US008697911B2

(12) United States Patent  
Cook et al.

(10) Patent No.: US 8,697,911 B2  
(45) Date of Patent: *Apr. 15, 2014

(54) RHO KINASE INHIBITORS

(75) Inventors: Brian Nicholas Cook, Danbury, CT (US); Jennifer A. Kowalski, New Milford, CT (US); Xiang Li, New Milford, CT (US); Daniel Richard Marshall, Norwalk, CT (US); Sabine Schlyer, New Milford, CT (US); Robert Sibley, North Haven, CT (US); Lana Louise Smith-Keenan, Poughquag, NY (US); Fariba Soleymanzadeh, Danbury, CT (US); Ronald John Sorcek, Bethel, CT (US); Erick Richard Roush Young, Danbury, CT (US); Yunlong Zhang, North Haven, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 138 days.

This patent is subject to a terminal disclaimer.

(21) Appl. No.: 13/171,696

(22) Filed: Jun. 29, 2011

(65) Prior Publication Data  
US 2012/0165322 A1 Jun. 28, 2012

Related U.S. Application Data

(60) Provisional application No. 61/362,032, filed on Jul. 7, 2010.

(51) Int. Cl.  
*A01N 37/18* (2006.01)  
*A61K 31/165* (2006.01)  
*C07C 239/00* (2006.01)  
*C07C 279/16* (2006.01)  
*C07D 473/00* (2006.01)  
*C07D 417/00* (2006.01)  
*C07C 45/78* (2006.01)  
*C07C 271/06* (2006.01)  
*C07D 271/12* (2006.01)  
*C07D 413/00* (2006.01)  
*C07D 271/00* (2006.01)  
*C07D 285/02* (2006.01)  
*C07D 285/04* (2006.01)  
*C07D 498/00* (2006.01)  
*C07D 513/00* (2006.01)  
*C07D 277/82* (2006.01)  
*C07D 263/60* (2006.01)  
*C07D 249/04* (2006.01)  
*C07D 249/08* (2006.01)  
*C07D 233/02* (2006.01)  
*C07D 231/00* (2006.01)

(52) U.S. Cl.  
USPC ............ 564/155; 514/617; 544/51; 544/264; 546/269.7; 568/473; 568/469; 568/304.3; 548/131; 548/125; 548/136; 548/148; 548/161; 548/217; 548/255; 548/262.4; 548/300.1; 548/356.1

(58) Field of Classification Search  
CPC .. C07C 233/57; C07C 233/64; C07D 251/10; C07D 251/04; C07D 233/00; C07D 239/20; C07D 239/84; C07D 237/04; C07D 277/20; C07D 409/04; C07D 401/04; C07D 279/16; C07D 239/94; C07D 277/62; C07D 249/02; C07D 265/30; C07D 413/04; C07D 419/04; C07D 221/04  
USPC ................ 514/617; 564/155; 548/148, 262.4, 548/356.1, 131, 125, 255, 136, 300.1, 161, 548/217; 544/51, 264; 546/269.7; 568/473, 568/469, 304.4  
See application file for complete search history.

(56) References Cited

U.S. PATENT DOCUMENTS 7,795,249 B2 * 9/2010 Adams et al. .............. 514/222.2  
8,093,266 B2 1/2012 Dahmann et al.  
2004/0082563 A1 4/2004 Dorsch et al.  
2007/0173530 A1 7/2007 deLong et al.  
2009/0270359 A1 10/2009 Ito et al.

(Continued)

FOREIGN PATENT DOCUMENTS

DE 10112768 A1 9/2002  
EP 1256574 A1 11/2002

(Continued)

OTHER PUBLICATIONS

Sheridan, R.P. "The Most Common Chemical Replacements in Drug-Like Compounds" J. Chem. Inf. Comput. Sci., 2002, vol. 42, pp. 103-108.*

(Continued)

*Primary Examiner* — Kendra D Carter  
(74) *Attorney, Agent, or Firm* — Michael P. Morris; Edward S. Lazer

(57) ABSTRACT

The present invention relates to compounds of formula (I):

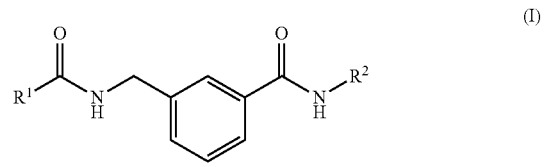

and pharmaceutically acceptable salts thereof, wherein $R^1$ and $R^2$ are as defined herein. The invention also relates to pharmaceutical compositions comprising these compounds, methods of using these compounds in the treatment of various diseases and disorders, processes for preparing these compounds and intermediates useful in these processes.

12 Claims, No Drawings

(56) References Cited

U.S. PATENT DOCUMENTS

| | | |
|---|---|---|
| 2010/0041645 A1 | 2/2010 | Dahmann et al. |
| 2010/0227846 A1 | 9/2010 | Ito et al. |
| 2012/0165322 A1 | 6/2012 | Cook et al. |
| 2012/0178752 A1 | 7/2012 | Ginn et al. |
| 2012/0270868 A1 | 10/2012 | Kirrane et al. |

FOREIGN PATENT DOCUMENTS

| | | |
|---|---|---|
| EP | 1403255 A1 | 3/2004 |
| JP | 11130751 A | 5/1999 |
| WO | 9205145 A1 | 4/1992 |
| WO | 9304682 A1 | 3/1993 |
| WO | 9304684 A1 | 3/1993 |
| WO | 0244126 A2 | 6/2002 |
| WO | 03015774 A1 | 2/2003 |
| WO | 2004071448 A2 | 8/2004 |
| WO | 2005051892 A1 | 6/2005 |
| WO | 2006034441 A1 | 3/2006 |
| WO | 2006052542 A2 | 5/2006 |
| WO | 2006129199 A1 | 12/2006 |
| WO | 2007008926 A1 | 1/2007 |
| WO | 2008053319 A1 | 5/2008 |
| WO | 2008083124 A1 | 7/2008 |
| WO | 2008086047 A1 | 7/2008 |
| WO | 2008157330 A1 | 12/2008 |
| WO | 2009027392 A1 | 3/2009 |
| WO | 2009028543 A1 | 3/2009 |
| WO | 2009065131 A1 | 5/2009 |
| WO | 2009119880 A1 | 10/2009 |
| WO | 2012006202 A1 | 1/2012 |
| WO | 2012006203 A1 | 1/2012 |
| WO | 2012054367 A1 | 4/2012 |

OTHER PUBLICATIONS

Chen, Jichou, et al; Synthesis of Carboxyphenoxyacetic Acid Derivatives Using Liquid-Liquid Phase Transfer Catalysis; Gaodeng Xuexiao Huaxue Xuebao (1991) vol. 12, No. 9, abstract.

Hoering, Heidi, et al; From Bench to Clinic and Back: Perspective on the 1st IQPC Translational Research Conference; Journal of Translational Medicine (2004) vol. 2, Chapter 44 pp. 1-8.

International Search Report and Written Opinion for PCT/US2008/050014 mailed May 8, 2008.

International Search Report and Written Opinion for PCT/US2011/042507 mailed Oct. 11, 2011.

International Search Report and Written Opinion for PCT/US2011/042508 mailed Oct. 12, 2011.

International Search Report and Written Opinion for PCT/US2011/056505 mailed Dec. 23, 2011.

Loirand, Gervaise, et al; Rho Kinases in Cardiovasculasr Physiology and Phathophysiology; Circulation Research (2006) vol. 98 pp. 322-334.

Lorthioir, Olivier, et al; Single Bead Characterization Using Analytical Constructs: Application to Quality Control of Libraries; Analytical Chemistry (2001) vol. 73 pp. 963-970.

Morwick, Tina, et al; Hit to Lead Account of the Discovery of Bisbenzamide and Related Ureidobenzamide inhibitors nhibitors of Rho Kinase; Journal of Medicinal Chemistry (2010) vol. 53 pp. 759-777.

Schaefer, Stefan, et al; Failure is an Option: Learning From Unsuccessfull Proof-Of-Concept Trials; Drug Discovery Today (2008) vol. 13, No. 21/22 pp. 913-916.

Tawara, Shunsuke, et al; Progress of the Study of Rho-Kinase and Future Perspective of the Inhibitor; Yakugarku Zasshi (2007) vol. 127, No. 3 Abstract p. 501.

\* cited by examiner

RHO KINASE INHIBITORS

FIELD OF THE INVENTION

This invention relates to substituted amide derivatives which are useful as inhibitors of Rho kinase and are thus useful for treating a variety of diseases and disorders that are mediated or sustained through the activity of Rho kinase, including cardiovascular diseases, cancer, neurological diseases, renal diseases, bronchial asthma, erectile dysfunction, and glaucoma. This invention also relates to pharmaceutical compositions comprising these compounds, methods of using these compounds in the treatment of various diseases and disorders, processes for preparing these compounds and intermediates useful in these processes.

BACKGROUND

Rho-Kinase (ROCK) is a member of the serine-threonine protein kinase family. ROCK exists in two isoforms, ROCK1 and ROCK2 (T. Ishizaki et al., EMBO J., 1996, 15, 1885-1893). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (K. Riento and A. J. Ridley, Nat Rev Mol Cell Biol, 2003, 4, 446-56). It is also directly involved in regulating smooth muscle contraction (A. P. Somlyo, Nature, 1997, 389, 908-911). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the RhoA/ROCK signaling pathway plays an important role in signal transduction initiated by several vasoactive factors, for example angiotensin II (T. Yamakawa et al., Hypertension, 2000, 35, 313-318), urotension II (V. Sauzeau et al., Circ. Res., 2001, 88, 1102-1104), endothelin-1 (P. Tangkijvanich et al., Hepatology, 2001, 33, 74-80), serotonin (H. Shimokawa, Jpn. Circ. J., 2000, 64, 1-12), norepinephrine (M. C. Martinez, et al., Am. J. Physiol., 2000, 279, H1228-H1238) and platelet-derived growth factor (PDGF) (H. Kishi et al., J. Biochem., 2000, 128, 719-722). Many of these factors are implicated in the pathogenesis of cardiovascular disease.

Additional studies in the literature, some using the known ROCK inhibitors fasudil (T. Asano et al., J. Pharmacol. Exp. Ther., 1987, 241, 1033-1040) or Y-27632 (M. Uehata et al., Nature, 1997, 389, 990-994) further illustrate the link between ROCK and cardiovascular disease. For example, ROCK expression and activity have been shown to be elevated in spontaneously hypertensive rats, suggesting a link to the development of hypertension in these animals (Y. Mukai et al., FASEB J., 2001, 15, 1062-1064). The ROCK inhibitor Y-27632 (M. Uehata et al., Nature, ibid) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Y. Eto et al., Am. J. Physiol. Heart Circ. Physiol., 2000, 278, H1744-H1750). In a similar model, ROCK inhibitor Y-27632 also inhibited neointimal formation in rats (N. Sawada et al., Circulation, 2000, 101, 2030-2033). In a porcine model of IL-1 beta-induced coronary stenosis, long term treatment with the ROCK inhibitor fasudil was shown to progressively reduce coronary stenosis, as well as promote a regression of coronary constrictive remodeling (H. Shimokawa et al., Cardiovascular Res., 2001, 51, 169-177).

Additional investigations suggest that a ROCK inhibitor would be useful in treating other cardiovascular diseases. For example, in a rat stroke model, fasudil was shown to reduce both the infarct size and neurologic deficit (Y. Toshima, Stroke, 2000, 31, 2245-2250). The ROCK inhibitor Y-27632 was shown to improve ventricular hypertrophy and function in a model of congestive heart failure in Dahl salt-sensitive rats (N. Kobayashi et al., Cardiovascular Res., 2002, 55, 757-767).

Other animal or clinical studies have implicated ROCK in additional diseases including coronary vasospasm (H. Shimokawa et al., Cardiovasc. Res., 1999, 43, 1029-1039), cerebral vasospasm (M. Sato et al., Circ. Res., 2000, 87, 195-200), ischemia/reperfusion injury (T. Yada et al., J. Am. Coll. Cardiol., 2505, 45, 599-607), pulmonary hypertension (Y. Fukumoto et al., Heart, 2005, 91, 391-392), angina (H. Shimokawa et al., J. Cardiovasc. Pharmacol., 2002, 39, 319-327), renal disease (S. Satoh et al., Eur. J. Pharmacol., 2002, 455, 169-174) and erectile dysfunction (N. F. Gonzalez-Cadavid and J. Rajifer, Endocrine, 2004, 23, 167-176).

In another study, it has been demonstrated that inhibition of the RhoA/ROCK signaling pathway allows formation of multiple competing lamellipodia that disrupt the productive migration of monocytes (R. A. Worthylake et al. The Journal of Biol. Chem., 2003, 278, 13578-13584). It has also been reported that small molecule inhibitors of Rho Kinase are capable of inhibiting MCP-1 mediated chemotaxis in vitro (H. Iijima, Biorganic and Medicinal Chemistry, 2007, 15, 1022-1033). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (H. Shimokawa et al., Arterioscler. Thromb. Vasc. Biol., 2005, 25, 1767-1775). Furthermore, Rho-kinase has been indicated as a drug target for the treatment of various other diseases, including airway inflammation and hyperresponsiveness (P. J. Henry et al., Pulm Pharmacol Ther., 2005, 18, 67-74), cancer (R. Rattan et al., J Neurosci. Res., 2006, 83, 243-55. D. Lepley et al., Cancer Res., 2005, 65, 3788-95), as well as neurological disorders, such as spinal-cord injury, Alzheimer disease, multiple sclerosis, stroke and neuropathic pain (B. K. Mueller et al., Nat Rev Drug Disc, 2005, 4, 387-398; X. Sun et. al., J. Neuroimmunology, 2006, 180, 126-134).

There remains an unmet medical need for new drugs to treat cardiovascular disease. A study published in 2003 estimated that almost 29% of the adult U.S. population had hypertension in 1999-2000 (I. Hajjar et al., JAMA, 2003, 290, 199-206). Furthermore, 69% of the hypertensive individuals studied during this period did not have their hypertension controlled at the time their blood pressure was measured. This figure was worse in patients with diabetes and hypertension where 75% of those patients studied did not have their blood pressure controlled to the target level. Another more recent study showed similar results, with less than one-third of hypertensive patients studied having blood pressure controlled to the target level (V. Andros, Am. J. Manag. Care, 2005, 11, S215-S219). Therefore, despite the number of medications available to treat hypertension, including diuretics, beta blockers, angiotensin converting enzyme inhibitors, angiotensin blockers and calcium channel blockers, hypertension remains poorly controlled or resistant to current medication for many patients. If not adequately treated, hypertension can lead to other cardiovascular diseases and organ failure including coronary artery disease, stroke, myocardial infarction, cardiac failure, renal failure and peripheral artery disease.

Although there are many reports of ROCK inhibitors under investigation (see, for example, U.S. 20100041645 A1, U.S. 20080161297 A1 and E. Hu and D. Lee, Expert Opin. Ther. Targets, 2005, 9, 715-736), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, bronchial asthma, erectile dysfunction, and glaucoma.

BRIEF SUMMARY OF THE INVENTION

In a general aspect, the present invention is directed to the compounds of the formula I:

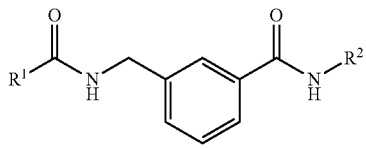

wherein $R^1$ and $R^2$ are as defined herein, as well as the tautomers and pharmaceutically acceptable salts thereof. It has been found that the compounds of formula I have valuable pharmacological properties, particularly on inhibiting activity on Rho kinase.

In another aspect, the present invention is directed to a method of inhibiting Rho kinase activity in a warm blooded animal comprising administering to said warm blooded animal a compound of the present invention as described above.

In another aspect, the present invention is directed to a method for treating a disease or disorder associated with the activation of Rho kinase which method comprises administering to a warm blooded animal in need of such treatment a compound of the present invention as described above.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, cardiac failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma and glaucoma, which method comprises administering to a patient in need of such treatment a compound of the present invention as described above.

In another aspect, the present invention is directed to a method of treating diseases mediated at least partially by Rho kinase including spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

DETAILED DESCRIPTION OF THE INVENTION

In an embodiment, there are provided compounds of the formula I

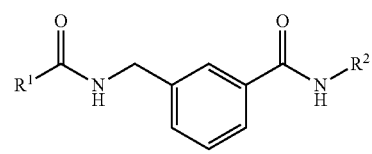

wherein:

$R^1$ is a substituted aryl, heteroaryl or heterocyclyl moiety selected from

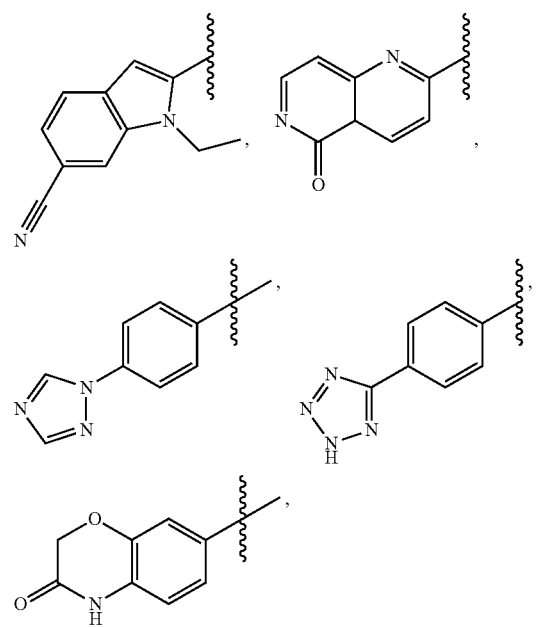

-continued
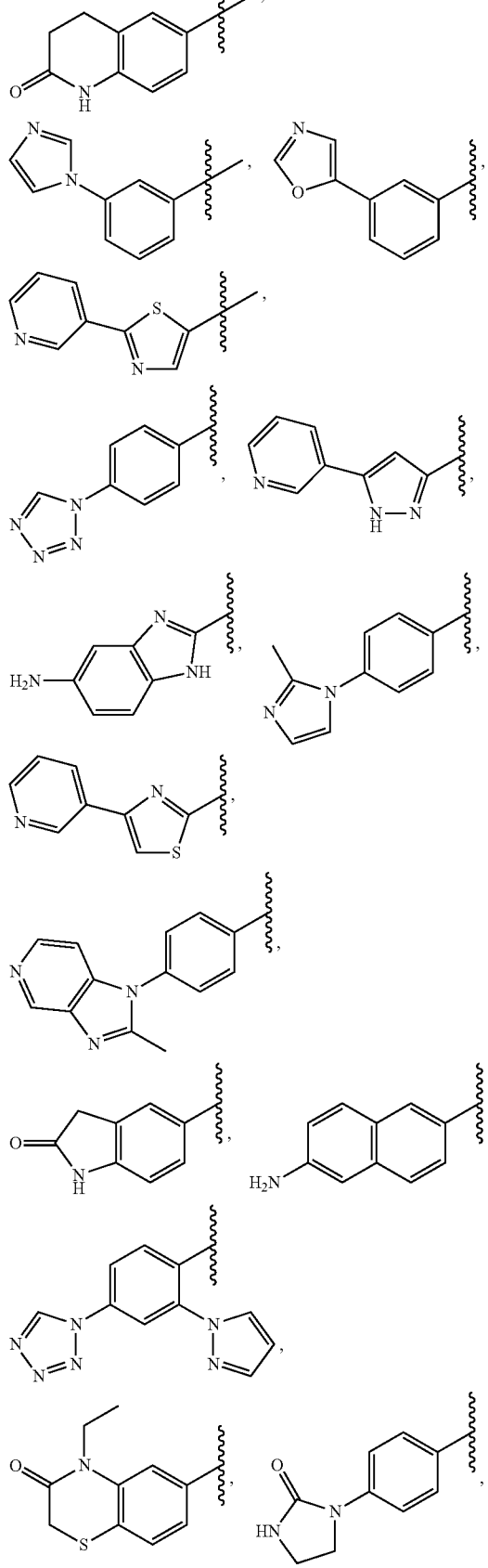
-continued
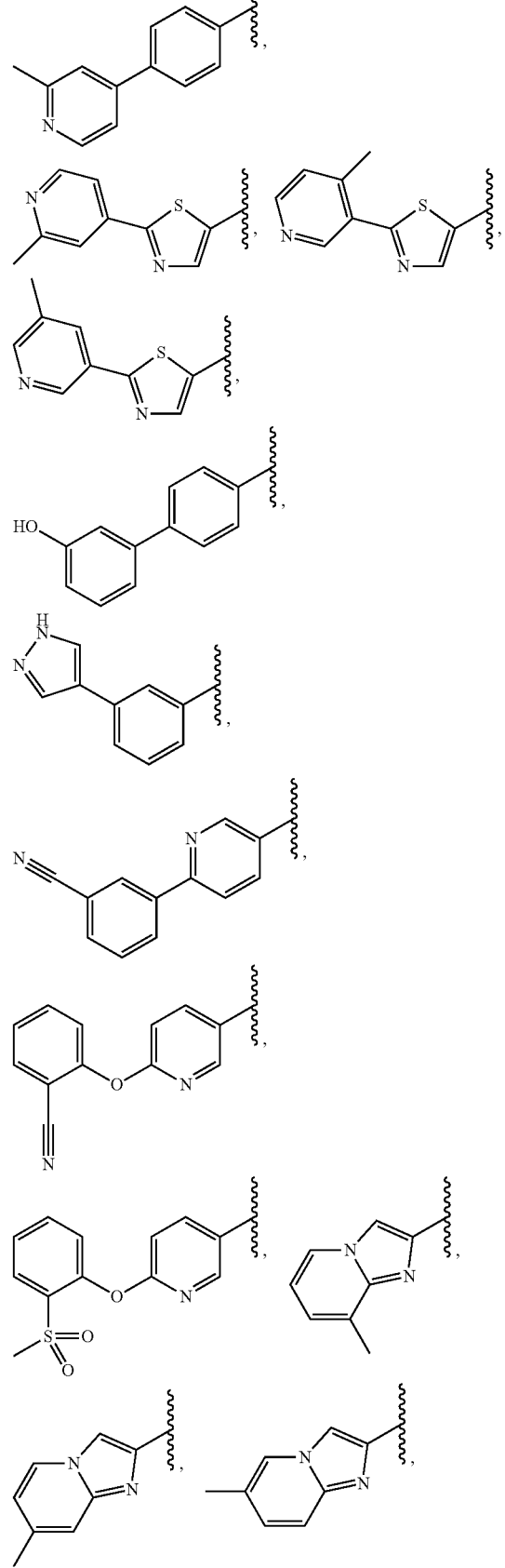

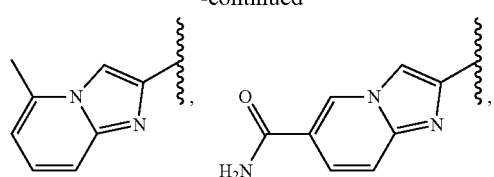
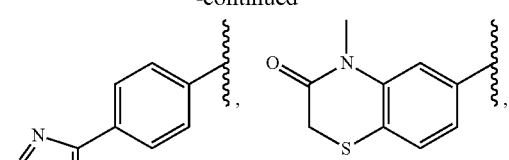
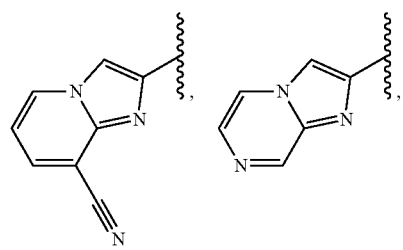
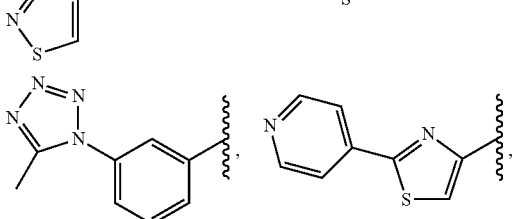
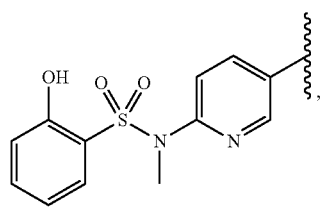
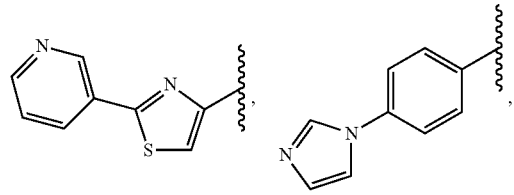
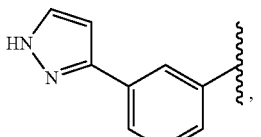
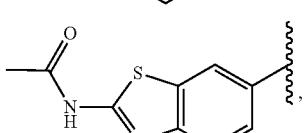
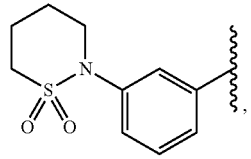
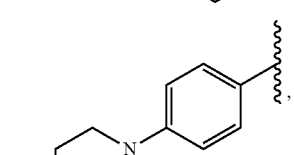
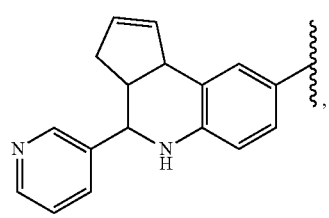
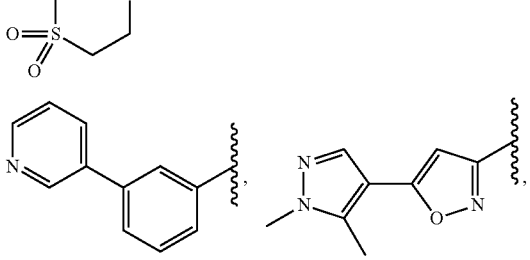
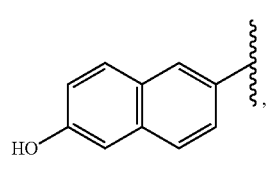
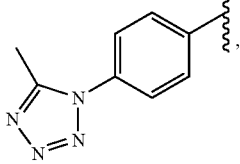
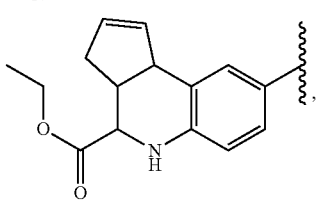
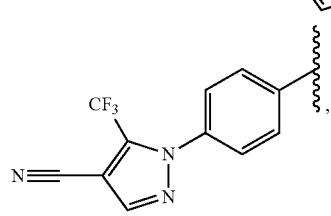
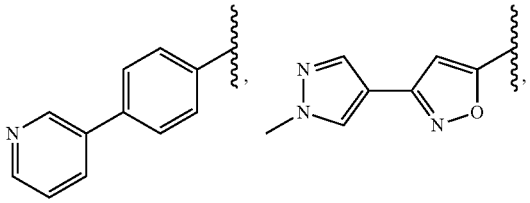

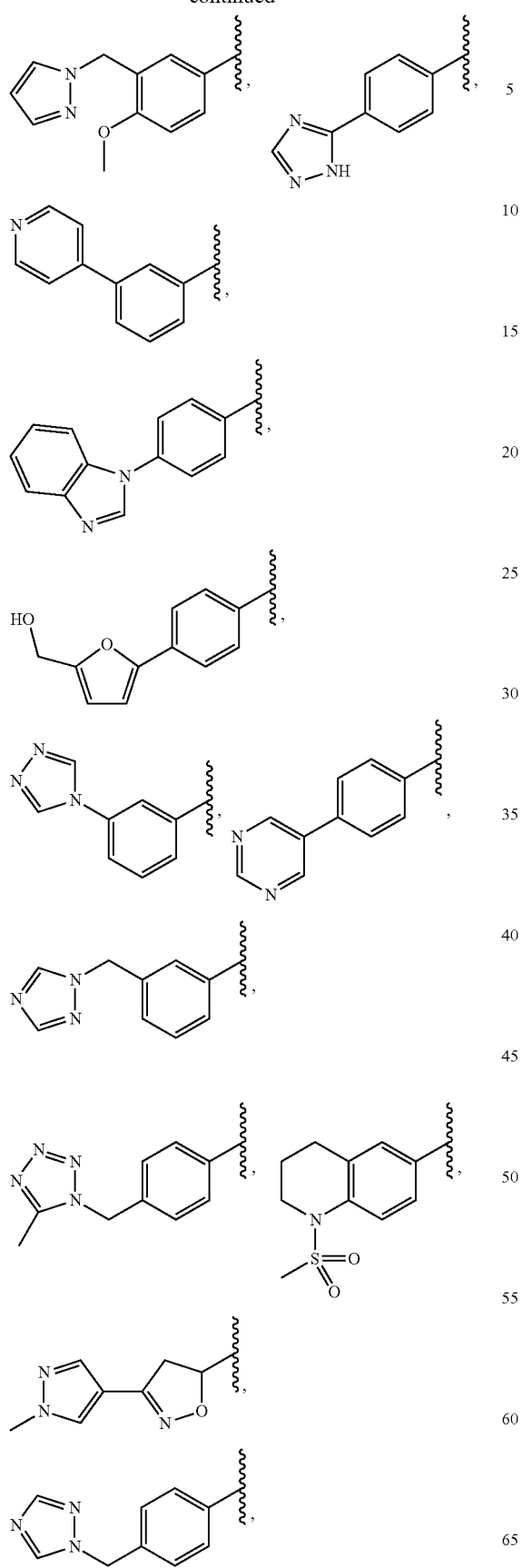
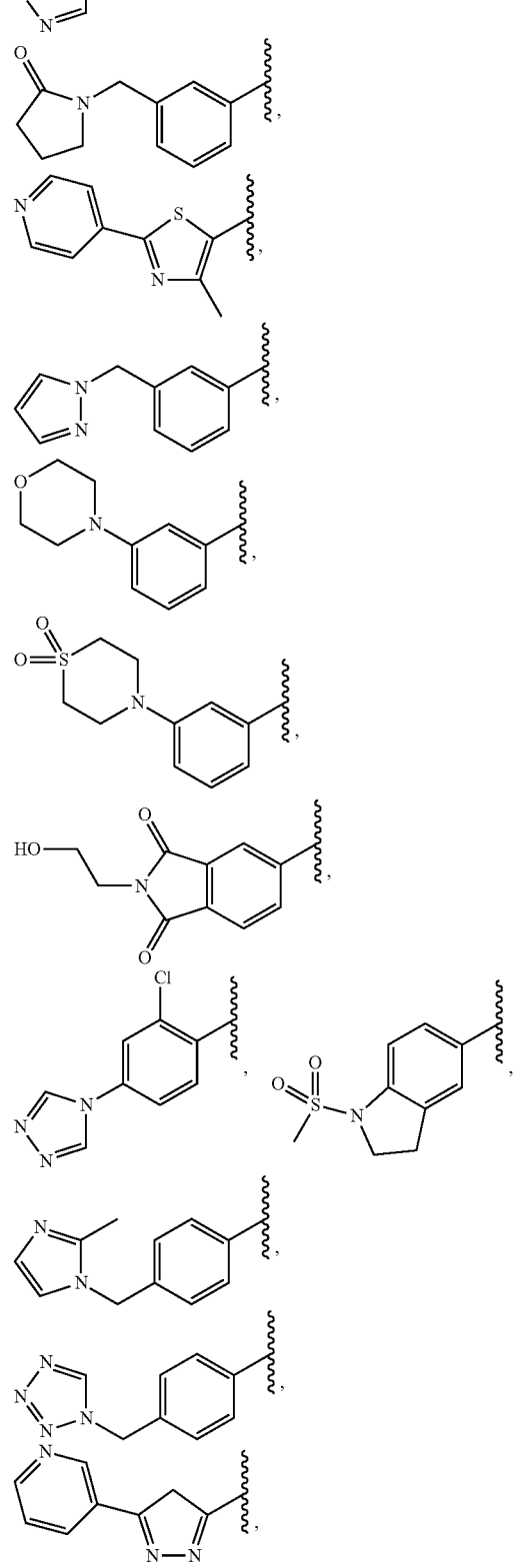

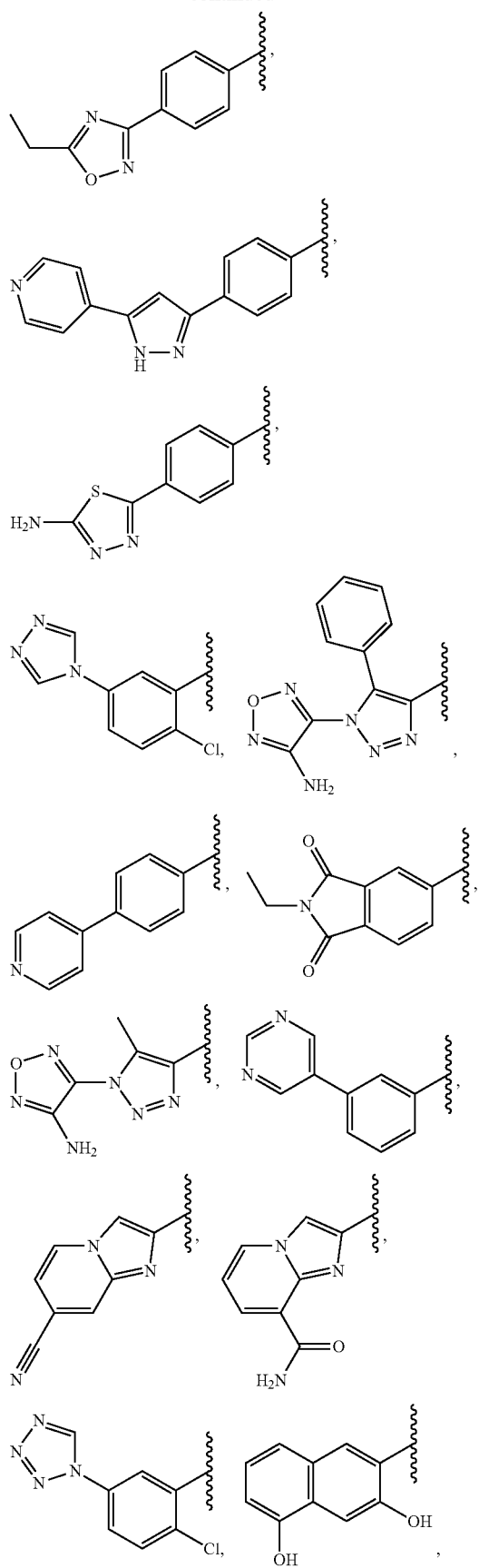
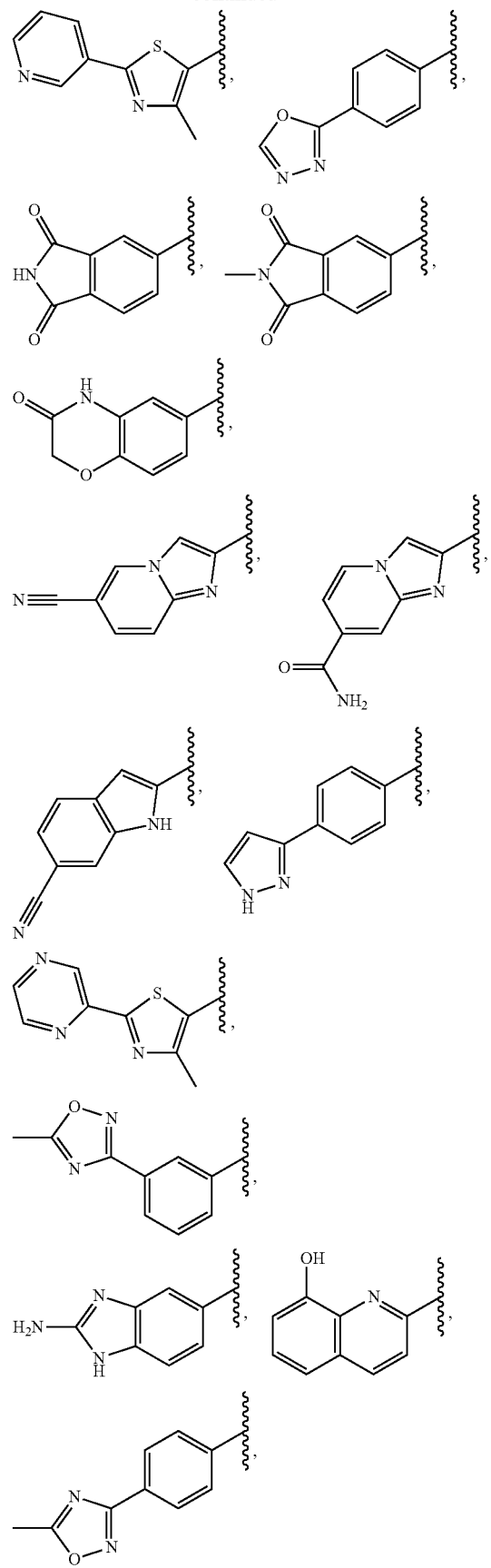

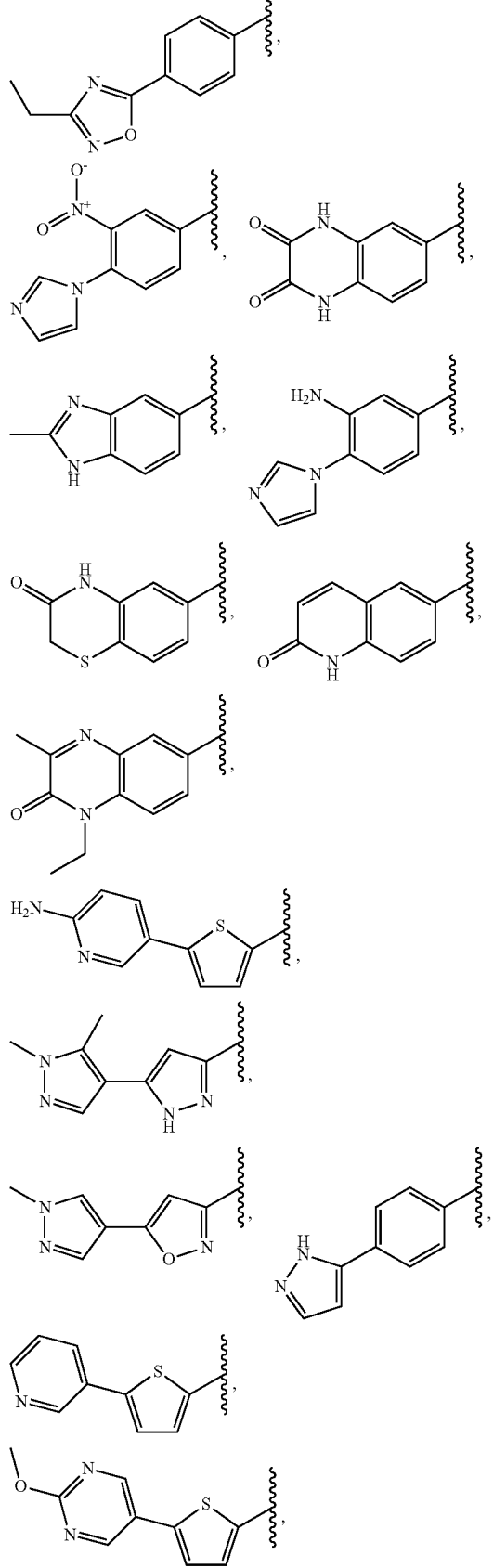
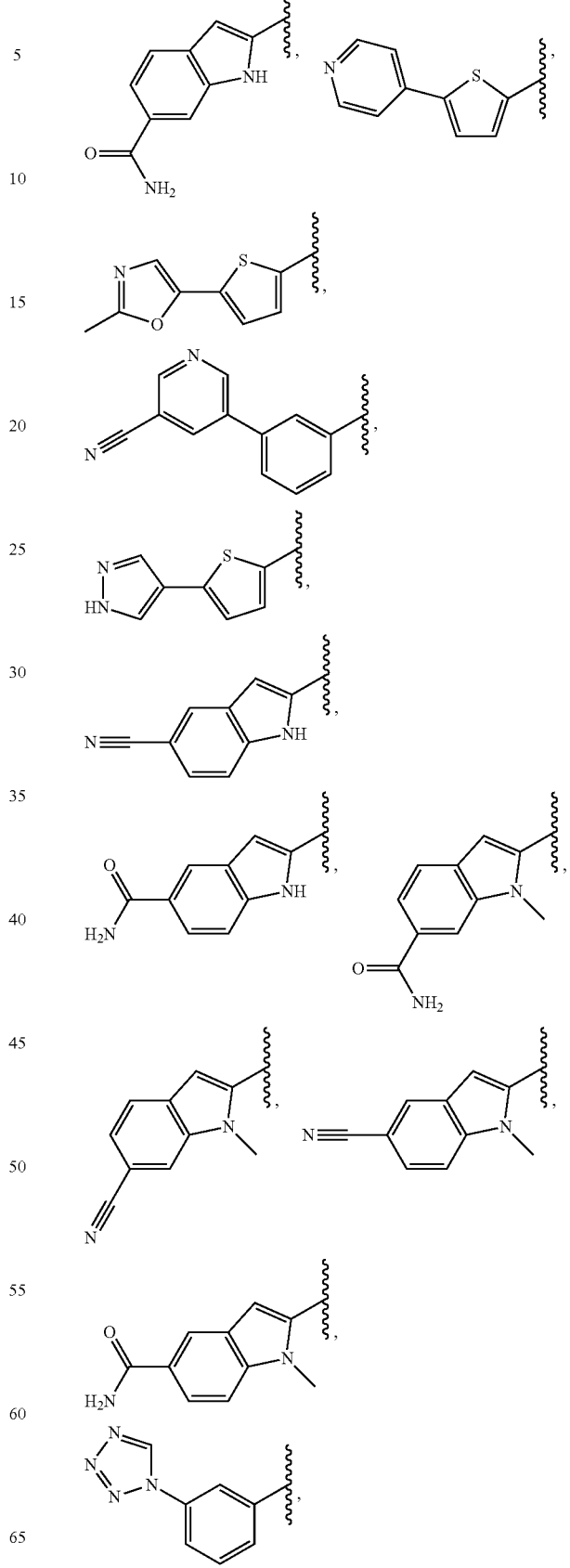

-continued

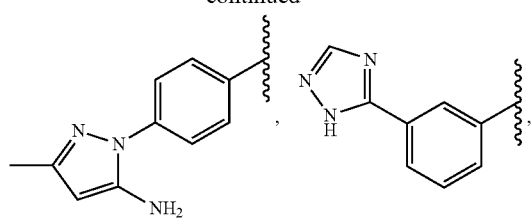,

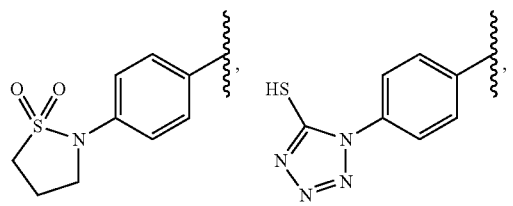,

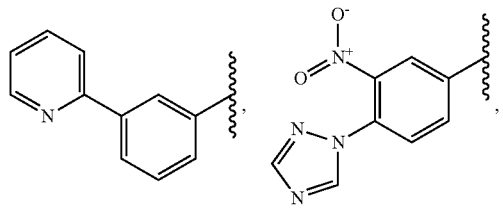,

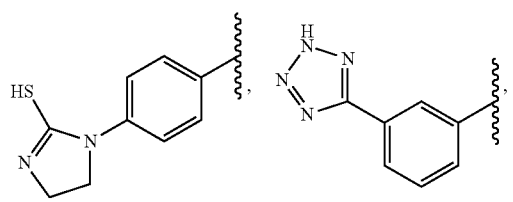,

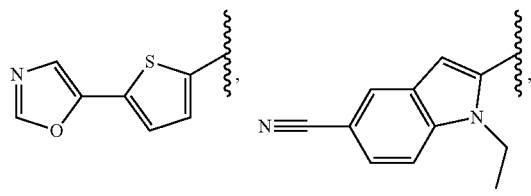;

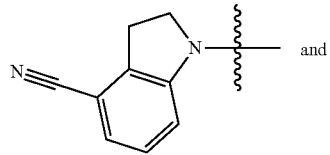

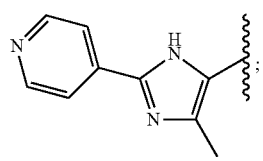 and

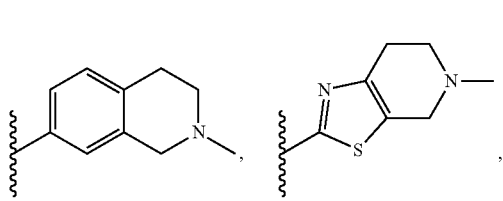

R² is selected from

-continued

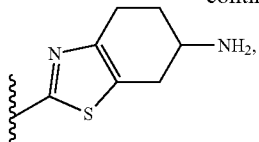,

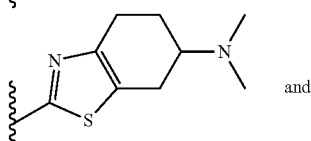 and

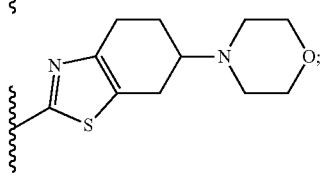;

or a salt thereof.

In another embodiment there are provided compounds of formula I as described above and wherein:
R² is

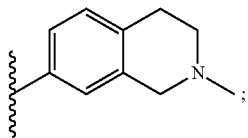 [SMILES: *c1ccc2c(c1)CN(C)CC2];

or a salt thereof.

In another embodiment there are provided compounds of formula I as described in the first embodiment and wherein:
R² is

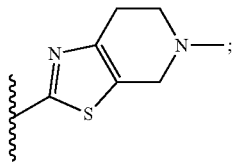 [SMILES: *c1nc2c(s1)CN(C)CC2];

or a salt thereof.

In another embodiment there are provided compounds of formula I as described in the first embodiment and wherein:
R² is selected from

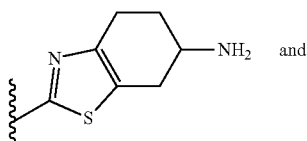 and

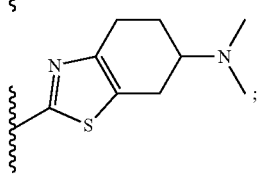;

or a salt thereof.

In another embodiment there are provided compounds of formula I as described in the first embodiment and wherein:
R² is
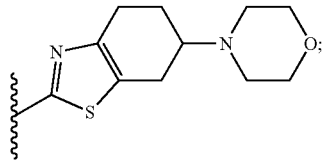 [SMILES: *c1nc2c(s1)CC(N1CCOCC1)CC2]
or a salt thereof.
In another embodiment there are provided compounds of formula I as described in the first embodiment and wherein:
R¹ is a substituted aryl, heteroaryl or heterocyclyl moiety selected from
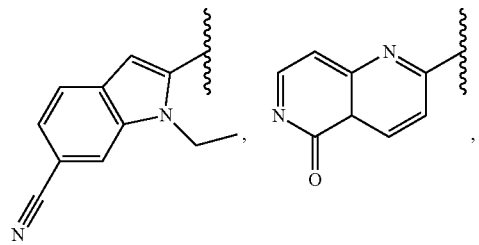,
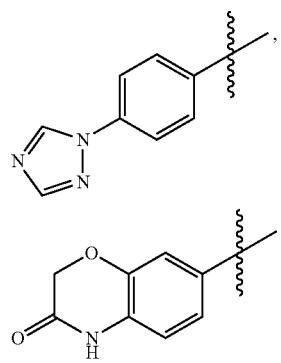,
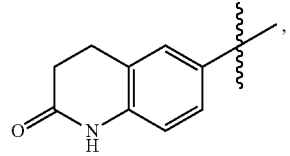,
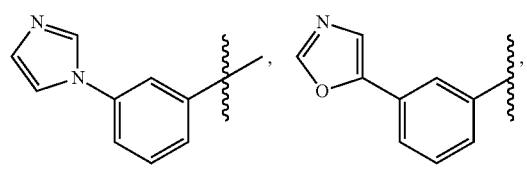,
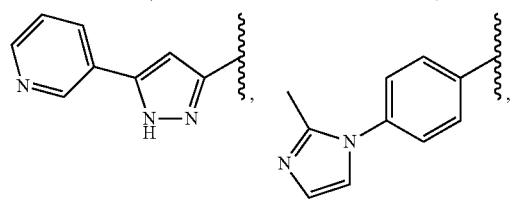,
-continued
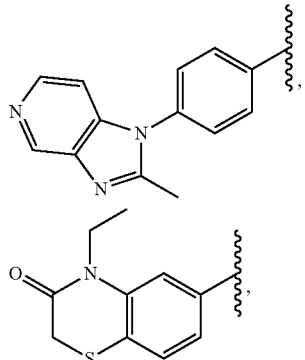,
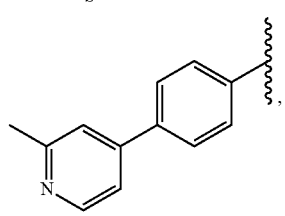,
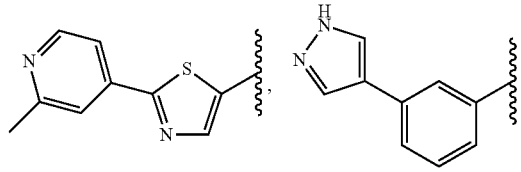,
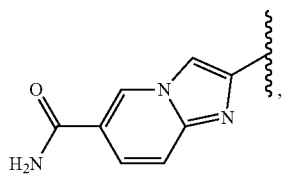,
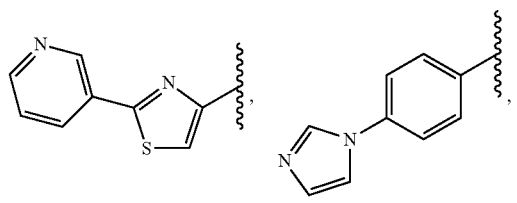,
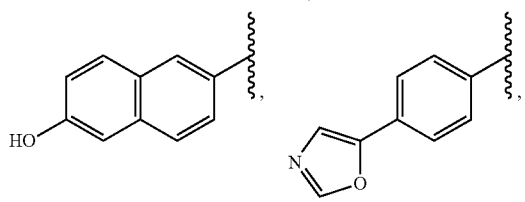,
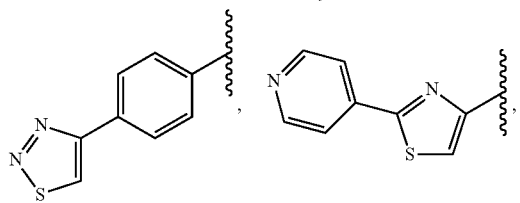,
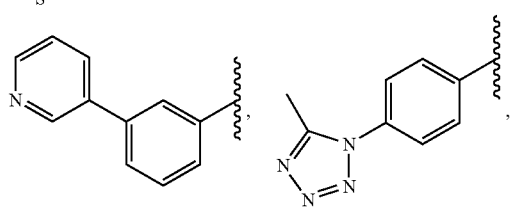,

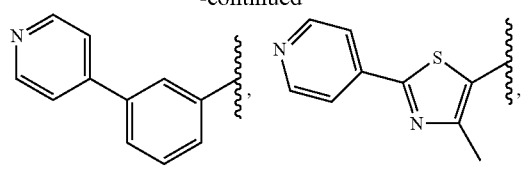
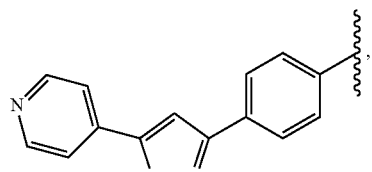
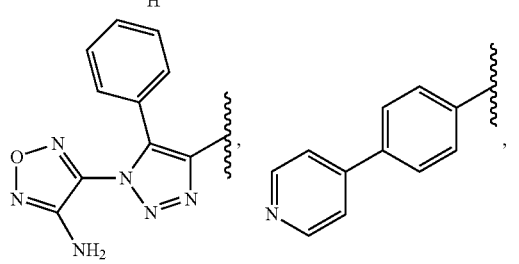
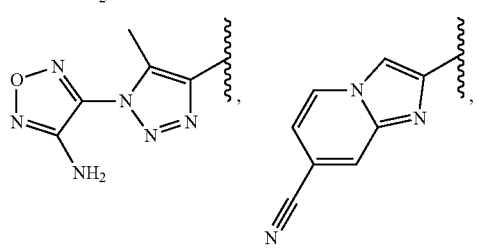
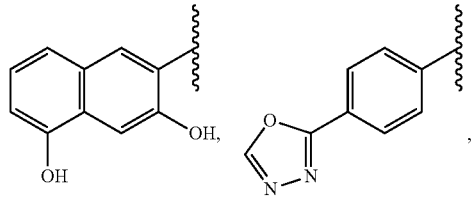
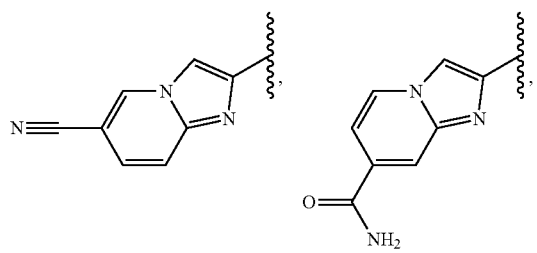
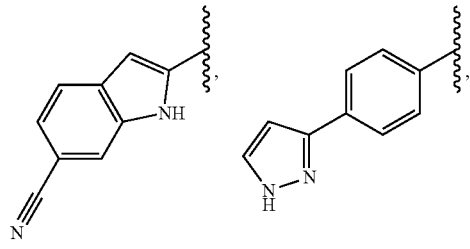
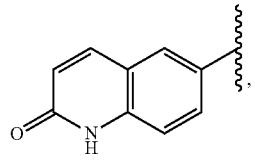
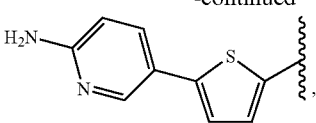
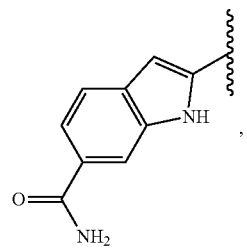
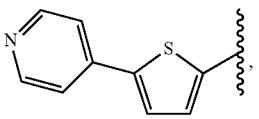
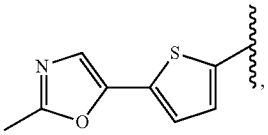
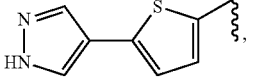
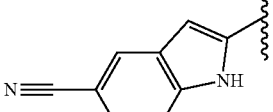
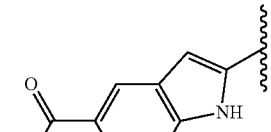
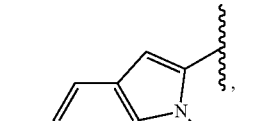
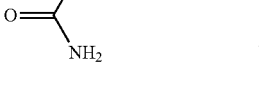
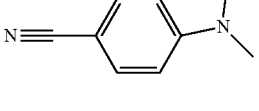
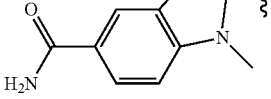

-continued

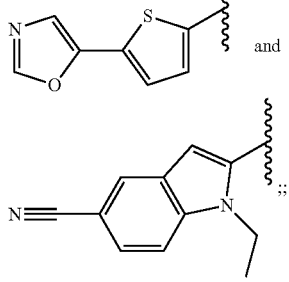 and

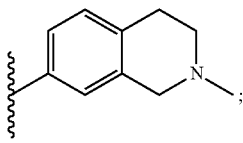 [SMILES: *c1ccc2c(c1)CN(C)CC2];

or a salt thereof.

In another embodiment there are provided compounds of formula I as described above and wherein:
R² is

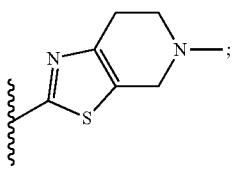 [SMILES: *c1nc2c(s1)CN(C)CC2];

or a salt thereof.

In another embodiment there are provided compounds of formula I as described in the embodiment two above and wherein:
R² is

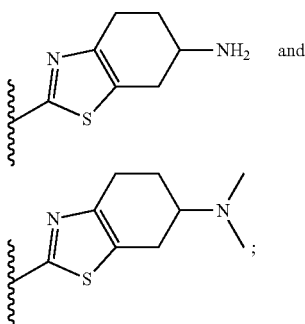

or a salt thereof.

In another embodiment there are provided compounds of formula I as described in the embodiment three above and wherein:
R² is selected from

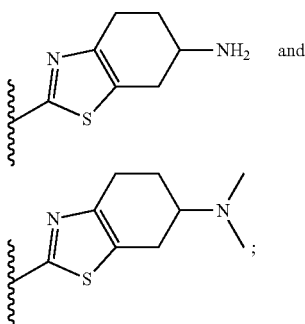

or a salt thereof.

In another embodiment there are provided compounds of formula I as described in the embodiment four above and wherein:

R² is

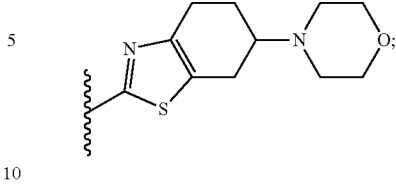

or a salt thereof.

In another embodiment there are provided compounds of formula I as described in the first embodiment and wherein:
R¹ is a substituted phenyl or naphthyl moiety selected from

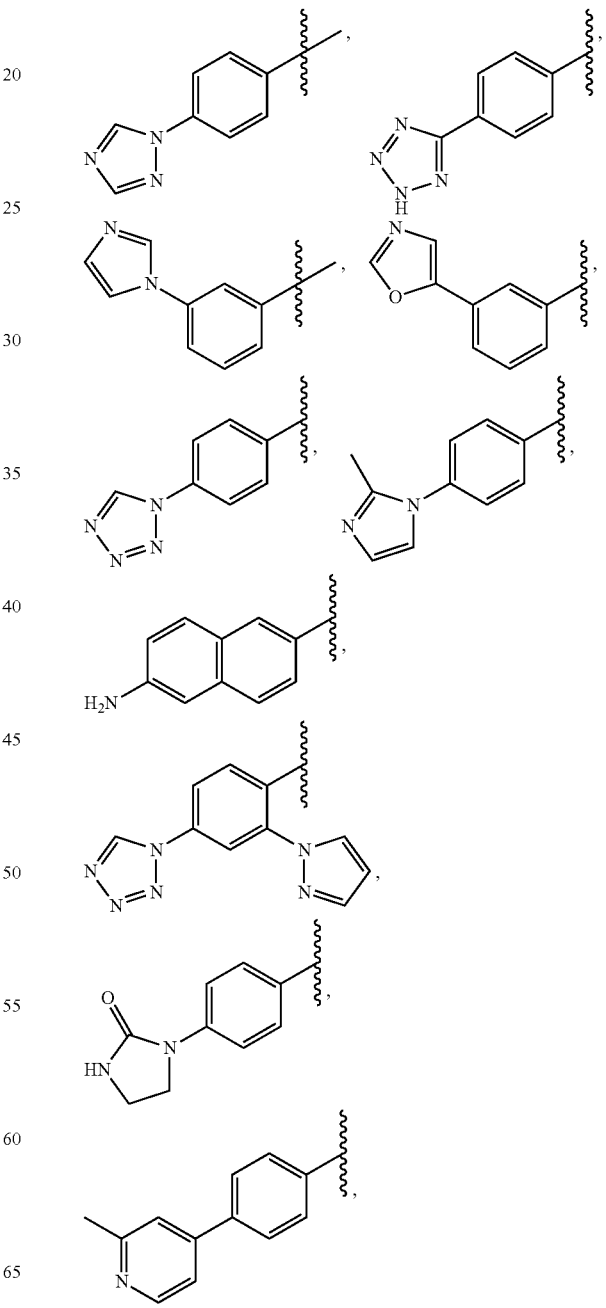

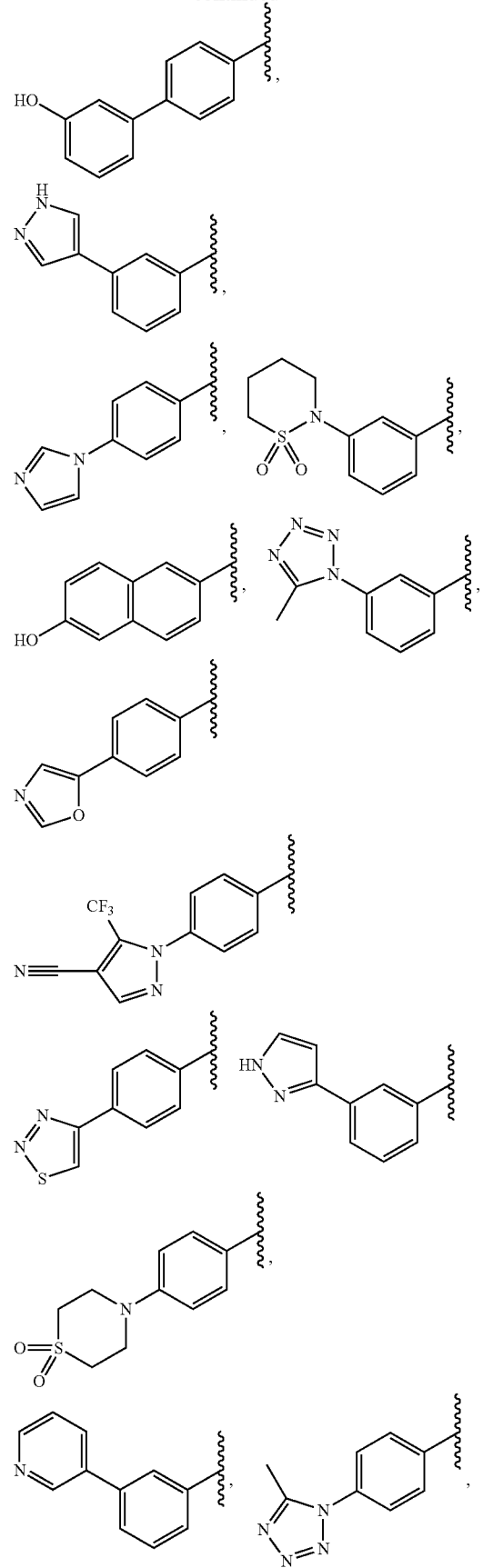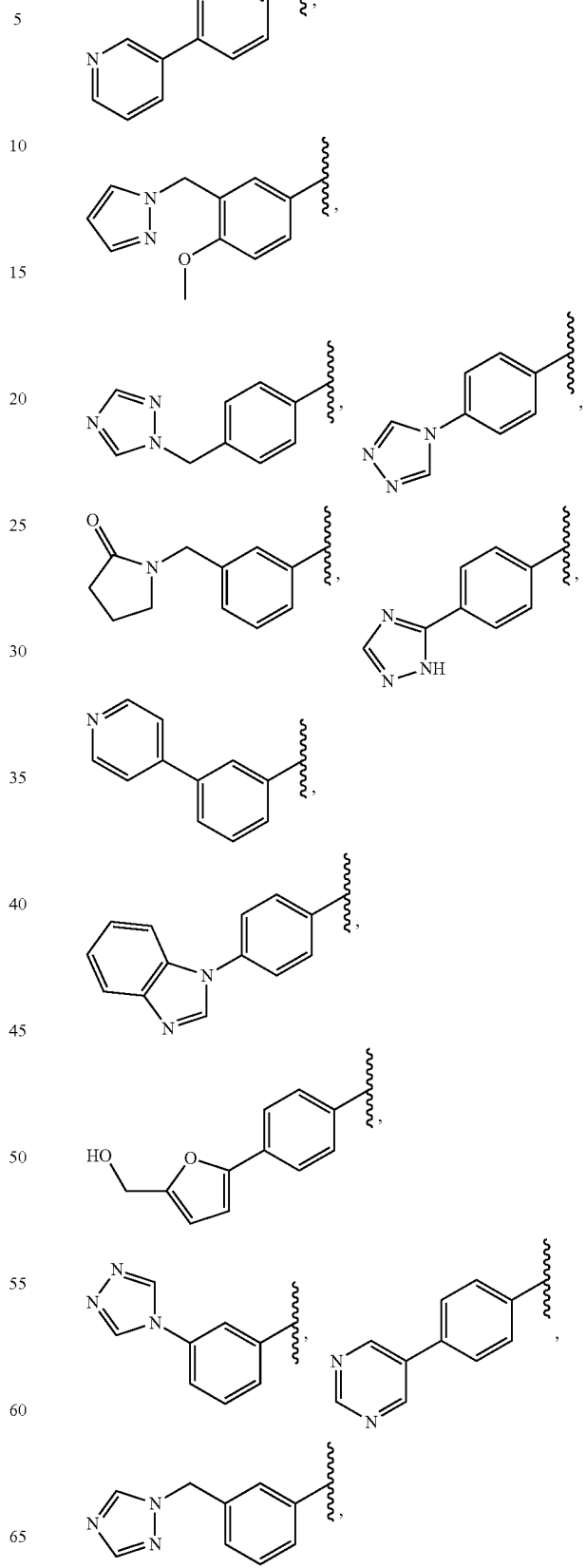

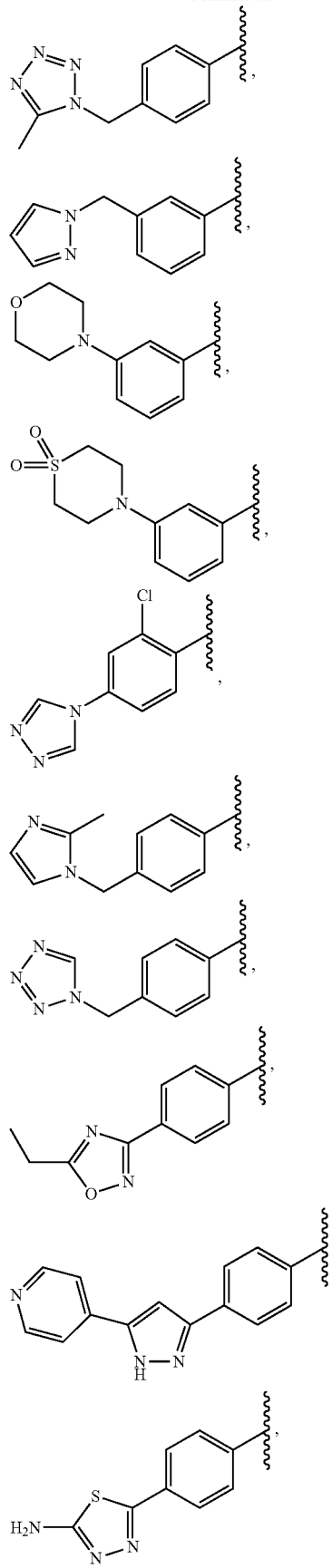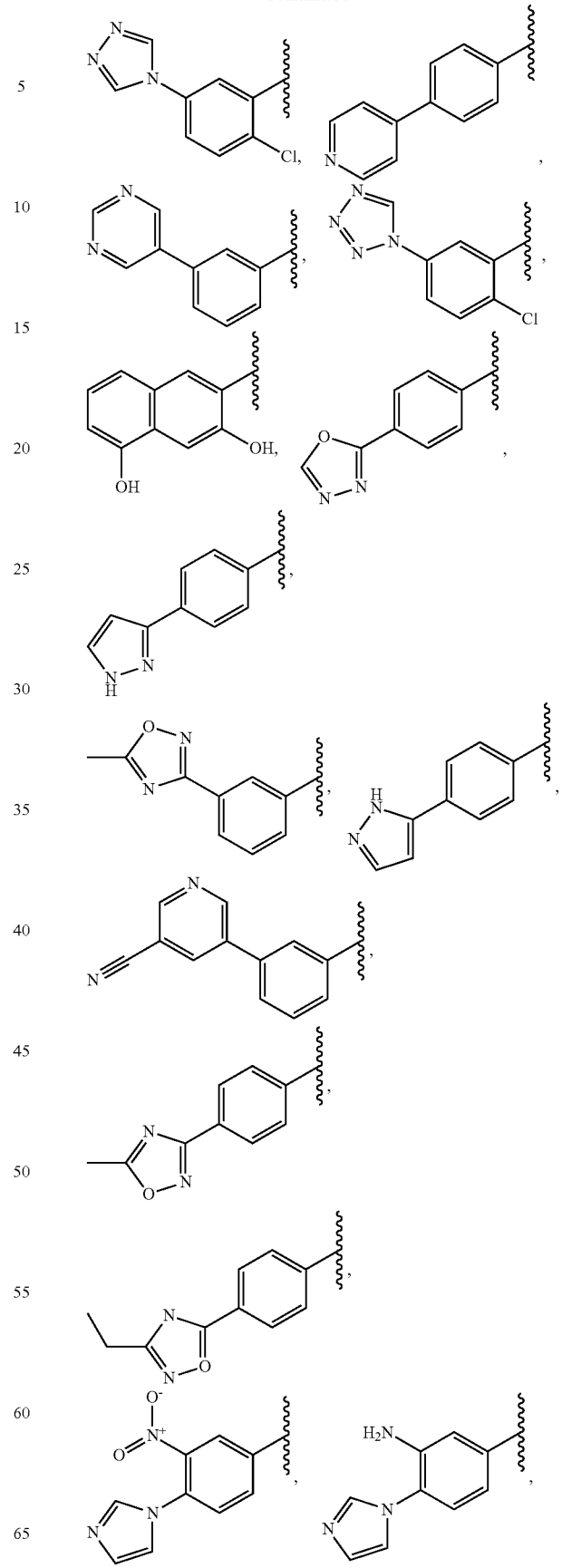

-continued

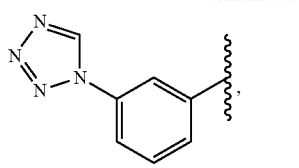

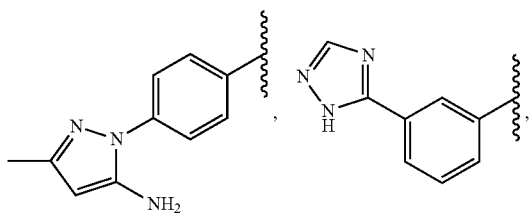

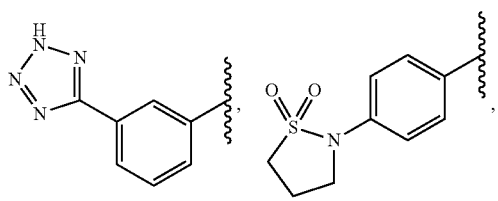

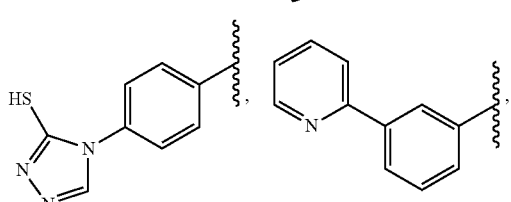

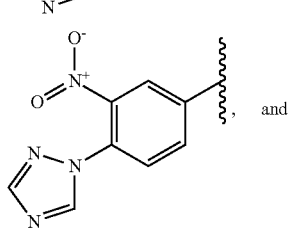

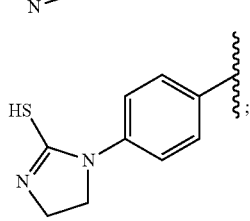

, and

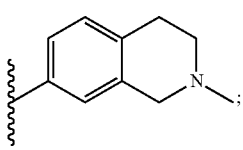 [SMILES: *c1ccc2c(c1)CN(C)CC2]

or a salt thereof.

In another embodiment there are provided compounds of formula I as described above and wherein:
R² is

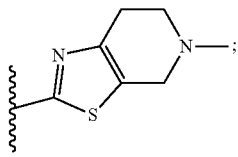 [SMILES: *c1nc2c(s1)CN(C)CC2]

or a salt thereof.

In another embodiment there are provided compounds of formula I as described in the embodiment two above and wherein:

R² is

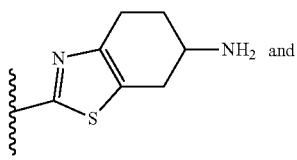

or a salt thereof.

In another embodiment there are provided compounds of formula I as described in the embodiment three above and wherein:
R² is selected from

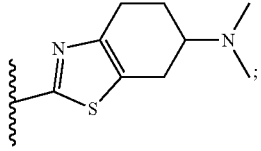

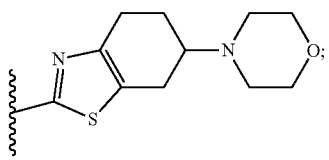 [SMILES: *c1nc2c(s1)CC(N1CCOCC1)CC2]

or a salt thereof.

In another embodiment there are provided compounds of formula I as described in the embodiment four above and wherein:
R² is

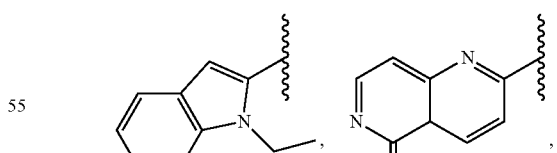

or a salt thereof.

In another embodiment there are provided compounds of formula I as described in the first embodiment and wherein:
R¹ is a substituted heteroaryl or heterocyclyl moiety selected from

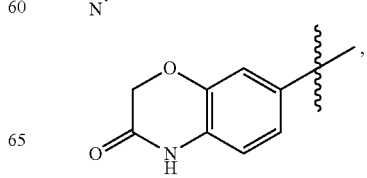

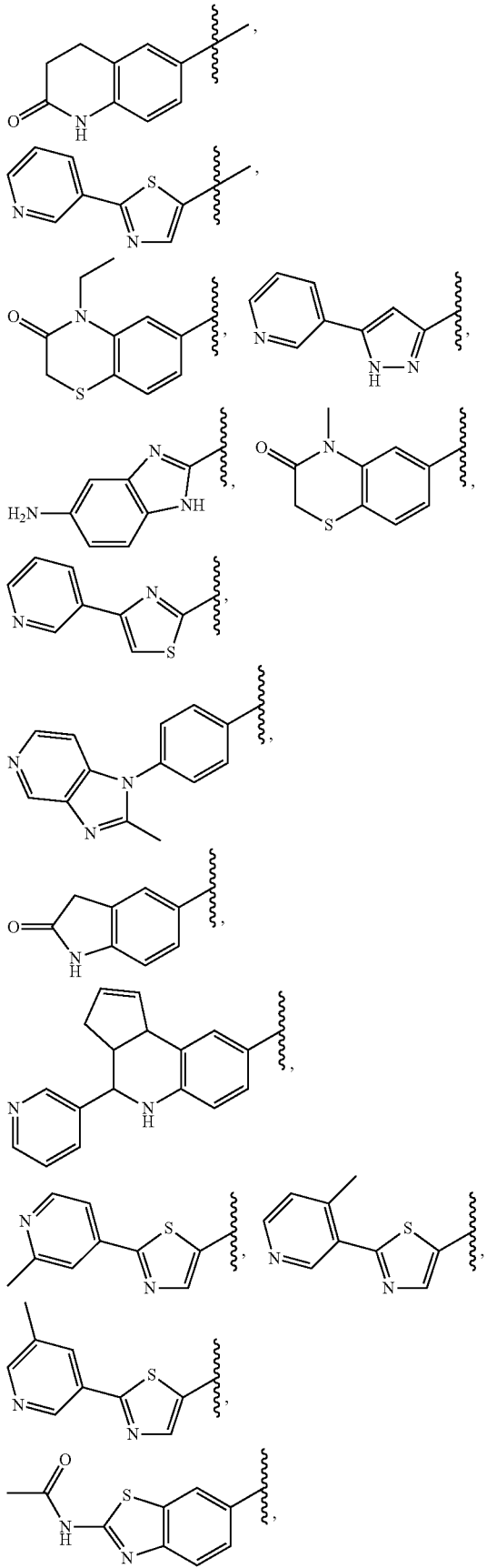
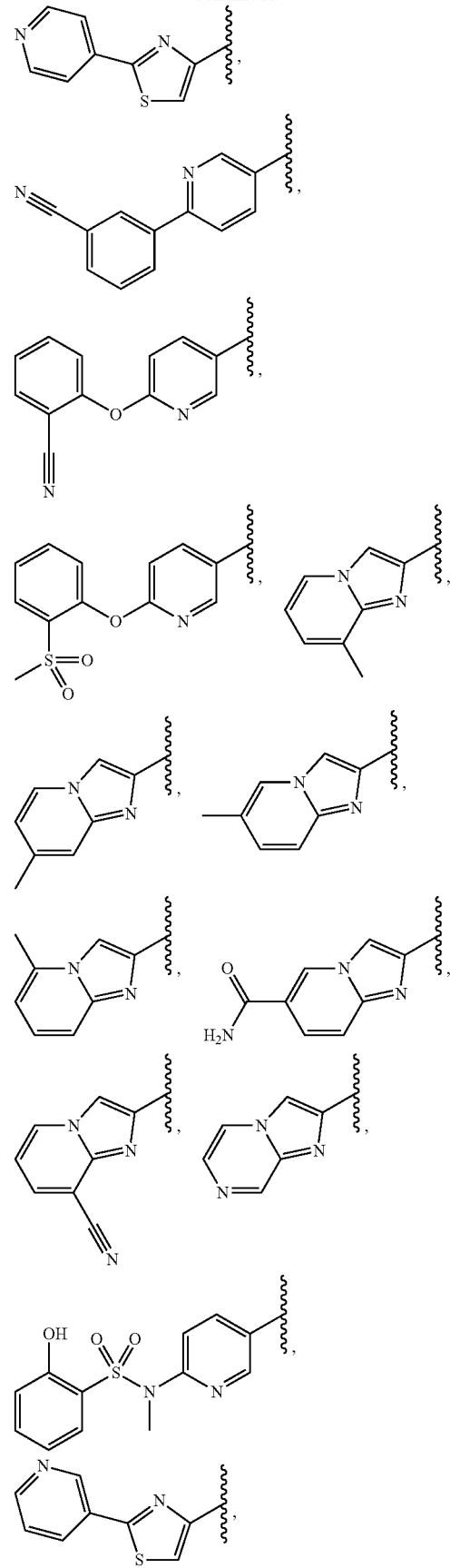

31
-continued
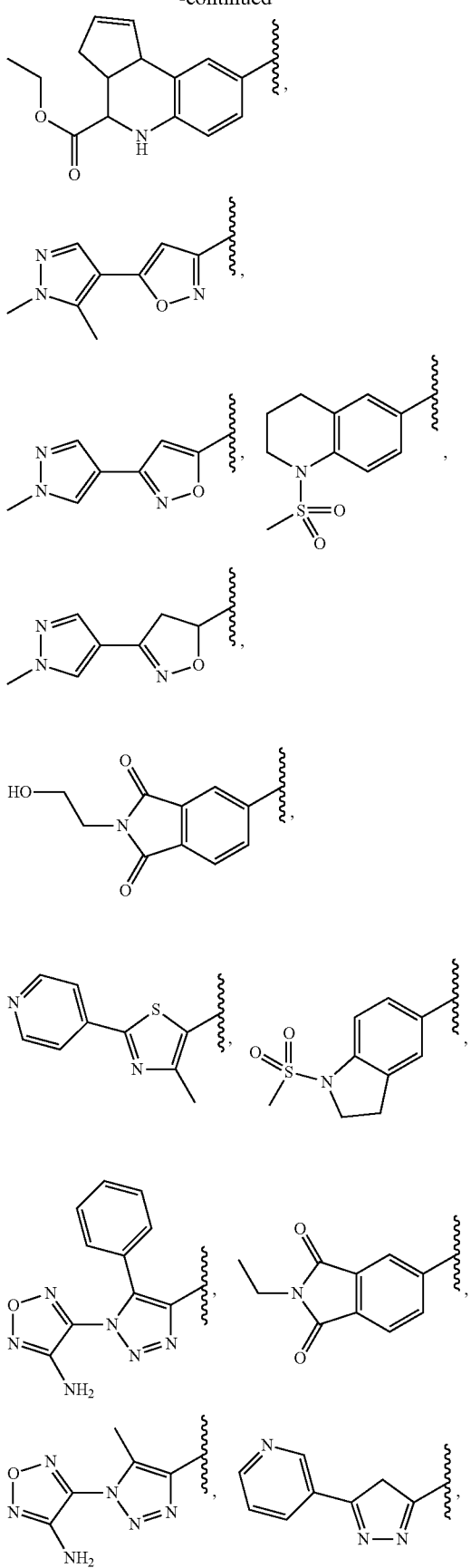
32
-continued
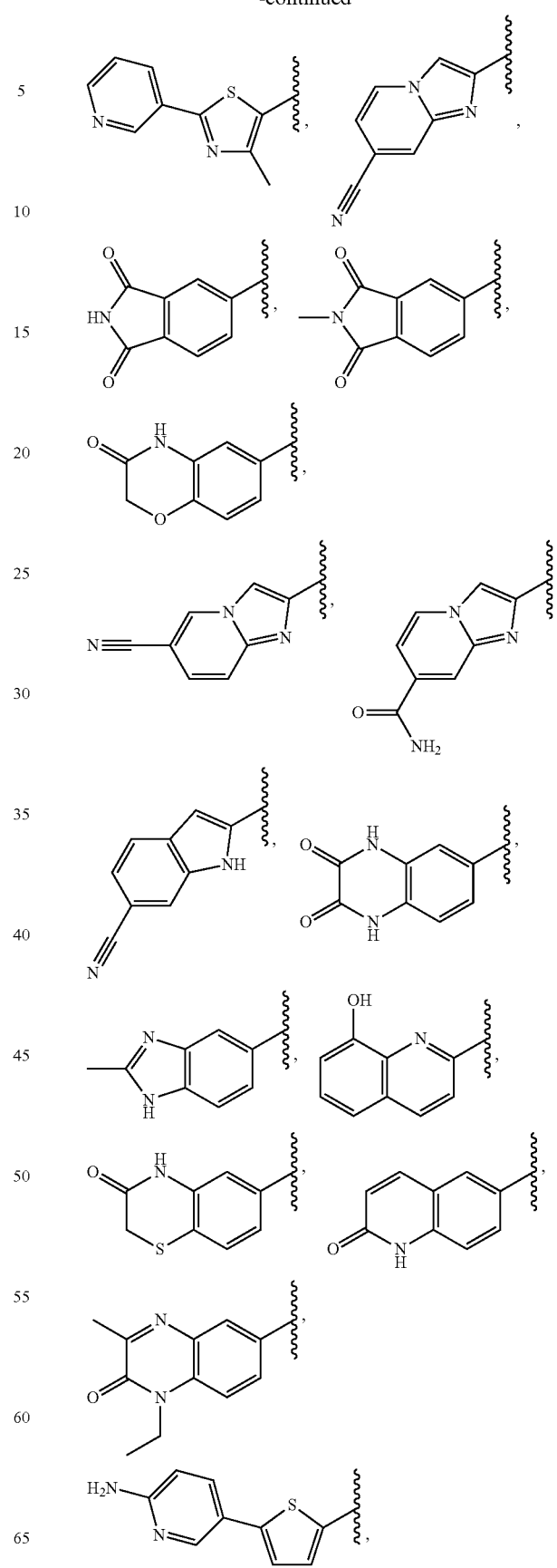

-continued
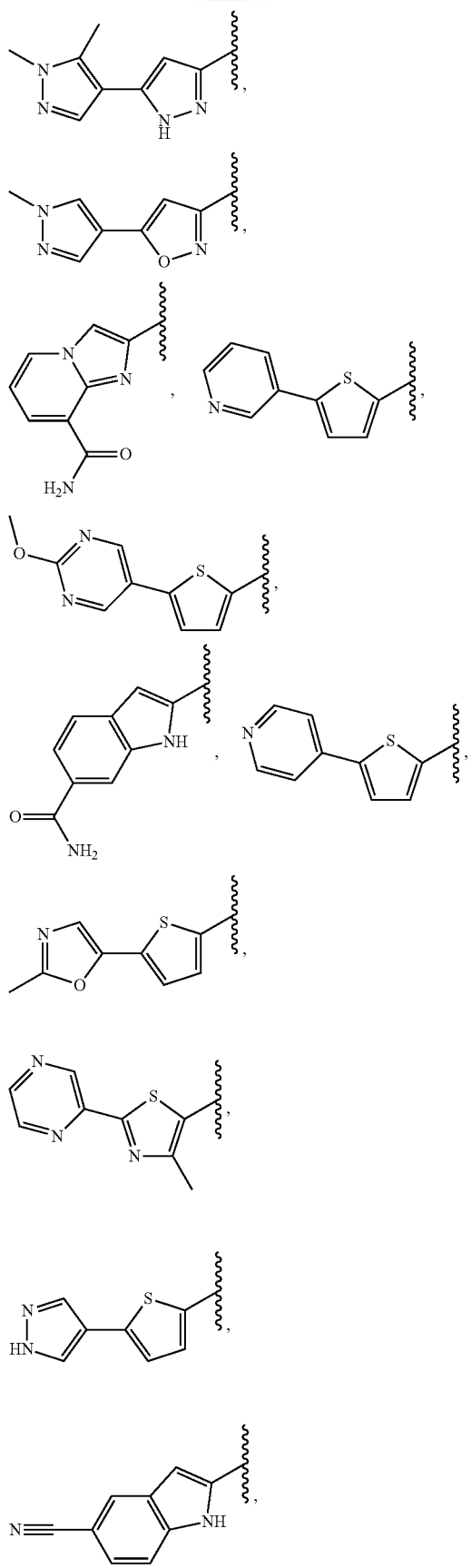
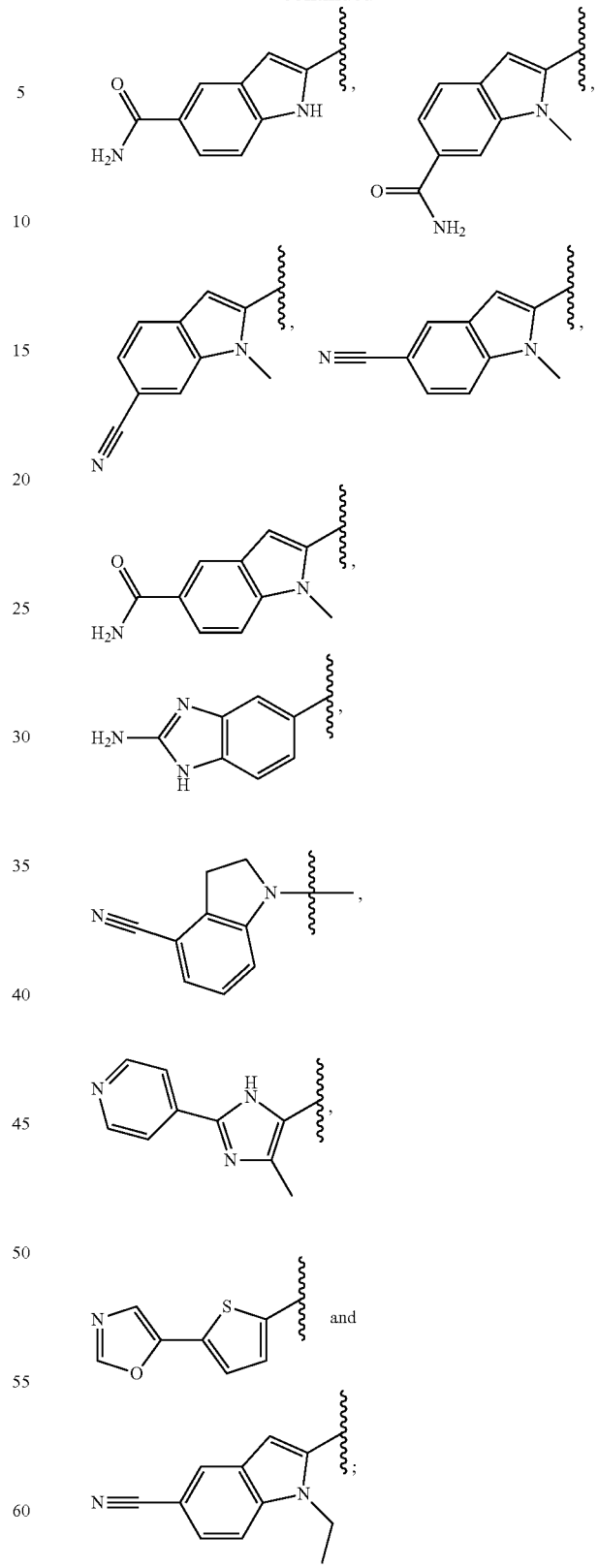
or a salt thereof.
In another embodiment there are provided compounds of formula I as described above and wherein:

R² is

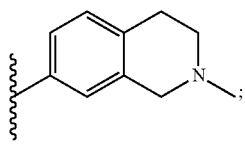 [SMILES: *c1ccc2c(c1)CN(C)CC2]

or a salt thereof.

In another embodiment there are provided compounds of formula I as described in the embodiment two above and wherein:
R² is

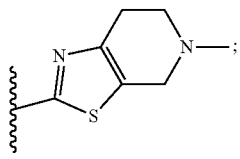

or a salt thereof.

In another embodiment there are provided compounds of formula I as described in the embodiment three above and wherein:
R² is selected from

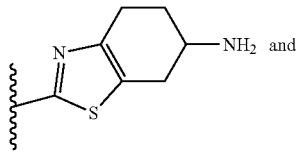

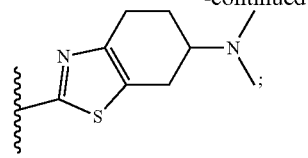

or a salt thereof.

In another embodiment there are provided compounds of formula I as described in the embodiment four above and wherein:
R² is

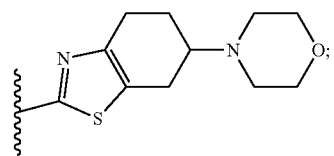 [SMILES: *c1nc2c(s1)CC(N1CCOCC1)CC2]

or a salt thereof.

The following are representative compounds of the invention which can be made by the methods described in the general synthetic schemes, the synthetic examples, and methods known in the art.

TABLE 1

| Cpd # |
| --- |

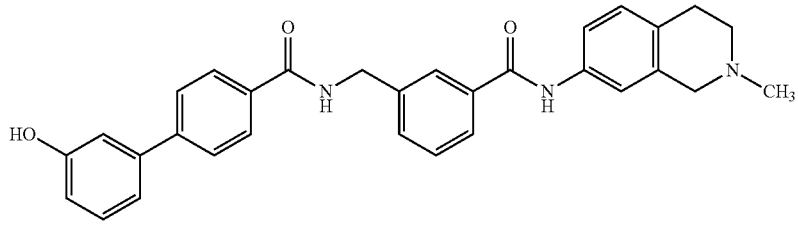 [SMILES: CN1CCc2ccc(NC(=O)c3cccc(CNC(=O)c4ccc(-c5cccc(O)c5)cc4)c3)cc2C1]

1

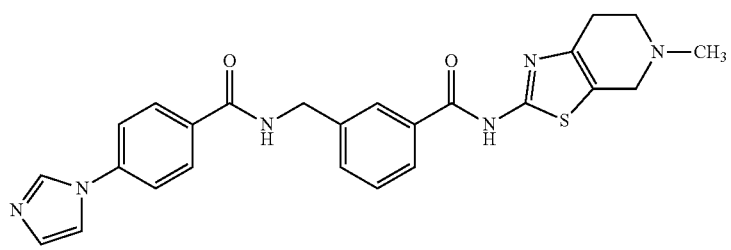 [SMILES: CN1CCc2nc(NC(=O)c3cccc(CNC(=O)c4ccc(-n5ccnc5)cc4)c3)sc2C1]

2

TABLE 1-continued

| Cpd # |
|---|

TABLE 1-continued
| Cpd # |
|---|
| 10 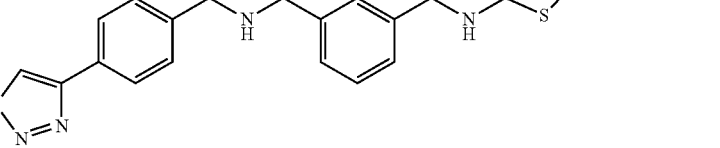 |
| 11 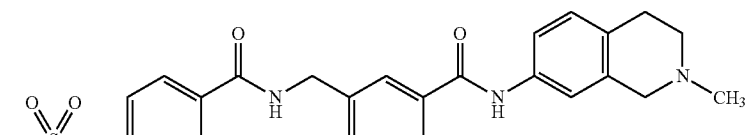 |
| 12  |
| 13 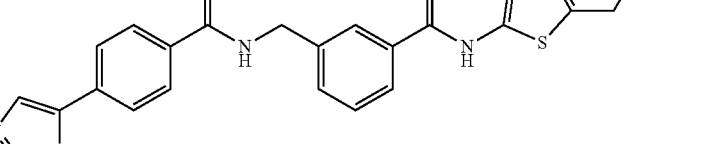 |
| 14 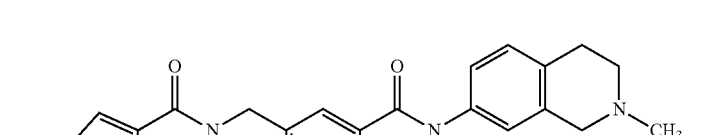 |
| 15 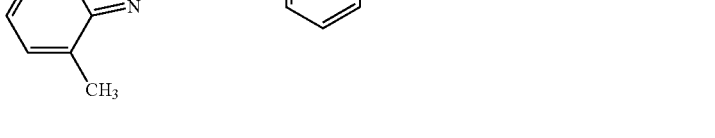 |

TABLE 1-continued

| Cpd # | |
|---|---|
| 16 | |
| 17 | |
| 18 | |
| 19 | |
| 20 | |
| 21 | |
| 22 | |

TABLE 1-continued

| Cpd # |
|---|
| 23 |
| 24 |
| 25 |
| 26 |
| 27 |
| 28 |

TABLE 1-continued
| Cpd # |
|---|
| 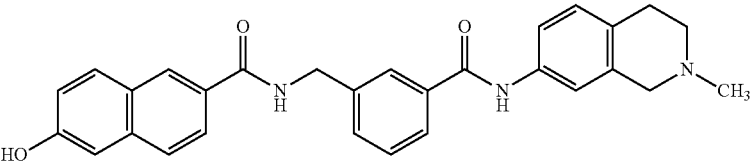 29 |
| 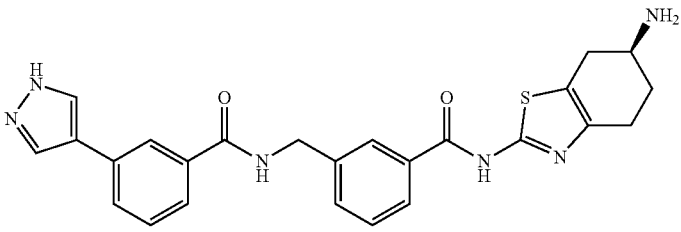 30 |
| 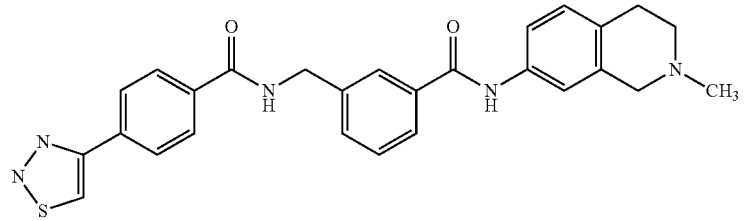 31 |
| 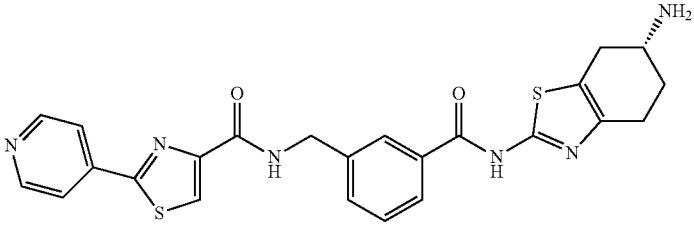 32 |
| 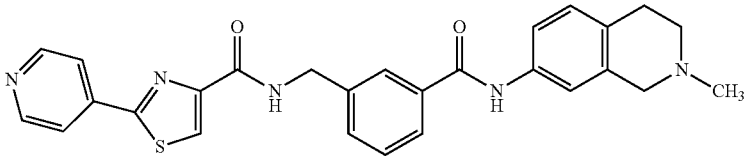 33 |
| 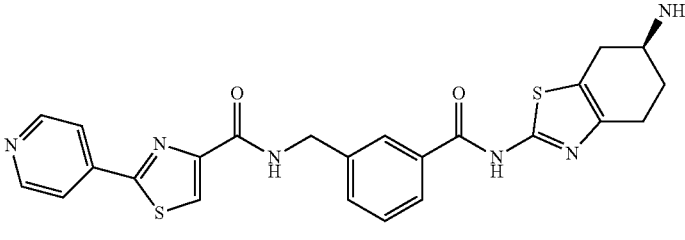 34 |
| 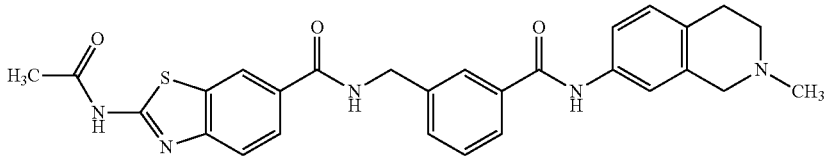 35 |

TABLE 1-continued

| Cpd # |
|---|
| 36 |
| 37 |
| 38 |
| 39 |
| 40 |
| 41 |

TABLE 1-continued
| Cpd # |
|---|
| 42 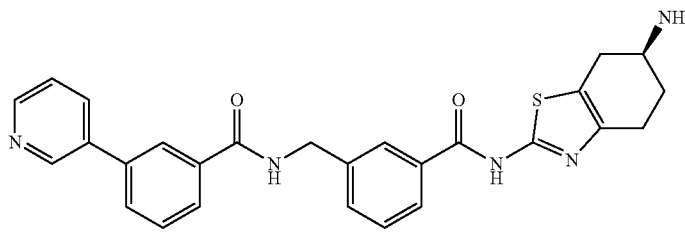 |
| 43 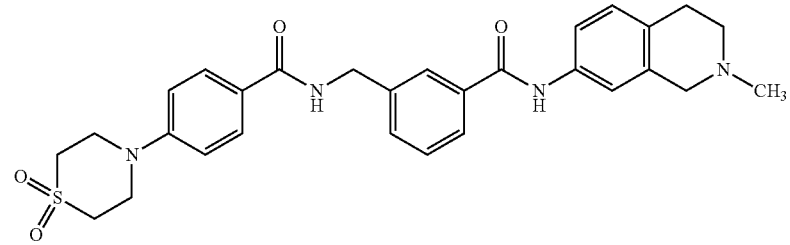 |
| 44 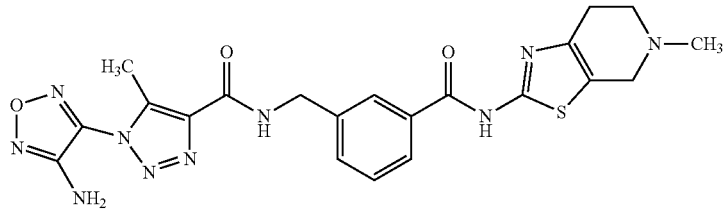 |
| 45 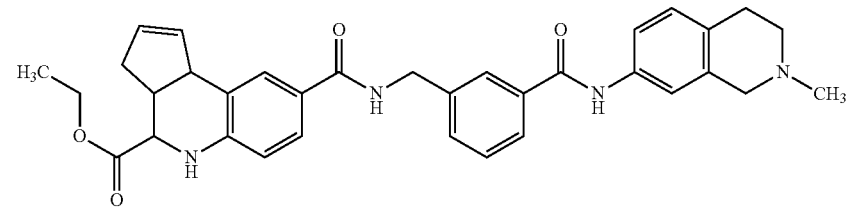 |
| 46 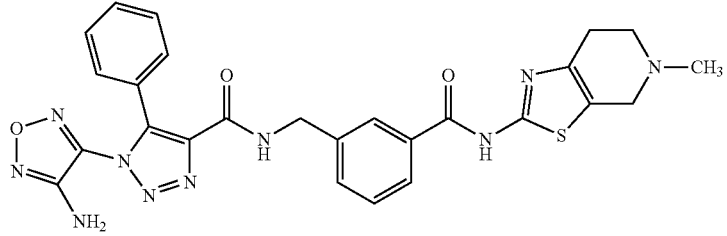 |
| 47 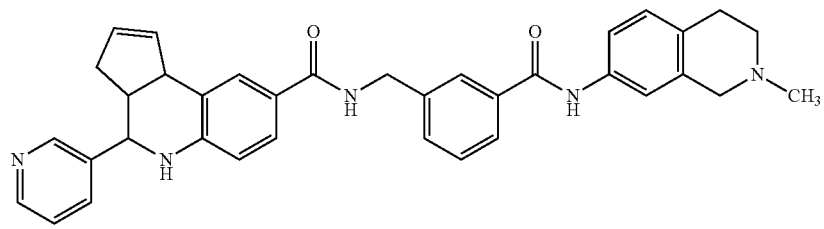 |
| 48 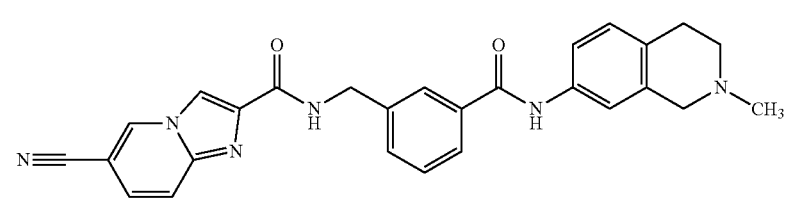 |

TABLE 1-continued
| Cpd # |
| --- |
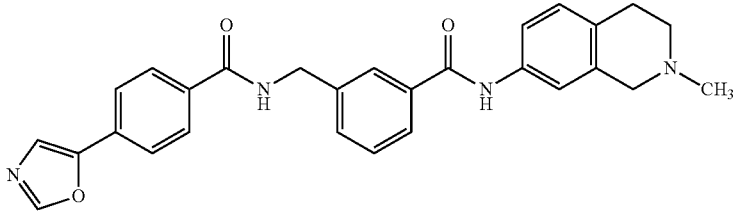
49
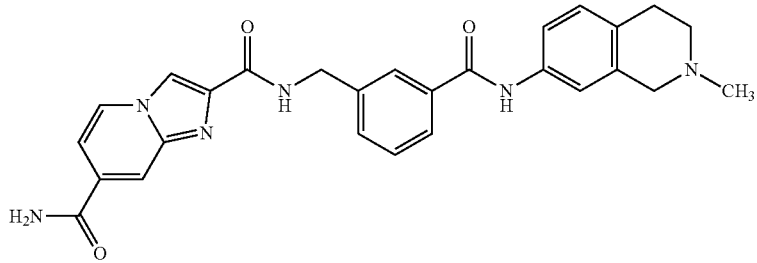
50
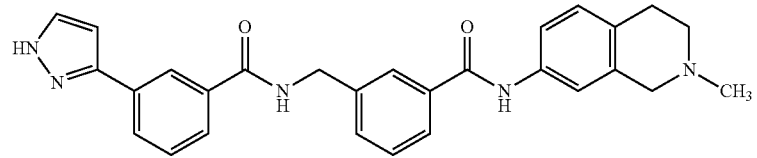
51
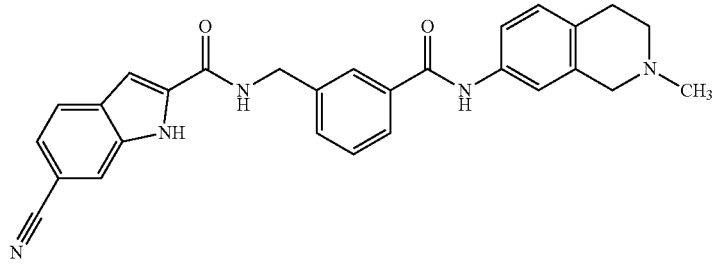
52
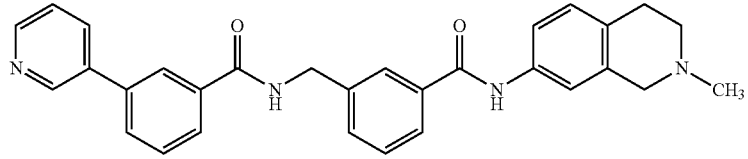
53
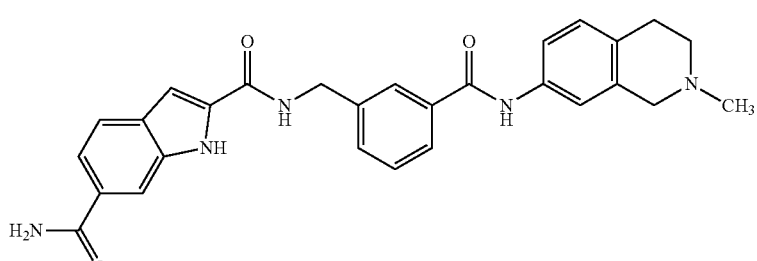
54

TABLE 1-continued

| Cpd # |
|---|
| 55 |
| 56 |
| 57 |
| 58 |
| 59 |
| 60 |
| 61 |
| 62 |

TABLE 1-continued

| Cpd # |
| --- |
| 63 |
| 64 |
| 65 |
| 66 |
| 67 |
| 68 |
| 69 |
| 70 |

TABLE 1-continued
| Cpd # |
|---|
| 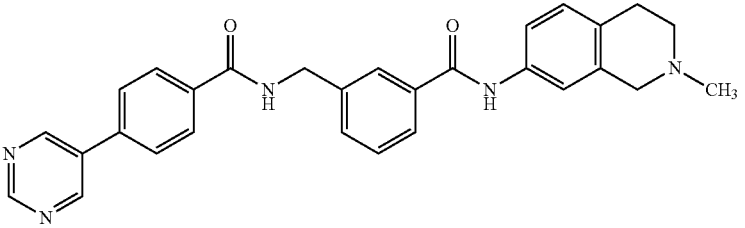 71 |
| 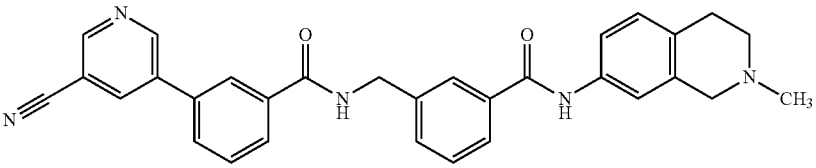 72 |
| 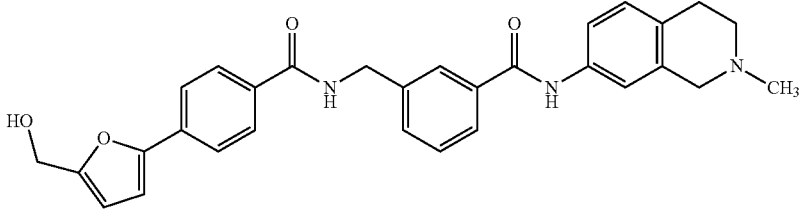 73 |
| 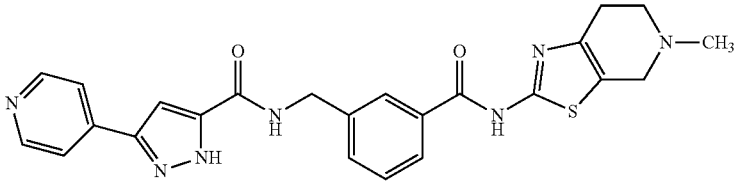 74 |
| 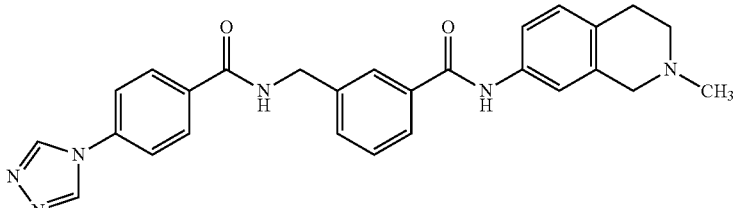 75 |
| 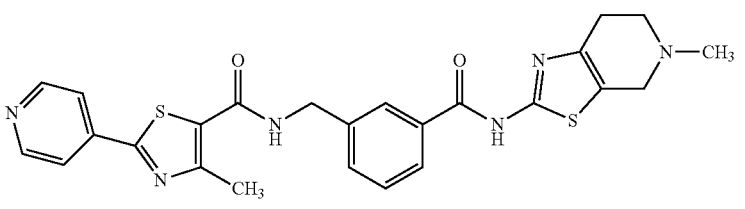 76 |
| 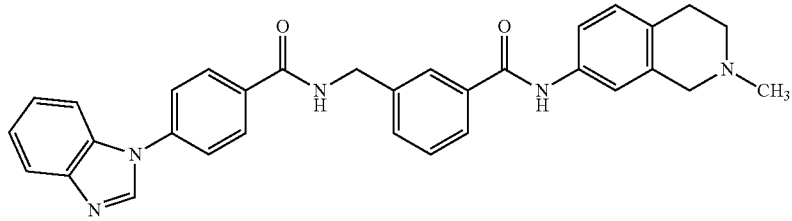 77 |

TABLE 1-continued

| Cpd # |
|---|
| 78 |
| 79 |
| 80 |
| 81 |
| 82 |
| 83 |
| 84 |
| 85 |

TABLE 1-continued

| Cpd # |
|---|
| 86 |
| 87 |
| 88 |
| 89 |
| 90 |
| 91 |
| 92 |

TABLE 1-continued

| Cpd # |
|---|
| 93 |
| 94 |
| 95 |
| 96 |
| 97 |
| 98 |
| 99 |

TABLE 1-continued

| Cpd # |
|---|
| 100 |
| 101 |
| 102 |
| 103 |
| 104 |
| 105 |

TABLE 1-continued
| Cpd # |
|---|
| 106 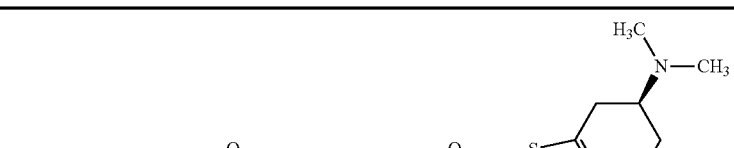 |
| 107 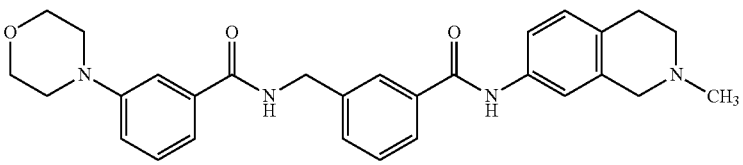 |
| 108 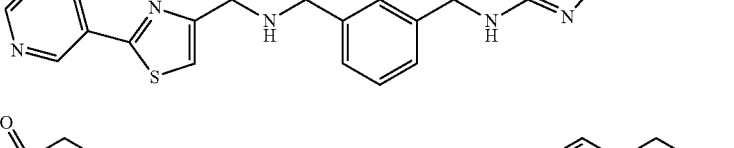 |
| 109 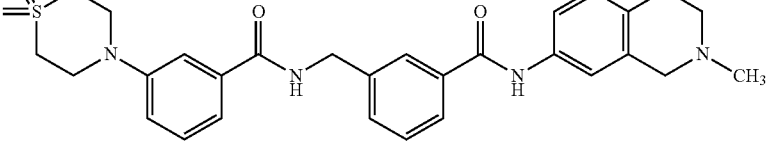 |
| 110 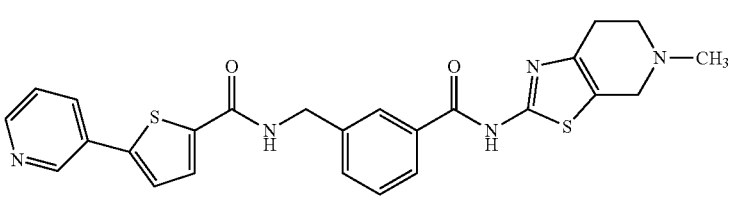 |
| 111 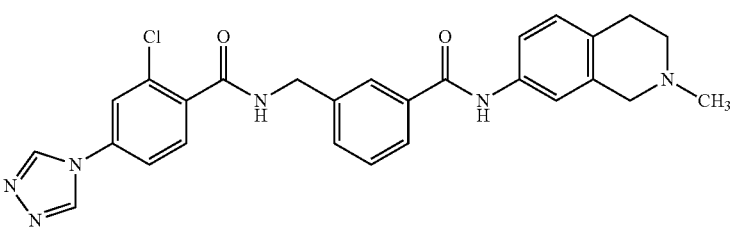 |
| 112 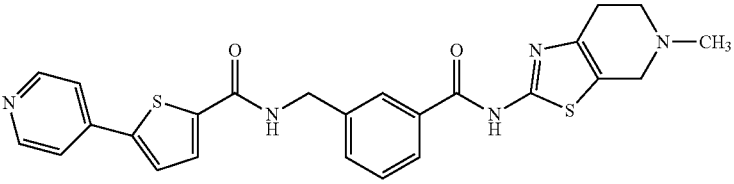 |

TABLE 1-continued

Cpd #

| 113 |
| 114 |
| 115 |
| 116 |
| 117 |
| 118 |
| 119 |

TABLE 1-continued

Cpd #

120, 121, 122, 123, 124, 125, 126

TABLE 1-continued
| Cpd # | |
|---|---|
| 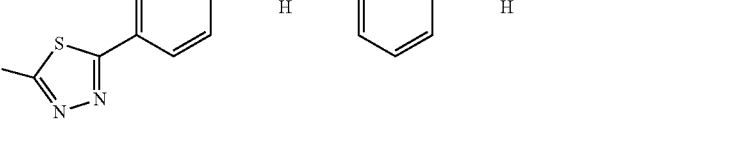 | 127 |
|  | 128 |
| 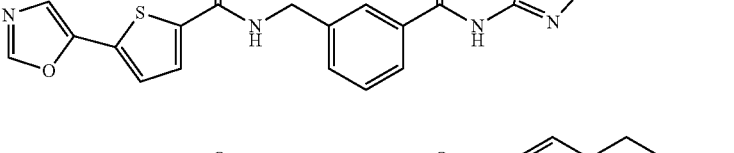 | 129 |
| 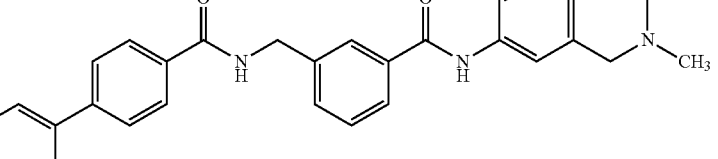 | 130 |
|  | 131 |
| 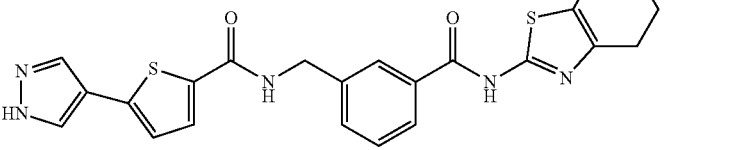 | 132 |

TABLE 1-continued
| Cpd # | |
|---|---|
| 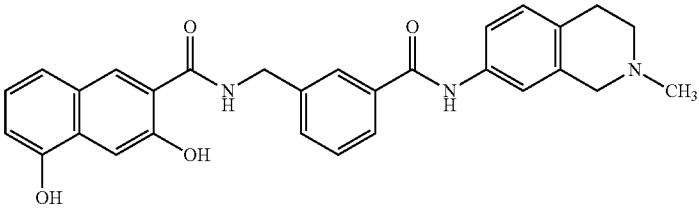 | 133 |
| 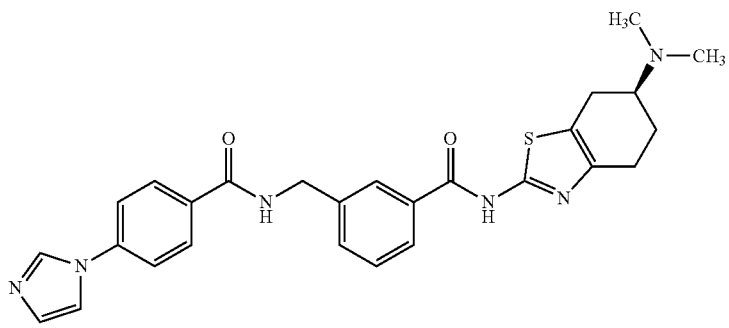 | 134 |
| 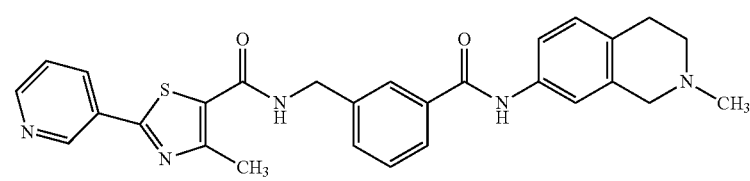 | 135 |
| 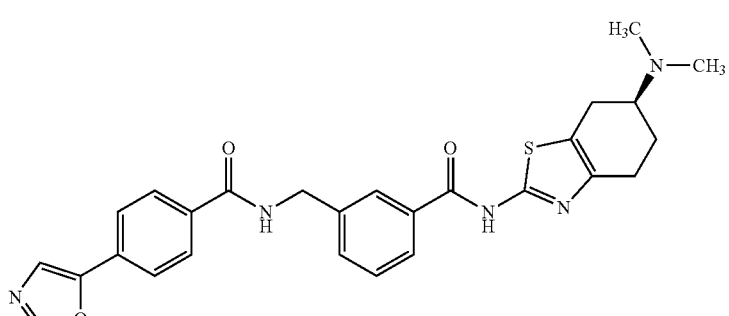 | 136 |
| 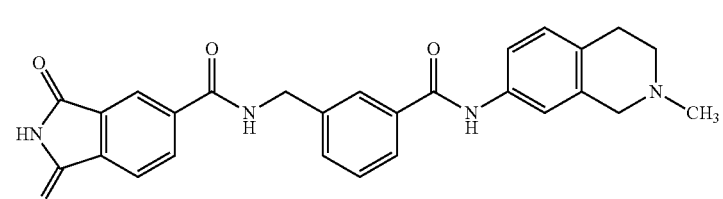 | 137 |
| 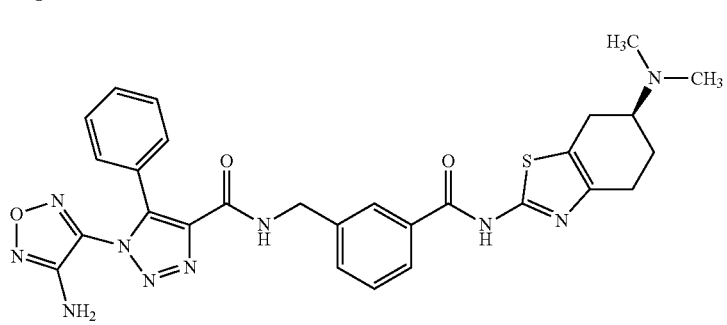 | 138 |

TABLE 1-continued
| Cpd # | |
|---|---|
| 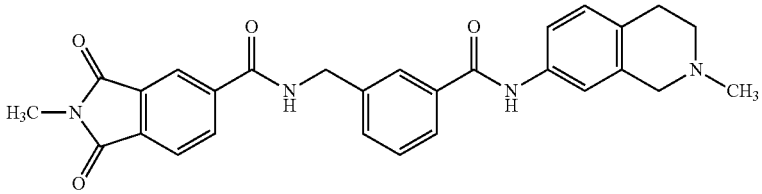 | 139 |
| 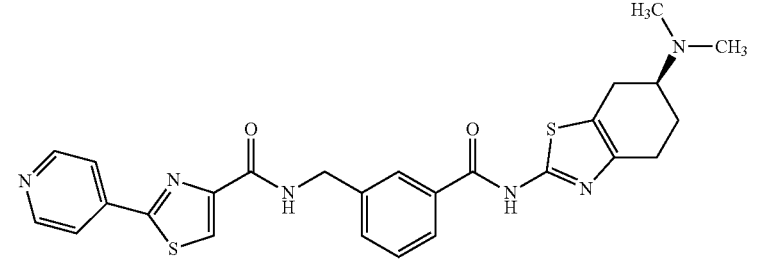 | 140 |
| 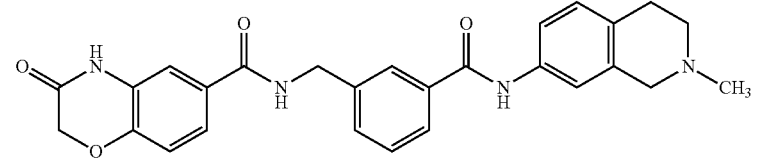 | 141 |
| 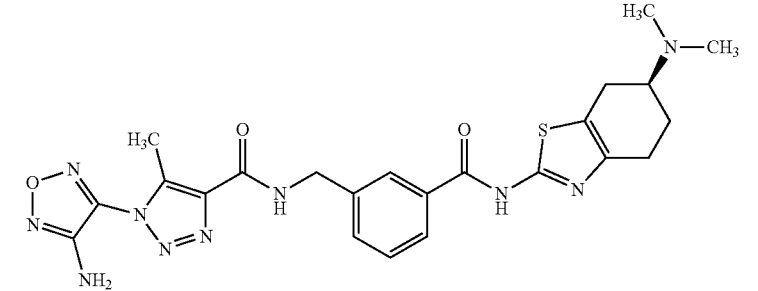 | 142 |
| 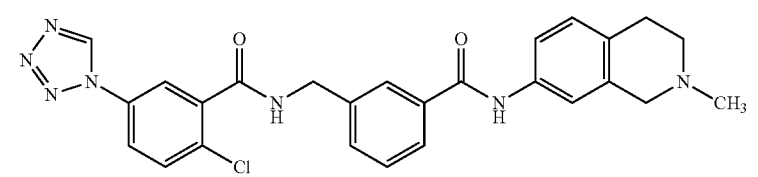 | 143 |
| 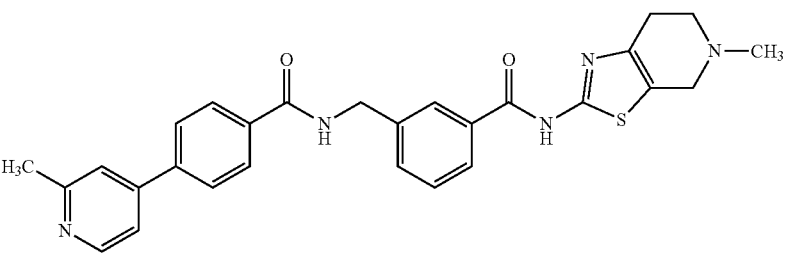 | 144 |

TABLE 1-continued
Cpd #
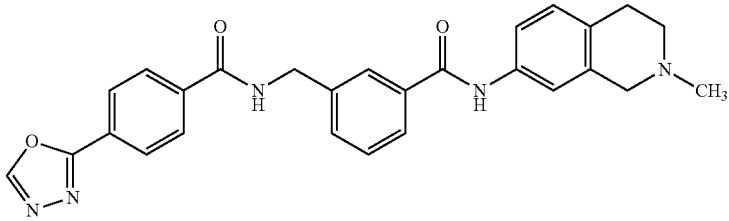
145
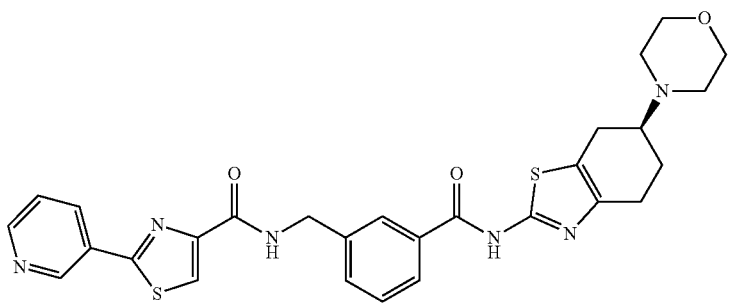
146
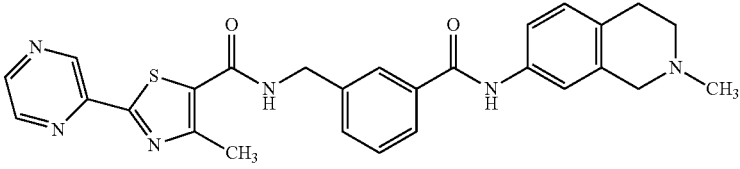
147
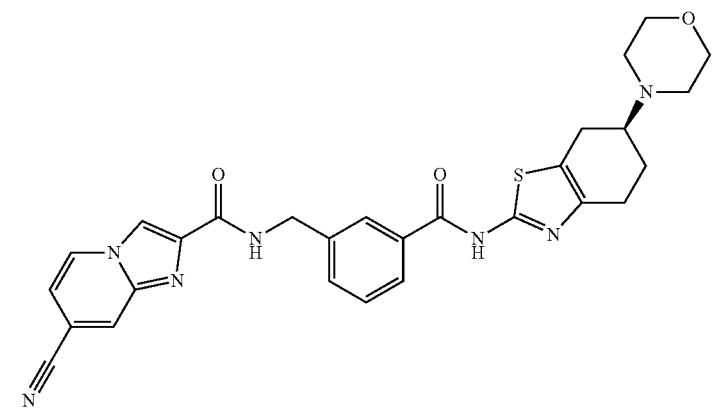
148
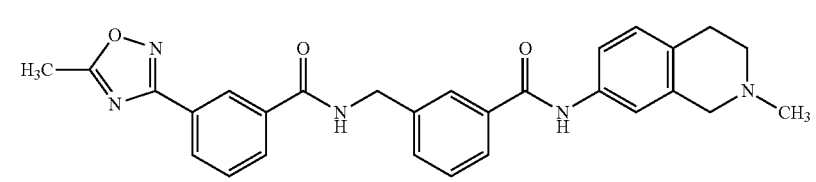
149

TABLE 1-continued

Cpd #

150

151

152

153

154

155

TABLE 1-continued

Cpd #

156, 157, 158, 159, 160, 161

TABLE 1-continued
| Cpd # | |
|---|---|
| 162 | 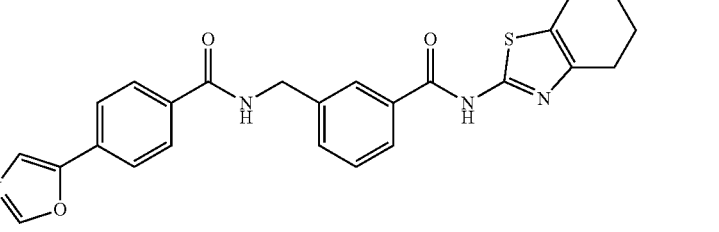 |
| 163 | 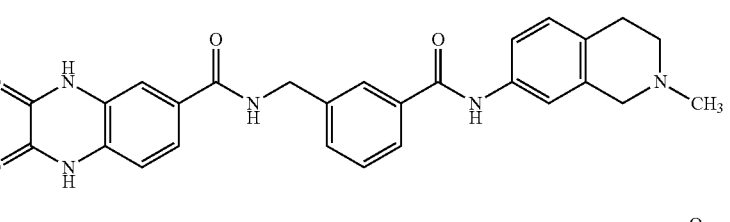 |
| 164 | 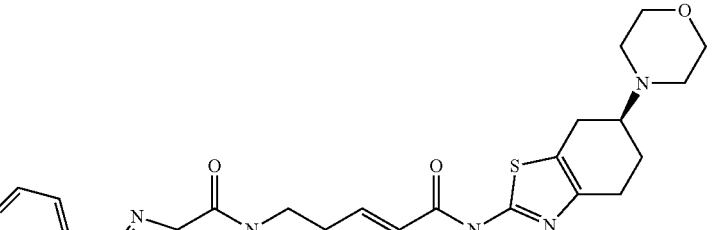 |
| 165 | 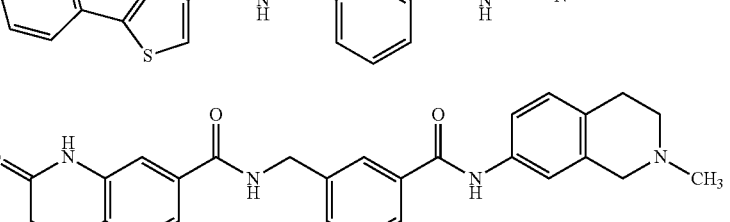 |
| 166 | 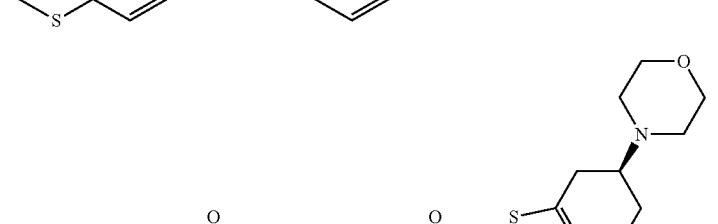 |
| 167 | 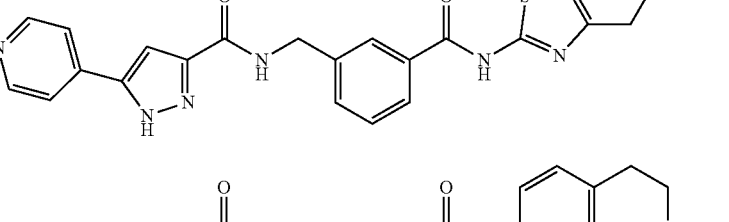 |

TABLE 1-continued
| Cpd # |
|---|
| 168  |
| 169 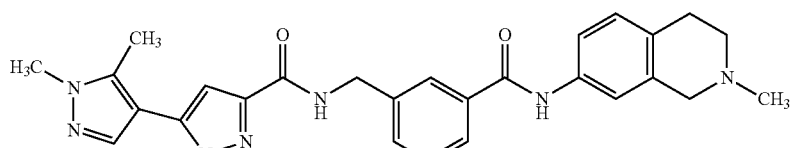 |
| 170 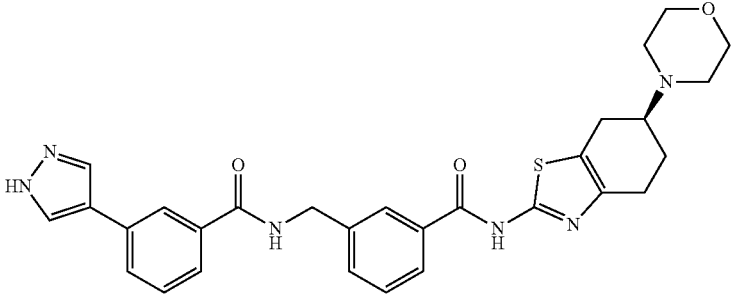 |
| 171 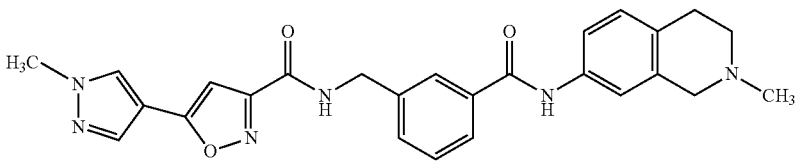 |
| 172 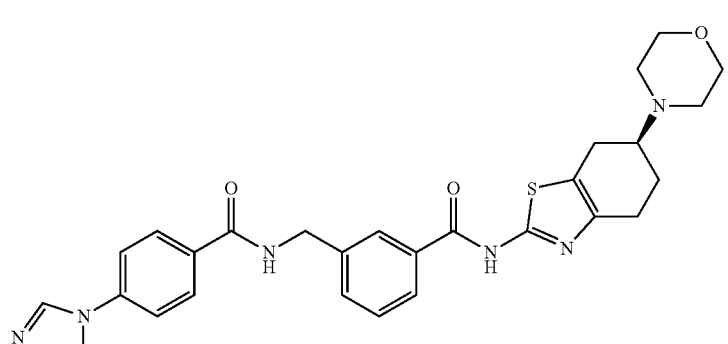 |
| 173 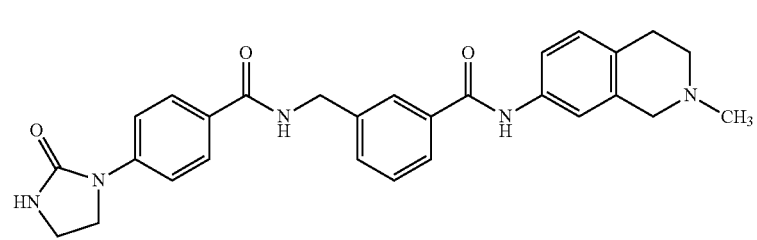 |

TABLE 1-continued

| Cpd # |
| --- |
| 174 |
| 175 |
| 176 |
| 177 |
| 178 |
| 179 |

TABLE 1-continued
| Cpd # | |
|---|---|
| 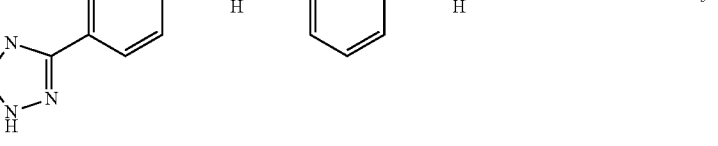 | 180 |
| 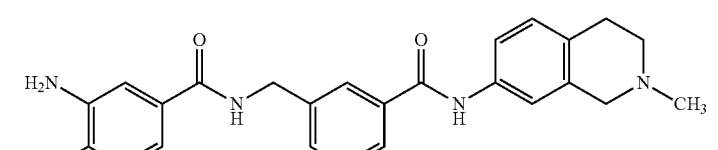 | 181 |
| 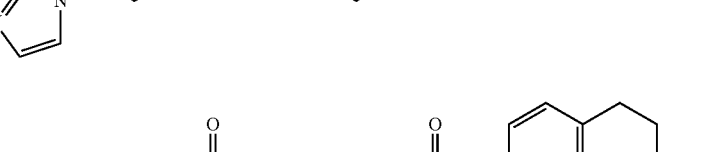 | 182 |
| 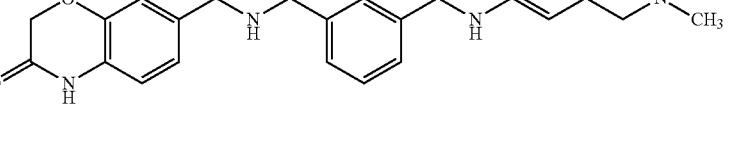 | 183 |
| 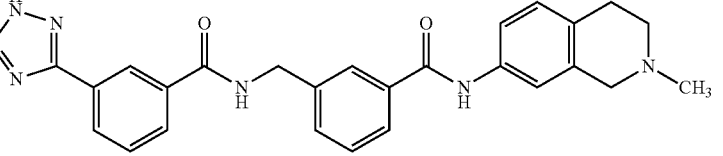 | 184 |
| 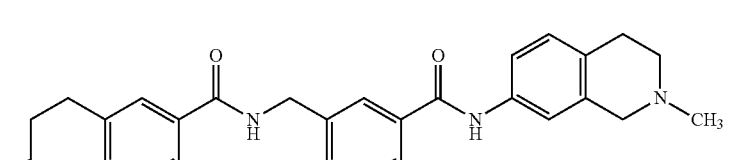 | 185 |
| 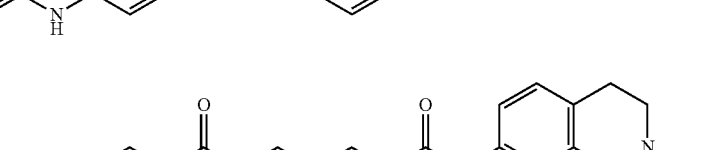 | 186 |

TABLE 1-continued
| Cpd # |
|---|
| 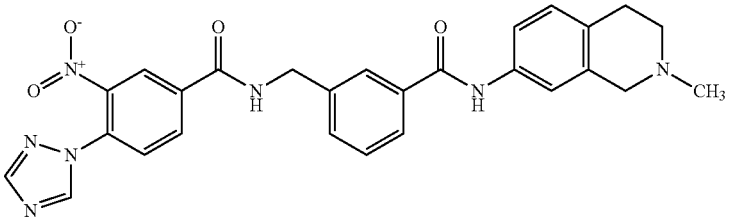 187 |
| 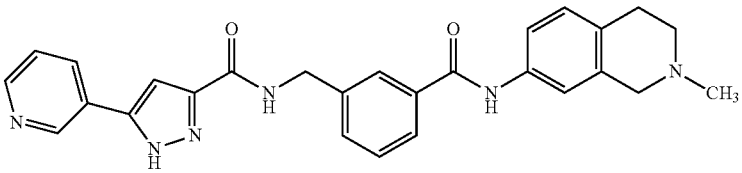 188 |
| 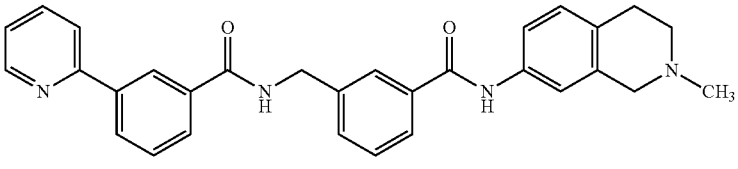 189 |
| 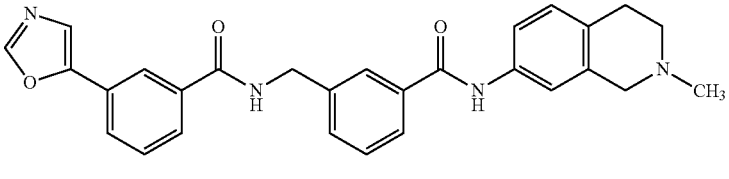 190 |
| 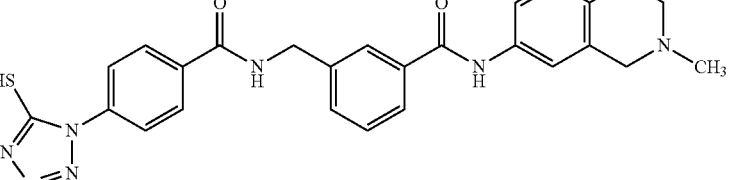 191 |
| 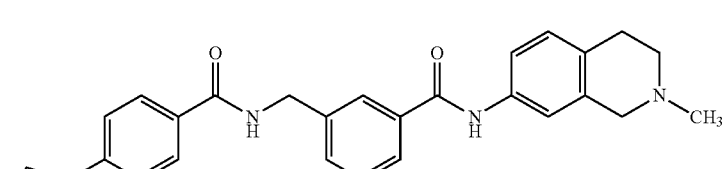 192 |
| 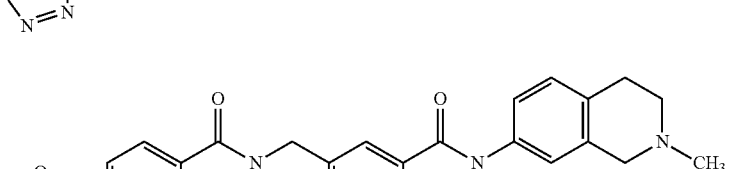 193 |

TABLE 1-continued

| Cpd # |
|---|
| 194 |
| 195 |
| 196 |
| 197 |
| 198 |
| 199 |
| 200 |

TABLE 1-continued

| Cpd # |
|---|
| 201 |
| 202 |
| 203 |
| 204 |
| 205 |
| 206 |
| 207 |

TABLE 1-continued

Cpd #

208

209

210

In another embodiment, the invention relates to a compound selected from compounds described in Table 1, and the pharmaceutically acceptable salts thereof.

In another embodiment, the invention relates to a compound selected from compounds 2-4, 6, 8, 12, 14, 18, 20-22, 24, 26-34, 36-40, 42, 44, 46, 48-50, 52-54, 56, 58, 62, 64, 66, 68-70, 74, 76, 78, 80, 84, 86, 88, 90, 92, 94-96, 98, 100, 102, 104, 106, 108, 110, 112, 114, 116, 118-120, 122-126, 128-130, 132-134, 136, 138, 140, 142, 144-146, 148, 150, 152, 154, 155, 160, 162, 164, 166, 168, 170, 172, 174-179, 182, 184, 186, 188, 190, 194, 198, 200-202, 205, 207, 209 and 210 in Table 1, and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula I can exist in more than one tautomeric form. The invention includes methods for using all such tautomers.

The invention includes pharmaceutically acceptable derivatives of compounds of formula I. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula I.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate and formate salts) also comprise a part of the invention.

In addition, within the scope of the invention is use of prodrugs of compounds of the formula I. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency' or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic-ring systems containing one or more heteroatoms selected from N, O or $S(O)_r$ with r=0, 1 or 2 wherein at least one of the heteroatoms is part of aromatic ring. The term "heteroaryl" is intended to include all the possible isomeric forms.

The term "heterocyclyl" means a saturated or unsaturated mono- or polycyclic-ring systems including aromatic ring system containing one or more heteroatoms selected from N, O or $S(O)_r$ with r=0, 1 or 2 wherein none of the heteroatoms is part of the aromatic ring. The term "heterocycle" is intended to include all the possible isomeric forms.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-$S(O)_m$— when $R_a$ is phenyl and where m is 0, 1 or 2.

General Synthetic Methods

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carbocylic acid and an amine in the presence of 1-(3-dimethylaminopropyl)-3-ethylcarbodiimide (EDC) and 1-hydroxybenzotriazole (HOBt). Intermediates used in the syntheses below are either commercially available or easily prepared by methods known to those skilled in the art or illustrated in the Synthetic Examples below. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of formula I. Initial products of formula (I) may be modified further by methods known in the art to produce additional compounds of formula (I).

Compounds of formula I may be prepared as described in Scheme 1.

Scheme 1

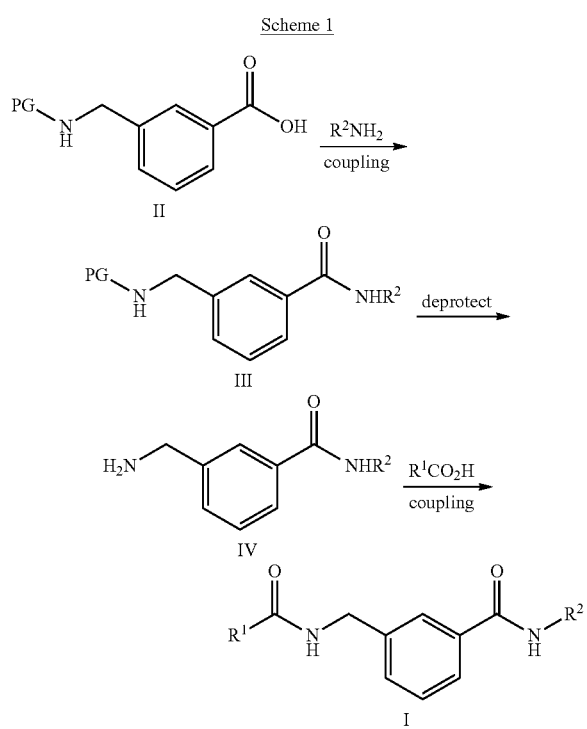

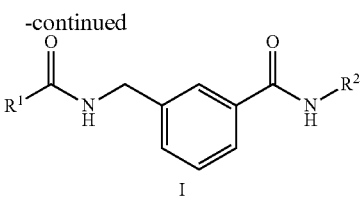

As illustrated in Scheme 1, R²NH₂ is coupled with intermediate II, where PG is an amine protecting group such as a tert-butoxycarbonyl (t-Boc) group, using standard coupling conditions known in the art, for example reaction in the presence of EDC, HOBt and Et₃N or in the presence of TBTU and (i-Pr)₂NEt, or in the presence of HATU and N-methylmorpholine to provide III. Deprotection of the amine on intermediate III, for example by treatment with acid if PG is a t-Boc group, provides IV. Coupling of intermediate IV with R¹CO₂H under standard coupling conditions as noted above provides the desired compound of formula I.

Alternatively, the couplings may be performed in reverse order as illustrated in Scheme 2

Scheme 2

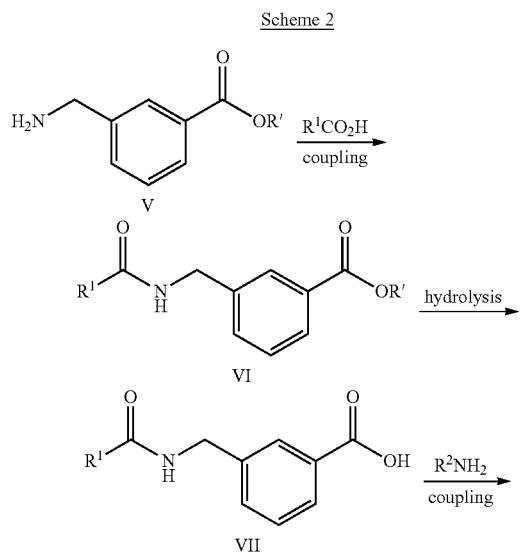

As illustrated above R¹CO₂H is coupled with V, where R' is an alkyl group such as methyl or ethyl, using standard coupling conditions known in the art as noted above, to provide VI. The ester on intermediate VI is hydrolyzed, for example by treatment with base such as LiOH to provide the carboxylic acid VII. Coupling with R²NH₂ then provides the desired compound of formula I.

All of the compounds in Table I were prepared by the methods illustrated above and in the Synthetic Examples section below.

Retention times (RT) reported for compounds in the Synthetic Examples section were obtained using one of the following methods:

| HPLC Method | Time (min) | Mobile Phase H₂O (0.1% Formic Acid) | CH₃CN (0.1% Formic Acid) | Flow (mL/min) | Column |
|---|---|---|---|---|---|
| A1 | 0 | 95 | 5 | 2.5 | Agilent Zorbax C18 |
|  | 1.7 | 5 | 95 | 2.5 | SB 3.5 um |
|  | 2 | 5 | 95 | 2.5 | 4.6 × 30 mm |
|  | 2.1 | 95 | 5 | 2.5 | cartridge |
|  | 2.3 | 95 | 5 | 2.5 |  |
| B1 | 0 | 70 | 30 | 2.5 | Agilent Zorbax C18 |
|  | 1.7 | 5 | 95 | 2.5 | SB 3.5 um |
|  | 2 | 5 | 95 | 2.5 | 4.6 × 30 mm |
|  | 2.1 | 70 | 30 | 2.5 | cartridge |
|  | 2.3 | 70 | 30 | 2.5 |  |
| C1 | 0 | 99 | 1 | 2.5 | Agilent Zorbax C18 |
|  | 1.7 | 50 | 50 | 2.5 | SB 3.5 um |
|  | 2 | 5 | 95 | 2.5 | 4.6 × 30 mm |
|  | 2.1 | 5 | 95 | 2.5 | cartridge |
|  | 2.3 | 99 | 1 | 2.5 |  |
| D1 | 0 | 95 | 5 | 1.5 | Agilent Zorbax |
|  | 7 | 5 | 95 | 1.5 | Eclipse XDB- |
|  | 9 | 5 | 95 | 1.5 | C8 5 um |
|  | 9.3 | 95 | 5 | 1.5 | 4.6 × 150 mm |
|  | 10 | 95 | 5 | 1.5 |  |
| C2 | 0 | 99 | 1 | 2.5 | Agilent Zorbax C18 |
|  | 1.6 | 80 | 20 | 2.5 | SB 3.5 um |
|  | 1.7 | 5 | 95 | 2.5 | 4.6 × 30 mm |
|  | 2 | 5 | 95 | 2.5 | cartridge |
|  | 2.1 | 99 | 1 | 2.5 |  |
|  | 2.3 | 99 | 1 | 2.5 |  |
| D2 | 0 | 99 | 1 | 1.5 | Agilent Zorbax |
|  | 2 | 80 | 20 | 1.5 | Eclipse XDB- |
|  | 7 | 5 | 95 | 1.5 | C8 5 um |
|  | 9 | 5 | 95 | 1.5 | 4.6 × 150 mm |
|  | 9.3 | 99 | 1 | 1.5 | column |
|  | 10 | 99 | 1 | 1.5 |  |
| A3 | 0 | 88 | 12 | 1.5 | Agilent SB-C18 |
|  | 0.25 | 70 | 30 | 1.5 | 1.8 um 3 × 50 mm |
|  | 0.3 | 60 | 40 | 1.5 | column |
|  | 1.19 | 5 | 95 | 1.5 |  |
|  | 1.75 | 0 | 100 | 1.5 |  |
| B3 | 0 | 60 | 40 | 1.5 | Agilent Eclipse C8 |
|  | 1.19 | 15 | 85 | 1.5 | 1.8 um 3 × 50 mm |
|  | 1.75 | 0 | 100 | 1.5 | column |
| C3 | 0 | 95 | 5 | 1.5 | Agilent SB- |
|  | 0.25 | 50 | 50 | 1.5 | AQ 1.8 um |
|  | 0.3 | 70 | 30 | 1.5 | 3 × 50 mm |

| HPLC Method | Time (min) | Mobile Phase H₂O (0.1% Formic Acid) | CH₃CN (0.1% Formic Acid) | Flow (mL/min) | Column |
|---|---|---|---|---|---|
| | 1.3 | 10 | 90 | 1.5 | column |
| | 1.7 | 0 | 100 | 1.5 | |
| D3 | 0 | 95 | 5 | 1.5 | Agilent SB-C18 |
| | 3.8 | 10 | 90 | 1.5 | 1.8 um 3 × 50 mm |
| | 4.5 | 0 | 100 | 1.5 | column |

| HPLC Method | Time (min) | Mobile Phase 95% H₂O + 5% CH₃CN (0.05% Formic Acid) | CH₃CN (0.05% Formic Acid) | Flow (mL/min) | Column |
|---|---|---|---|---|---|
| E | 0 | 90 | 10 | 0.8 | BEH 2.1 × 50 mm |
| | 1.19 | 5 | 95 | 0.8 | C18, 1.7 um |
| | 1.7 | 5 | 95 | 0.8 | particle diameter |

Synthetic Examples

Synthesis of Intermediates

The following intermediates are prepared as described in *Il Farmaco*, 1977, 32, 735-748 and *J. Med. Chem.* 2003, 46, 3914-3929:

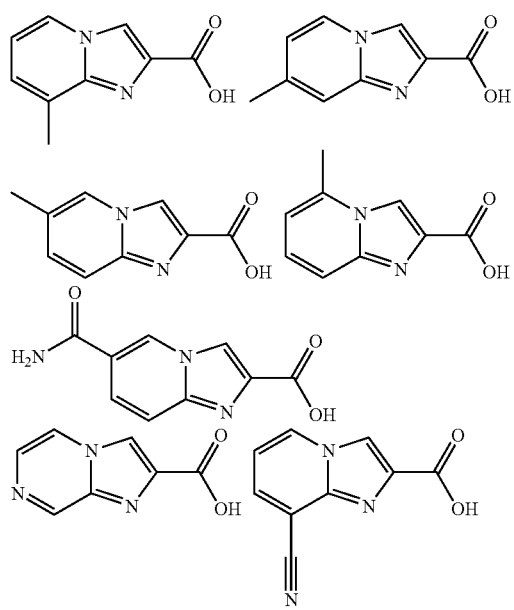

The following intermediates are prepared as described in WO2008086047:

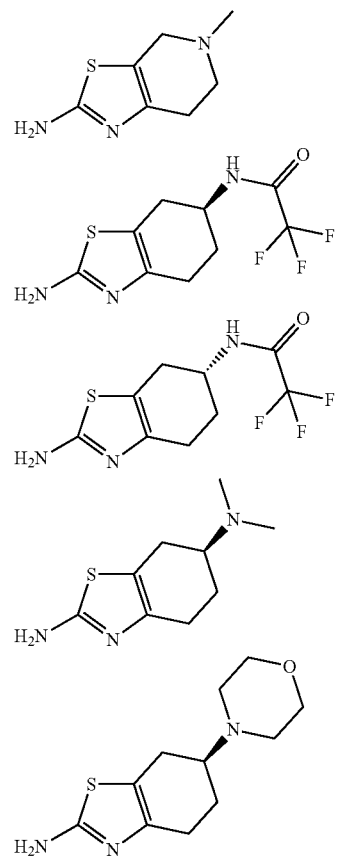

The following intermediates are prepared as described in WO050079791:

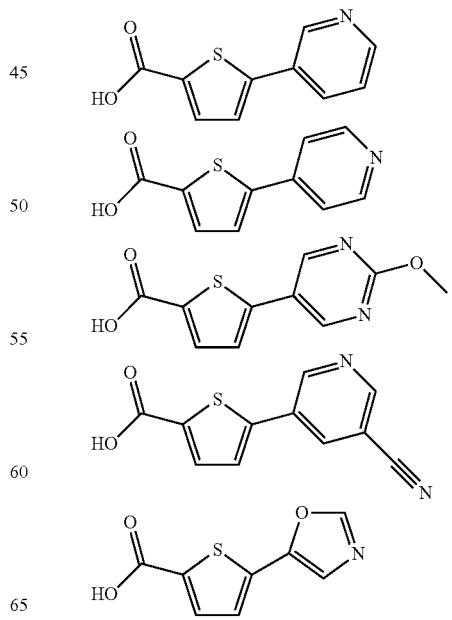

The following intermediate is prepared as described in WO050079791 using 4-(1-trityl)-1H-pyrazole boronic acid as a coupling partner:

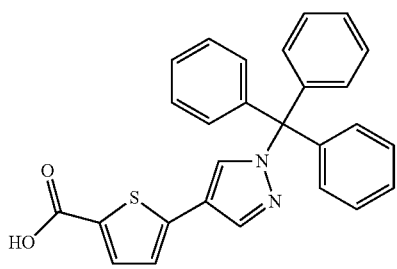

The following intermediate is prepared as described in Goddard, C. J., J. Het. Chem., 1991, 28, 1, 17-28:

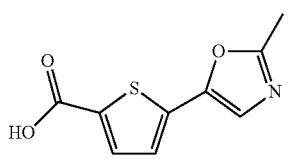

Synthesis of
5-oxo-5,6-dihydro-[1,6]naphthyridine-2-carboxylic acid

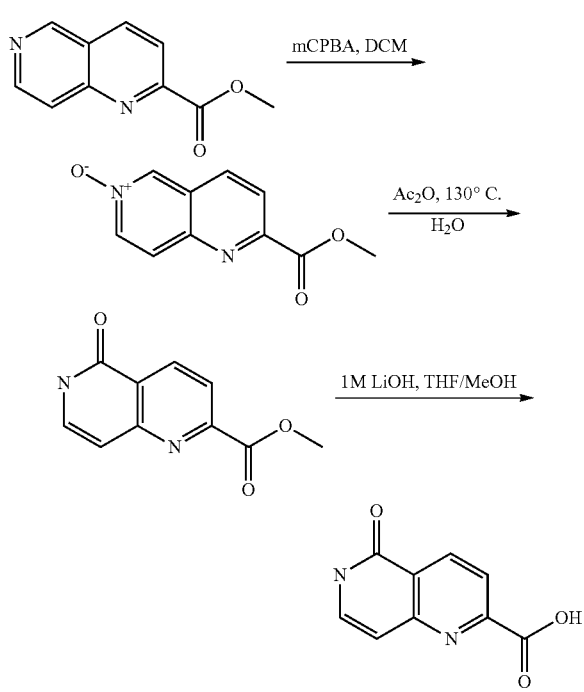

Treat a solution of [1,6]naphthyridine-2-carboxylic acid methyl ester (2.00 g, 10.4 mmol) in DCM (dichloromethane) (50 mL) with mCPBA (m-chloroperoxybenzoic acid) (65%, 3.10 g, 12.0 mmol)) at rt (room temperature) and stir for 2 h. Dilute the reaction mixture with EtOAc and water. Wash the organic layers with sat. NaHCO₃ and brine. Extract the organic layer with DCM (4×50 mL) and dry the combined organics over MgSO₄, filter and concentrate. Purify the compound by silica gel chromatography eluting with a gradient of 0% to 100% EtOAc/hexanes to obtain the desired product 6-oxy-[1,6]naphthyridine-2-carboxylic acid methyl ester in (930 mg, 4.56 mmol).

Heat a mixture of 6-oxy-[1,6]naphthyridine-2-carboxylic acid methyl ester (905 mg, 4.43 mmol) in acetic anhydride (15 mL) to 130° C. for 18 h. Cool the solution to 100° C. and add water (5 mL). Further cool the solution to rt and dilute with DCM and sat. NaHCO₃. Separate the layers and extract the aqueous layer with DCM (5×50 mL). Combine the organic layers and dry (MgSO₄) and concentrate to afford the desired product 5-oxo-5,6-dihydro-[1,6]naphthyridine-2-carboxylic acid methyl ester (470 mg, 2.30 mmol).

Stir a solution of 5-oxo-5,6-dihydro-[1,6]naphthyridine-2-carboxylic acid methyl ester (920 mg, 4.51 mmol) in a solution of THF/MeOH/1N LiOH (3:1:1) (30 mL) at rt for 18 h. Concentrate the solution and suspend the residue in water. Treat the solution with AcOH (1 mL) and let sit 1 h until a solid forms. Collect this by filtration to give desired product 5-oxo-5,6-dihydro-[1,6]naphthyridine-2-carboxylic acid (730 mg, 3.84 mmol).

Synthesis of
7-cyano-imidazo[1,2-a]pyridine-2-carboxylic acid
and
7-carbamoyl-imidazo[1,2-a]pyridine-2-carboxylic acid

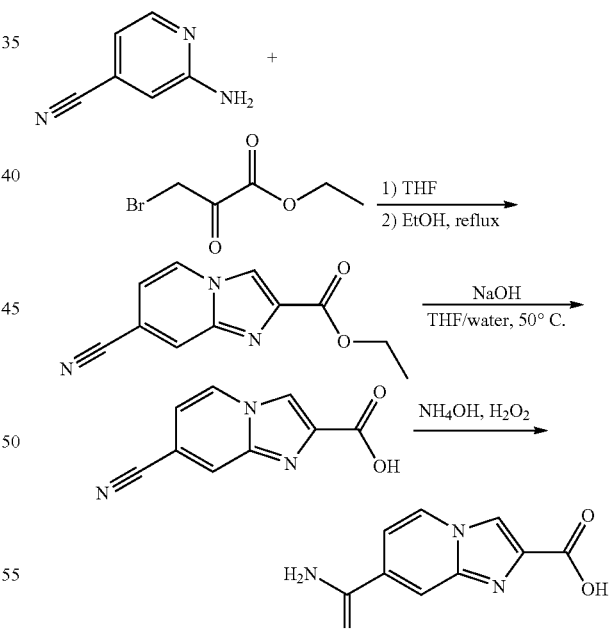

To a solution of 2-amino-4-cyanopyridine (4.00 g, 33.6 mmol) in THF (100 mL) add ethyl bromopyruvate (6.55 g, 33.6 mmol). Stir the mixture at rt overnight. A light yellow suspension forms. After filtration and washing with THF, dissolve the light yellow solid in EtOH (50 mL) and heat to reflux for 4 h. Concentrate in vacuo to afford the desired product 7-cyano-imidazo[1,2-a]pyridine-2-carboxylic acid ethyl ester as a solid (6.21 g, 28.9 mmol).

To a suspension of 7-cyano-imidazo[1,2-a]pyridine-2-carboxylic acid ethyl ester (501 mg, 2.33 mmol) in 5:1 dioxane/water (30 mL) add sodium hydroxide (130 mg, 3.26 mmol) and stir at 50° C. overnight. Concentrate to a solid and acidify with 4 M HCl in dioxane. Concentrate again to afford the desired product 7-cyano-imidazo[1,2-a]pyridine-2-carboxylic acid and use without further purification.

To a suspension of 7-cyano-imidazo[1,2-a]pyridine-2-carboxylic acid (98 mg, 0.52 mmol) in ammonium hydroxide (3 mL) add hydrogen peroxide (0.5 mL). Stir the mixture for 2 h at rt to form a clear solution. LCMS analysis indicates desired product and absence of starting material. Concentrate to a white solid, dissolve in water to form a clear solution, and acidify with 1M HCl to give a solid. Collect this by filtration and dry to afford the desired product 7-carbamoyl-imidazo[1,2-a]pyridine-2-carboxylic acid as a solid (52 mg, 0.25 mmol).

The following intermediates were synthesized in an analogous fashion:

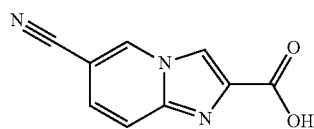

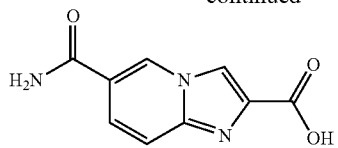

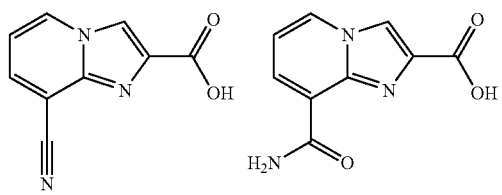

Synthesis of 6-cyano-1H-indole-2-carboxylic acid and 6-carbamoyl-1H-indole-2-carboxylic acid

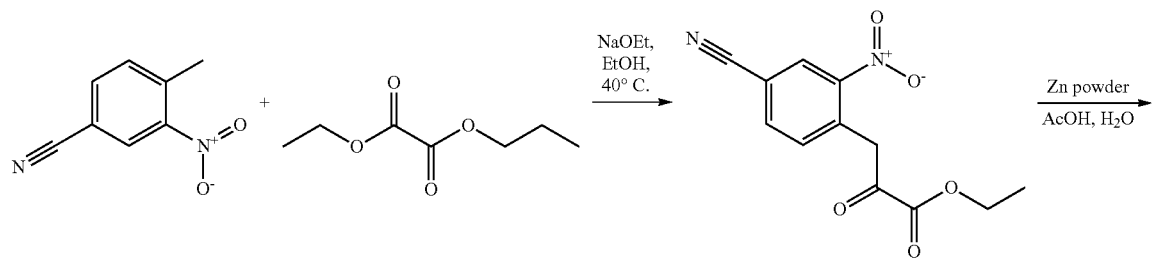

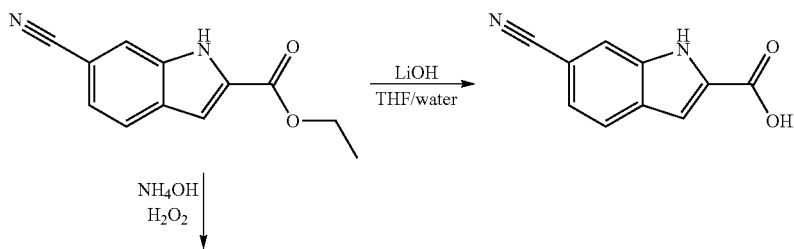

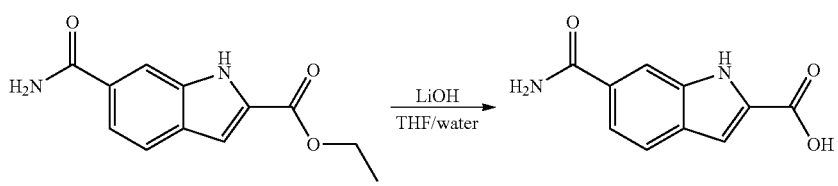

Treat a suspension of 4-methyl-3-nitro-benzonitrile (2.11 g, 12.5 mmol) and oxalic acid ethyl ester propyl ester (2.99 g, 18.7 mmol) in EtOH (80 mL) with NaOEt (21% w/w, 18.2 mL). Stir the mixture at 40° C. overnight. Quench the reaction with water and acidify with 1 M HCl solution. Concentrate to a residue and partition between EtOAc and water. Concentrate the organic layer and purify by silica gel chromatography to give the desired product 3-(4-cyano-2-nitro-phenyl)-2-oxo-propionic acid ethyl ester (3:1 keto/enol mixture) as a solid in 37% yield (1.21 g, 4.62 mmol).

To a suspension of 3-(4-cyano-2-nitro-phenyl)-2-oxo-propionic acid ethyl ester (1.21 g, 4.62 mmol) in acetic acid (50 mL) and water (8 mL) add zinc powder (1.81 g, 27.7 mmol) portionwise over 2 h. Stir at rt for 3 h then filter to remove the solids. Concentrate the filtrate to a volume of 10 mL, dilute with EtOAc (40 mL), and filter again to remove insoluble material. Concentrate the filtrate to give the desired product 6-cyano-1H-indole-2-carboxylic acid ethyl ester as a solid (670 mg, 3.13 mmol).

Treat a solution of 6-cyano-1H-indole-2-carboxylic acid ethyl ester (101 mg, 0.47 mmol) in dioxane/water (5:1, 18 mL) with lithium hydroxide monohydrate (28 mg, 0.66 mmol).

Stir the reaction at rt overnight. Concentrate the reaction to dryness and dissolve the residue in water (5 mL) to form a clear solution. Acidify with 1M HCl solution to form a solid. Collect by filtration and dry to give the desired product 6-cyano-1H-indole-2-carboxylic acid as a solid in 51% yield (45 mg, 0.24 mmol).

To a suspension of 6-cyano-1H-indole-2-carboxylic acid ethyl ester (102 mg, 0.48 mmol) in ammonium hydroxide (3 mL) add hydrogen peroxide (0.5 mL). Stir the mixture for 2 h at rt to form a clear solution. LCMS analysis indicates desired product and absence of starting material. Concentrate to a solid, dissolve in water to form a solution, and acidify with 1M HCl to give a solid. Collect by filtration and dry to afford the desired product 6-carbamoyl-1H-indole-2-carboxylic acid ethyl ester as a solid (54 mg, 0.23 mmol).

Treat a solution of 6-carbamoyl-1H-indole-2-carboxylic acid ethyl ester (54 mg, 0.23 mmol) in dioxane/water (5:1, 12 mL) with LiOH monohydrate (14 mg, 0.33 mmol). Stir the reaction at rt overnight. Concentrate the reaction to dryness and dissolve the residue in water (5 mL) to form a solution. Acidify with 1 M HCl solution to form a solid. Collect by filtration and dry to give the desired product 6-carbamoyl-1H-indole-2-carboxylic acid as a solid in 70% yield (33 mg, 0.16 mmol).

The following intermediates were synthesized in an analogous fashion:

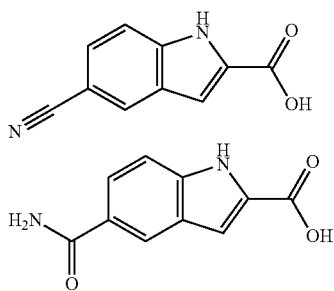

Synthesis of 6-cyano-1-methyl-1H-indole-2-carboxylic acid and 6-carbamoyl-1-methyl-1H-indole-2-carboxylic acid

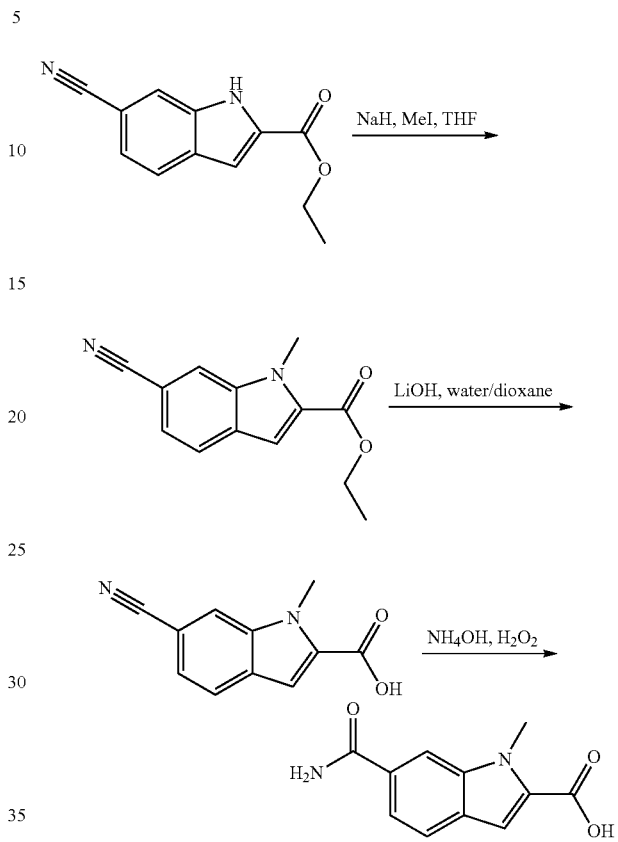

Treat a solution of 6-cyano-1H-indole-2-carboxylic acid ethyl ester (86 mg, 0.40 mmol) in THF (3 mL) with sodium hydride (60% disp. in mineral oil, 18 mg, 0.44 mmol) under $N_2$. After stirring for 10 min, add iodomethane (68 mg, 0.48 mmol) and stir at rt for 3 h. Quench the reaction with sat. $NH_4Cl$ solution and extract several times with EtOAc. Dry the combined organic layers ($Na_2SO_4$) and concentrate to give a solid. Purify the crude product by silica gel chromatography (MeOH/DCM: 0% to 10%) to give the desired 6-cyano-1-methyl-1H-indole-2-carboxylic acid ethyl ester in 59% yield (54 mg, 0.24 mmol).

To a solution of 6-Cyano-1-methyl-1H-indole-2-carboxylic acid ethyl ester (51 mg, 0.22 mmol) in 1,4-dioxane/water (5:1, 6 mL) add LiOH monohydrate (13 mg, 0.31 mmol). Stir the reaction mixture at rt overnight. Remove the solvent in vacuo and dissolve the residue in water (2 mL) to form a solution. Acidify with 1 M HCl solution to form a white suspension. Collect the solid by filtration and dry to give the desired product 6-cyano-1-methyl-1H-indole-2-carboxylic acid as a solid (44 mg, 0.22 mmol).

Dissolve 6-cyano-1-methyl-1H-indole-2-carboxylic acid (21 mg, 0.11 mmol) in ammonium hydroxide (1 mL) and treat the solution with hydrogen peroxide (0.5 mL). Stir the reaction mixture at rt for 2 h. Concentrate in vacuo and dissolve the residue in water (1 mL), followed by acidification with 1 M HCl and filtration of the resulting solid. Collect the desired product 6-carbamoyl-1-methyl-1H-indole-2-carboxylic acid as a solid in 66% yield (15 mg, 0.069 mmol).

The following intermediates were synthesized in an analogous fashion:

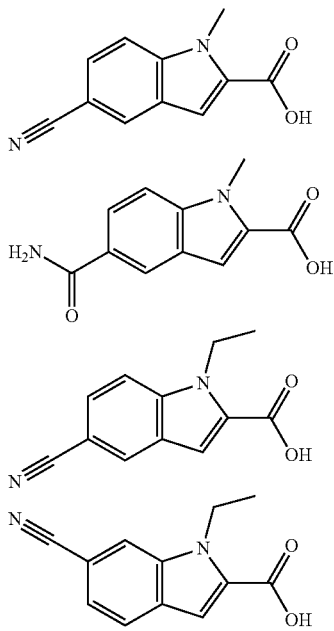

Synthesis of 4-(2-methyl-imidazol-1-yl)-benzoic acid

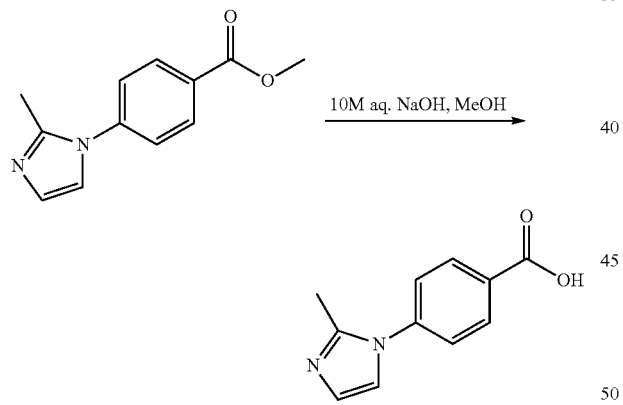

To a stirring solution of 4-(2-methyl-imidazol-1-yl)-benzoic acid methyl ester (250 mg) in MeOH (2 mL) add 10 M NaOH aqueous solution (2.3 mL) and stir the reaction at rt for 20 h. Dilute with water (25 mL) and cool to −15° C. Quench with careful dropwise addition of conc. HCl (2.2 mL) over 5 min to a final pH of 1-2. Wash the suspension with EtOAc (50 mL). Concentrate the aqueous layer to a solid, and further dry in vacuo under $P_2O_5$ to remove all moisture. Triturate the solid in MeOH and filter to remove inorganic salts, washing with MeOH. Concentrate the filtrate, triturate the residue in EtOAc/hexane, and filter, washing with hexane. Suspend the solid in 10% MeOH/EtOAc (20 mL) and stir/sonicate. Syringe filter the suspension to remove inorganics solids, concentrate the organic to a solid residue, and repeat this procedure. Triturate the organic residue in EtOAc/hexane and filter/dry the solid to afford the desired product 4-(2-methyl-imidazol-1-yl)-benzoic acid as a solid in 93% yield (238 mg, 1.06 mmol).

The following intermediates were synthesized in an analogous fashion:

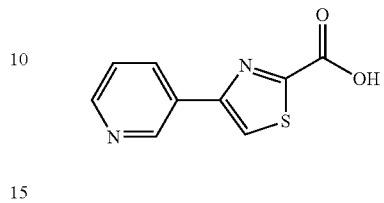

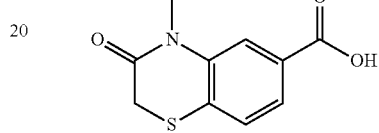

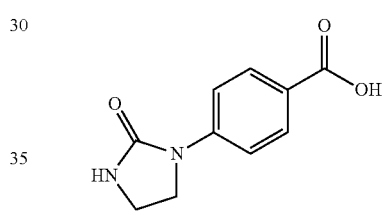

Synthesis of 3-aminomethyl-N-(5-methyl-4,5,6,7-tetrahydro-thiazolo[5,4-c]pyridin-2-yl)-benzamide

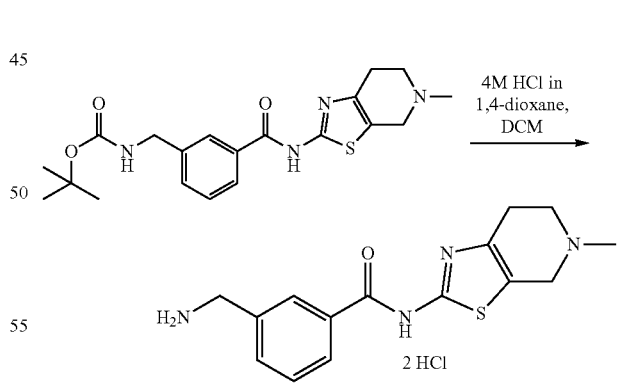

To a solution of [3-(5-methyl-4,5,6,7-tetrahydro-thiazolo[5,4-c]pyridin-2-ylcarbamoyl)-benzyl]-carbamic acid tert-butyl ester (3.56 g, 8.76 mmol) in anhydrous DCM (175 mL) at rt add HCl (44 mL 4M solution in 1,4-dioxane, 175 mmol) and stir the reaction at rt for 24 h. Dilute the solid suspension with $Et_2O$ (300 mL) and hexane (500 mL), stir vigorously for 20 min Filter and wash with $Et_2O$ and hexane to afford the desired product 3-aminomethyl-N-(5-methyl-4,5,6,7-tetrahydro-thiazolo[5,4-c]pyridin-2-yl)-benzamide dihydrochloride as a solid (3.28 g, 8.64 mmol).

Synthesis of 2-(2-methyl-pyridin-4-yl)-thiazole-5-carboxylic acid

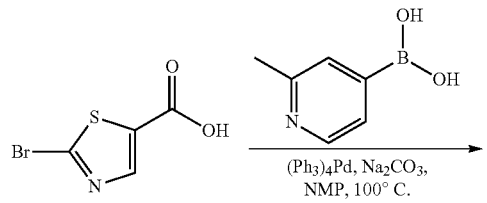

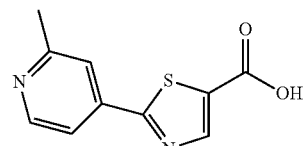

Bubble argon through a suspension of 2-bromothiazole-5-carboxylic acid (75 mg, 0.36 mmol), 2-picoline-4-boronic acid (59 mg, 0.43 mmol), and tetrakis-(triphenylphosphine)-palladium(0) (42 mg) in NMP (1 mL) and 2M $Na_2CO_3$ (0.25 mL). Stir the sealed vial at 100° C. for 4 h. Quench the reaction with aq. $NH_4Cl$ and concentrate in vacuo. Triturate the residue in 30% MeOH/DCM, filter, and concentrate the filtrate in vacuo to an oil. Addition of $H_2O$ gives a precipitate. Filter the solid, wash with $H_2O$ and ether, and dry to give a residue containing impure product. Extract the aqueous filtrate with 1:1 EtOAc/n-butanol (4×), wash with $H_2O$ (4×), and concentrate in vacuo to get more impure product. Purify both crops by prep-TLC developing with 10% MeOH/DCM with 1% HOAc. Further purify the desired band by the same method developing with 50% MeOH/DCM to give desired product 2-(2-methyl-pyridin-4-yl)-thiazole-5-carboxylic acid as a resin (8 mg, 0.036 mmol). MS, electrospray (M+H) 221.5, rt 0.51 min.

The following intermediates were synthesized in an analogous fashion:

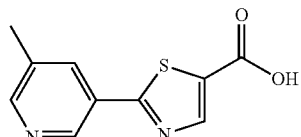

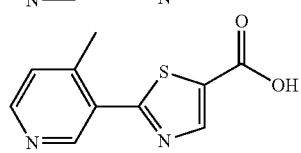

Synthesis of 3-aminomethyl-N—((S)-6-dimethylamino-4,5,6,7-tetrahydro-benzothiazol-2-yl)-benzamide

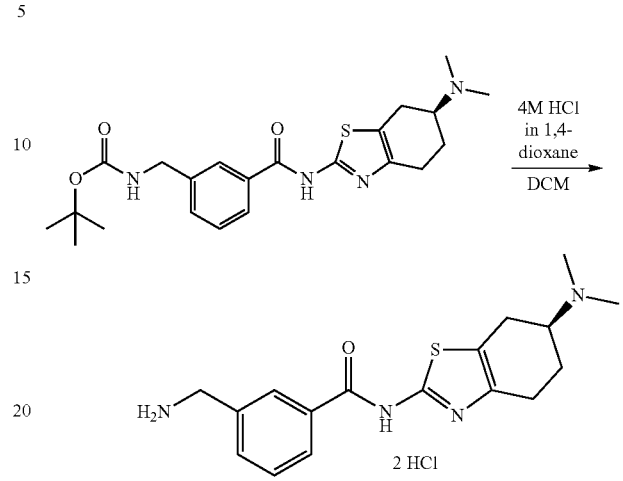

To a solution of [3-((S)-6-Dimethylamino-4,5,6,7-tetrahydro-benzothiazol-2-ylcarbamoyl)-benzyl]-carbamic acid tert-butyl ester (1.60 g, 3.72 mmol) in DCM (40 mL) and MeOH (0.5 mL) at rt add 4M HCl in dioxane (4.65 mL, 18.6 mmol) and stir the reaction at rt overnight. Dilute the solid suspension with $Et_2O$ (300 mL) then filter and wash with $Et_2O$ to afford the desired product 3-aminomethyl-N—((S)-6-dimethylamino-4,5,6,7-tetrahydro-benzothiazol-2-yl)-benzamide dihydrochloride as a solid (1.32 g, 3.27 mmol).

Synthesis of 3-aminomethyl-N—((S)-6-morpholin-4-yl-4,5,6,7-tetrahydro-benzothiazol-2-yl)-benzamide

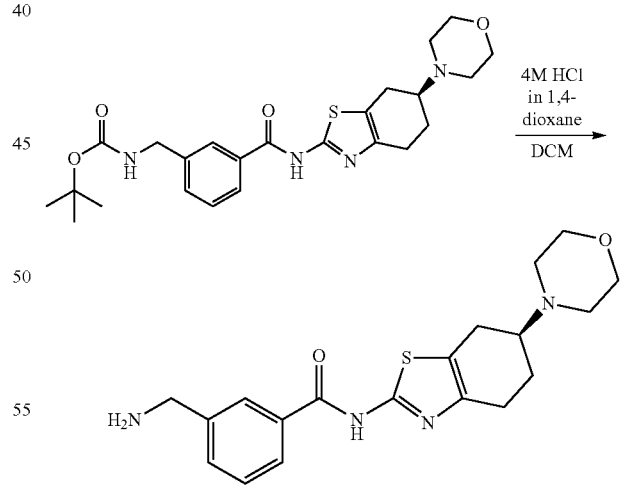

Dissolve [3-((S)-6-morpholin-4-yl-4,5,6,7-tetrahydro-benzothiazol-2-ylcarbamoyl)-benzyl]-carbamic acid tert-butyl ester (4.82 g, 10.2 mmol) in DCM (5 mL) and add TFA (trifluoroacetic acid) (20 mL). Stir the mixture at rt for 1 h. LCMS analysis indicates the desired deprotected material. Concentrate to give the desired product 3-aminomethyl-N—((S)-6-morpholin-4-yl-4,5,6,7-tetrahydro-benzothiazol-2-yl)-benzamide as a foam (4.80 g, 9.87 mmol).

Example 1

Synthesis of 3'-hydroxy-biphenyl-4-carboxylic acid 3-(2-methyl-1,2,3,4-tetrahydro-isoquinolin-7-ylcarbamoyl)-benzylamide (Compound 1, Table 1)

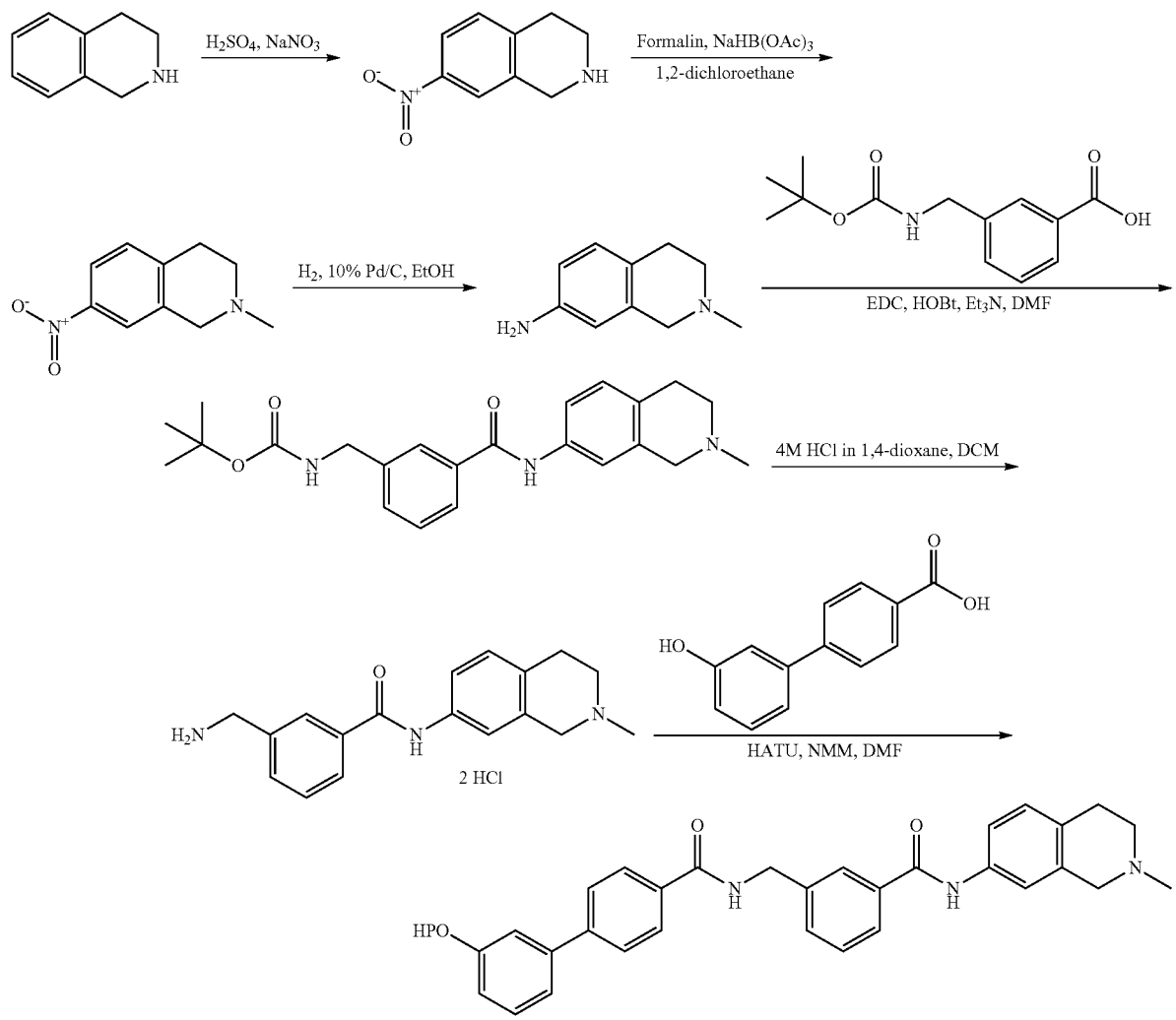

1

To concentrated $H_2SO_4$ (100 mL) at 4° C. add 1,2,3,4-tetrahydro-isoquinoline (24.01 g, 180.3 mmol) dropwise keeping the temp below 15° C. To the stirring mixture at 4° C. add $NaNO_3$ (20.04 g, 198.2 mmol) carefully keeping internal temp below 10° C. and stir the mixture overnight at rt. Carefully add the reaction to stirring $NH_4OH$ (300 mL) to a final pH=8. Extract the mixture with DCM (3×200 mL) and wash the organic phase with brine (100 mL). Dry the mixture ($Na_2SO_4$), filter and concentrate. Dissolve the crude residue in EtOH (80 mL) and add concentrated HCl (25 mL) resulting in a light brown solid which crystallizes in MeOH to give the desired product 7-nitro-1,2,3,4-tetrahydro-isoquinoline (21.91 g, 123.0 mmol).

To a stirring solution of 7-nitro-1,2,3,4-tetrahydro-isoquinoline (5.00 g, 23.3 mmol) in dry 1,2-dichloroethane (200 mL) add formalin (37% aq. formaldehyde) (1.91 mL, 25.6 mmol) followed by sodium triacetoxyborohydride (23.4 g, 104.8 mmol). Stir the reaction vigorously at rt for 24 h. TLC (10% MeOH/DCM) indicates formation of desired product (Rf=0.35) and absence of starting material. Concentrate the reaction in vacuo and dilute the residue with EtOAc (400 mL). Quench this with portionwise addition of sat. $NaHCO_3$ (400 mL) and vigorous stirring (delayed onset of vigorous bubbling). Extract the aqueous with more EtOAc (400 mL), dry the combined organics ($Na_2SO_4$), and concentrate in vacuo to give a brown oil. Purify the crude product by silica gel chromatography eluting with a gradient of 0% to 2.5% MeOH/DCM to afford an oil. This crystallizes to a solid overnight in vacuo to give the desired product 2-methyl-7-nitro-1,2,3,4-tetrahydro-isoquinoline as a solid (3.43 g, 17.3 mmol).

To a stirring solution of 2-methyl-7-nitro-1,2,3,4-tetrahydro-isoquinoline (3.43 g, 17.3 mmol) in 95% EtOH (200 mL) add 10% Pd/C (200 mg) and hydrogenate the reaction at rt and 1 atm for 24 h. TLC analysis (10% MeOH/DCM) indicates desired product (Rf=0.15, streak) and absence of starting materials. Remove the solids by filtration washing with EtOH, and concentrate the solvent in vacuo to give a gum. Purify the crude product by silica gel chromatography eluting with a gradient of 0% to 25% MeOH/DCM to afford an oil.

The desired product 2-methyl-1,2,3,4-tetrahydro-isoquinolin-7-ylamine crystallizes on standing to a solid (2.80 g, 17.3 mmol).

To a solution of 3-(tert-butoxycarbonylamino-methyl)-benzoic acid (4.69 g, 18.5 mmol), EDC (1-ethyl-3-(3-dimethylaminopropyl)carbodiimide) (3.72 g, 19.0 mmol), and HOBt (1-hydroxybenzotriazole) (2.63 g, 18.5 mmol) in anhyd. DMF (50 mL) add Et₃N (3.91 ml, 27.7 mmol) and stir the thick suspension at rt for 1 h. To this add 2-methyl-1,2,3,4-tetrahydro-isoquinolin-7-ylamine (3.00 g, 18.5 mmol) as a solution in DMF (10 mL) and stir the solution at rt for 24 h. TLC analysis (10% MeOH/DCM) indicates desired product (Rf=0.20, streak) and absence of starting materials. Dilute the reaction in EtOAc (600 mL) and wash with sat. NaHCO₃ (500 mL) then water (500 mL). Extract the aqueous layers with more EtOAc (2×400 mL), dry the combined organics (Na₂SO₄), filter and concentrate in vacuo to give an amber gum. Purify this by silica gel chromatography eluting with 0% to 25% MeOH/DCM to afford the desired product [3-(2-methyl-1,2,3,4-tetrahydro-isoquinolin-7-ylcarbamoyl)-benzyl]-carbamic acid tert-butyl ester as a solid foam (6.35 g, 15.6 mmol).

To a solution of [3-(2-methyl-1,2,3,4-tetrahydro-isoquinolin-7-ylcarbamoyl)-benzyl]-carbamic acid tert-butyl ester (6.35 g, 15.6 mmol) in anhydrous DCM (250 mL) at rt add 4M HCl in 1,4-dioxane (58.4 mL, 233.6 mmol) and stir the reaction at rt for 24 h. Dilute the solid suspension with Et₂O (500 mL) and hexane (800 mL), stir vigorously for 20 min then filter and wash with Et₂O then hexane to afford the desired product 3-aminomethyl-N-(2-methyl-1,2,3,4-tetrahydro-isoquinolin-7-yl)-benzamide dihydrochloride as a hydroscopic solid (5.68 g, 14.7 mmol).

To a vial containing 3'-hydroxy-biphenyl-4-carboxylic acid (26 mg, 0.12 mmol) add a solution of HATU (2-(1H-7-azabenzotriazol-1-yl)-1,1,3,3-tetramethyl uronium hexafluorophosphate) (57 mg, 0.15 mmol) in DMF (1 mL) followed by a solution of 3-aminomethyl-N-(2-methyl-1,2,3,4-tetrahydro-isoquinolin-7-yl)-benzamide dihydrochloride (37 mg, 0.10 mmol) and 4-methylmorpholine (0.044 mL, 0.40 mmol) in DMF (1 mL). Shake the reaction at rt for 24 h. Concentrate in vacuo to an oil. Dissolve the residue in 10% water in DMSO (0.9 mL) and purify by prep-HPLC (10% to 90%, CH₃CN/H₂O). Concentrate fractions to afford the desired product 3'-hydroxy-biphenyl-4-carboxylic acid 3-(2-methyl-1,2,3,4-tetrahydro-isoquinolin-7-ylcarbamoyl)-benzylamide as a solid in 45% yield (22 mg, 0.045 mmol). MS, electrospray (M+H) 492.4, rt 2.29 min.

The following compounds were prepared analogously to Example 1. Compound numbers refer to number in Table 1:

Cpd 3:

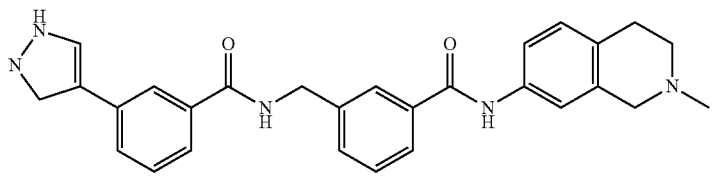

MS, electrospray 466.4 (M + H), rt 1.86 min.

Cpd 5:

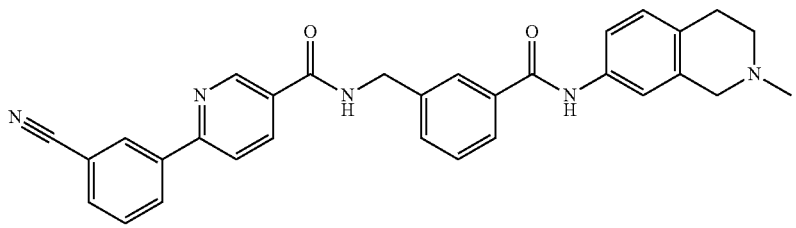

MS, electrospray 502.4 (M + H), rt 2.28 min.

Cpd 7:

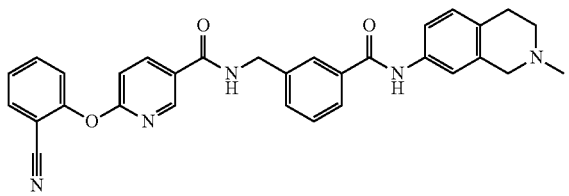

MS, electrospray 518.4 (M + H), rt 2.26 min.

Cpd 9:

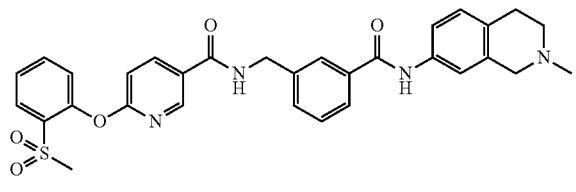

MS, electrospray 571.4 (M + H), rt 1.97 min.

-continued

Cpd 11:

MS, electrospray 586.4 (M + H), rt 2.20 min.

Cpd 13:

MS, electrospray 454.4 (M + H), rt 1.63 min.

Cpd 15:

MS, electrospray 454.4 (M + H), rt 1.66 min.

Cpd 17:

MS, electrospray 454.4 (M + H), rt 1.54 min.

Cpd 19:

MS, electrospray 454.4 (M + H), rt 1.54 min.

Cpd 21:

MS, electrospray 483.3 (M + H), rt 1.75 min.

Cpd 23:

MS, electrospray 465.4 (M + H), rt 1.79 min.

Cpd 25:

MS, electrospray 441.3 (M + H), rt 1.74 min.

Cpd 27:

MS, electrospray 484.2 (M + H), rt 2.09 min.

Cpd 29:

MS, electrospray 466.3 (M + H), rt 2.22 min.

Cpd 31:

MS, electrospray 483.2 (M + H), rt 1.85 min.

-continued
Cpd 33:
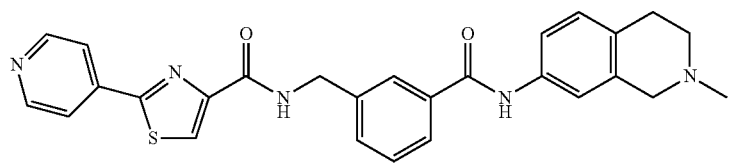
MS, electrospray 484.2 (M + H), rt 1.81 min.
Cpd 35:
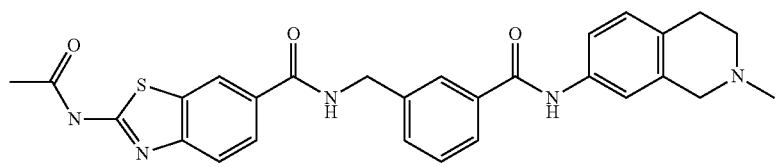
MS, electrospray 514.2 (M + H), rt 2.16 min.
Cpd 37:
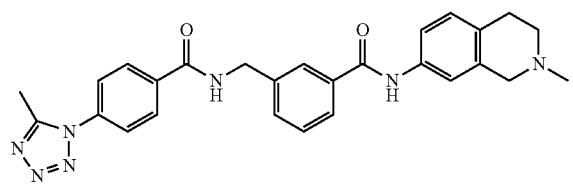
MS, electrospray 482.3 (M + H), rt 1.99 min.
Cpd 39:
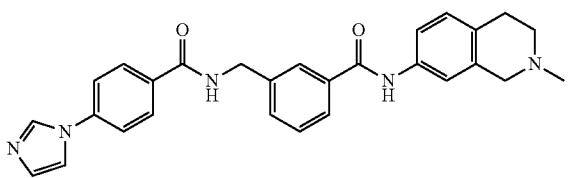
MS, electrospray 466.3 (M + H), rt 1.39 min.
Cpd 41:
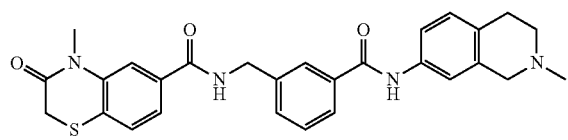
MS, electrospray 501.3 (M + H), rt 2.28 min.
Cpd 43:
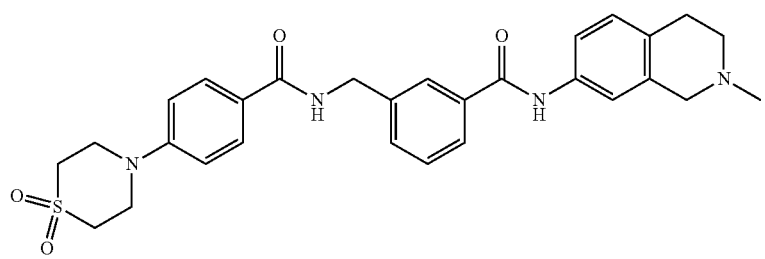
MS, electrospray 533.3 (M + H), rt 1.97 min.
Cpd 45:
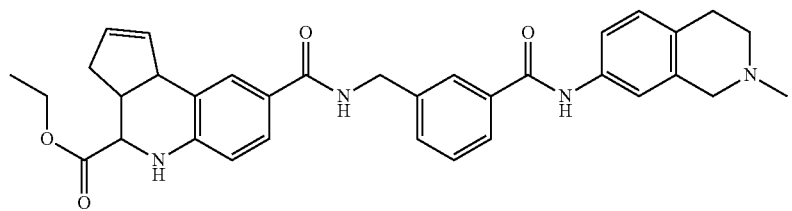
MS, electrospray 565.3 (M + H), rt 2.88 min.

Cpd 47:
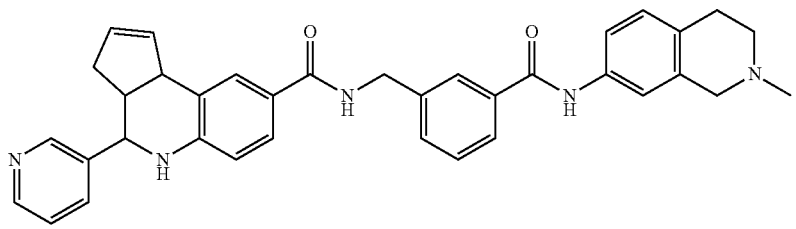
MS, electrospray 570.3 (M + H), rt 1.98 min.
Cpd 49:
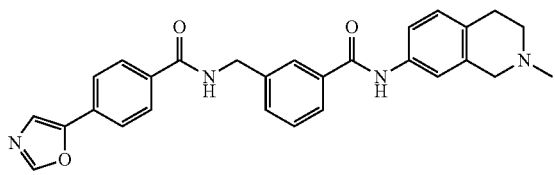
MS, electrospray 467.3 (M + H), rt 2.20 min.
Cpd 51:
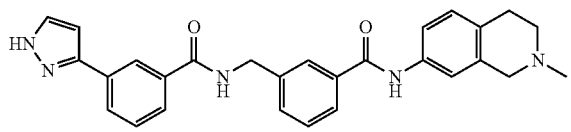
MS, electrospray 466.3 (M + H), rt 2.15 min.
Cpd 53:
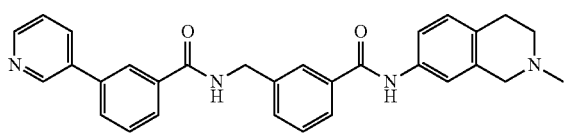
MS, electrospray 477.3 (M + H), rt 1.74 min.
Cpd 55:
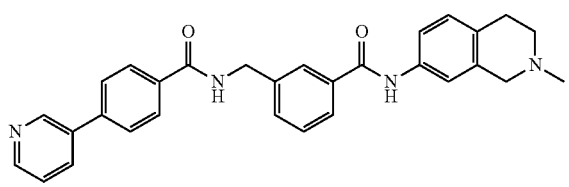
MS, electrospray 477.3 (M + H), rt 1.70 min.
Cpd 57:
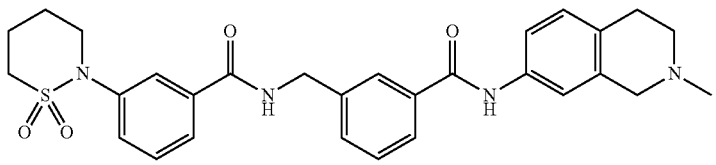
MS, electrospray 533.2 (M + H), rt 2.23 min.
Cpd 59:
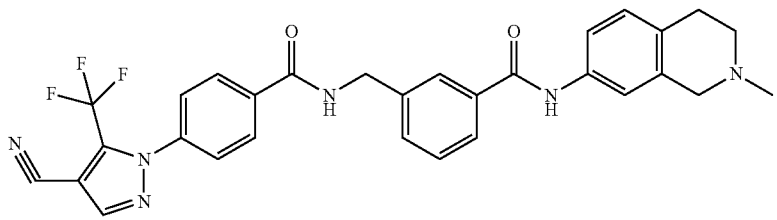
MS, electrospray 559.3 (M + H), rt 2.77 min.
Cpd 61:
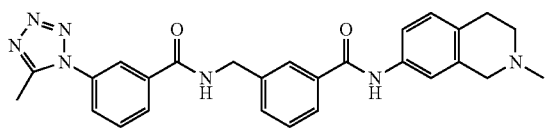
MS, electrospray 482.3 (M + H), rt 2.00 min.
Cpd 63:
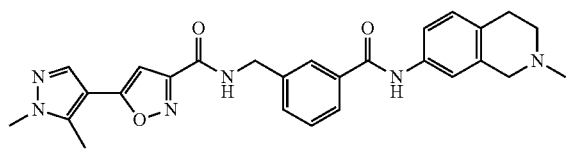
MS, electrospray 485.3 (M + H), rt 2.27 min.

-continued

Cpd 65:
MS, electrospray 472.3 (M + H), rt 2.01 min.

Cpd 67:
MS, electrospray 510.3 (M + H), rt 2.38 min.

Cpd 69:
MS, electrospray 477.3 (M + H), rt 1.64 min.

Cpd 71:
MS, electrospray 478.3 (M + H), rt 2.06 min.

Cpd 73:
MS, electrospray 478.2 (M + H), rt 2.31 min.

Cpd 75:
MS, electrospray 467.3 (M + H), rt 1.76 min.

Cpd 77:
MS, electrospray 516.3 (M + H), rt 2.18 min.

Cpd 79:
MS, electrospray 533.3 (M + H), rt 2.36 min.

Cpd 81:
MS, electrospray 473.3 (M + H), rt 1.75 min.

Cpd 83:
MS, electrospray 496.3 (M + H), rt 1.96 min.

Cpd 85:
MS, electrospray 481.3 (M + H), rt 1.89 min.

Cpd 87:
MS, electrospray 481.3 (M + H), rt 1.87 min.

Cpd 89:
MS, electrospray 497.3 (M + H), rt 2.08 min.

Cpd 91:
MS, electrospray 467.3 (M + H), rt 1.88 min.

-continued

Cpd 93:

MS, electrospray 467.3 (M + H), rt 1.79 min.

Cpd 95:

MS, electrospray 498.3 (M + H), rt 1.63 min.

Cpd 97:

MS, electrospray 513.4 (M + H), rt 1.67 min.

Cpd 99:

MS, electrospray 480.4 (M + H), rt 1.94 min.

Cpd 101:

MS, electrospray 519.4 (M + H), rt 1.92 min.

Cpd 103:

MS, electrospray 482.4 (M + H), rt 1.64 min.

Cpd 105:

MS, electrospray 467.4 (M + H), rt 1.33 min.

Cpd 107:

MS, electrospray 485.4 (M + H), rt 1.88 min.

Cpd 109:

MS, electrospray 533.4 (M + H), rt 1.79 min.

Cpd 111:

MS, electrospray 501.3 (M + H), rt 1.50 min.

Cpd 113:

MS, electrospray 494.4 (M + H), rt 1.20 min.

-continued
Cpd 115:
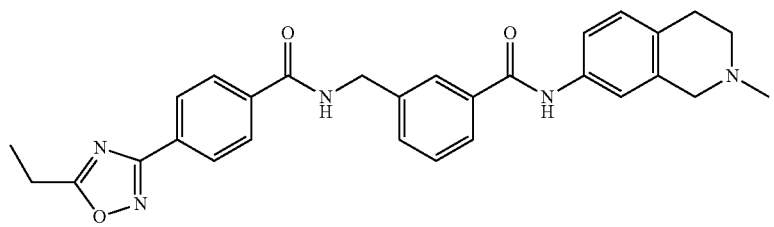
MS, electrospray 496.4 (M + H), rt 2.33 min.
Cpd 117:
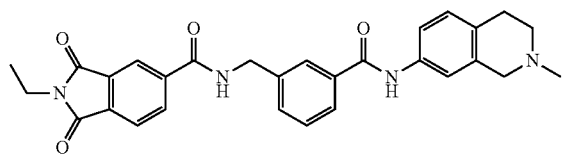
MS, electrospray 497.4 (M + H), rt 2.11 min.
Cpd 119:
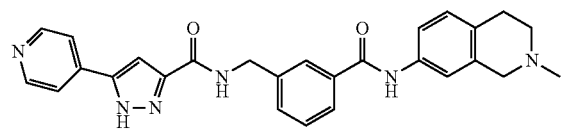
MS, electrospray 467.4 (M + H), rt 1.21 min.
Cpd 121:
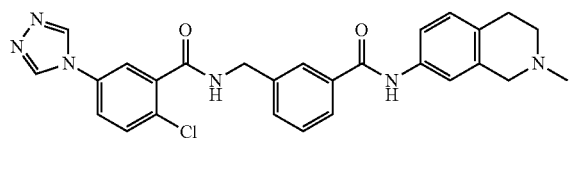
MS, electrospray 501.3 (M + H), rt 1.56 min.
Cpd 123:
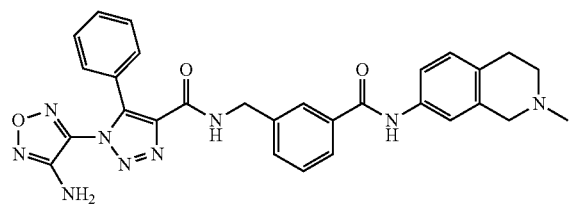
MS, electrospray 550.4 (M + H), rt 2.35 min.
Cpd 125:
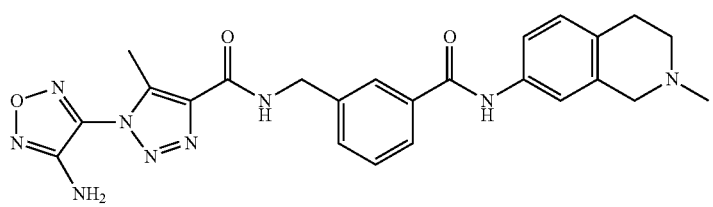
MS, electrospray 488.4 (M + H), rt 2.00 min.
Cpd 127:
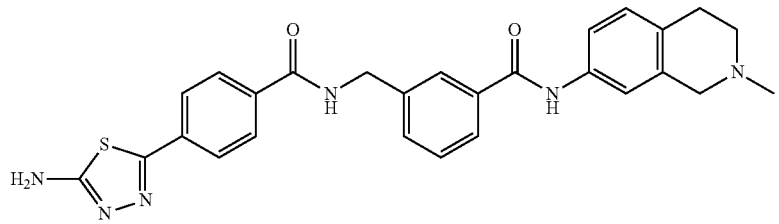
MS, electrospray 499.4 (M + H), rt 1.72 min.
Cpd 129:
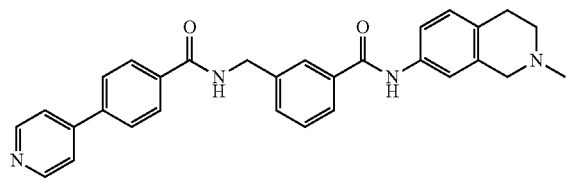
MS, electrospray 477.4 (M + H), rt 1.37 min.
Cpd 131:
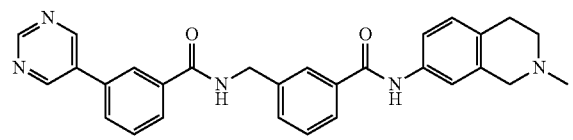
MS, electrospray 478.4 (M + H), rt 1.82 min.

-continued
Cpd 133:
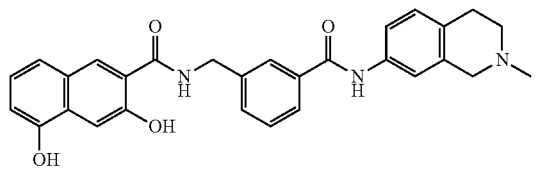
MS, electrospray 482.3 (M + H), rt 2.13 min.
Cpd 135:
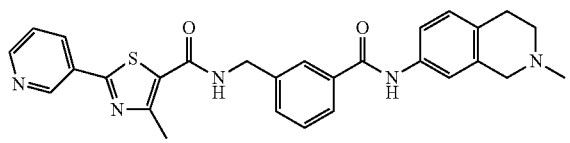
MS, electrospray 498.3 (M + H), rt 1.79 min.
Cpd 137:
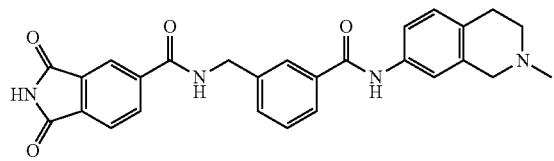
MS, electrospray 469.3 (M + H), rt 1.63 min.
Cpd 139:
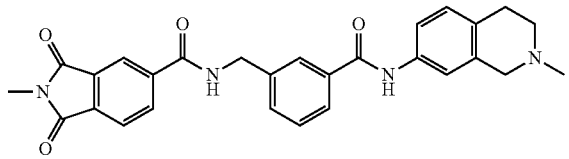
MS, electrospray 483.3 (M + H), rt 1.85 min.
Cpd 141:
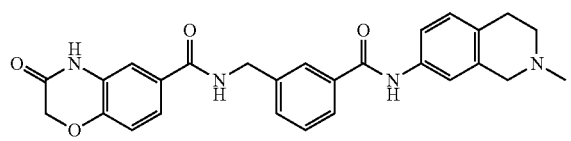
MS, electrospray 471.3 (M + H), rt 1.67 min.
Cpd 143:
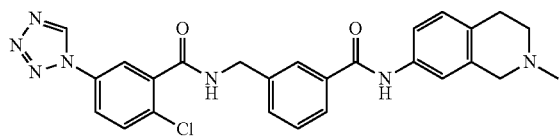
MS, electrospray 502.3 (M + H), rt 1.76 min.
Cpd 145:
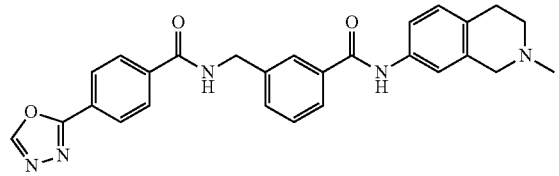
MS, electrospray 468.4 (M + H), rt 1.69 min.
Cpd 147:
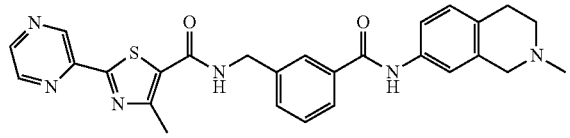
MS, electrospray 499.4 (M + H), rt 1.88 min.
Cpd 149:
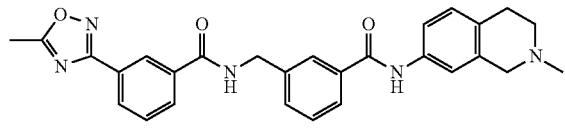
MS, electrospray 482.4 (M + H), rt 2.01 min.
Cpd 151:
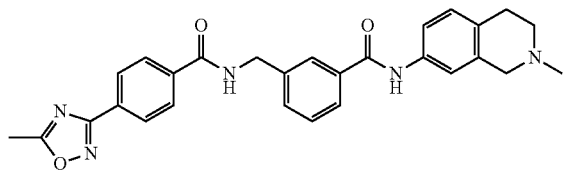
MS, electrospray 482.4 (M + H), rt 2.04 min.
Cpd 153:
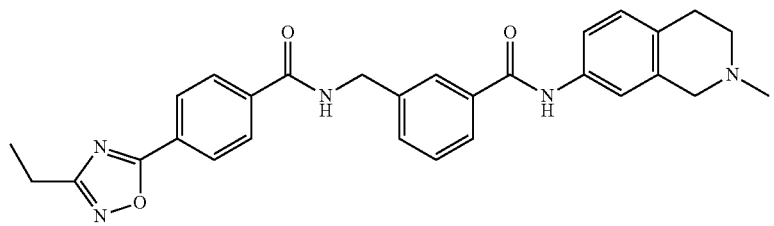
MS, electrospray 496.4 (M + H), rt 2.25 min.

-continued

Cpd 155:

MS, electrospray 466.4 (M + H), rt 1.80 min.

Cpd 157:

MS, electrospray 455.3 (M + H), rt 0.19 min.

Cpd 159:

MS, electrospray 467.4 (M + H), rt 2.25 min.

Cpd 161:

MS, electrospray 511.4 (M + H), rt 1.26 min.

Cpd 163:

MS, electrospray 484.4 (M + H), rt 1.36 min.

Cpd 165:

MS, electrospray 487.4 (M + H), rt 1.78 min.

Cpd 167:

MS, electrospray 510.4 (M + H), rt 1.90 min.

Cpd 169:

MS, electrospray 484.4 (M + H), rt 1.69 min.

Cpd 171:

MS, electrospray 471.4 (M + H), rt 1.83 min.

Cpd 175:

MS, electrospray 467.4 (M + H), rt 1.57 min.

Cpd 177:

MS, electrospray 498.4 (M + H), rt 1.38 min.

Cpd 179:

MS, electrospray 466.4 (M + H), rt 1.82 min.

Cpd 181:

MS, electrospray 481.4 (M + H), rt 1.09 min.

-continued

Cpd 183:

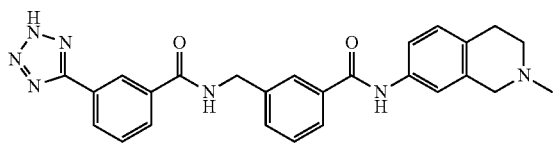

MS, electrospray 468.4 (M + H), rt 1.64 min.

Cpd 185:

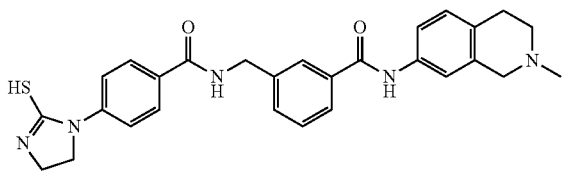

MS, electrospray 500.5 (M + H), rt 1.67 min.

Cpd 187:

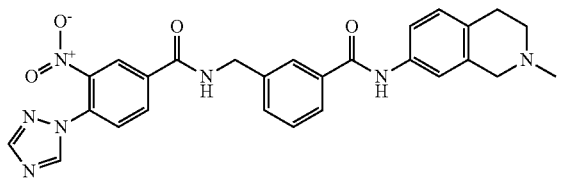

MS, electrospray 512.4 (M + H), rt 1.75 min.

Cpd 189:

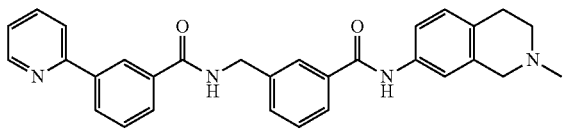

MS, electrospray 477.4 (M + H), rt 1.66 min.

Cpd 191:

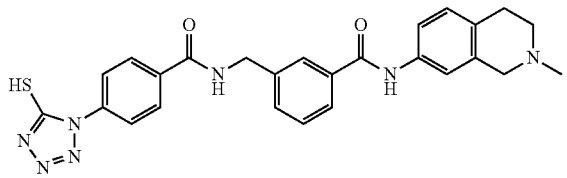

MS, electrospray 500.4 (M + H), rt 1.85 min.

Cpd 193:

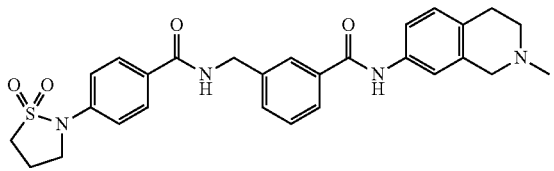

MS, electrospray 519.5 (M + H), rt 1.72 min.

Cpd 195:

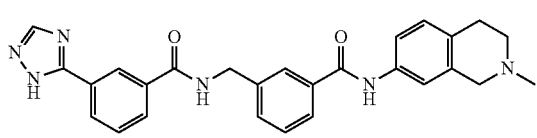

MS, electrospray 467.4 (M + H), rt 1.59 min.

Cpd 197:

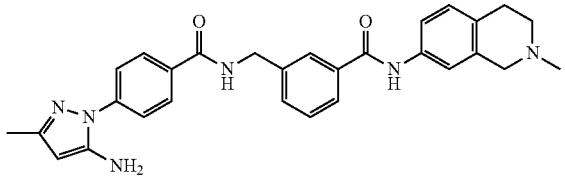

MS, electrospray 495.4 (M + H), rt 1.42 min.

Cpd 199:

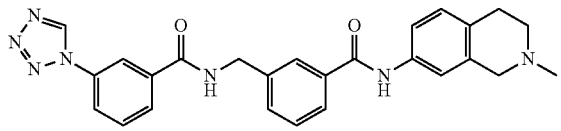

MS, electrospray 468.4 (M + H), rt 1.69 min.

Cpd 203:

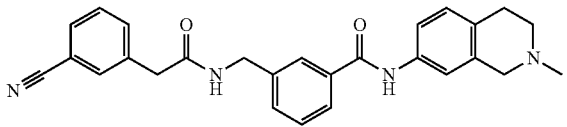

MS, electrospray 439.5 (M + H), rt 1.66 min.

Cpd 205:

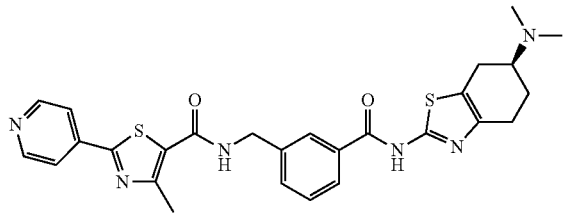

MS, electrospray 533.3 (M + H), rt 0.90 min.

Cpd 207:

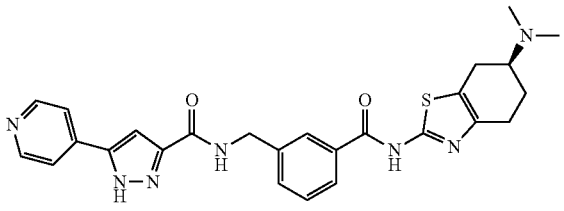

MS, electrospray 502.2 (M + H), rt 0.34 min.

-continued
Cpd 150:
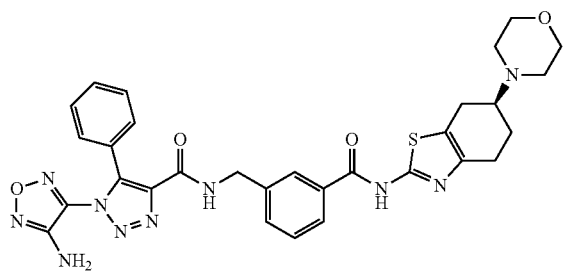
MS, electrospray 627.82 (M + H), rt 1.39 min.
Cpd 152:
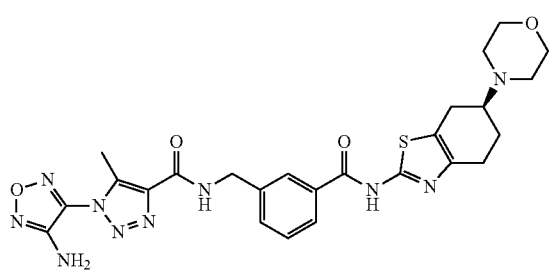
MS, electrospray 565.78 (M + H), rt 1.29 min.
Cpd 172:
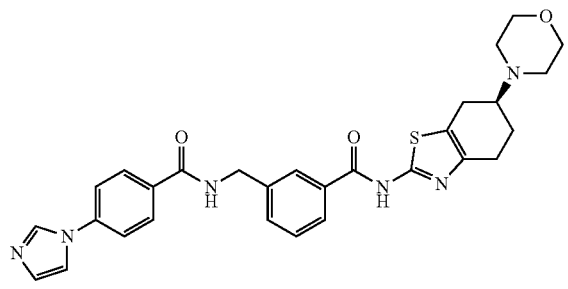
MS, electrospray 543.74 (M + H), rt 1.04 min.
Cpd 174:
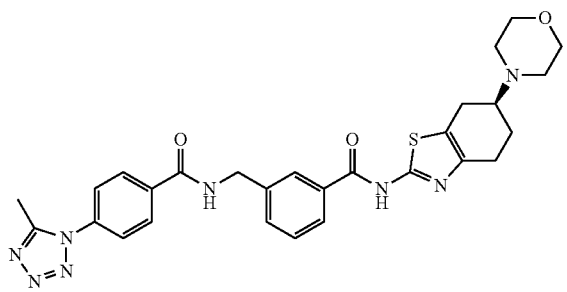
MS, electrospray 559.84 (M + H), rt 1.18 min.
Cpd 170:
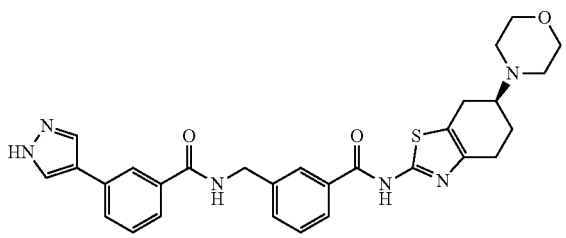
MS, electrospray 543.85 (M + H), rt 1.22 min.
Cpd 176:
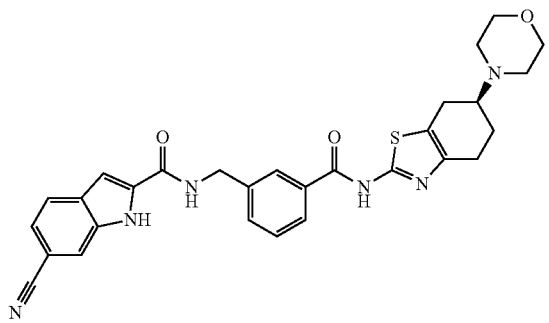
MS, electrospray 541.81 (M + H), rt 1.29 min.
Cpd 148:
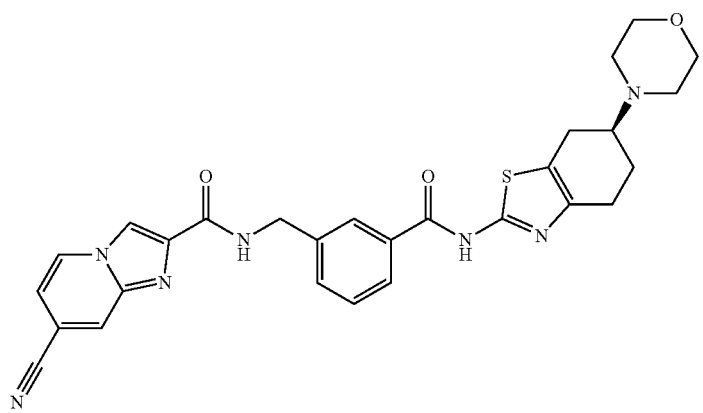
MS, electrospray 542.77 (M + H), rt 1.18 min.

Example 2

Synthesis of 5-pyridin-3-yl-thiophene-2-carboxylic acid 3-(2-methyl-1,2,3,4-tetrahydro-isoquinolin-7-ylcarbamoyl)-benzylamide (Cpd 62, Table 1)

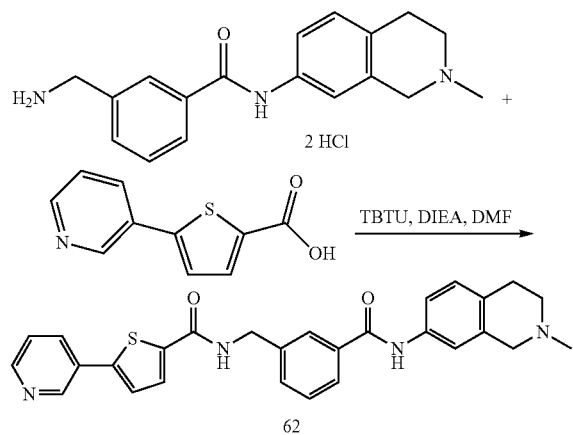

To a solution of 5-pyridin-3-yl-thiophene-2-carboxylic acid (31 mg, 0.15 mmol) in DMF (1 mL) add Hunig's Base (0.10 mL, 0.54 mmol) and TBTU (52 mg, 0.16 mmol) and stir at rt for 20 min. To this add 3-aminomethyl-N-(2-methyl-1,2,3,4-tetrahydro-isoquinolin-7-yl)-benzamide dihydrochloride (50 mg, 0.1 mmol) and stir the solution for 18 h at rt. Concentrate the solution and purify the residue by prep-HPLC (10% to 90%, $CH_3CN/H_2O$) to provide the desired product 5-pyridin-3-yl-thiophene-2-carboxylic acid 3-(2-methyl-1,2,3,4-tetrahydro-isoquinolin-7-ylcarbamoyl)-benzylamide (62 mg, 0.087 mmol). MS, electrospray 483.8 (M+H), rt 0.88 min.

The following examples were prepared analogously to Example 2:

Cpd 60:

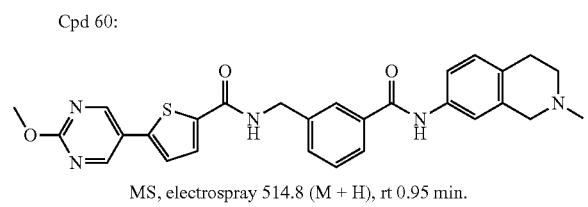

MS, electrospray 514.8 (M + H), rt 0.95 min.

Cpd 70:

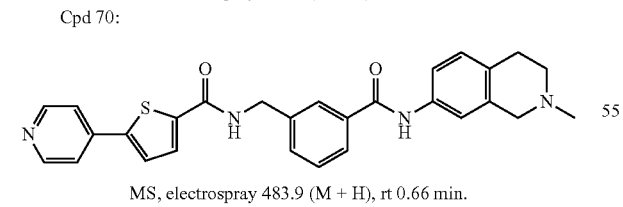

MS, electrospray 483.9 (M + H), rt 0.66 min.

Cpd 68:

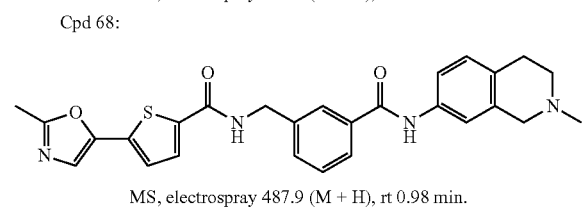

MS, electrospray 487.9 (M + H), rt 0.98 min.

Cpd 72:

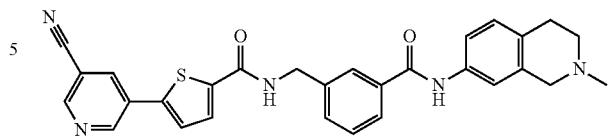

MS, electrospray 502.9 (M + H), rt 1.01 min.

Cpd 64:

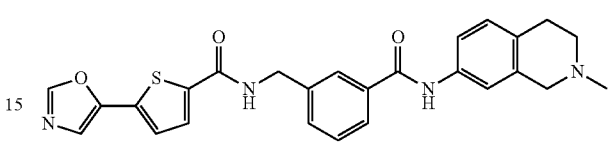

MS, electrospray 473.8 (M + H), rt 0.97 min.

Cpd 122:

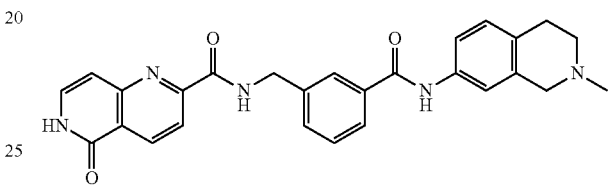

MS, electrospray 468.3 (M + H), rt 0.42 min.

Cpd 18:

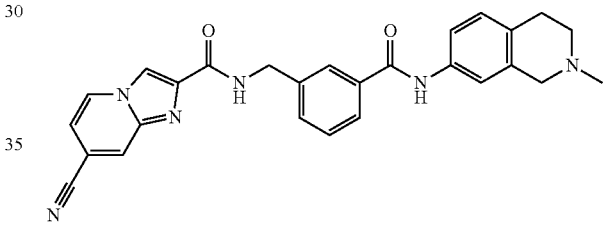

MS, electrospray 465.8 (M + H), rt 0.88 min.

Cpd 16:

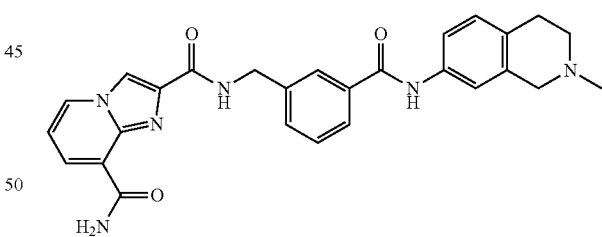

MS, electrospray 483.76 (M + H), rt 0.82 min.

Cpd 52:

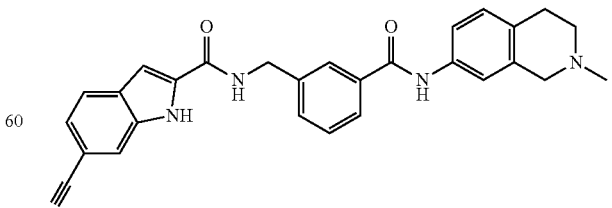

MS, electrospray 464.16 (M + H), rt 0.54 min.

Cpd 54:

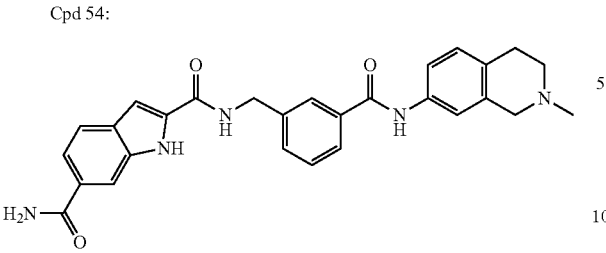

MS, electrospray 482.20 (M + H), rt 0.46 min.

Cpd 80:

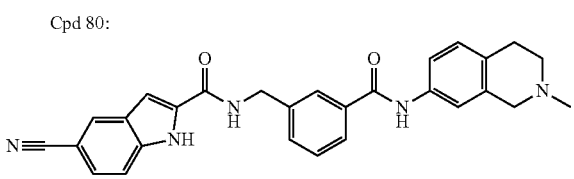

MS, electrospray 464.86 (M + H), rt 1.04 min.

Cpd 86:

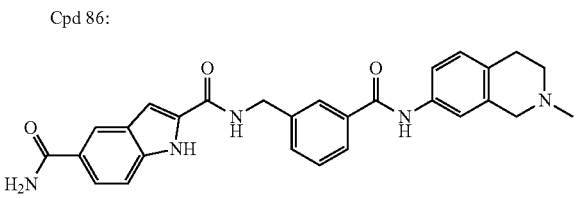

MS, electrospray 482.90 (M + H), rt 0.80 min.

Cpd 84:

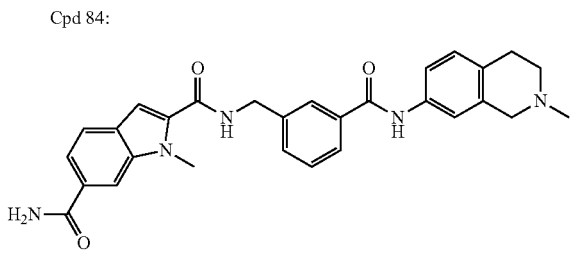

MS, electrospray 496.93 (M + H), rt 0.87 min.

Cpd 92:

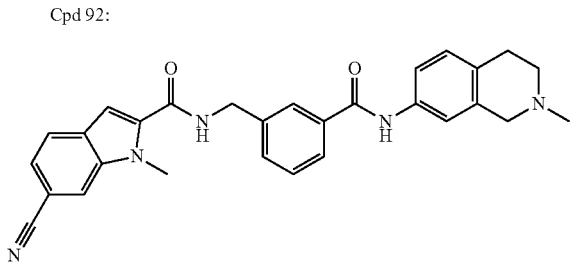

MS, electrospray 478.25 (M + H), rt 0.65 min.

Cpd 94:

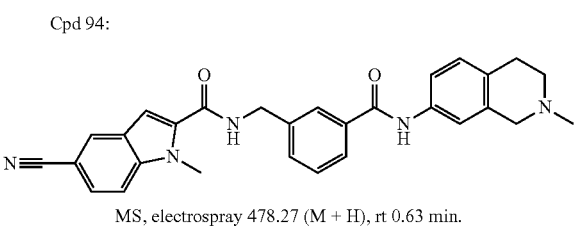

MS, electrospray 478.27 (M + H), rt 0.63 min.

Cpd 96:

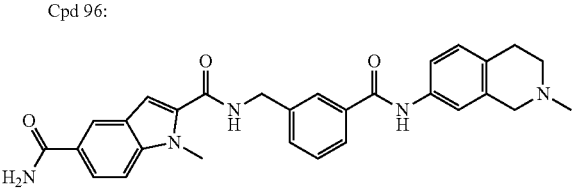

MS, electrospray 496.27 (M + H), rt 0.50 min.

Cpd 102:

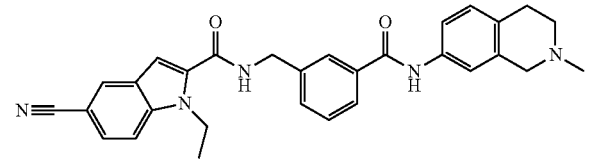

MS, electrospray 492.96 (M + H), rt 1.14 min.

Cpd 118:

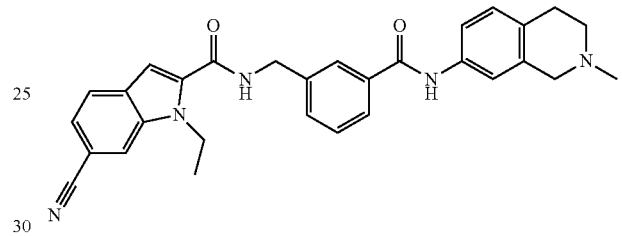

MS, electrospray 492.30 (M + H), rt 0.62 min.

Cpd 66:

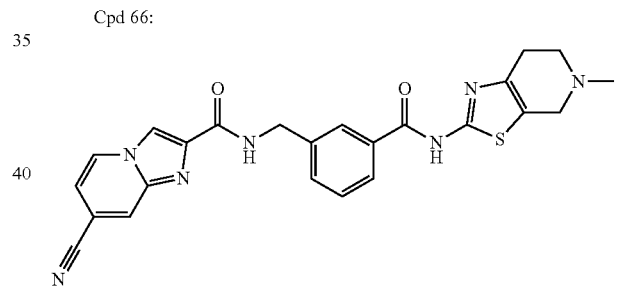

MS, electrospray 472.85 (M + H), rt 0.83 min.

Cpd 88:

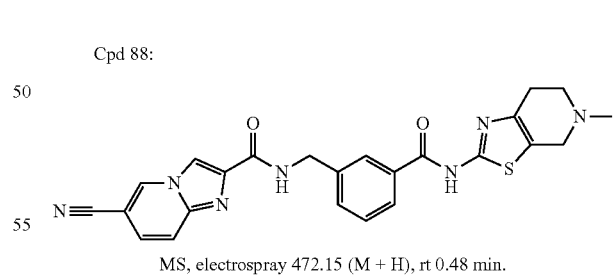

MS, electrospray 472.15 (M + H), rt 0.48 min.

Cpd 124:

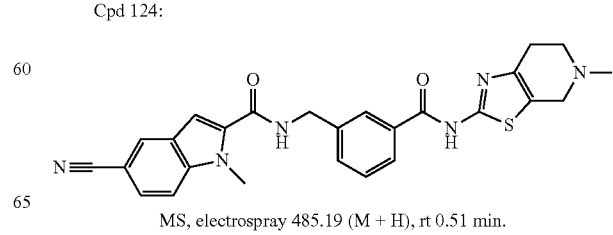

MS, electrospray 485.19 (M + H), rt 0.51 min.

-continued

Cpd 116:

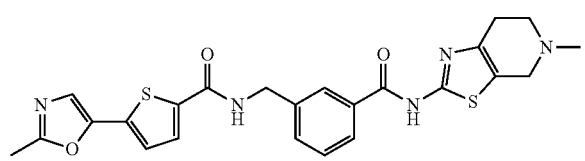

MS, electrospray 494.2 (M + H), rt 0.50 min.

Cpd 114:

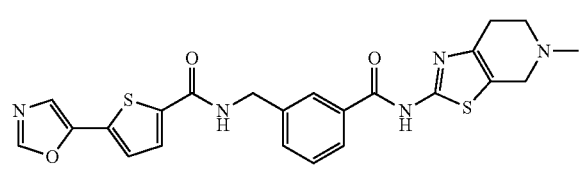

MS, electrospray 480.2 (M + H), rt 0.48 min.

Cpd 112:

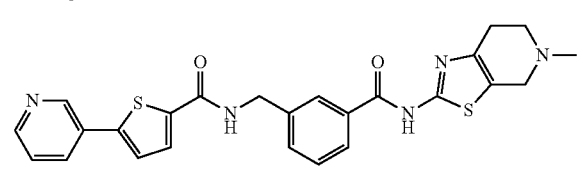

MS, electrospray 490.2 (M + H), rt 0.35 min.

Cpd 110:

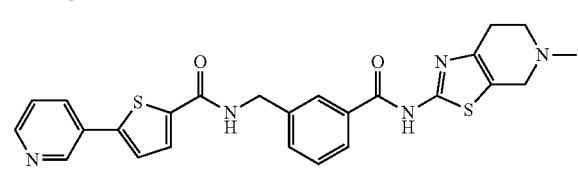

MS, electrospray 490.2 (M + H), rt 0.44 min.

Cpd 154:

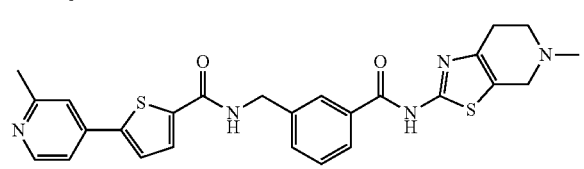

MS, electrospray 505.5 (M + H), rt 1.00 min.

Cpd 156:

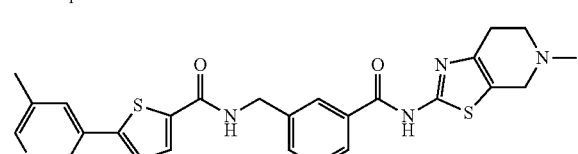

MS, electrospray 505.5 (M + H), rt 1.13 min.

Cpd 158:

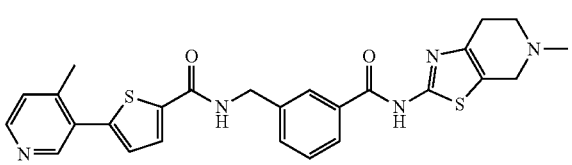

MS, electrospray 505.5 (M + H), rt 1.06 min.

Cpd 98:

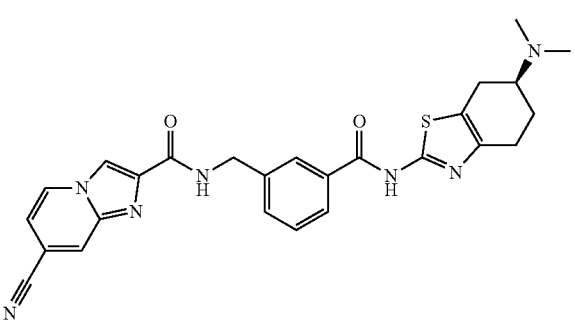

MS, electrospray 500.22 (M + H), rt 0.67 min.

Cpd 100:

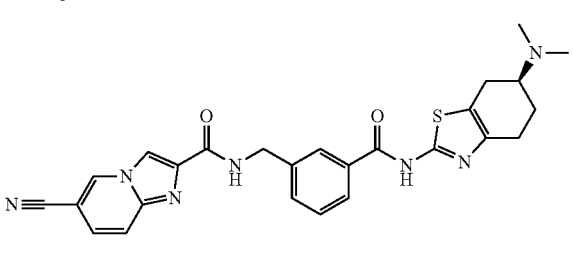

MS, electrospray 500.20 (M + H), rt 0.98 min.

Example 3

Synthesis of 5-(1H-pyrazol-4-yl)-thiophene-2-carboxylic acid 3-(2-methyl-1,2,3,4-tetrahydro-isoquinolin-7-ylcarbamoyl)-benzylamide (Cpd 78, Table 1)

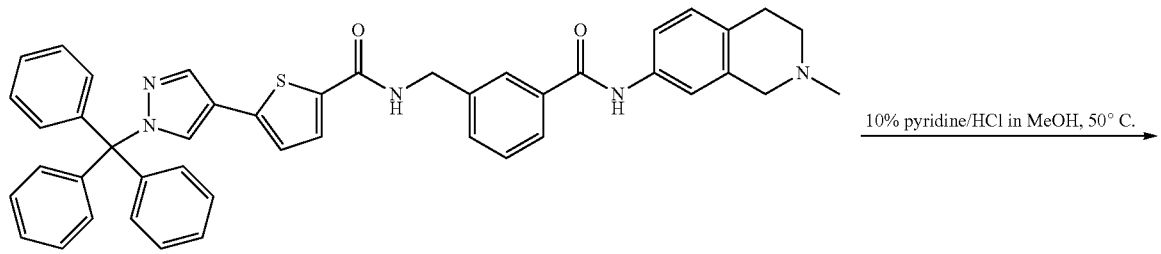

10% pyridine/HCl in MeOH, 50° C.

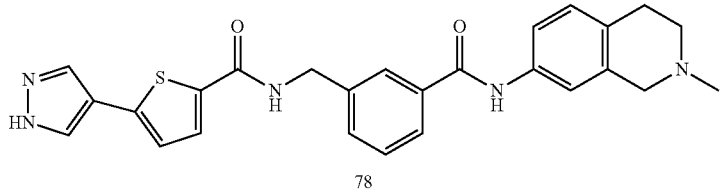

78

Heat a solution of 5-(1-trityl-1H-pyrazol-4-yl)-thiophene-2-carboxylic acid 3-(2-methyl-1,2,3,4-tetrahydro-isoquinolin-7-ylcarbamoyl)-benzylamide (167 mg, 0.234 mmol) in 10% pyridine/HCl in MeOH (50 mL) at 50° C. overnight. Cool the reaction to rt, concentrate, and purify the residue by prep-HPLC (10% to 90%, $CH_3CN$/water). Further purify the residue through a short silica plug to remove baseline impurity affording desired product 5-(1H-pyrazol-4-yl)-thiophene-2-carboxylic acid 3-(2-methyl-1,2,3,4-tetrahydro-isoquinolin-7-ylcarbamoyl)-benzylamide (68 mg, 0.097 mmol). MS, electrospray 472.2 (M+H), rt 0.94 min.

The following examples were prepared analogously to Example 3:

Cpd 120:

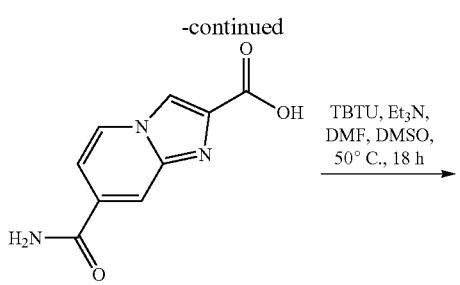

MS, electrospray 479.2 (M + H), rt 0.41 min.

Cpd 130:

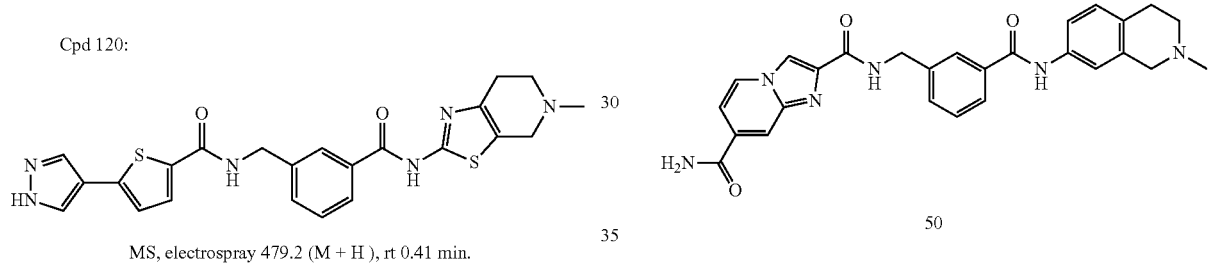

MS, electrospray 507.2 (M + H), rt 0.38 min.

Example 4

Synthesis of imidazo[1,2-a]pyridine-2,7-dicarboxylic acid 7-amide 2-[3-(2-methyl-1,2,3,4-tetrahydro-isoquinolin-7-ylcarbamoyl)-benzylamide] (Cpd 50, Table 1)

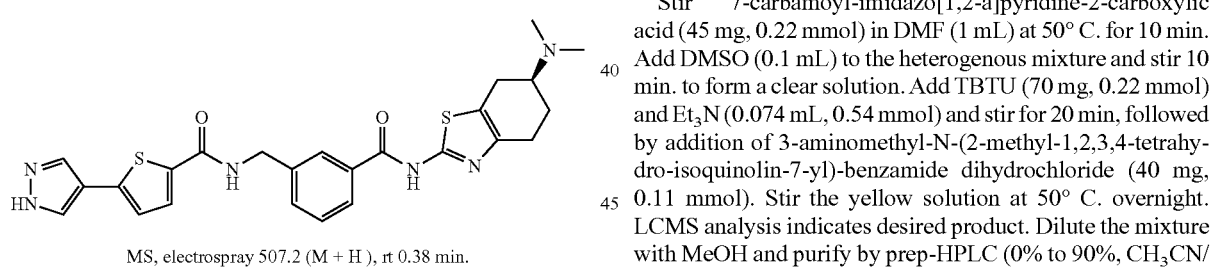

50

Stir 7-carbamoyl-imidazo[1,2-a]pyridine-2-carboxylic acid (45 mg, 0.22 mmol) in DMF (1 mL) at 50° C. for 10 min. Add DMSO (0.1 mL) to the heterogenous mixture and stir 10 min. to form a clear solution. Add TBTU (70 mg, 0.22 mmol) and $Et_3N$ (0.074 mL, 0.54 mmol) and stir for 20 min, followed by addition of 3-aminomethyl-N-(2-methyl-1,2,3,4-tetrahydro-isoquinolin-7-yl)-benzamide dihydrochloride (40 mg, 0.11 mmol). Stir the yellow solution at 50° C. overnight. LCMS analysis indicates desired product. Dilute the mixture with MeOH and purify by prep-HPLC (0% to 90%, $CH_3CN$/water). Concentration of product fractions gives desired product imidazo[1,2-a]pyridine-2,7-dicarboxylic acid 7-amide 2-[3-(2-methyl-1,2,3,4-tetrahydro-isoquinolin-7-ylcarbamoyl)-benzylamide] as a solid (22 mg, 0.046 mmol). MS, electrospray 483.16 (M+H), rt 0.39 min.

The following compound is prepared analogously to Example 4:

Cpd 48:

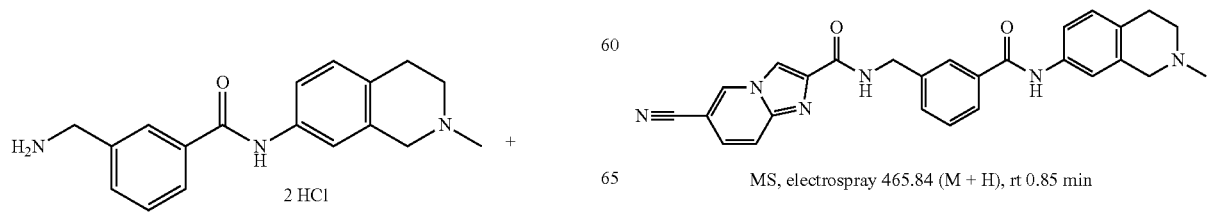

MS, electrospray 465.84 (M + H), rt 0.85 min

Example 5

Synthesis of 4-[1,2,4]triazol-1-yl-benzoic acid 3-(2-methyl-1,2,3,4-tetrahydro-isoquinolin-7-ylcarbamoyl)-benzylamide (Cpd 178, Table 1)

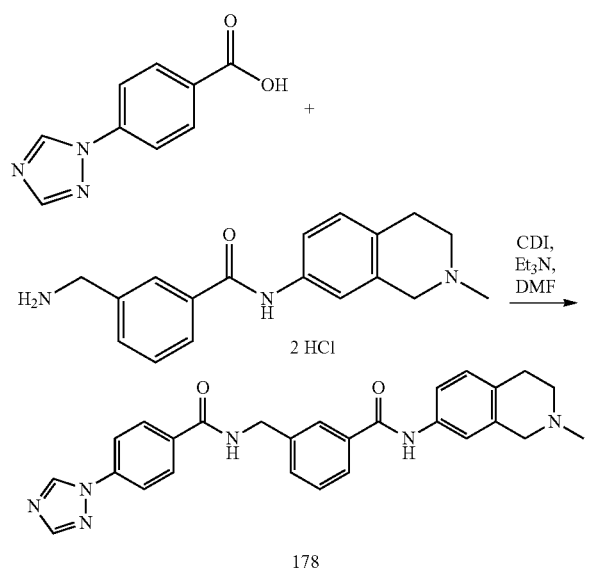

178

Dissolve 4-[1,2,4]triazol-1-yl-benzoic acid (29 mg, 0.15 mmol) and CDI (N,N'-carbonyldiimidazole) (25 mg, 0.15 mmol) in DMF (2 mL) and stir the mixture for 1 h. To this add 3-aminomethyl-N-(2-methyl-1,2,3,4-tetrahydro-isoquinolin-7-yl)-benzamide dihydrochloride (50 mg, 0.14 mmol) and triethylamine (0.095 mL, 0.68 mmol) and stir the mixture overnight. Dilute the mixture with water (1 mL) and trifluoroacetic acid (0.2 mL) and purify by prep-HPLC (5%-70%, CH$_3$CN/H$_2$O) to give the desired product 4-[1,2,4]triazol-1-yl-benzoic acid 3-(2-methyl-1,2,3,4-tetrahydro-isoquinolin-7-ylcarbamoyl)-benzylamide (51 mg, 0.086 mmol). MS, electrospray 467.4 (M+H), rt 1.05 min.

The following examples were prepared analogously to Example 5:

Cpd 180:

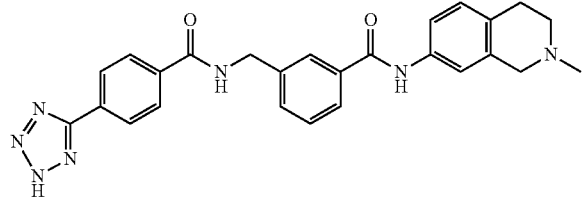

MS, electrospray 468.4 (M + H), rt 1.03 min.

Cpd 182:

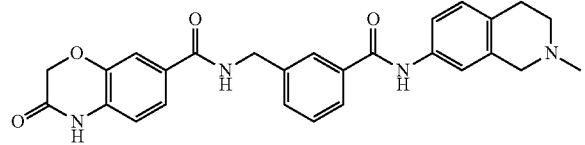

MS, electrospray 471.4 (M + H), rt 1.03 min.

Cpd 184:

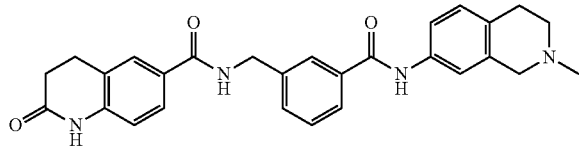

MS, electrospray 469.4 (M + H), rt 1.02 min.

Cpd 186:

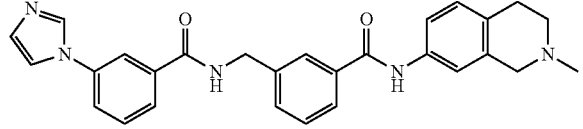

MS, electrospray 466.7 (M + H), rt 0.90 min.

Cpd 190:

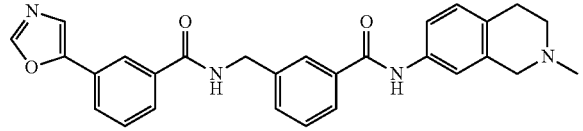

MS, electrospray 467.7 (M + H), rt 1.13 min.

Cpd 194:

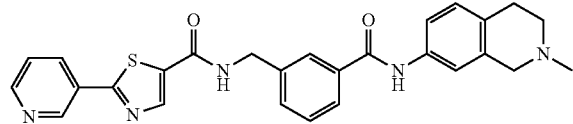

MS, electrospray 484.4 (M + H), rt 1.10 min.

Cpd 192:

MS, electrospray 468.4 (M + H), rt 1.07 min.

Cpd 188:

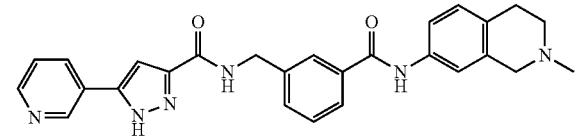

MS, electrospray 467.7 (M + H), rt 0.93 min.

Cpd 196:

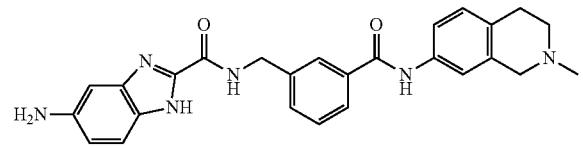

MS, electrospray 455.7 (M + H), rt 0.94 min.

-continued

Cpd 198:

MS, electrospray 531.7 (M + H), rt 0.98 min.

Cpd 204:

MS, electrospray 455.7 (M + H), rt 1.02 min.

Cpd 206:

MS, electrospray 465.7 (M + H), rt 1.14 min.

Cpd 208:

MS, electrospray 534.7 (M + H), rt 1.11 min.

Cpd 200:

MS, electrospray 480.7 (M + H), rt 0.94 min.

Cpd 202:

MS, electrospray 484.7 (M + H), rt 1.08 min.

Cpd 210:

MS, electrospray 515.7 (M + H), rt 1.27 min.

-continued

Cpd 173:

MS, electrospray 484.8 (M + H), rt 1.06 min.

Cpd 2:

MS, electrospray 473.1 (M + H), rt 0.33 min.

Cpd 4:

MS, electrospray 484.1 (M + H), rt 0.44 min.

Cpd 10:

MS, electrospray 474.9 (M + H), rt 0.49 min.

Cpd 12:

MS, electrospray 474.9 (M + H), rt 0.49 min.

Cpd 8:

MS, electrospray 489.2 (M + H), rt 0.47 min.

Cpd 20:

MS, electrospray 473.1 (M + H), rt 0.51 min.

Cpd 44:

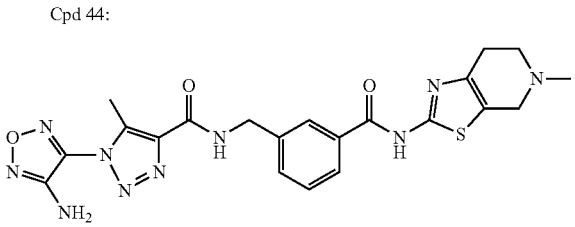

MS, electrospray 495.2 (M + H), rt 0.53 min.

Cpd 46:

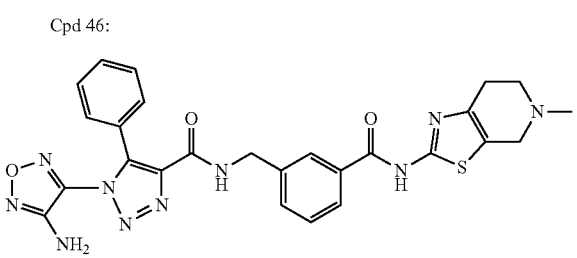

MS, electrospray 555.3 (M + H), rt 0.58 min.

Cpd 142:

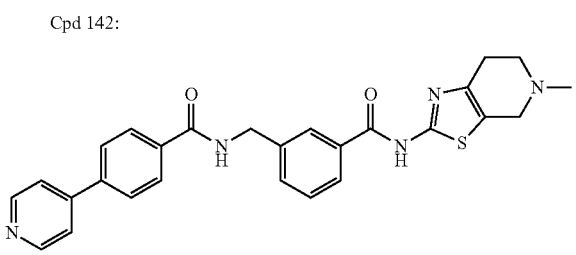

MS, electrospray 484.1 (M + H), rt 0.39 min.

Cpd 14:

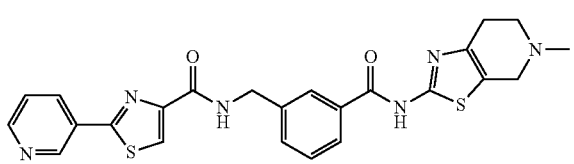

MS, electrospray 491.2 (M + H), rt 0.49 min.

Cpd 6:

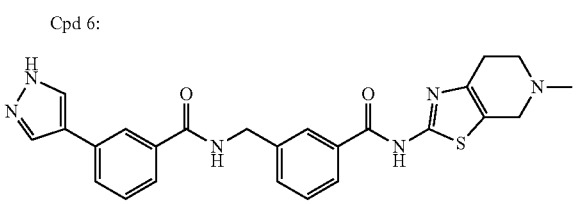

MS, electrospray 473.1 (M + H), rt 0.49 min.

Cpd 22:

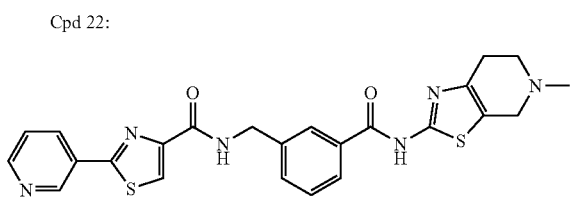

MS, electrospray 491.1 (M + H), rt 0.44 min.

Cpd 58:

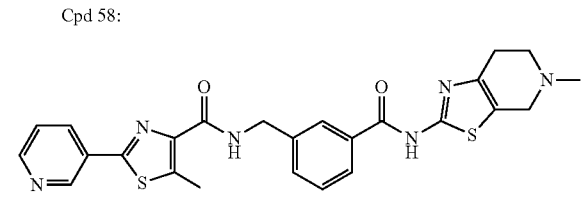

MS, electrospray 503.3 (M − H), rt 0.48 min.

Cpd 76:

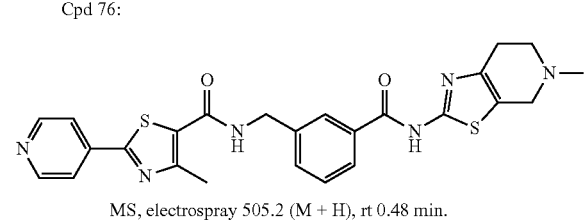

MS, electrospray 505.2 (M + H), rt 0.48 min.

Cpd 74:

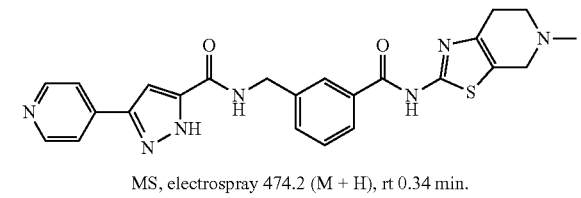

MS, electrospray 474.2 (M + H), rt 0.34 min.

Cpd 82:

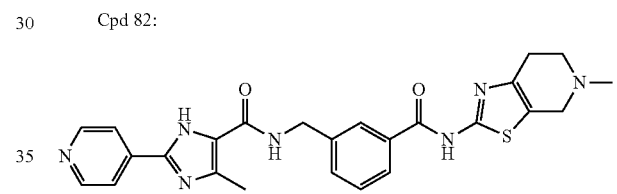

MS, electrospray 488.2 (M + H), rt 0.58 min.

Cpd 104:

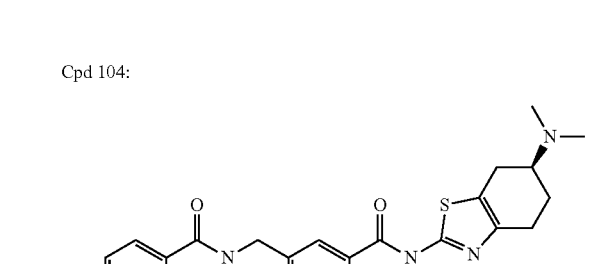

MS, electrospray 517.30 (M + H), rt 0.52 min.

Cpd 106:

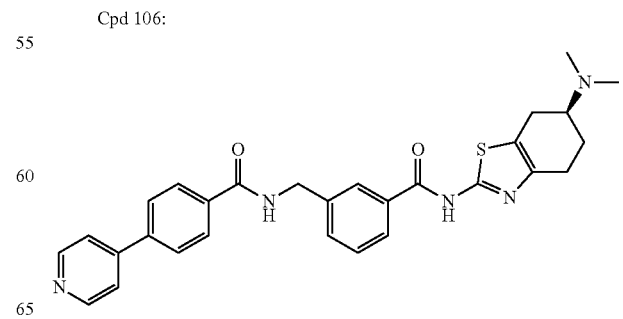

MS, electrospray 512.29 (M + H), rt 0.44 min.

Cpd 108:
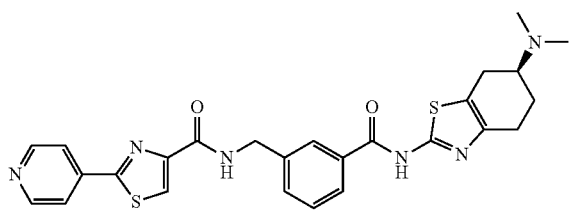
MS, electrospray 519.2 (M + H), rt 0.55 min.
Cpd 126:
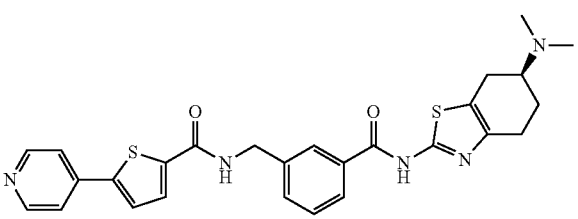
MS, electrospray 518.2 (M + H), rt 0.35 min.
Cpd 128:
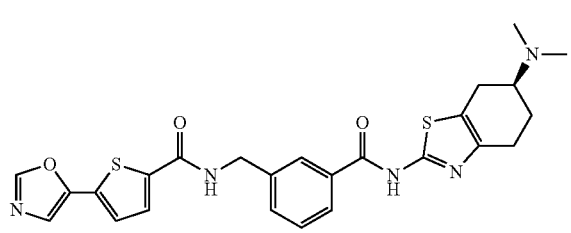
MS, electrospray 508.2 (M + H), rt 0.43 min.
Cpd 138:
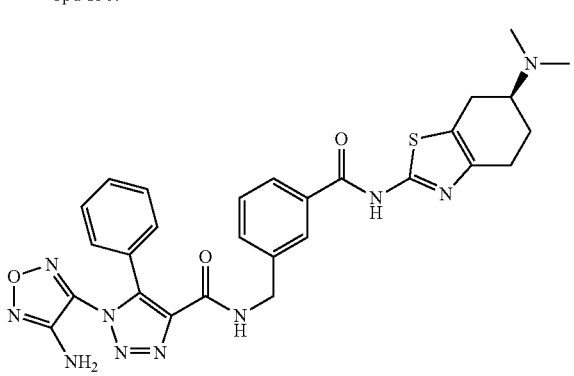
MS, electrospray 584.33 (M + H), rt 1.23 min.
Cpd 142:
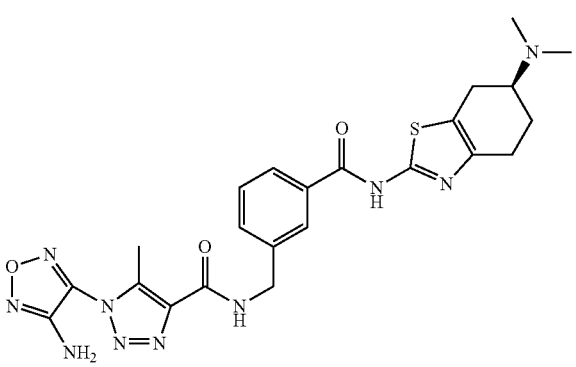
MS, electrospray 524.05 (M + H), rt. 1.15 min.
Cpd 132:
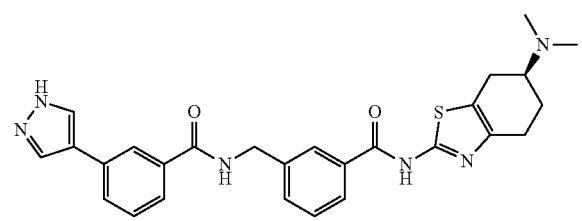
MS, electrospray 501.8 (M + H), rt 1.15 min.
Cpd 134:
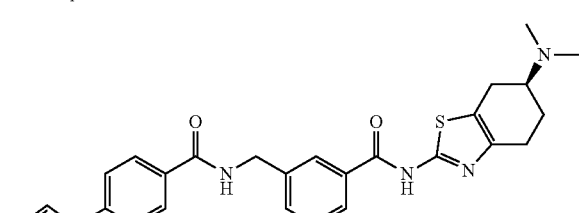
MS, electrospray 501.8 (M + H), rt 0.95 min.
Cpd 136:
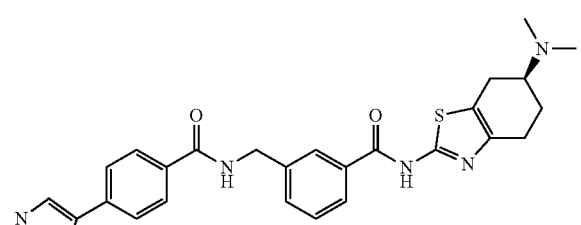
MS, electrospray 501.2 (M + H), rt 1.07 min.
Cpd 140: MS, electrospray 520.1 (M + H), rt 1.02 min.
Cpd 140:
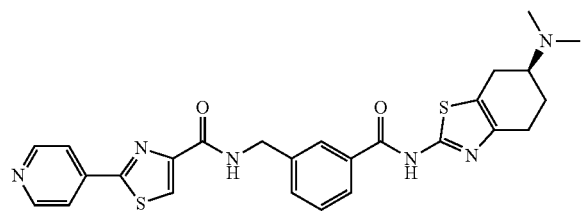
MS, electrospray 520.1 (M + H), rt 1.02 min.

Cpd 146:

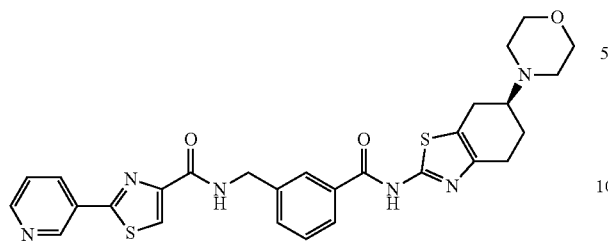

MS, electrospray 561.6 (M + H), rt 1.12 min.

Cpd 162:

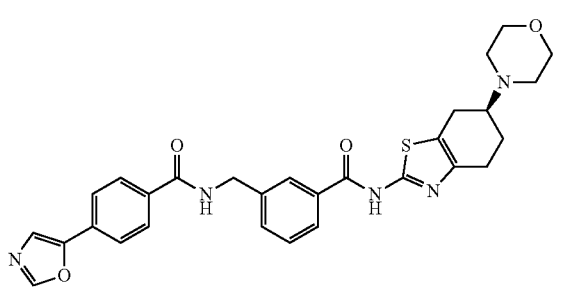

MS, electrospray 544.5 (M + H), rt 1.13 min.

Cpd 166:

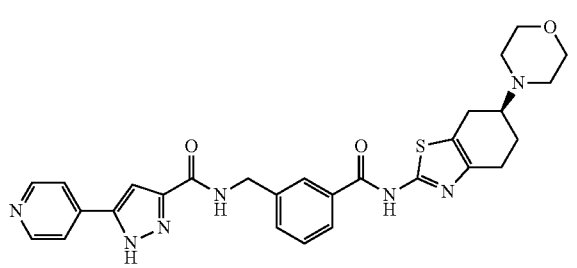

MS, electrospray 544.5 (M + H), rt 0.83 min.

Cpd 160:

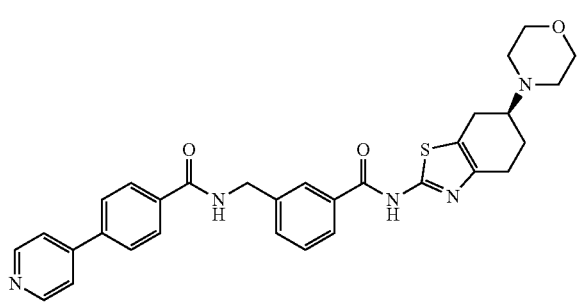

MS, electrospray 554.5 (M + H), rt 0.91 min.

Cpd 168:

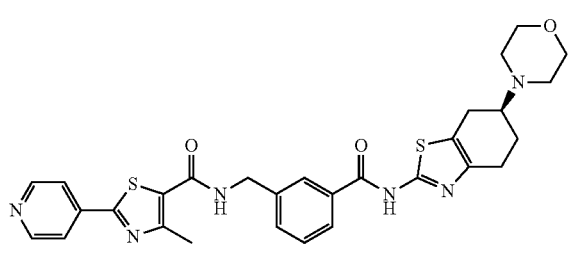

MS, electrospray 575.5 (M + H), rt 1.02 min.

Cpd 164:

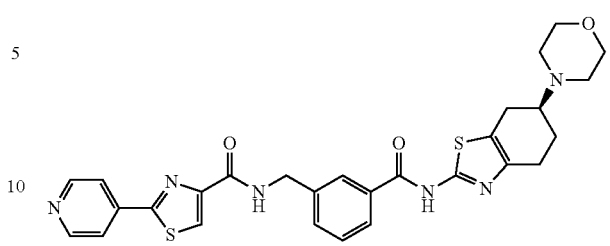

MS, electrospray 561.5 (M + H), rt 1.00 min.

Example 6

Synthesis of 4-cyano-2,3-dihydro-indole-1-carboxylic acid 3-(2-methyl-1,2,3,4-tetrahydro-isoquinolin-7-ylcarbamoyl)-benzylamide (Cpd 201, Table 1)

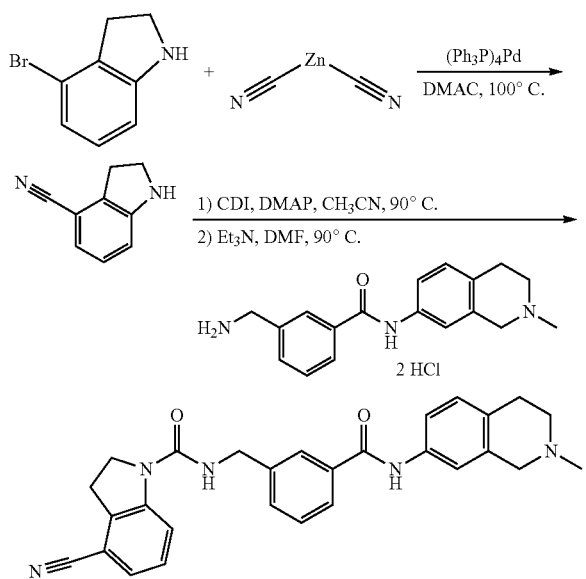

Degas a solution of 4-bromo-2,3-dihydro-1H-indole (250 mg, 1.224 mmol) in dimethylacetamide (2 mL) under Ar. To this add zinc cyanide (147 mg, 1.224 mmol) followed by tetrakis-(triphenylphosphine) palladium(0) (143 mg, 0.123 mmol) and heat the reaction under argon in a sealed tube at 100° C. for 4 h. Quench the cooled reaction with sat. NH$_4$Cl (50 mL) and extract with EtOAc (3×50 mL). Wash the organics with water (50 mL), dry (Na$_2$SO$_4$), then concentrate in vacuo to give a gum. Purify by silica gel chromatography eluting with 5% to 30% EtOAc/hexane. Pool and concentrate fractions containing product then dissolve the residue in Et$_2$O (5 mL) and hexane (50 mL). Reconcentrate this to a solid. Suspend in hexane and filter washing with hexane to afford the product 2,3-dihydro-1H-indole-4-carbonitrile as a powder (131 mg, 0.863 mmol). MS, electrospray 145.2 (M+H), rt 1.02 min.

To a solution of 2,3-dihydro-1H-indole-4-carbonitrile (25 mg, 0.168 mmol) in acetonitrile (3 ml) add CDI (28 mg, 0.168 mmol) followed by 4-dimethylaminopyridine (DMAP) (42 mg, 0.340 mmol) and stir the sealed vial at 90° C. for 4 h. Concentrate the reaction to dryness and add a solution of 3-aminomethyl-N-(2-methyl-1,2,3,4-tetrahydro-isoquinolin-7-yl)-benzamide dihydrochloride (62 mg, 0.17 mmol) and Et$_3$N (0.081 mL, 0.588 mmol) in DMF (3 mL). Stir the sealed vial at 90° C. for 4 h. Dilute the reaction with water (1 mL) and quench with TFA (0.3 mL). Purify this by prep HPLC (10% to 90% CH$_3$CN/water. Pool and concentrate fractions containing product. Suspend the residue in EtOAc (3 mL) and precipitate with hexane (100 mL). Filter washing with hexane to afford the desired product 4-cyano-2,3-dihydro-indole-1-carboxylic acid 3-(2-methyl-1,2,3,4-tetrahydro-isoquinolin-7-ylcarbamoyl)-benzylamide as a solid (12 mg, 0.02 mmol). MS, electrospray 467.1 (M+H), rt 1.22 min.

The following compounds were prepared analogously to Example 6:

Cpd 90:

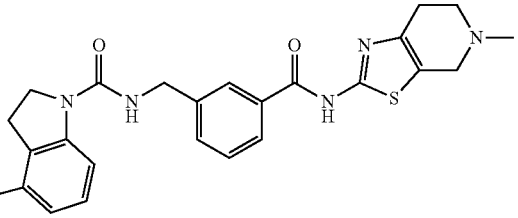

MS, electrospray 474.0 (M + H), rt 1.20 min.

Example 7

Synthesis of 3-[4-(2-picoline-4-yl)-benzamidomethyl-N-(5-methyl-4,5,6,7-tetrahydro-thiazolo[5,4-c]pyridin-2-yl)-benzamide] (Cpd 144, Table 1)

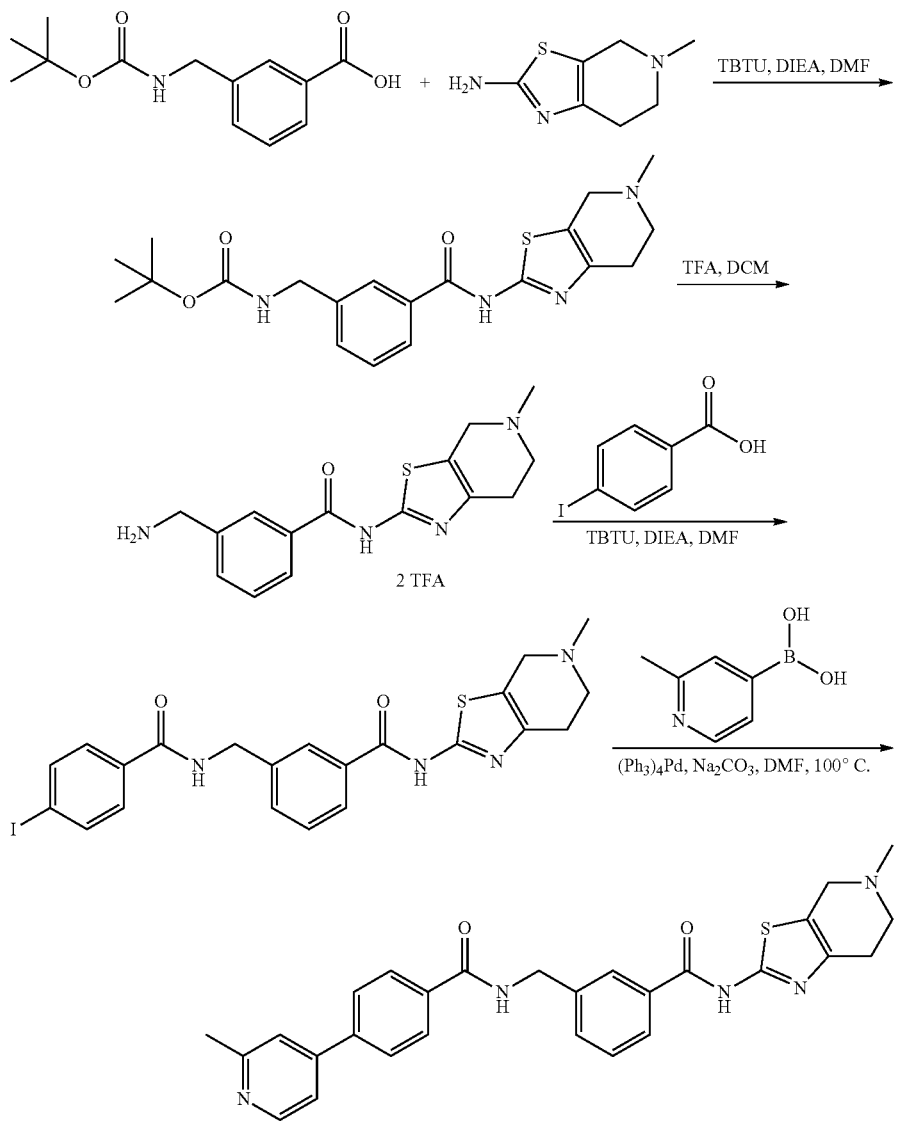

Stir a solution of tert-BOC-(3-aminomethyl)benzoic acid (7.42 g, 29.5 mmol), 5-methyl-4,5,6,7-tetrahydro[1,3]thiazolo[5,4-C]pyridin-2-amine (5.00 g, 29.5 mmol), TBTU (12.3 g, 38.4 mmol) and N,N-diisopropylethylamine (15.4 ml, 88.6 mmol) in DMF (50 mL) overnight at rt. Add $H_2O$ and extract with EtOAc (4×), washing with $H_2O$ (4×), aq. $NH_4Cl$ (3×), and aq. $Na_2CO_3$. Add $MgSO_4$ and activated carbon, filter and concentrate in vacuo to a solid. Triturate in 1:1 ether/hexane, filter, and wash with the same mixture. Dry the solid to obtain desired product [3-(5-methyl-4,5,6,7-tetrahydro-thiazolo[5,4-c]pyridin-2-ylcarbamoyl)-benzyl]-carbamic acid tert-butyl ester as an orange solid in 90% yield (10.67, 26.55 mmol). MS, electrospray (M+H) 404.0, rt 1.14 min.

Stir a solution of [3-(5-methyl-4,5,6,7-tetrahydro-thiazolo[5,4-c]pyridin-2-ylcarbamoyl)-benzyl]-carbamic acid tert-butyl ester (10.65 g, 26.50 mmol) in trifluoroacetic acid (20 mL) and DCM (20 mL) for 4 h in a capped flask. Concentrate the reaction in vacuo and co-evaporate with toluene (3×), MeOH (5×), and DCM (2×) to afford the desired product 3-aminomethyl-N-(5-methyl-4,5,6,7-tetrahydro-thiazolo[5,4-c]pyridin-2-yl)-benzamide di-trifluoroacetate as a foamy resin in 92% yield (12.85 g, 24.23 mmol). MS, electrospray (M+H) 303.6, rt 0.73 min.

Stir a solution of 4-iodobenzoic acid (351 mg, 1.41 mmol), 3-aminomethyl-N-(5-methyl-4,5,6,7-tetrahydro-thiazolo[5,4-c]pyridin-2-yl)-benzamide)di-trifluoroacetate (750 mg, 1.41 mmol), TBTU (590 mg, 1.84 mmol), and N,N-diisopropylethylamine (1.23 ml, 7.07 mmol) in DMF (5 mL) overnight at rt. Add $H_2O$ and ether to the reaction, and triturate to a solid. Filter, wash with $H_2O$ and ether, and dry the solid in vacuo to give desired product 3-(4-iodobenzamidomethyl-N-(5-methyl-4,5,6,7-tetrahydro-thiazolo[5,4-c]pyridin-2-yl)-benzamide) as a solid (609 mg, 1.15 mmol). MS, electrospray (M+H) 533.4, rt 1.27 min.

Stir a suspension of 3-(4-iodobenzamidomethyl-N-(5-methyl-4,5,6,7-tetrahydro-thiazolo[5,4-c]pyridin-2-yl)-benzamide) (50 mg, 0.094 mmol), 2-picoline-4-boronic acid (15.4 mg, 0.113 mmol), and tetrakis(triphenylphosphine)palladium(0) (10.9 mg, 0.011 mmol) in DMF (1 mL) and add aq. 2M $Na_2CO_3$ (0.25 ml). Heat the reaction to 100° C. for 2 h in a capped vial. Add activated carbon to the reaction and filter through diatomaceous earth, eluting with hot MeOH/EtOAc. Wash the filtrate with $H_2O$ (4×), dry ($MgSO_4$), and concentrate in vacuo to 47 mg oil. Purify by prep-TLC developing with 10% to 50% MeOH/DCM with 0.5% $NH_4OH$ to yield the semi-pure product. Repurification by the same method developing with 7.5% MeOH/DCM with 1% $NH_4OH$ affords pure desired product 3-[4-(2-picoline-4-yl)-benzamidomethyl-N-(5-methyl-4,5,6,7-tetrahydro-thiazolo[5,4-c]pyridin-2-yl)-benzamide] as a solid (10.2 mg, 0.020 mmol). MS, electrospray (M+H) 498.6, rt 0.95 min.

Example 8

Synthesis of imidazo[1,2-a]pyridine-2,6-dicarboxylic acid 6-amide 2-[3-(5-methyl-4,5,6,7-tetrahydro-thiazolo[5,4-c]pyridin-2-ylcarbamoyl)-benzylamide]

(Cpd 213, Table 1)

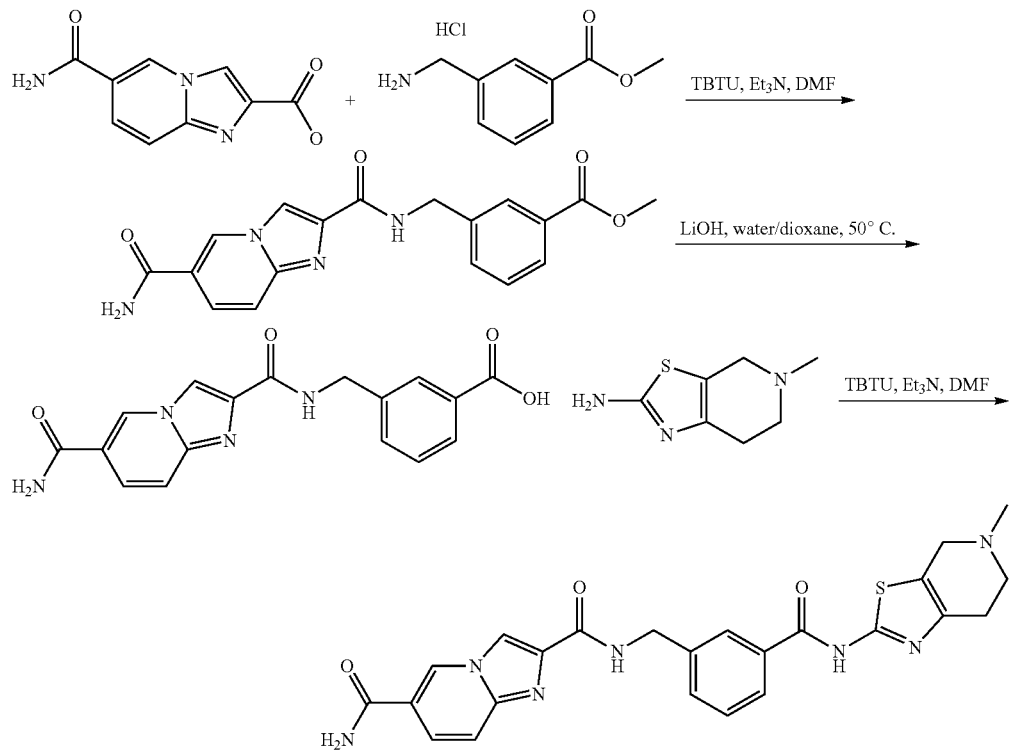

To a solution of 6-carbamoyl-imidazo[1,2-a]pyridine-2-carboxylic acid (500 mg, 2.44 mmol) in DMF (10 mL), add $Et_3N$ (0.67 mL, 4.9 mmol) and TBTU (939 mg, 2.92 mmol) and stir at rt for 30 min. Add methyl 3-aminomethyl-benzoic acid methyl ester hydrochloride (541 mg, 2.68 mmol). Stir the mixture at rt overnight. LCMS indicates desired product. Dilute the mixture with EtOAc, and pour into water to form a solid. Filter and set aside as crop 1. Extract the filtrate with EtOAc, dry the organic (Na₂SO₄), concentrate and purify by silica gel chromatography to afford additional desired product. Combine and dry the crops to give 3-{[(6-carbamoyl-imidazo[1,2-a]pyridine-2-carbonyl)-amino]-methyl}-benzoic acid methyl ester as a solid (722 mg, 2.05 mmol).

Example 9

Synthesis of N—((S)-6-amino-4,5,6,7-tetrahydro-benzothiazol-2-yl)-3-(4-[1,2,3]thiadiazol-4-yl)-aminomethyl)-benzamide (Cpd 26, Table 1)

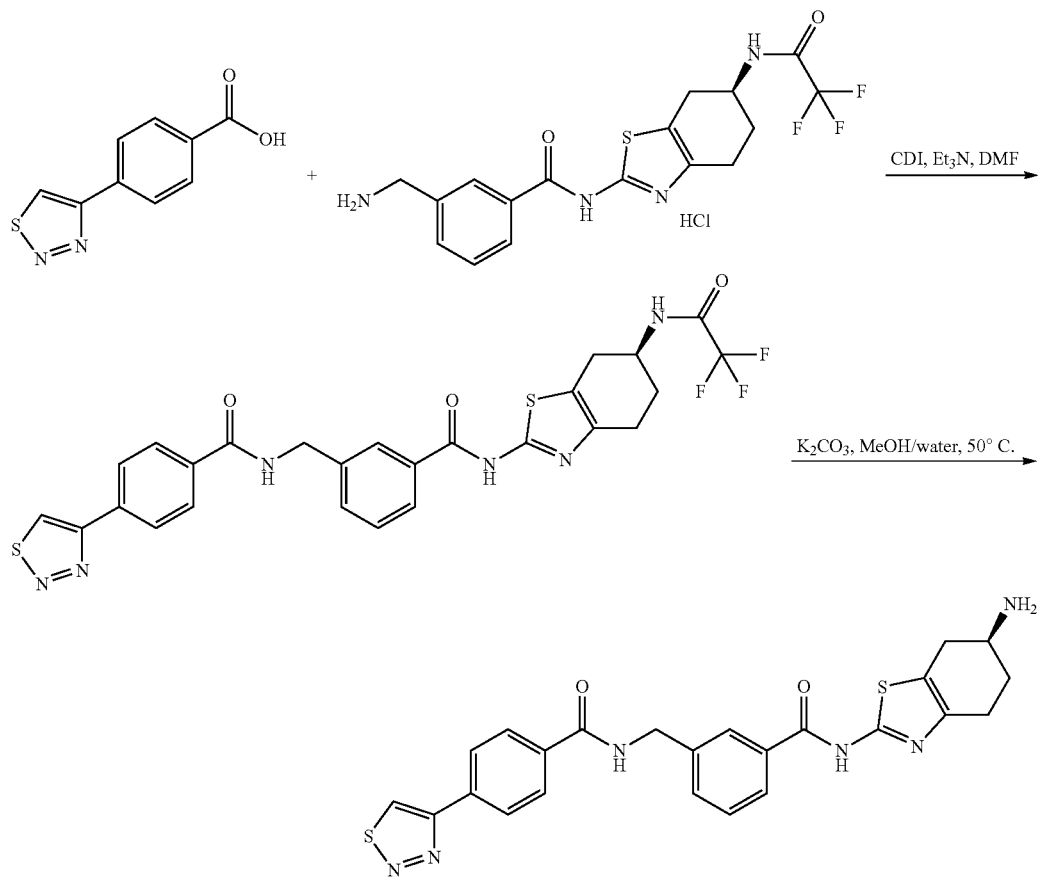

26

Treat 3-{[(6-carbamoyl-imidazo[1,2-a]pyridine-2-carbonyl)-amino]-methyl}-benzoic acid methyl ester (722 mg, 2.05 mmol) in 5:1 water/dioxane (36 mL) with LiOH (64 mg, 2.66 mmol). Stir the mixture at 50° C. overnight. LCMS indicates desired product. Concentrate to a residue and acidify with 1 M HCl to form a solid. Filter this washing with water and dry to afford the desired product 3-{[(6-carbamoyl-imidazo[1,2-a]pyridine-2-carbonyl)-amino]-methyl}-benzoic acid as a solid (610 mg, 1.80 mmol).

To a solution of 3-{[(6-carbamoyl-imidazo[1,2-a]pyridine-2-carbonyl)-amino]-methyl}-benzoic acid in DMF (3 mL) add Et₃N (0.081 ml, 0.59 mmol) and TBTU (104 mg, 0.325 mmol) and stir at rt for 30 min. Add 5-methyl-4,5,6,7-tetrahydro-thiazolo[5,4-c]pyridin-2-ylamine (50 mg, 0.30 mmol) and stir the solution at rt overnight. LCMS indicates the desired product. The mixture is diluted with water and extracted with EtOAc. Combine the organic layers, concentrate and purify by silica gel chromatography to give the desired product imidazo[1,2-a]pyridine-2,6-dicarboxylic acid 6-amide 2-[3-(5-methyl-4,5,6,7-tetrahydro-thiazolo[5,4-c]pyridin-2-ylcarbamoyl)-benzylamide] as a solid (81 mg, 0.17 mmol). MS, electrospray 490.7 (M+H), rt 0.61 min.

Stir a solution of 4-[1,2,3]thiadiazol-4-yl-benzoic acid (21 mg, 0.10 mmol) and CDI (19 mg, 0.11 mmol) in DMF (3 mL) at rt for 1.5 h. To the clear solution add 3-aminomethyl-N—[(S)-6-(2,2,2-trifluoro-acetylamino)-4,5,6,7-tetrahydro-benzothiazol-2-yl]-benzamide hydrochloride (45 mg, 0.10 mmol) followed by Et₃N (0.098 mL, 0.70 mmol). Stir the mixture at rt overnight. Concentrate and use the mixture in the next step without any purification. Dissolve the crude trifluoroacetamide (50 mg, 0.085 mmol) in 4:1 MeOH/H₂O (10 mL). Add potassium carbonate (47 mg, 0.34 mmol) to the mixture and stir at 50° C. for 48 h. Add a small amount of TFA to the mixture and purify by prep-HPLC (10% to 100%, CH₃CN/H₂O) to give the desired product N—((S)-6-amino-4,5,6,7-tetrahydro-benzothiazol-2-yl)-3-(4-[1,2,3]thiadiazol-4-yl)-aminomethyl)-benzamide in 48% yield (20 mg, 0.041 mmol) MS, electrospray 491.1 (M+H), rt 0.55 min.

The following compounds were prepared analogously to Example 9:

Cpd 30:

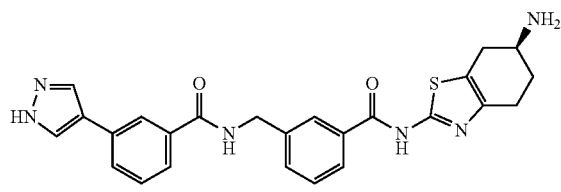

MS, electrospray 473.1 (M + H), rt 0.49 min.

Cpd 24:

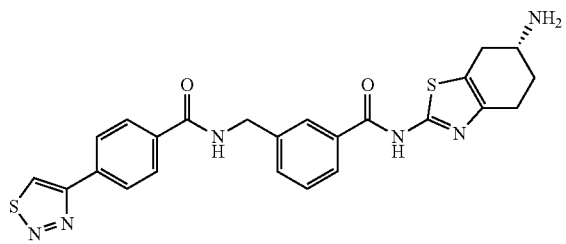

MS, electrospray 491.2 (M + H), rt 0.56 min.

Cpd 34:

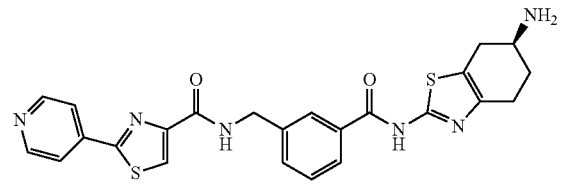

MS, electrospray 491.1 (M + H), rt 0.46 min.

Cpd 32:

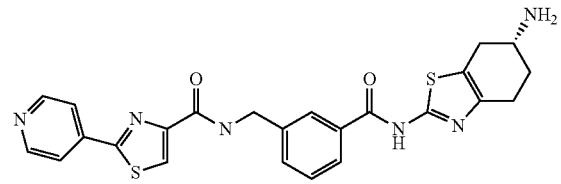

MS, electrospray 491.1 (M + H), rt 0.46 min.

Cpd 36:

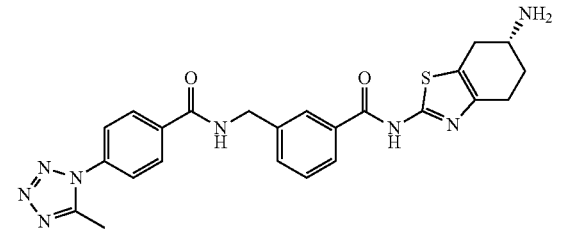

MS, electrospray 489.2 (M + H), rt 0.50 min.

Cpd 28:

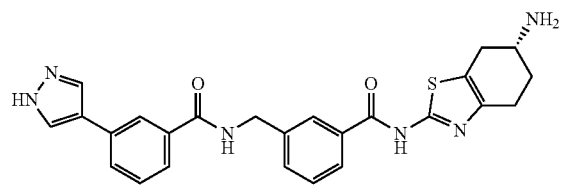

MS, electrospray 473.2 (M + H), rt 0.50 min.

Cpd 38:

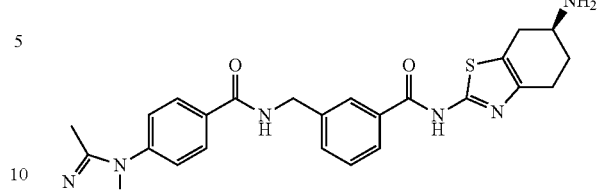

MS, electrospray 489.2 (M + H), rt 0.48 min.

Cpd 42:

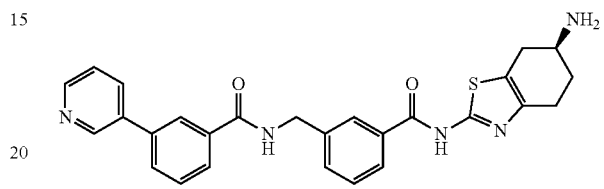

MS, electrospray 484.2 (M + H), rt 0.45 min.

Cpd 42:

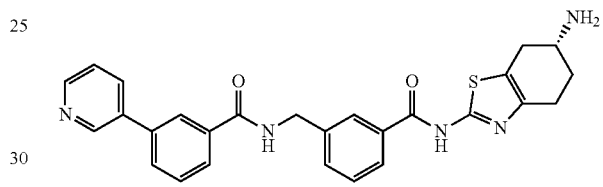

MS, electrospray 484.1 (M + H), rt 0.44 min.

Assessment of Biological Activity

Molecular Assays

The compounds of the invention may be evaluated in one or both of the following two molecular assays:

1. Luciferin-Luciferase Assay

The activity of ROCKII (1-543) kinase is measured utilizing Cambrex PKLight ATP Detection Reagent, a homogeneous assay technology using luciferin-luciferase to quantify residual ATP. The assay is performed in 384-well low-volume, white, non-binding surface microtiter plates (Corning). The assay buffer is 25 mM HEPES, pH 7.5, 10 mM $MgCl_2$, 50 mM KCl, 0.2% BSA, 0.01% CHAPS, 100 μM $Na_3VO_4$ and 0.5 mM DTT. Test compounds, dissolved in neat DMSO at 500 μg/mL, are serially diluted for dose response for a final starting concentration of 3 μg/mL in 1% DMSO of assay buffer. ROCKII (1-543) (62,408 Da) is diluted in assay buffer to a final concentration of 7.5 nM in a total volume of 15 μL. Positive controls are reaction mixtures containing no test compound; negative controls (blanks) are reaction mixtures containing no kinase. After 15 minutes of pre-incubation of the test compounds with the kinase, a mixture of ATP and peptide substrate (AKRRRLSSLRA) in assay buffer is added to each well for a final concentration of 750 nM ATP and 500 nM peptide, respectively. After 90 minutes of incubation of the kinase reaction at 28° C. temperature, 10 μL of PKLight ATP Detection Reagent (warmed to room temperature previously) is added to each well. The assay plate is incubated at room temperature for additional 15 minutes and then read on an Analyst in luminescence mode. Dose-response experiments for each of the test compounds are conducted in quadruplet. $IC_{50}$ values of test compounds represent 50% response of the positive control from the dose-response curve.

2. IMAP Assay

This assay is performed using FAM S6 substrate peptide (Catalogue #R7184) and IMAP FP Screening Express Kit detection reagents from Molecular Devices (Sunnyvale, Calif.) in IMAP kinase reaction buffer (Tris-HCl, pH 7.2, 10 mM MgCl2, 0.05% NaN3, 0.1% phosphate-free BSA) containing 1 mM DTT. Test compounds dissolved in neat DMSO at 0.3 mg/mL are serially diluted 1 to 3 for concentration response in 100% DMSO. The DMSO serial dilutions are further diluted 33.33-fold in kinase reaction buffer, and 10 μL of this buffer dilution is transferred to Corning black 96-well half area NBS plates for a final top concentration of 3 μg/mL in 1% DMSO. 10 μL aliquot of 3 nM ROCKII (1-543) diluted in kinase reaction buffer is added to each assay well for a final concentration of 1 nM kinase. 10 μL of a mixture of 600 nM FAM S6 peptide and 300 μM ATP diluted in kinase reaction buffer is added to each well for a final concentration of 200 nM peptide and 100 μM ATP. The kinase reaction mixture is incubated for 60 minutes at room temperature. Positive controls are reaction mixtures containing no test compound and negative controls (blanks) are reaction mixtures containing no kinase. The kinase reaction is stopped by addition of 60 μL IMAP progressive binding reagent (Catalog #R7284) diluted 400-fold in 1× Binding buffer A. After 30 min of incubation at room temperature, the plates are read for fluorescence polarization on Analyst Plate Reader using Ex 485 nm, Em 530 nm, and FL 505 dichroic minor. The mP signals are converted to percent of control (POC) values using the formula:

$$POC = 100 * (Signal - BCTRL) \div (PCTRL - BCTRL)$$

Where Signal is the test well signal, BCTRL is the average of background (negative control) well signals on the plate and PCTRL is the average of positive control well signals on the plate. For the concentration-responsive compounds, POC as a function of test compound concentration is fitted to a 4-parameter logistic equation of the form:

$$Y = A + (B-A)/[1+(x/C)^D]$$

Where A, B, C, and D are fitted parameters (parameter B is fixed at zero POC), and x and y are the independent and dependent variables, respectively. The $IC_{50}$ is determined as the inflection point parameter, C.

Representative compounds of the present invention were tested for activity in one or both of the above assays. Preferred compounds have an $IC_{50}<1,000$ nM and more preferred compounds have an $IC_{50}<100$ nM in these assays. As examples the following data were obtained for the compounds listed below:

| Compound Number (Table 1) | Assay 1 $IC_{50}$ (nM) | Assay 2 $IC_{50}$ (nM) | Compound Number (Table 1) | Assay 1 $IC_{50}$ (nM) | Assay 2 $IC_{50}$ (nM) |
|---|---|---|---|---|---|
| 2 | | 1.9 | 106 | | 0.22 |
| 3 | 4 | 5.1 | 108 | | 0.32 |
| 4 | 22.5 | 73 | 110 | 15.5 | |
| 6 | 2 | 0.53 | 112 | | 0.18 |
| 8 | 6 | 9.8 | 114 | | 0.45 |
| 12 | | 0.21 | 116 | 14.5 | |
| 14 | 4.8 | 7.9 | 118 | 24 | |
| 18 | 19.3 | | 119 | 1.3 | 0.22 |
| 20 | | 0.39 | 120 | | 0.77 |
| 21 | 5.9 | 25 | 122 | 27.5 | |
| 22 | 5.8 | 37 | 123 | 1.7 | 3.9 |
| 24 | 14.3 | | 124 | 3.8 | 11 |
| 26 | 7.6 | 40 | 125 | 5.9 | 26 |
| 27 | 9.8 | 45 | 126 | | 0.27 |
| 28 | 1.1 | 0.45 | 128 | | 0.37 |
| 29 | 2.6 | 2 | 129 | 1.3 | 0.195 |
| 30 | 0.72 | 0.16 | 130 | | 0.22 |
| 31 | 4.6 | 4.6 | 132 | | 0.32 |
| 32 | 1.8 | 4.8 | 133 | 80 | |
| 33 | 33 | | 134 | | 0.24 |
| 34 | 1.1 | 1.1 | 136 | | 0.2 |
| 36 | 1.4 | 3 | 138 | | 0.21 |
| 37 | 43.5 | | 140 | | 0.87 |
| 38 | 1.1 | 0.67 | 142 | | 0.33 |
| 39 | 4.9 | 9.9 | 144 | 2.6 | 4.35 |
| 40 | 1.9 | 10 | 145 | 49.3 | |
| 42 | 1.2 | 2 | 146 | | 0.73 |
| 44 | 1.8 | 9.3 | 148 | | 0.52 |
| 46 | 1.8 | 4.9 | 150 | | 2.65 |
| 48 | 35.5 | | 152 | 1.9 | 0.57 |
| 49 | 2.6 | 26 | 154 | 9.5 | 39 |
| 50 | 2.9 | 11 | 155 | 8.1 | 47 |
| 52 | 2.2 | 8.1 | 162 | | 0.43 |
| 53 | 28 | | 164 | | 0.93 |
| 54 | 1.3 | 0.45 | 166 | | 0.34 |
| 56 | | 0.26 | 168 | | 0.37 |
| 58 | 2.1 | 1.2 | 170 | | 0.41 |
| 62 | 18.5 | | 172 | | 0.38 |
| 64 | 1.5 | 1 | 174 | | 0.35 |
| 66 | 2.5 | 12 | 175 | 22.5 | |
| 68 | 64.2 | | 176 | | 0.87 |
| 69 | 44.5 | | 177 | 68 | |
| 70 | | 0.25 | 178 | 5.7 | 48 |
| 74 | 1.3 | 0.23 | 179 | 6.6 | 34 |
| 76 | 1.2 | 1.4 | 182 | 81 | |
| 78 | | 0.17 | 184 | 18 | |
| 80 | 1.5 | 0.58 | 186 | 14.5 | |
| 84 | | 0.26 | 188 | 91.5 | |
| 86 | 1.7 | 0.85 | 190 | 6.5 | 56 |
| 88 | 45.7 | | 194 | 4.8 | 30 |
| 90 | 3.1 | 17 | 198 | 38 | |
| 92 | 4.1 | 17 | 200 | 3 | 1.6 |
| 94 | 8.1 | 46 | 201 | 6.9 | 34 |
| 95 | 1.4 | 1.25 | 202 | 11.9 | 72 |
| 96 | 3.8 | 12.25 | 205 | | 0.25 |
| 98 | | 0.27 | 207 | | 0.2 |
| 100 | 1.7 | 2.6 | 209 | | 3.7 |
| 102 | 47 | | 210 | 86 | |
| 104 | | 0.43 | | | |

Methods of Therapeutic Use

In accordance with the invention, there are provided novel methods of using the compounds of formula I. The compounds disclosed herein effectively inhibit Rho kinase. The inhibition of Rho kinase is an attractive means for preventing and treating a variety of cardiovascular diseases or conditions associated with Rho kinase activation. Thus, the compounds are useful for the treatment of diseases and conditions as described in the Background section, including the following conditions and diseases: hypertension, atherosclerosis, restenosis, stroke, myocardial infarction, heart failure, coronary artery disease, peripheral artery disease, coronary vasospasm, cerebral vasospasm, ischemia/reperfusion injury, pulmonary hypertension, angina, erectile dysfunction, renal disease and organ failure. As disclosed in the Background section, the compounds of the invention will also be useful for treating diseases or conditions associated with smooth muscle hyper reactivity or with activated Rho-kinase under other pathophysiological conditions. These diseases include but are not limited to asthma, glaucoma, cancer, Alzheimer's disease, multiple sclerosis, spinal cord injury, neuropathic pain, rheumatoid arthritis, psoriasis and inflammatory bowel disease.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula I (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of the formula I

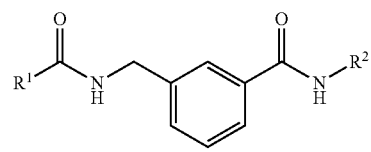

wherein:

$R^1$ is a substituted aryl, heteroaryl or heterocyclyl moiety selected from

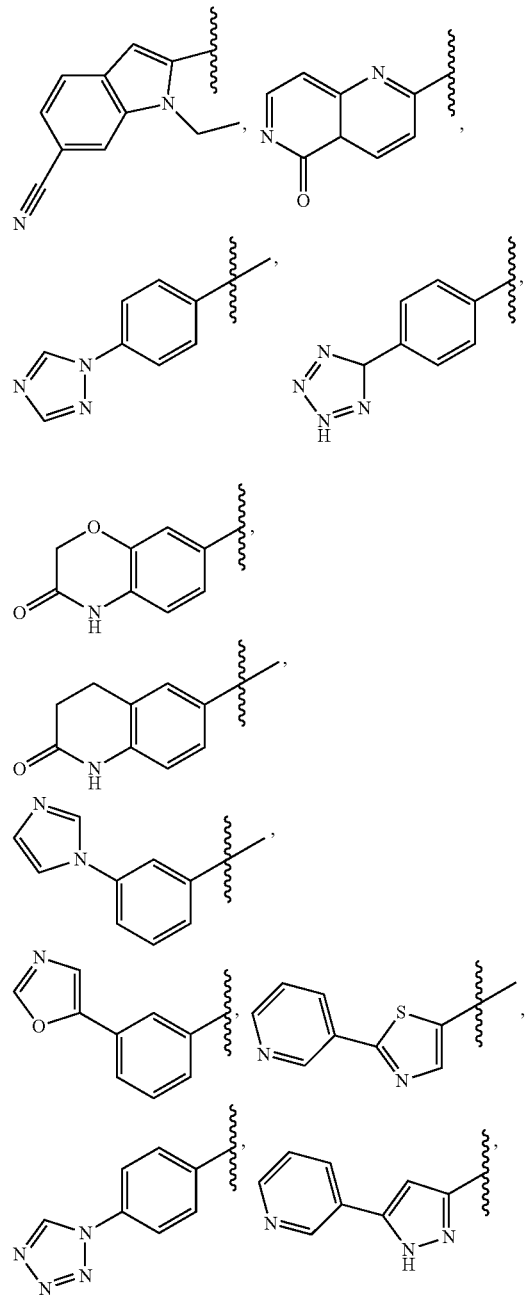

171
-continued
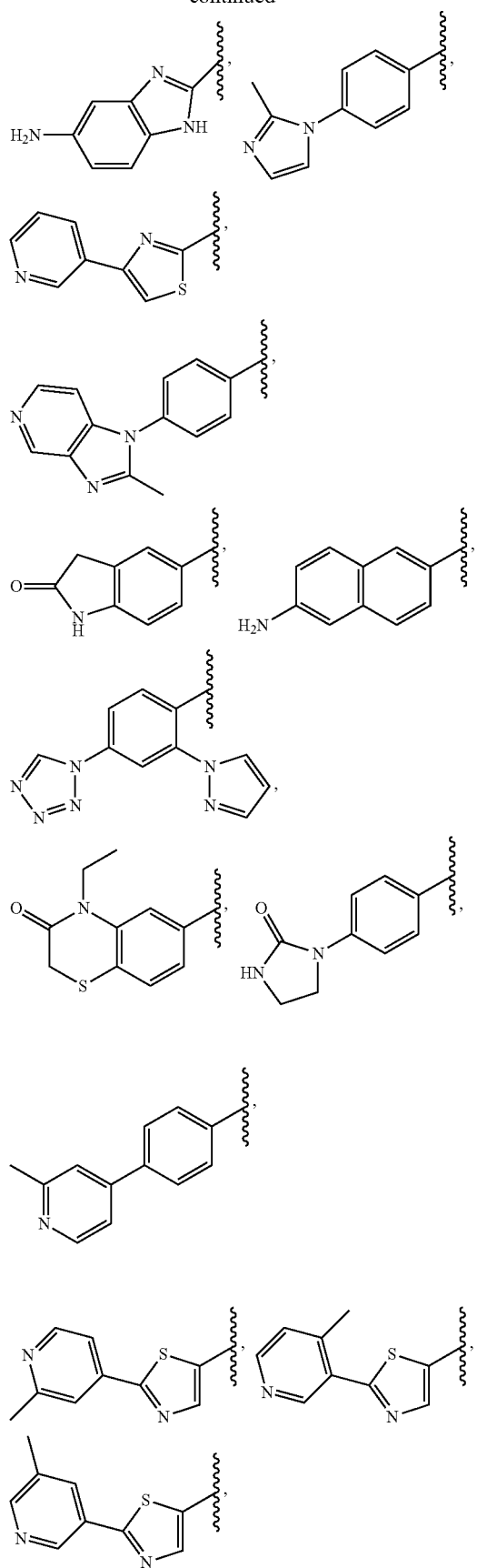
172
-continued
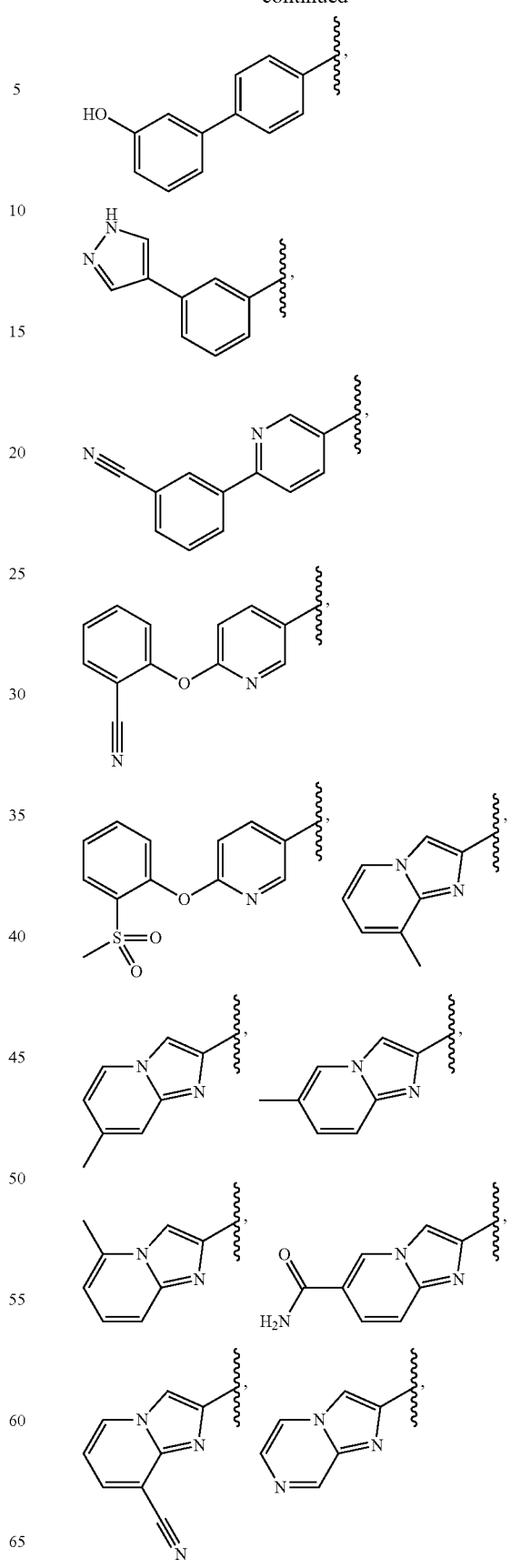

-continued
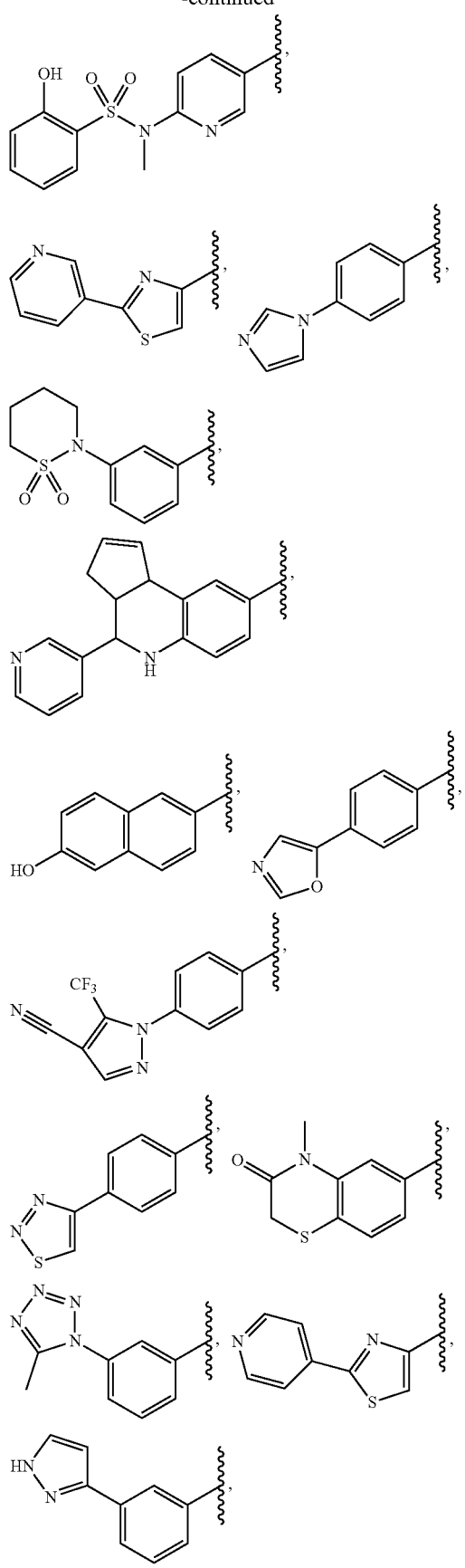
-continued
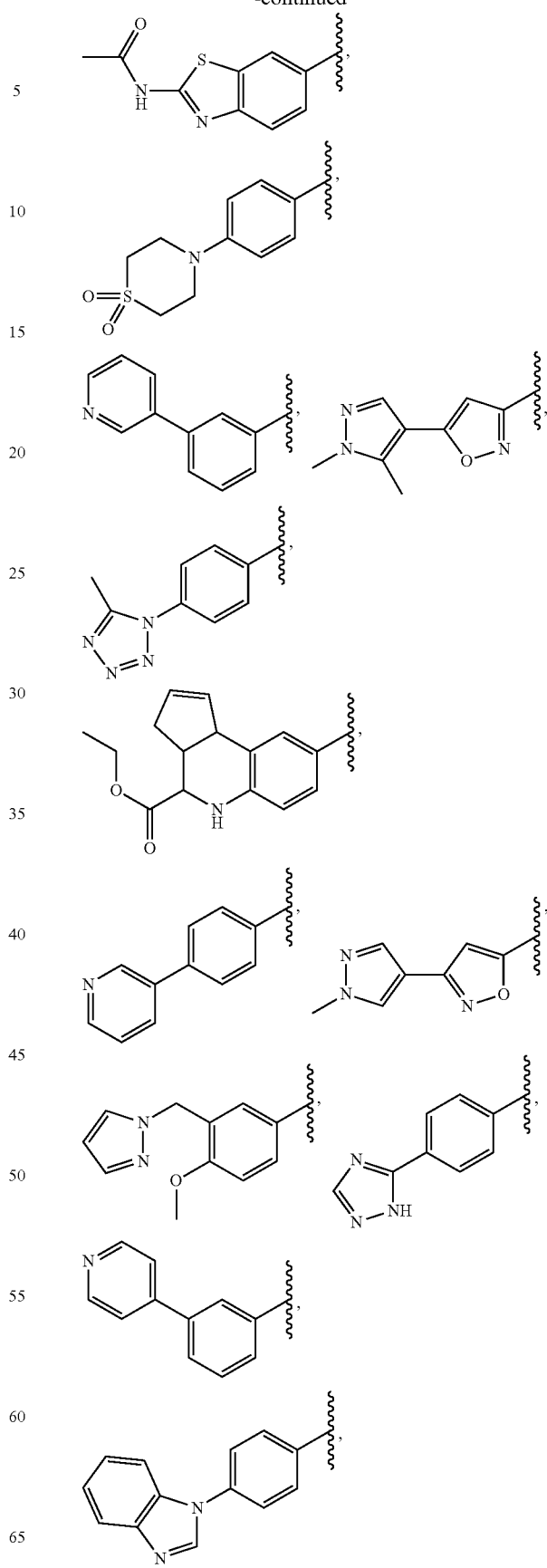

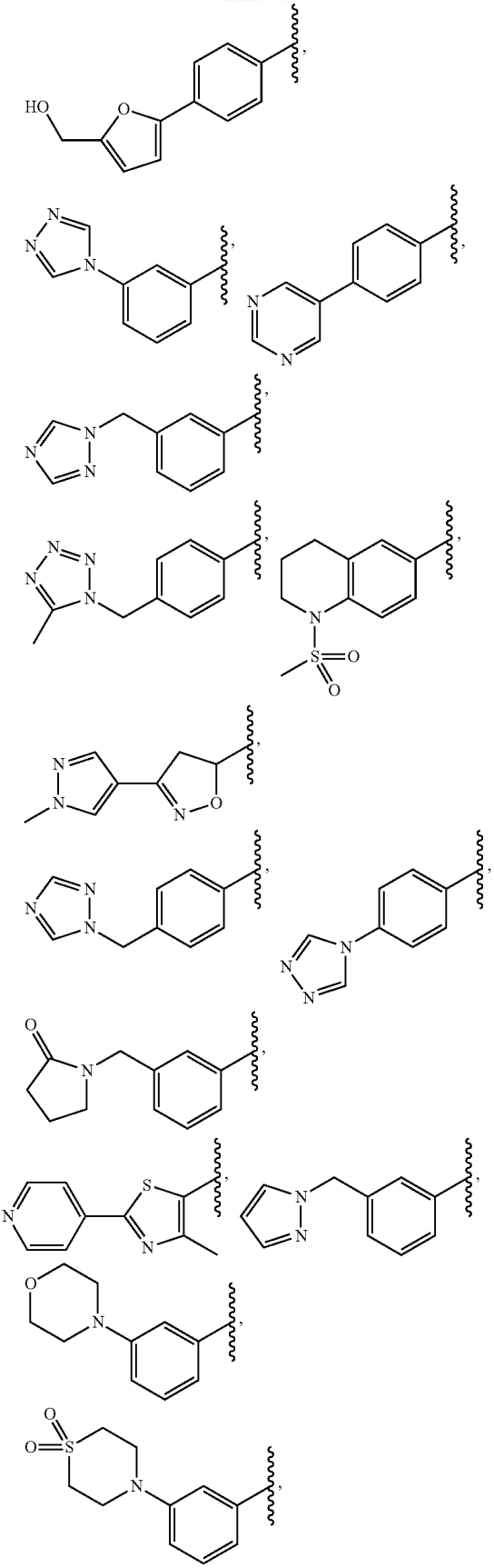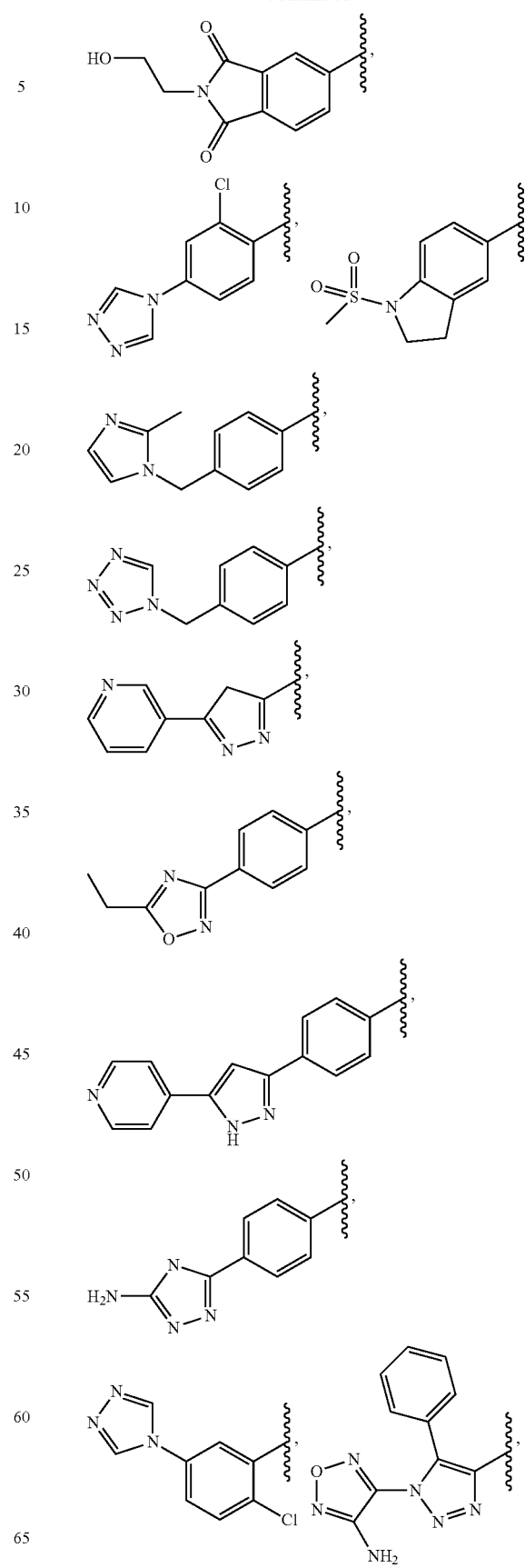

-continued
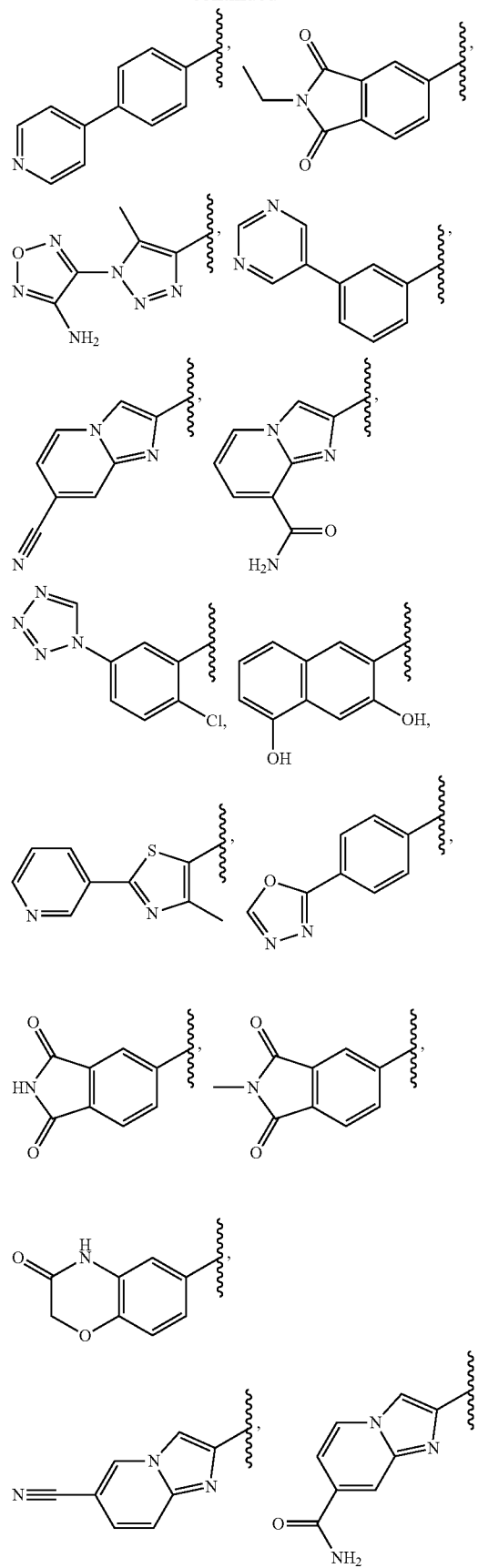
-continued
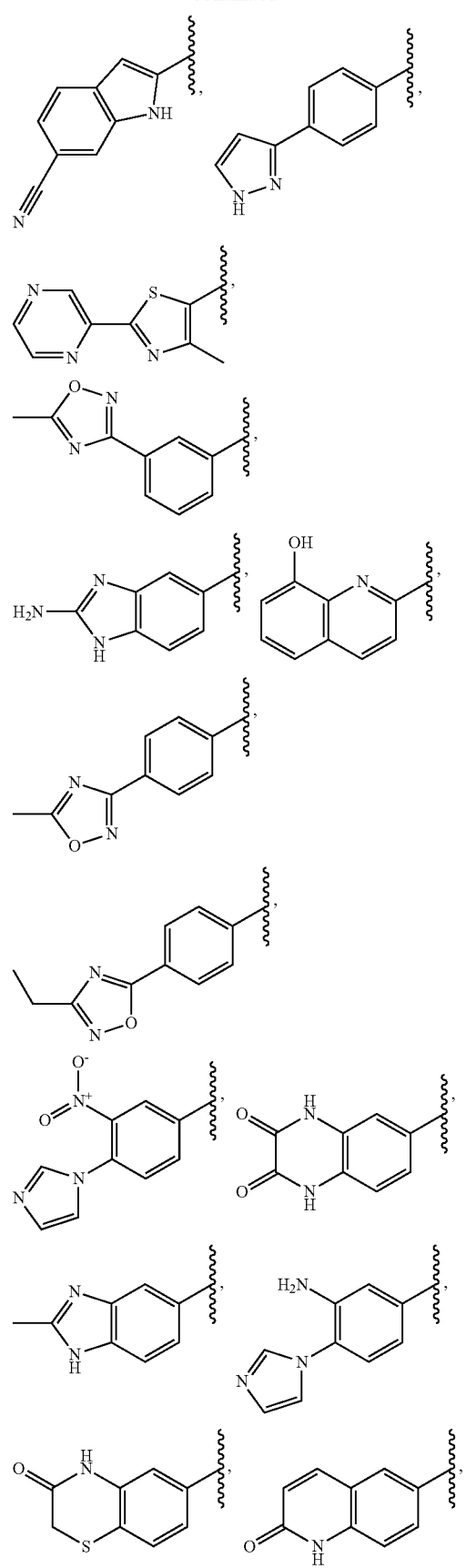

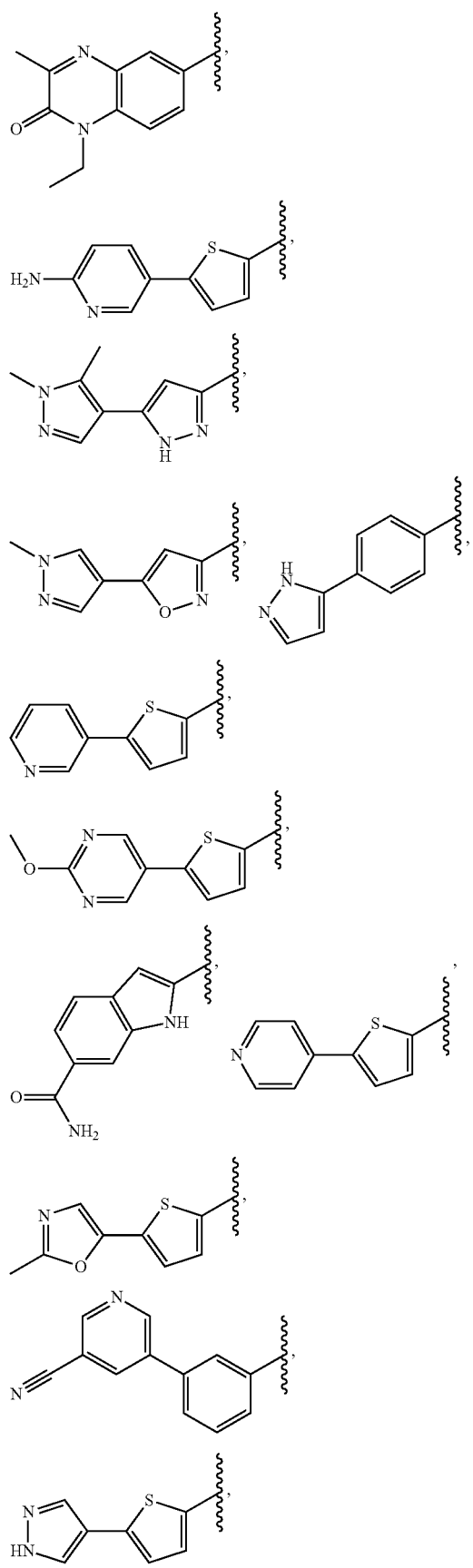
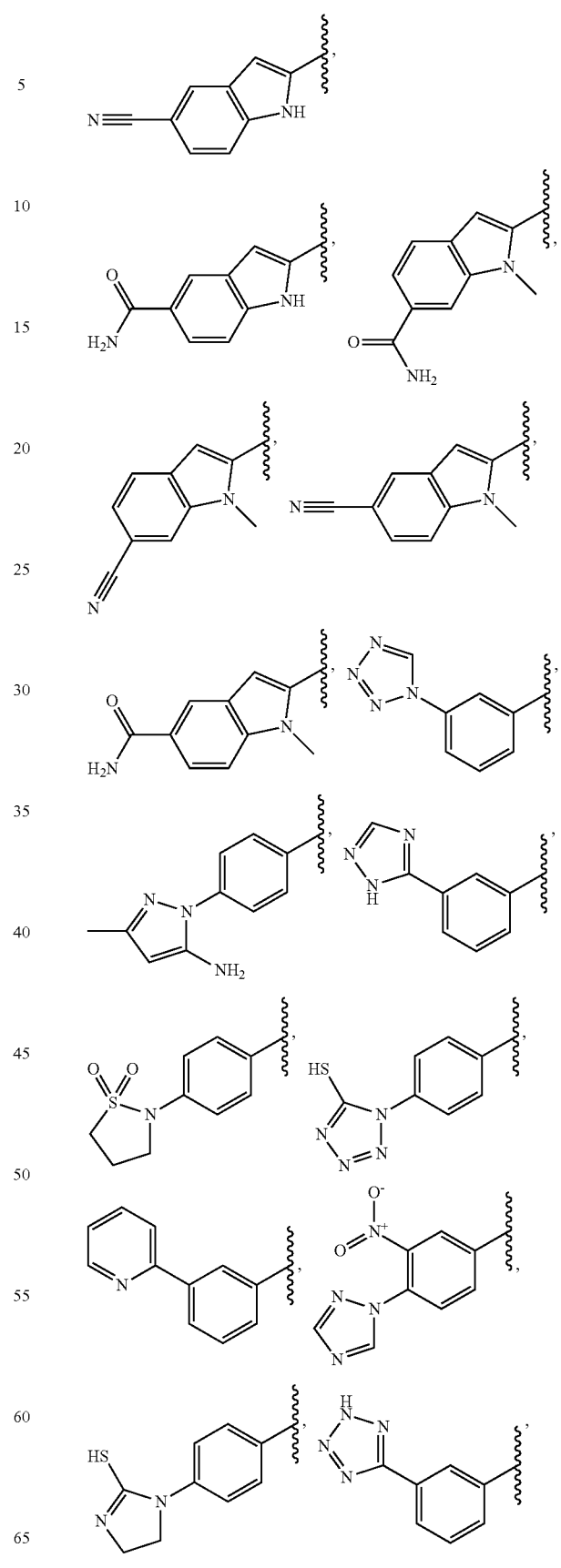

-continued

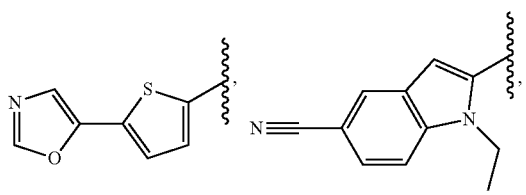

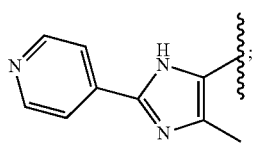

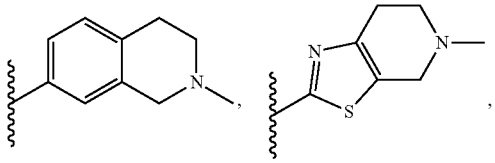

R² is selected from

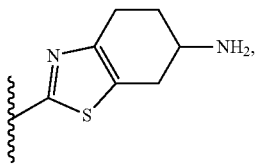

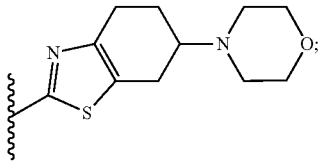

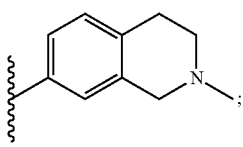

or a salt thereof.

2. The compound of claim 1 wherein:
R² is

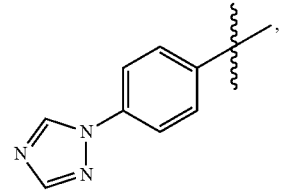

or a salt thereof.

3. The compound of claim 1 wherein:
R² is

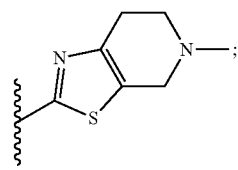

or a salt thereof.

4. The compound of claim 1 wherein:
R² is selected from

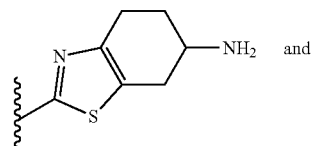

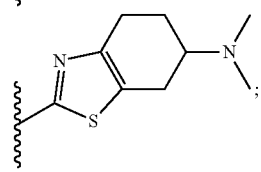

or a salt thereof.

5. The compound of claim 1 wherein:
R² is

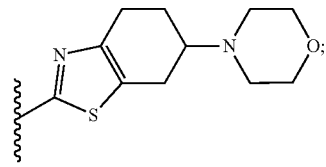

or a salt thereof.

6. The compound of claim 1 wherein:
R¹ is a substituted aryl, heteroaryl or heterocyclyl moiety selected from

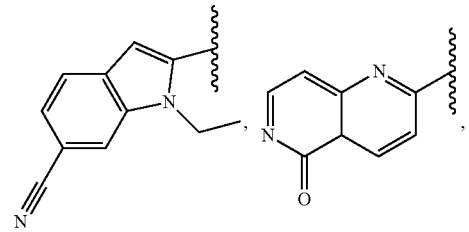

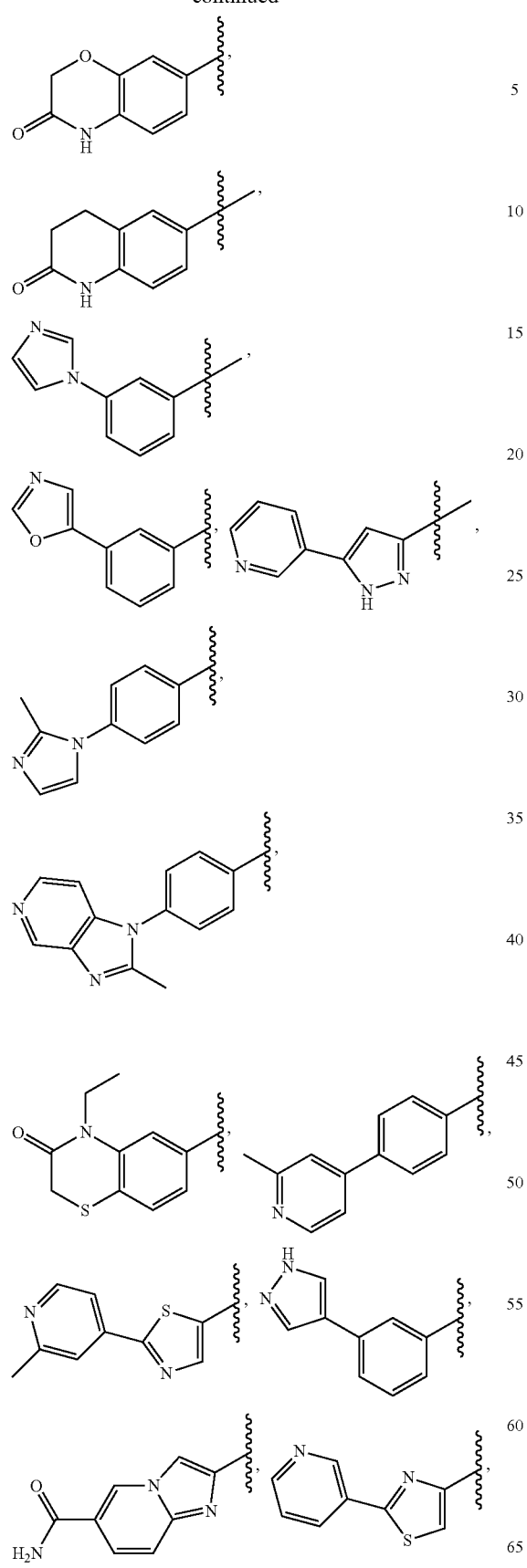
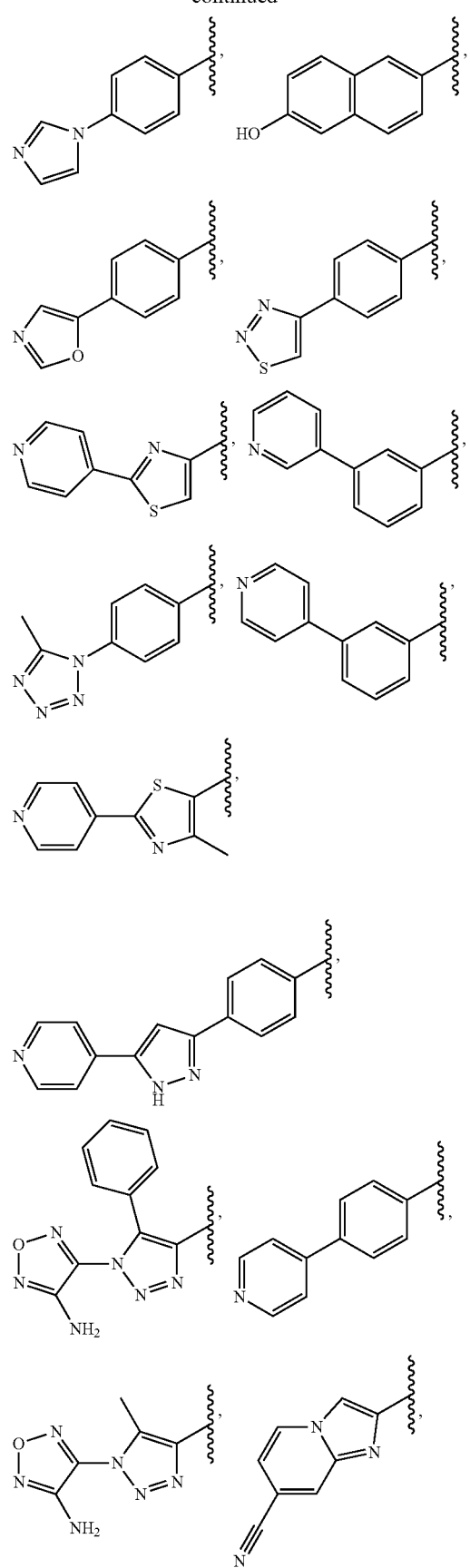

-continued
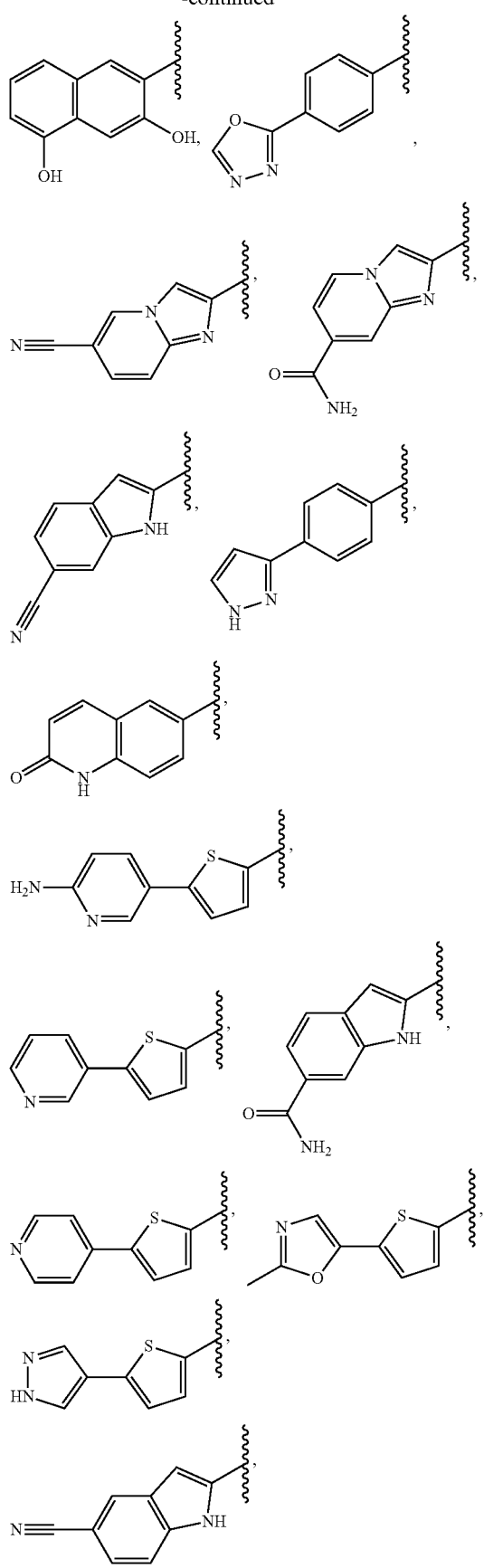
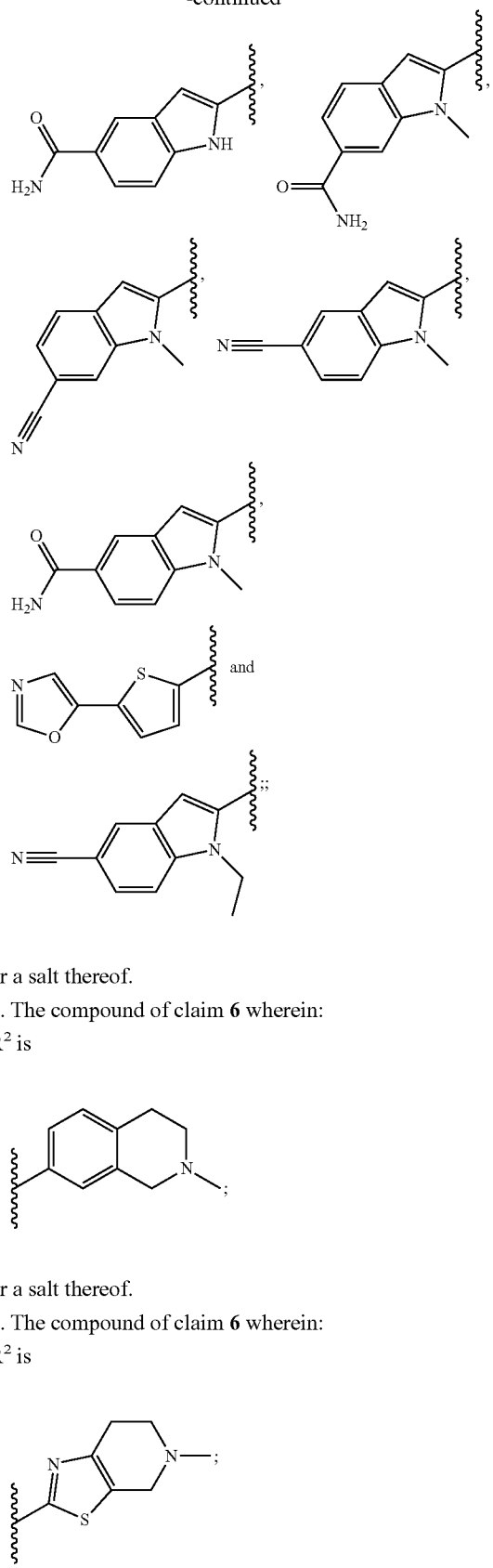
or a salt thereof.
7. The compound of claim 6 wherein:
R² is
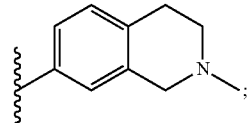
or a salt thereof.
8. The compound of claim 6 wherein:
R² is
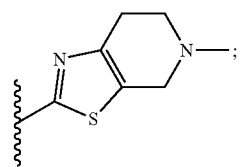
or a salt thereof.

9. The compound of claim 6 wherein:
R² is selected from
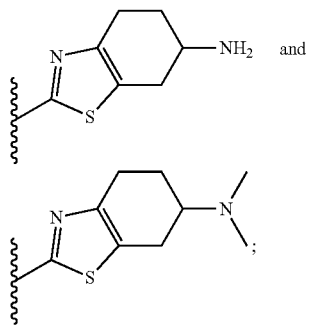
or a salt thereof.
10. The compound of claim 6 wherein:
R² is
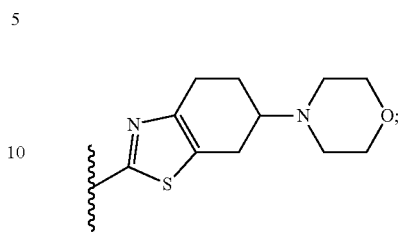
or a salt thereof.
11. A compound selected from the group consisting of:
211
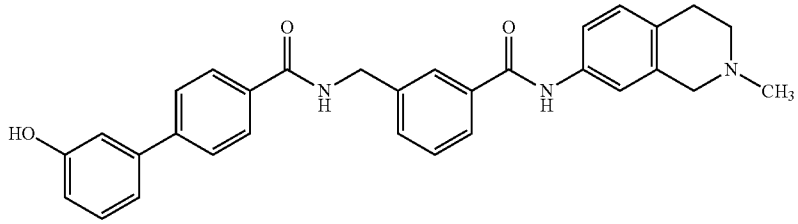
212
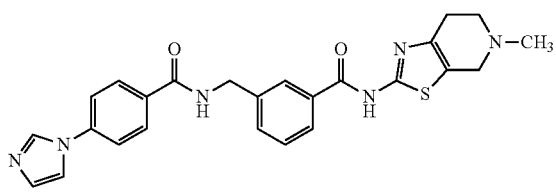
213
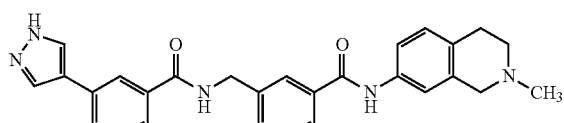
214
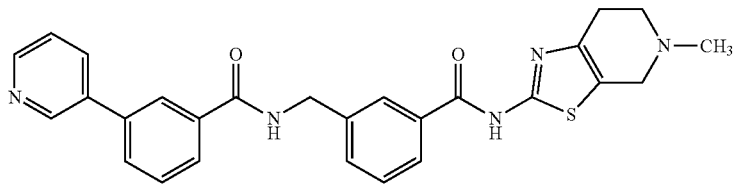 [SMILES: CN1CCc2nc(NC(=O)c3cccc(CNC(=O)c4cccc(-c5cccnc5)c4)c3)sc2C1]
215
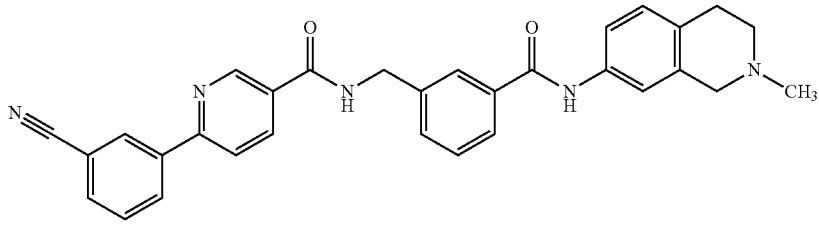 [SMILES: CN1CCc2ccc(NC(=O)c3cccc(CNC(=O)c4ccc(-c5cccc(C#N)c5)nc4)c3)cc2C1]
216
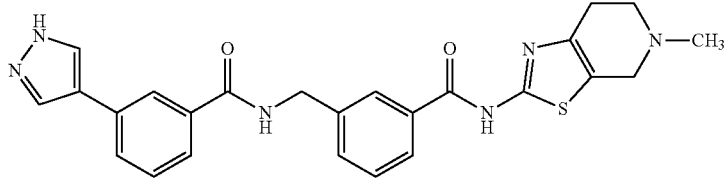 [SMILES: CN1CCc2nc(NC(=O)c3cccc(CNC(=O)c4cccc(-c5cn[nH]c5)c4)c3)sc2C1]

217
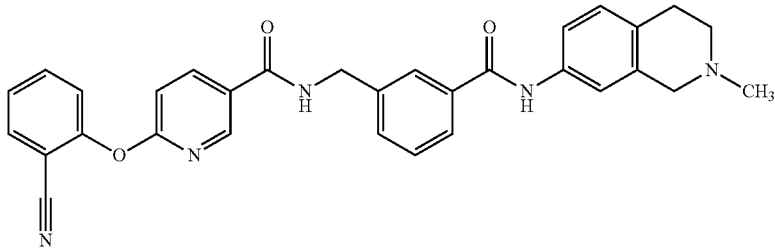 [SMILES: CN1CCc2ccc(NC(=O)c3cccc(CNC(=O)c4ccc(Oc5ccccc5C#N)nc4)c3)cc2C1]
218
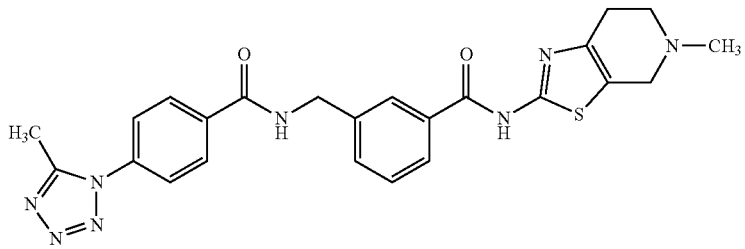 [SMILES: Cc1nnnn1-c1ccc(C(=O)NCc2cccc(C(=O)Nc3nc4c(s3)CN(C)CC4)c2)cc1]
219
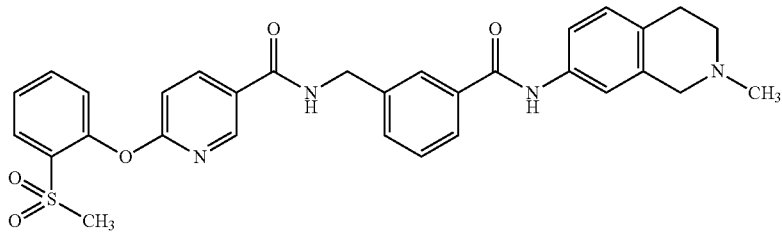
220
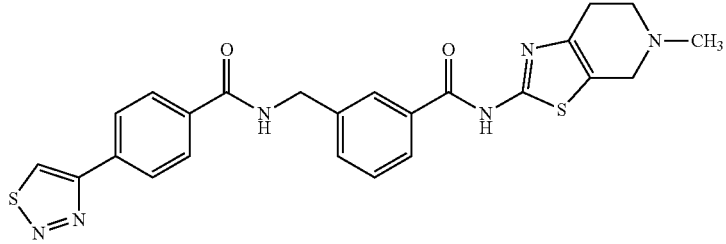 [SMILES: CN1CCc2nc(NC(=O)c3cccc(CNC(=O)c4ccc(-c5csnn5)cc4)c3)sc2C1]
221
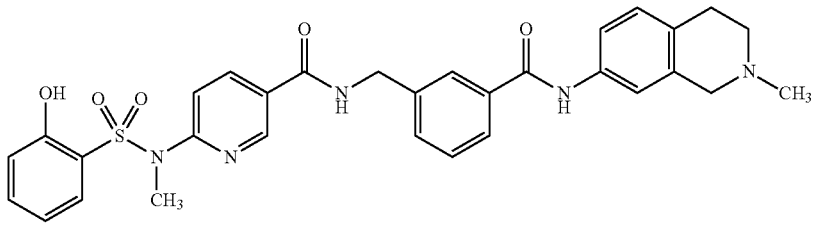 [SMILES: CN1CCc2ccc(NC(=O)c3cccc(CNC(=O)c4ccc(N(C)S(=O)(=O)c5ccccc5O)nc4)c3)cc2C1]
222
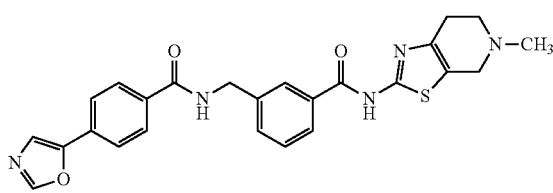
223

-continued
| 224 | 225 |
|---|---|
| 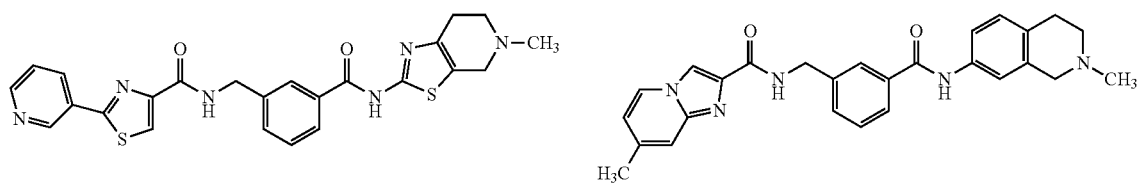 | |
| 226 |
|---|
| 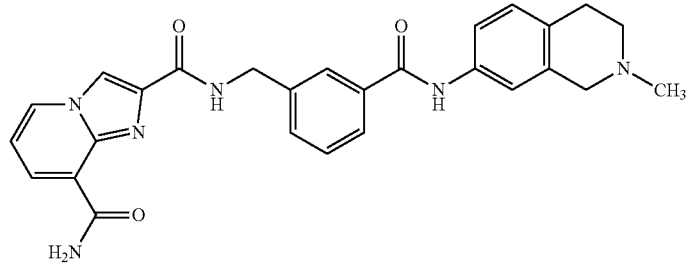 [SMILES: CN1CCc2ccc(NC(=O)c3cccc(CNC(=O)c4cn5cccc(C(N)=O)c5n4)c3)cc2C1] |
| 227 |
|---|
| 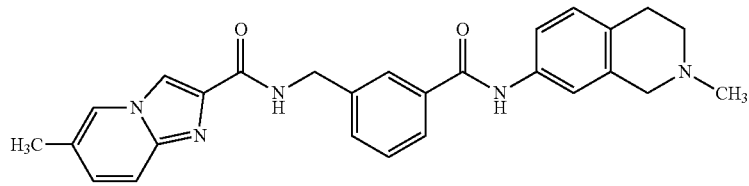 |
| 228 | 229 |
|---|---|
| 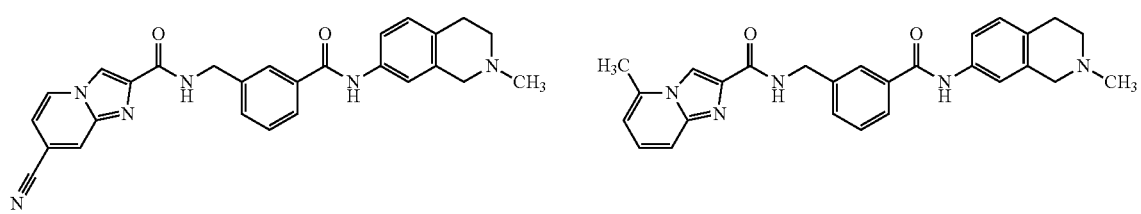 | |
| 230 |
|---|
| 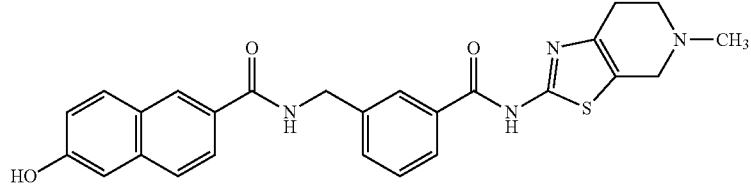 [SMILES: CN1CCc2nc(NC(=O)c3cccc(CNC(=O)c4ccc5cc(O)ccc5c4)c3)sc2C1] |
| 231 |
|---|
| 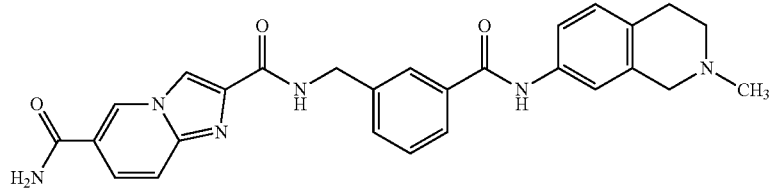 |
| 232 |
|---|
| 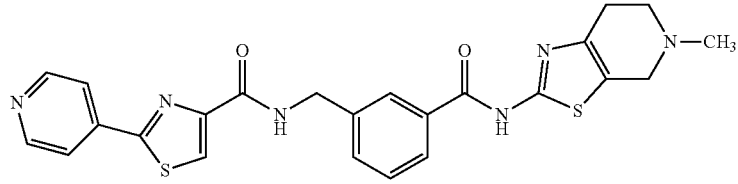 [SMILES: CN1CCc2nc(NC(=O)c3cccc(CNC(=O)c4csc(-c5ccncc5)n4)c3)sc2C1] |

-continued
233 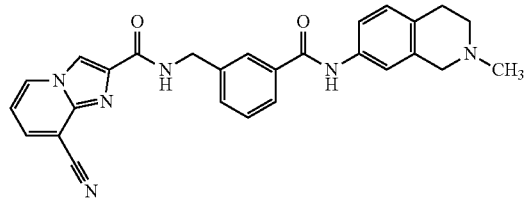
234 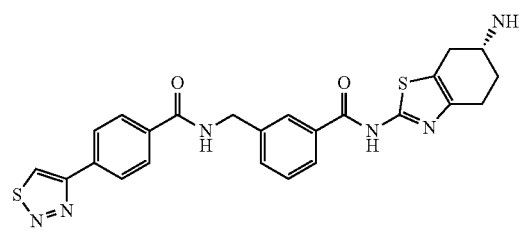 [SMILES: N[C@@H]1CCc2nc(NC(=O)c3cccc(CNC(=O)c4ccc(-c5csnn5)cc4)c3)sc2C1]
235 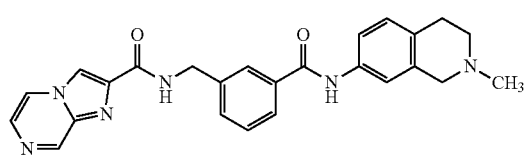
236 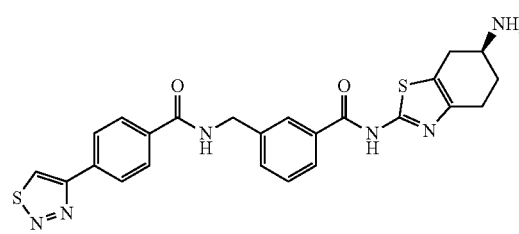 [SMILES: N[C@H]1CCc2nc(NC(=O)c3cccc(CNC(=O)c4ccc(-c5csnn5)cc4)c3)sc2C1]
237 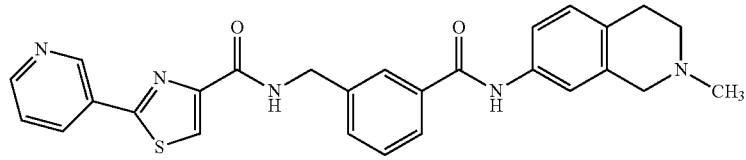 [SMILES: CN1CCc2ccc(NC(=O)c3cccc(CNC(=O)c4csc(-c5cccnc5)n4)c3)cc2C1]
238 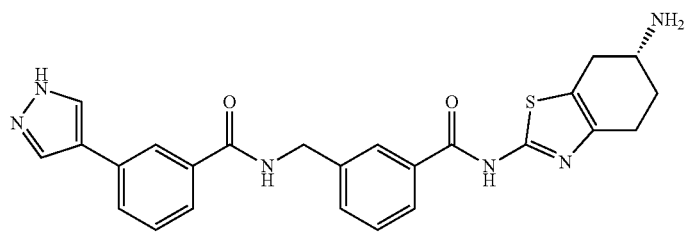 [SMILES: N[C@@H]1CCc2nc(NC(=O)c3cccc(CNC(=O)c4cccc(-c5cn[nH]c5)c4)c3)sc2C1]
239 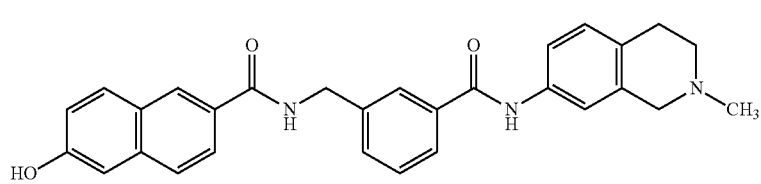
240 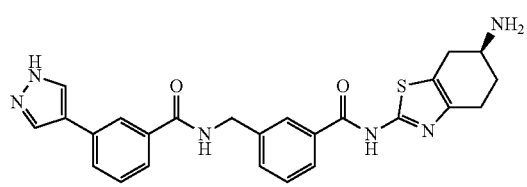
241 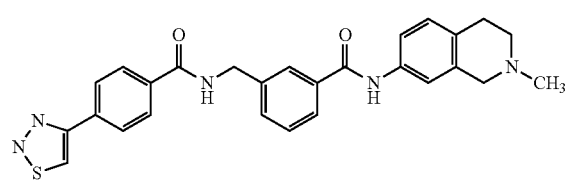
242 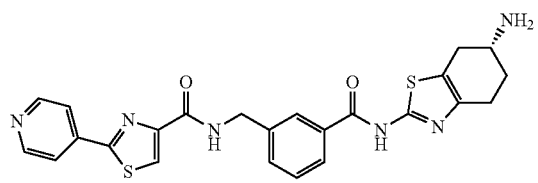
243 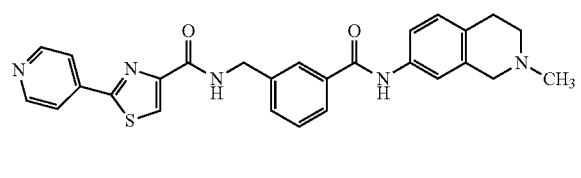

-continued
244
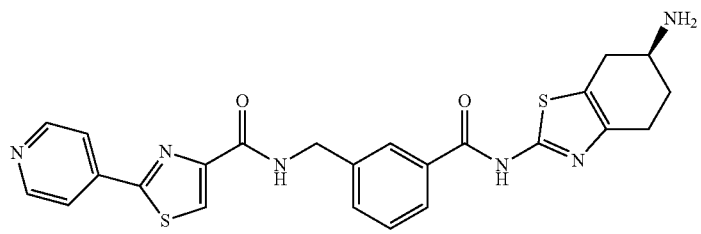 [SMILES: N[C@H]1CCc2nc(NC(=O)c3cccc(CNC(=O)c4csc(-c5ccncc5)n4)c3)sc2C1]
245
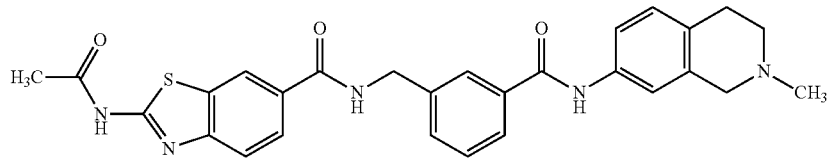 [SMILES: CC(=O)Nc1nc2ccc(C(=O)NCc3cccc(C(=O)Nc4ccc5c(c4)CN(C)CC5)c3)cc2s1]
246
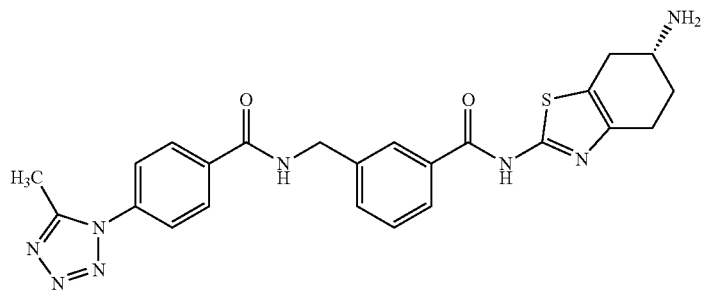 [SMILES: Cc1nnnn1-c1ccc(C(=O)NCc2cccc(C(=O)Nc3nc4c(s3)C[C@H](N)CC4)c2)cc1]
247
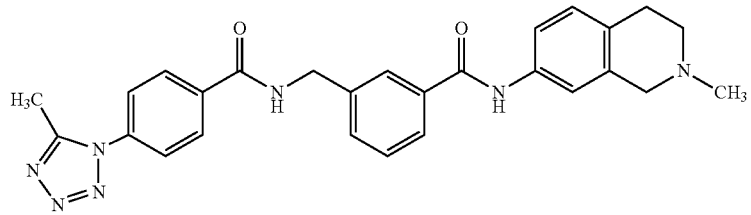
248
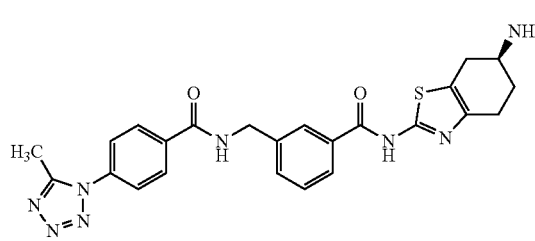
249
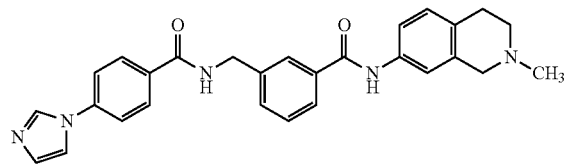
250
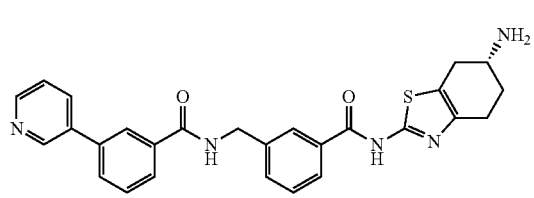
251
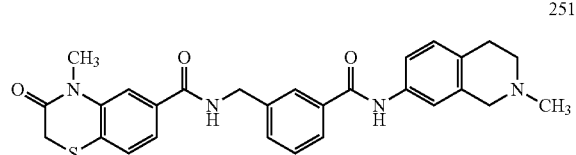
252
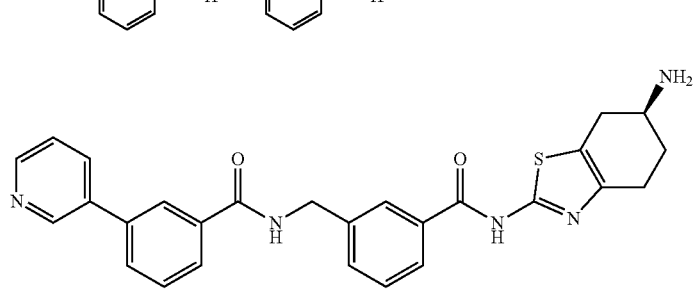

253
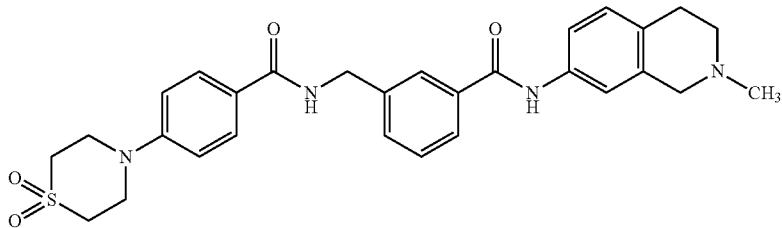
254
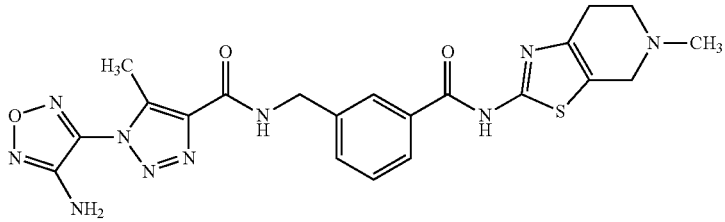
255
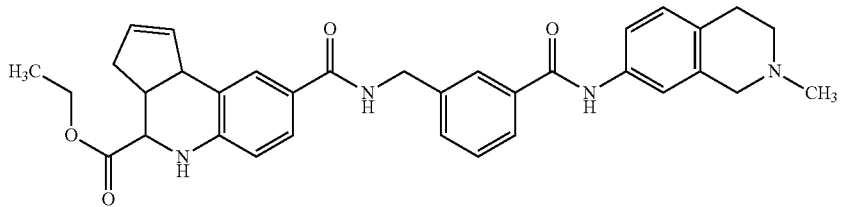 [SMILES: CCOC(=O)C1Nc2ccc(C(=O)NCc3cccc(C(=O)Nc4ccc5c(c4)CN(C)CC5)c3)cc2C2C=CCC12]
256
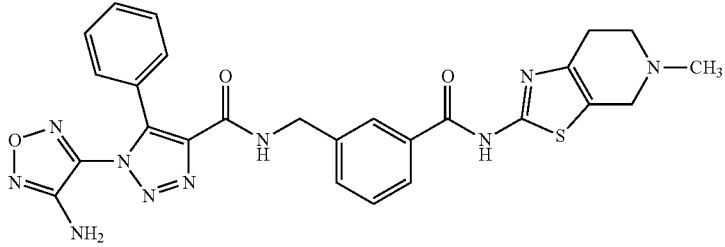
257
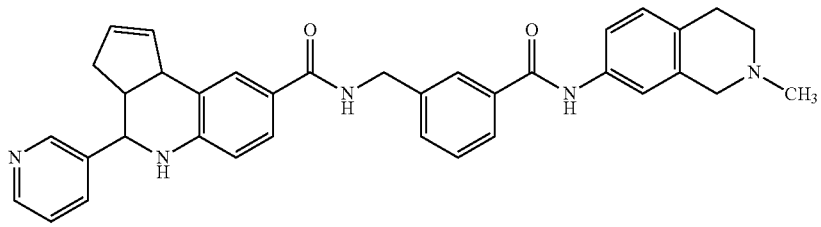 [SMILES: CN1CCc2ccc(NC(=O)c3cccc(CNC(=O)c4ccc5c(c4)C4C=CCC4C(c4cccnc4)N5)c3)cc2C1]
258
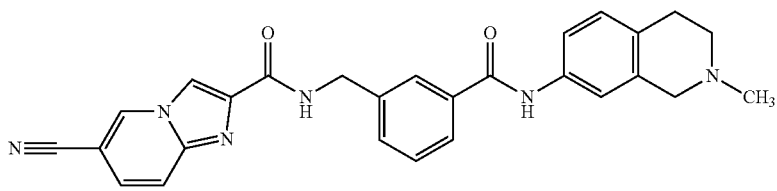 [SMILES: CN1CCc2ccc(NC(=O)c3cccc(CNC(=O)c4cn5cc(C#N)ccc5n4)c3)cc2C1]
259
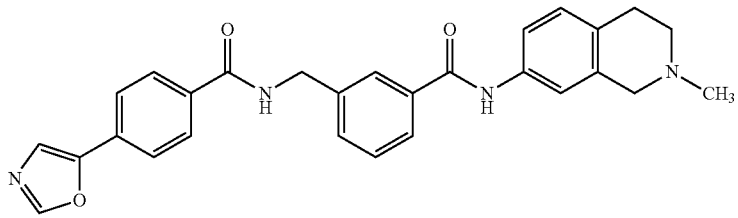 [SMILES: CN1CCc2ccc(NC(=O)c3cccc(CNC(=O)c4ccc(-c5cnco5)cc4)c3)cc2C1]

260
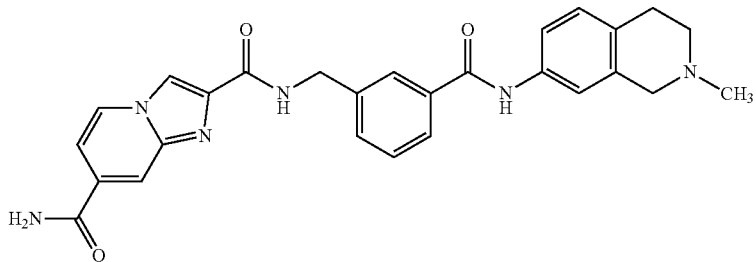 [SMILES: CN1CCc2ccc(NC(=O)c3cccc(CNC(=O)c4cn5ccc(C(N)=O)cc5n4)c3)cc2C1]
261
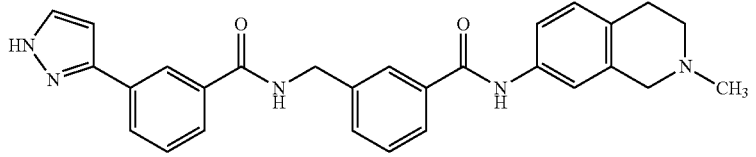 [SMILES: CN1CCc2ccc(NC(=O)c3cccc(CNC(=O)c4cccc(-c5cc[nH]n5)c4)c3)cc2C1]
262 263
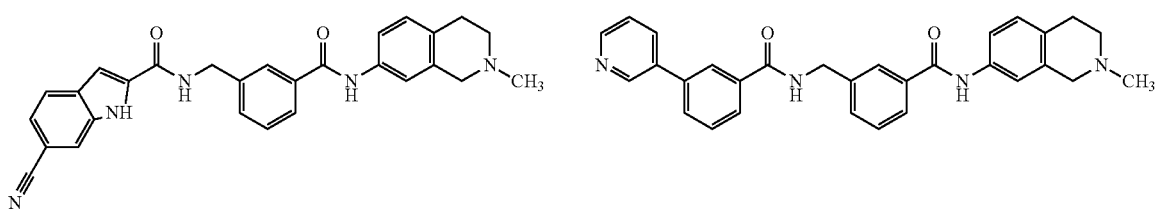
264
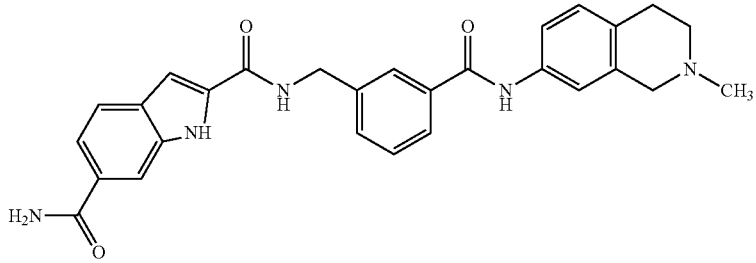 [SMILES: CN1CCc2ccc(NC(=O)c3cccc(CNC(=O)c4cc5ccc(C(N)=O)cc5[nH]4)c3)cc2C1]
265
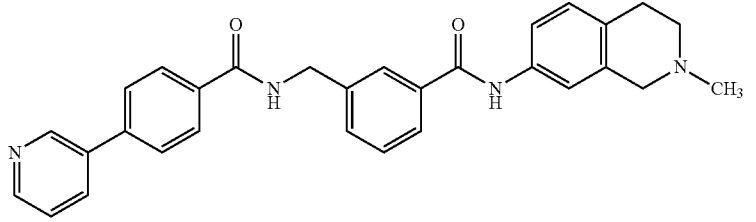 [SMILES: CN1CCc2ccc(NC(=O)c3cccc(CNC(=O)c4ccc(-c5cccnc5)cc4)c3)cc2C1]
266 267
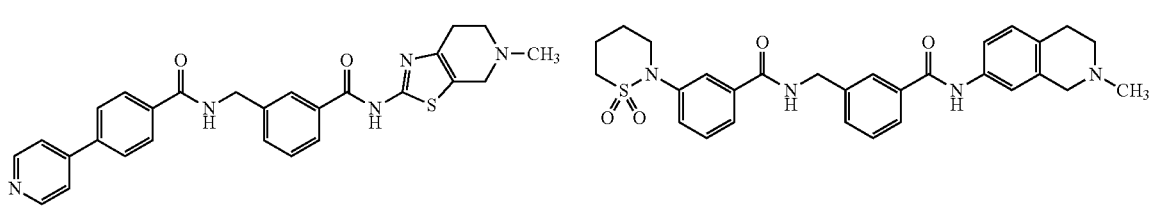
268
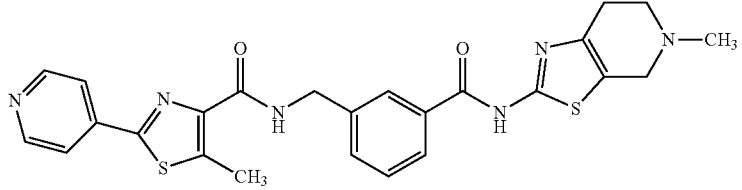 [SMILES: Cc1sc(-c2ccncc2)nc1C(=O)NCc1cccc(C(=O)Nc2nc3c(s2)CN(C)CC3)c1]

269 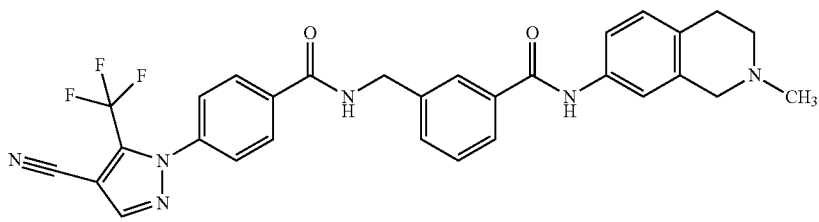 [SMILES: CN1CCc2ccc(NC(=O)c3cccc(CNC(=O)c4ccc(-n5ncc(C#N)c5C(F)(F)F)cc4)c3)cc2C1]
270 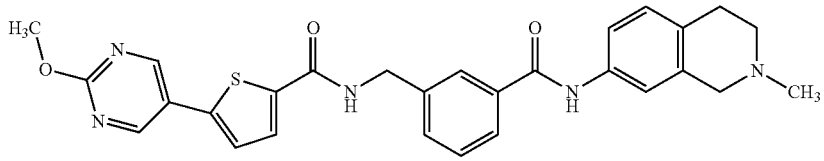
271 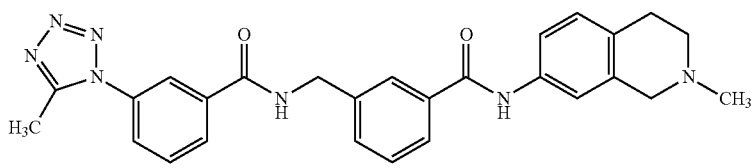 [SMILES: Cc1nnnn1-c1cccc(C(=O)NCc2cccc(C(=O)Nc3ccc4c(c3)CN(C)CC4)c2)c1]
272 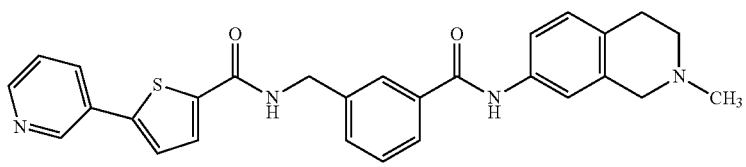 [SMILES: CN1CCc2ccc(NC(=O)c3cccc(CNC(=O)c4ccc(-c5cccnc5)s4)c3)cc2C1]
273 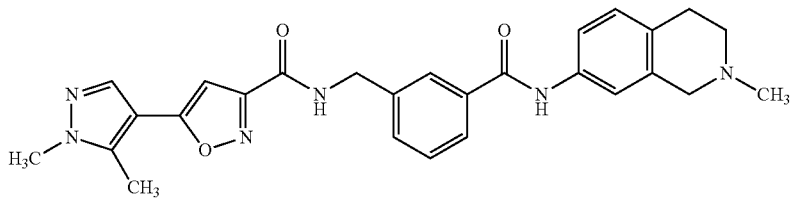
274 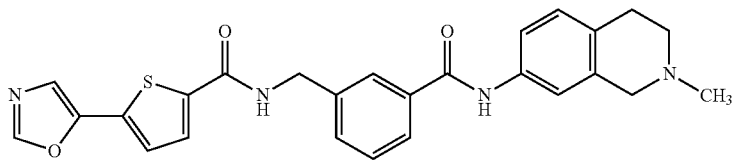
275 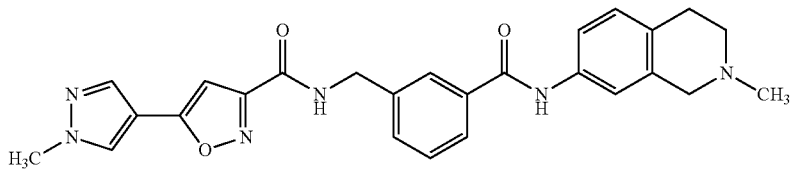
276 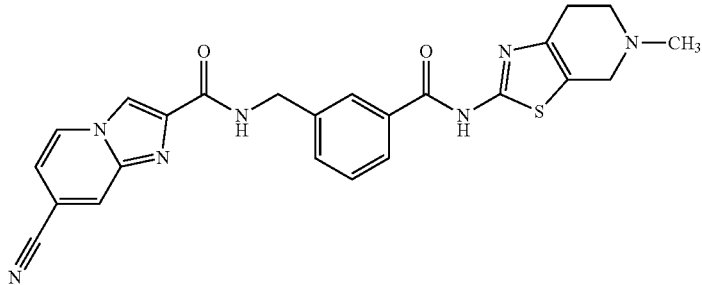 [SMILES: CN1CCc2nc(NC(=O)c3cccc(CNC(=O)c4cn5ccc(C#N)cc5n4)c3)sc2C1]

-continued
277
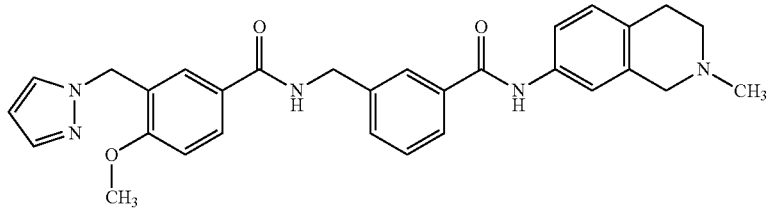 [SMILES: COc1ccc(C(=O)NCc2cccc(C(=O)Nc3ccc4c(c3)CN(C)CC4)c2)cc1Cn1cccn1]
278
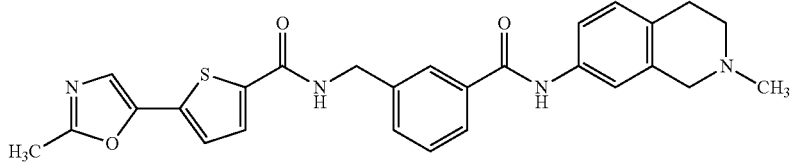
279
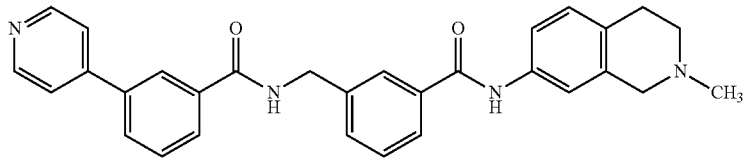 [SMILES: CN1CCc2ccc(NC(=O)c3cccc(CNC(=O)c4cccc(-c5ccncc5)c4)c3)cc2C1]
280
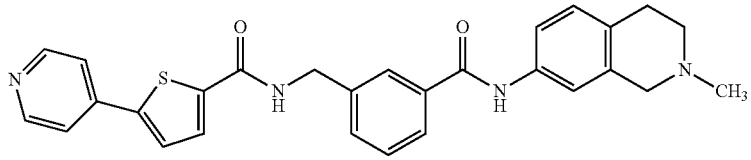 [SMILES: CN1CCc2ccc(NC(=O)c3cccc(CNC(=O)c4ccc(-c5ccncc5)s4)c3)cc2C1]
281
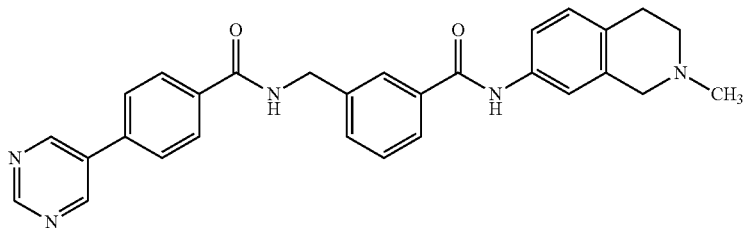 [SMILES: CN1CCc2ccc(NC(=O)c3cccc(CNC(=O)c4ccc(-c5cncnc5)cc4)c3)cc2C1]
282
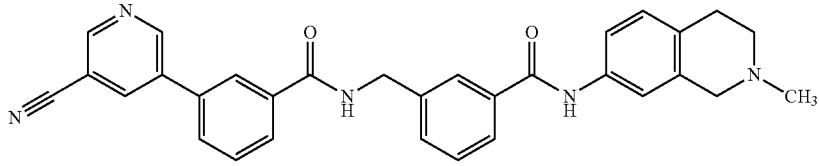 [SMILES: CN1CCc2ccc(NC(=O)c3cccc(CNC(=O)c4cccc(-c5cncc(C#N)c5)c4)c3)cc2C1]
283
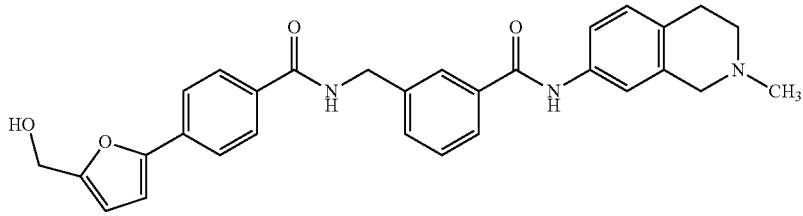 [SMILES: CN1CCc2ccc(NC(=O)c3cccc(CNC(=O)c4ccc(-c5ccc(CO)o5)cc4)c3)cc2C1]
284 285
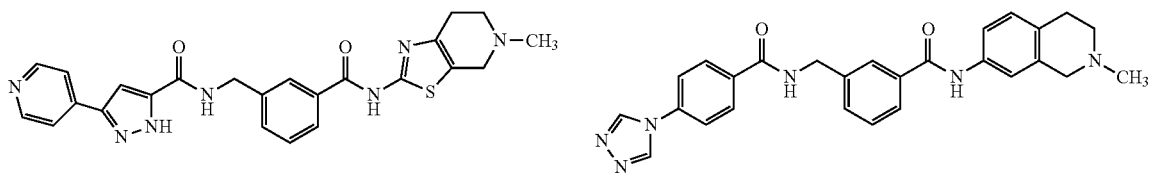

| | |
|---|---|
| 286 | 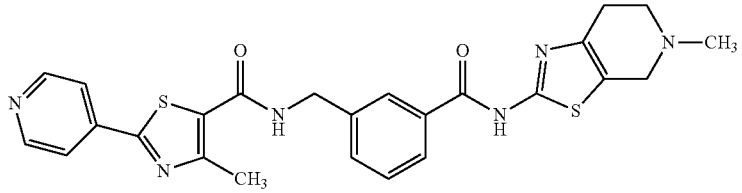 [SMILES: Cc1nc(-c2ccncc2)sc1C(=O)NCc1cccc(C(=O)Nc2nc3c(s2)CN(C)CC3)c1] |
| 287 | 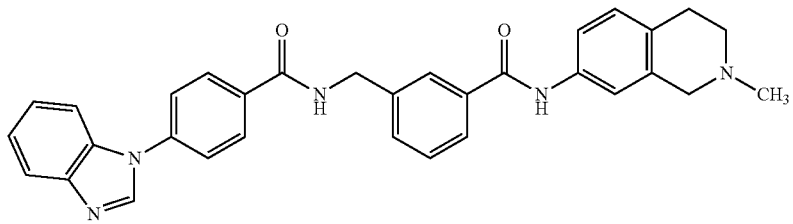 [SMILES: CN1CCc2ccc(NC(=O)c3cccc(CNC(=O)c4ccc(-n5cnc6ccccc65)cc4)c3)cc2C1] |
| 288 | 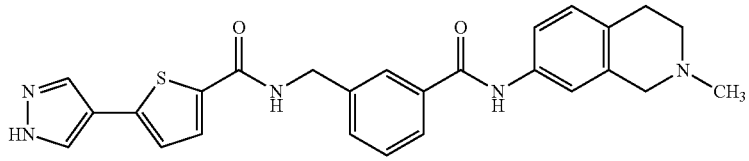 |
| 289 | 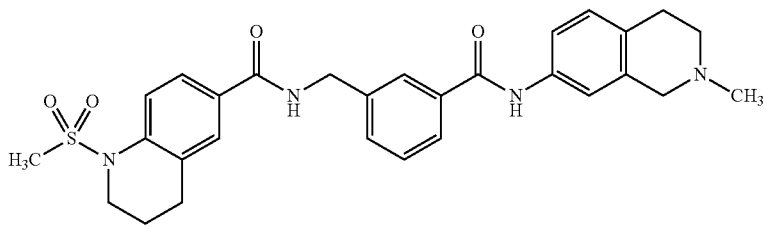 |
| 290 | 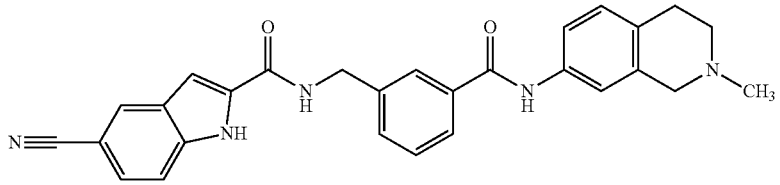 |
| 291 | 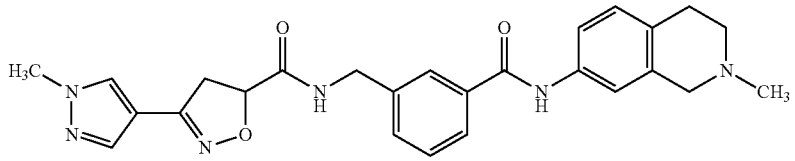 |
| 292 | 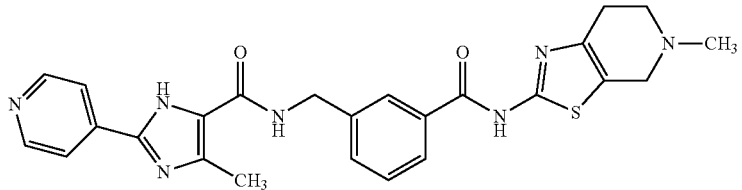 |
| 293 | 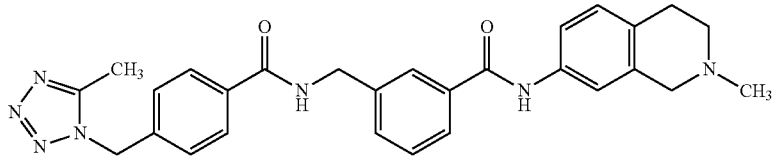 [SMILES: Cc1nnnn1Cc1ccc(C(=O)NCc2cccc(C(=O)Nc3ccc4c(c3)CN(C)CC4)c2)cc1] |

| 207 | 208 |
|---|---|
| -continued | |
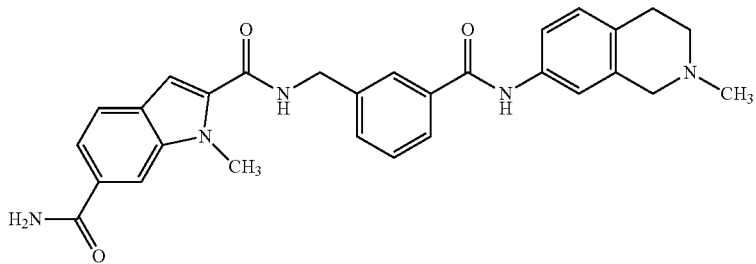 [SMILES: CN1CCc2ccc(NC(=O)c3cccc(CNC(=O)c4cc5ccc(C(N)=O)cc5n4C)c3)cc2C1]
294
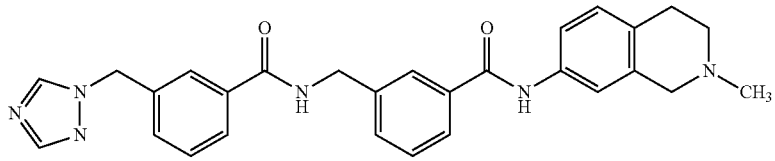 [SMILES: CN1CCc2ccc(NC(=O)c3cccc(CNC(=O)c4cccc(Cn5cncn5)c4)c3)cc2C1]
295
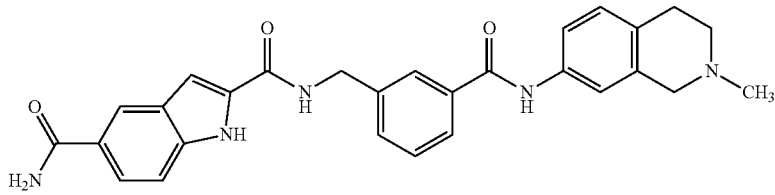 [SMILES: CN1CCc2ccc(NC(=O)c3cccc(CNC(=O)c4cc5cc(C(N)=O)ccc5[nH]4)c3)cc2C1]
296
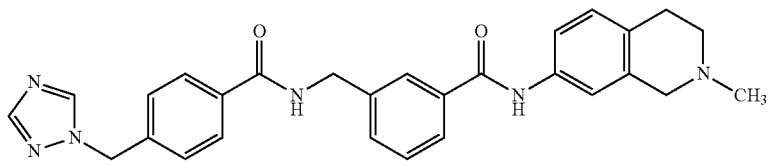 [SMILES: CN1CCc2ccc(NC(=O)c3cccc(CNC(=O)c4ccc(Cn5cncn5)cc4)c3)cc2C1]
297
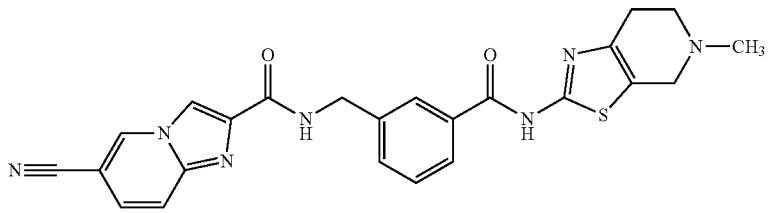 [SMILES: CN1CCc2nc(NC(=O)c3cccc(CNC(=O)c4cn5cc(C#N)ccc5n4)c3)sc2C1]
298
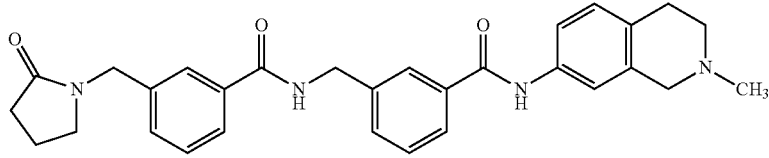 [SMILES: CN1CCc2ccc(NC(=O)c3cccc(CNC(=O)c4cccc(CN5CCCC5=O)c4)c3)cc2C1]
299
300 301
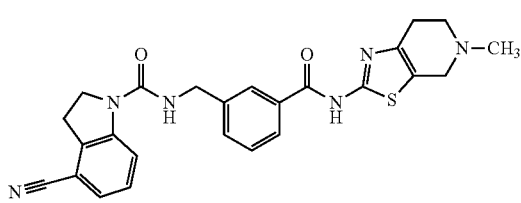 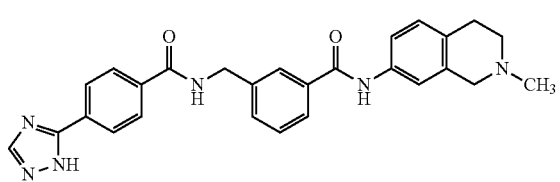

-continued
| 302 | 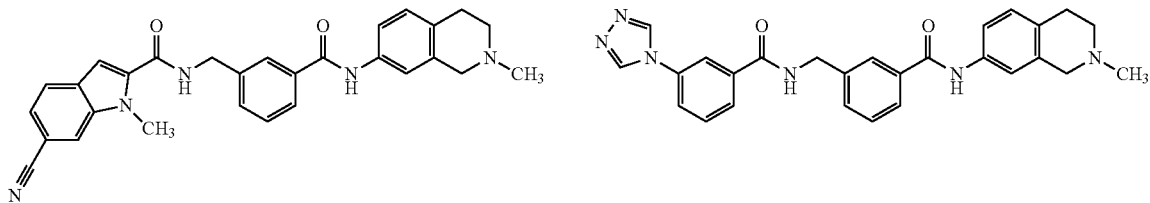 |
| --- | --- |
| 303 | |
| 304 | 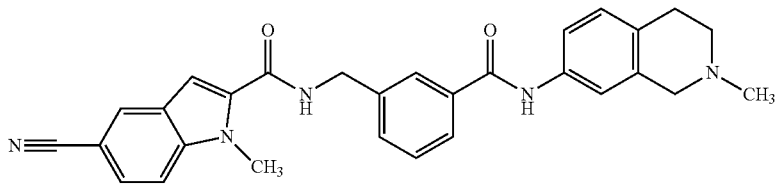 |
| 305 | 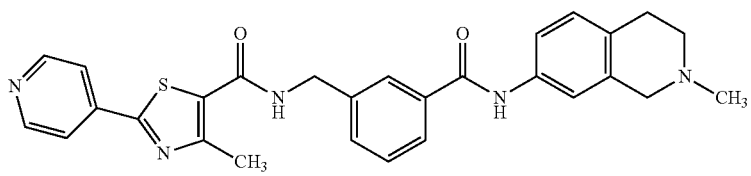 [SMILES: Cc1nc(-c2ccncc2)sc1C(=O)NCc1cccc(C(=O)Nc2ccc3c(c2)CN(C)CC3)c1] |
| 306 | 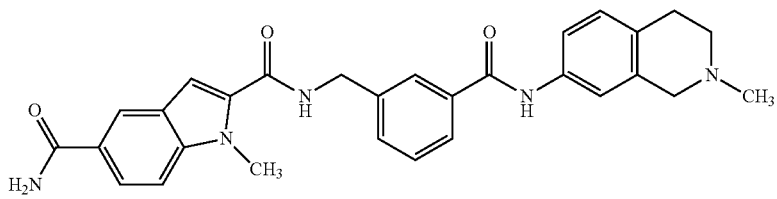 |
| 307 | 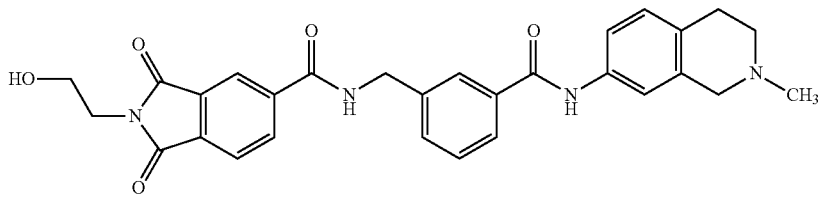 [SMILES: CN1CCc2ccc(NC(=O)c3cccc(CNC(=O)c4ccc5c(c4)C(=O)N(CCO)C5=O)c3)cc2C1] |
| 308 | 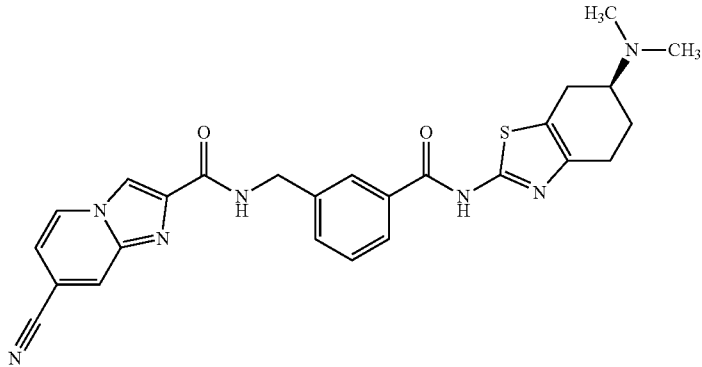 [SMILES: CN(C)[C@H]1CCc2nc(NC(=O)c3cccc(CNC(=O)c4cn5ccc(C#N)cc5n4)c3)sc2C1] |
| 309 | 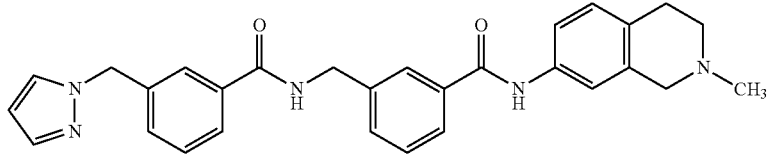 [SMILES: CN1CCc2ccc(NC(=O)c3cccc(CNC(=O)c4cccc(Cn5cccn5)c4)c3)cc2C1] |

| | |
|---|---|
| 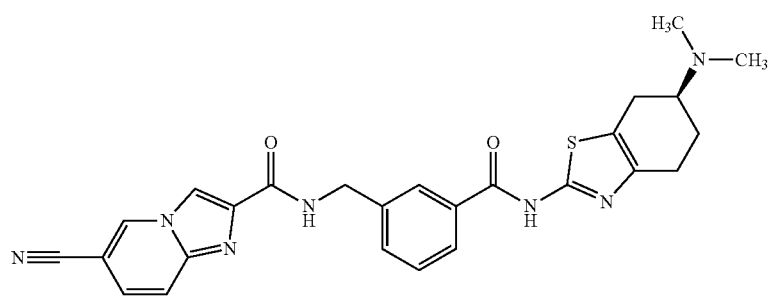 [SMILES: CN(C)[C@H]1CCc2nc(NC(=O)c3cccc(CNC(=O)c4cn5cc(C#N)ccc5n4)c3)sc2C1] | 310 |
| 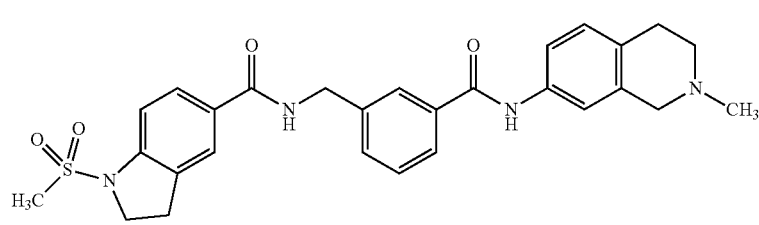 | 311 |
| 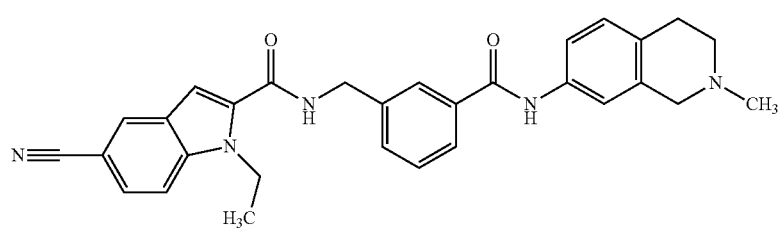 [SMILES: CCn1c(C(=O)NCc2cccc(C(=O)Nc3ccc4c(c3)CN(C)CC4)c2)cc2cc(C#N)ccc21] | 312 |
| 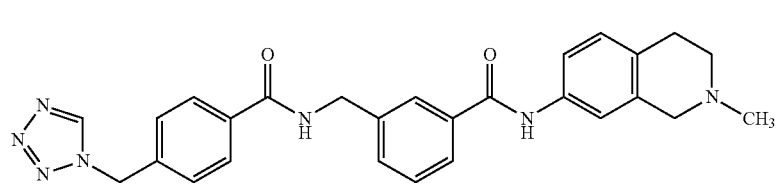 [SMILES: CN1CCc2ccc(NC(=O)c3cccc(CNC(=O)c4ccc(Cn5cnnn5)cc4)c3)cc2C1] | 313 |
| 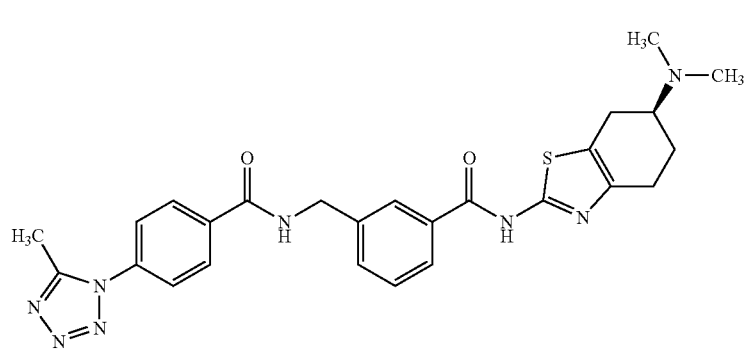 [SMILES: Cc1nnnn1-c1ccc(C(=O)NCc2cccc(C(=O)Nc3nc4c(s3)C[C@@H](N(C)C)CC4)c2)cc1] | 314 |
| 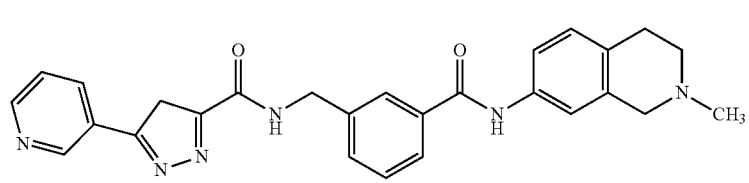 [SMILES: CN1CCc2ccc(NC(=O)c3cccc(CNC(=O)C4=NN=C(c5cccnc5)C4)c3)cc2C1] | 315 |

-continued
316
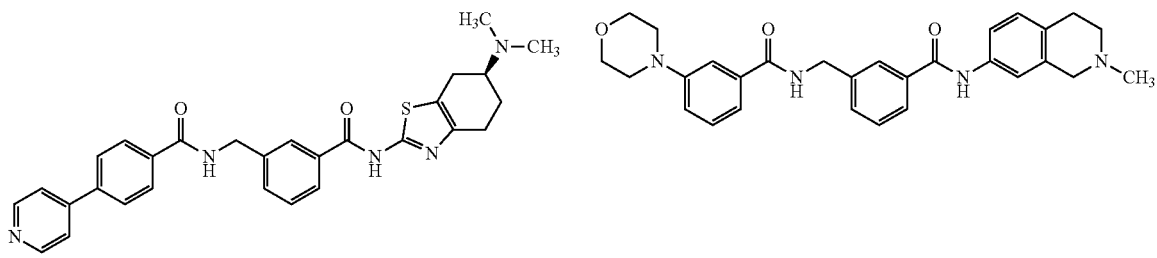
317
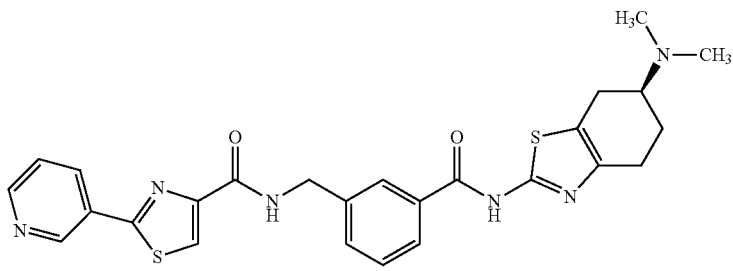 [SMILES: CN(C)[C@H]1CCc2nc(NC(=O)c3cccc(CNC(=O)c4csc(-c5cccnc5)n4)c3)sc2C1]
318
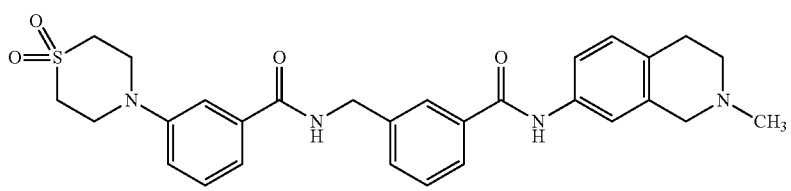 [SMILES: CN1CCc2ccc(NC(=O)c3cccc(CNC(=O)c4cccc(N5CCS(=O)(=O)CC5)c4)c3)cc2C1]
319
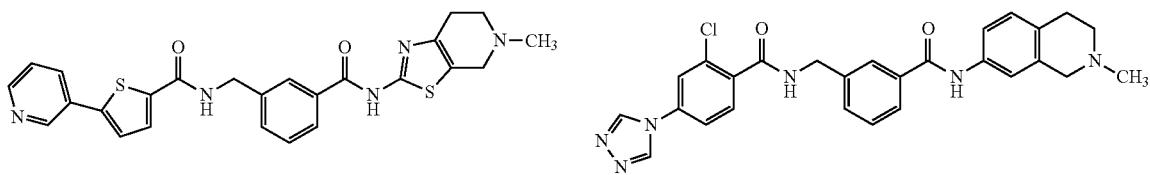
320
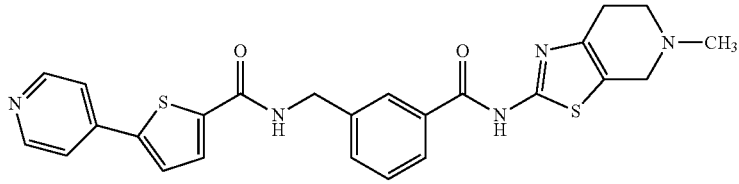 [SMILES: CN1CCc2nc(NC(=O)c3cccc(CNC(=O)c4ccc(-c5ccncc5)s4)c3)sc2C1]
321
322
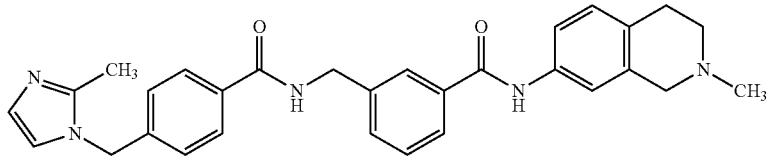 [SMILES: Cc1nccn1Cc1ccc(C(=O)NCc2cccc(C(=O)Nc3ccc4c(c3)CN(C)CC4)c2)cc1]
323
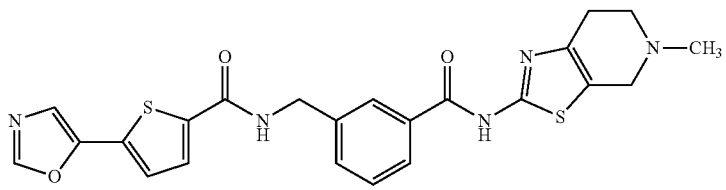
324

325
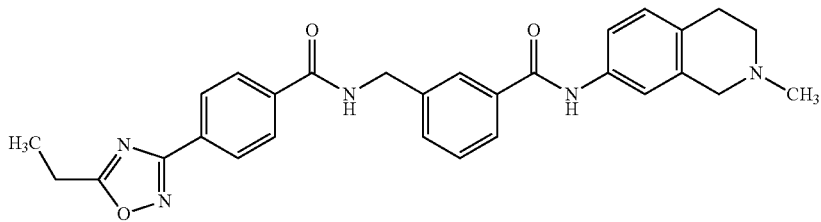
326
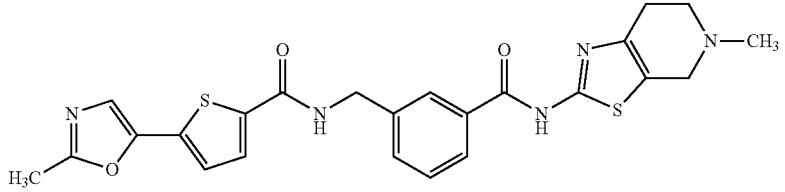
327
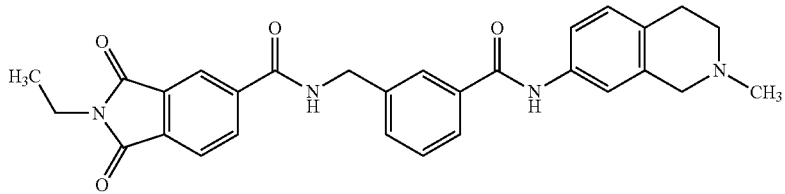 [SMILES: CCN1C(=O)c2ccc(C(=O)NCc3cccc(C(=O)Nc4ccc5c(c4)CN(C)CC5)c3)cc2C1=O]
328 329
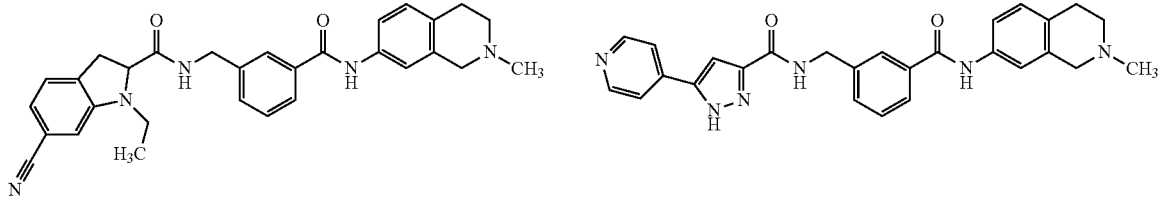
330
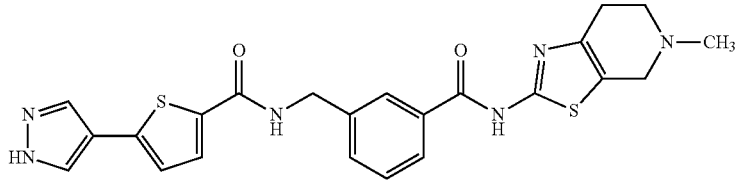
331 332
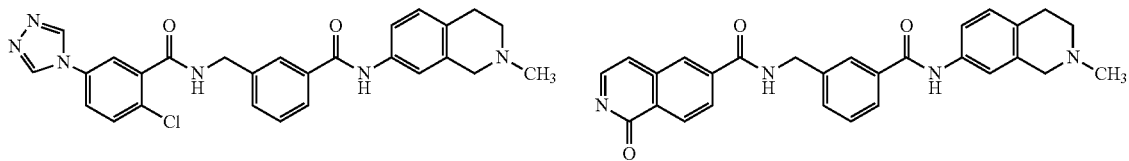
333
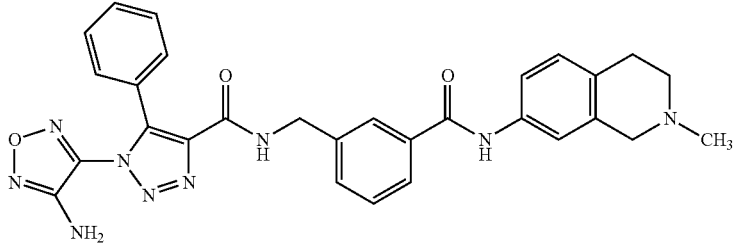

| 217 | 218 |
|---|---|
| -continued | |
334
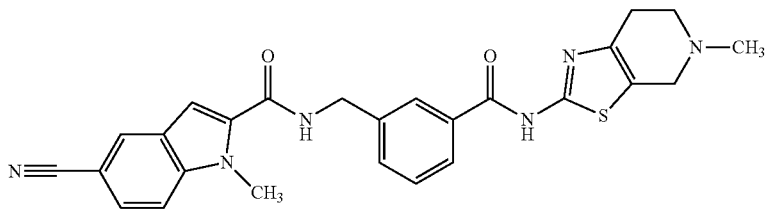 [SMILES: CN1CCc2nc(NC(=O)c3cccc(CNC(=O)c4cc5cc(C#N)ccc5n4C)c3)sc2C1]
335
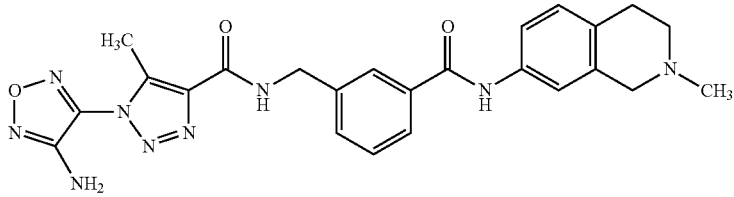
336
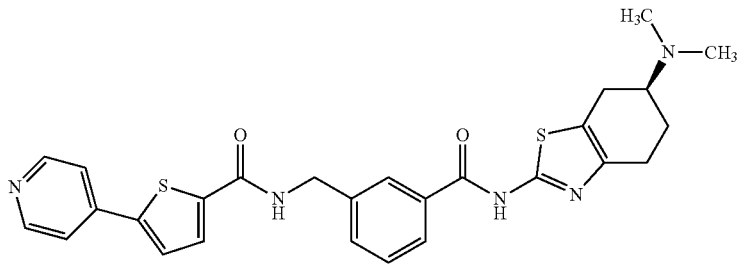 [SMILES: CN(C)[C@H]1CCc2nc(NC(=O)c3cccc(CNC(=O)c4ccc(-c5ccncc5)s4)c3)sc2C1]
337
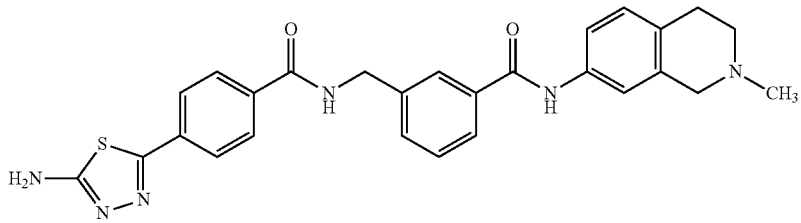 [SMILES: CN1CCc2ccc(NC(=O)c3cccc(CNC(=O)c4ccc(-c5nnc(N)s5)cc4)c3)cc2C1]
| 338 | 339 |
|---|---|
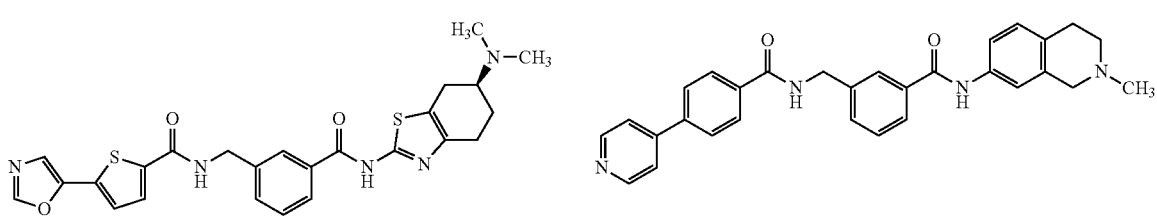
| 340 | 341 |
|---|---|
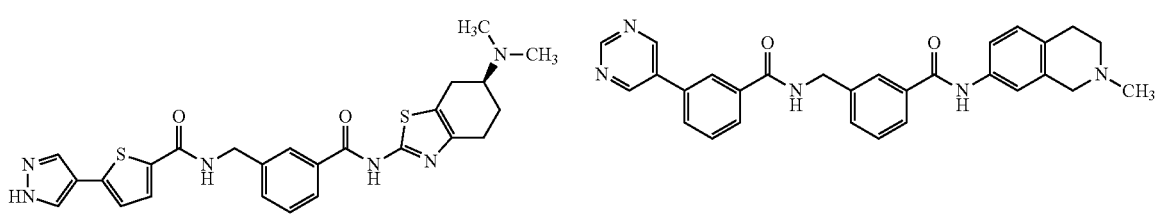
| 342 | 343 |
|---|---|
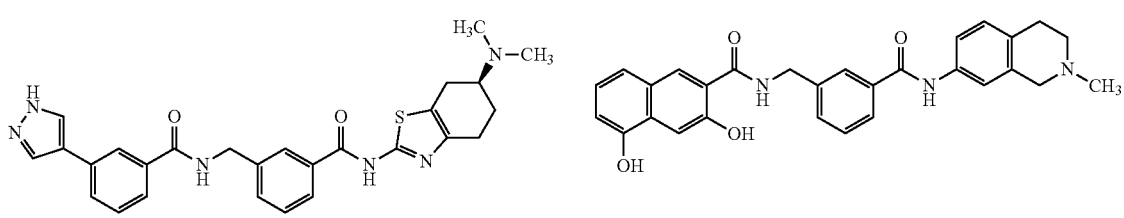

344
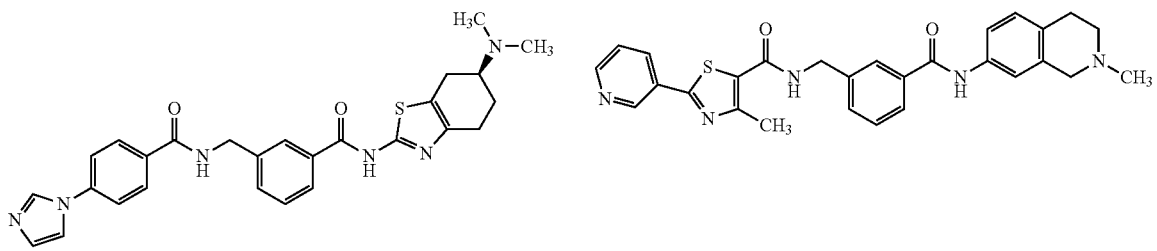
345
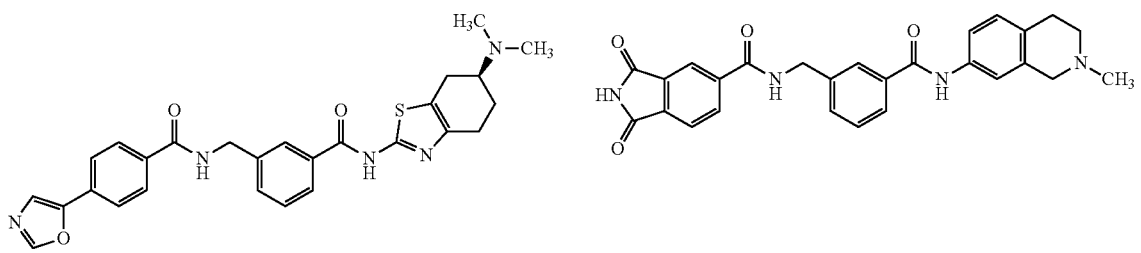
346
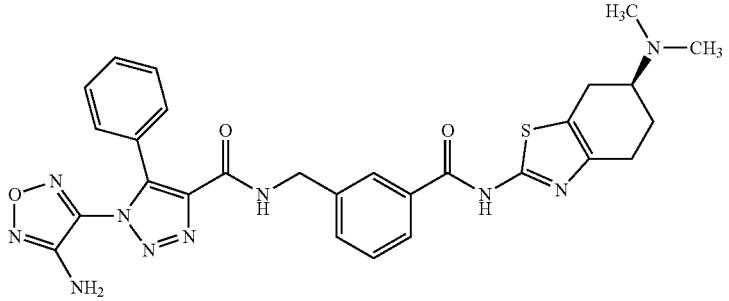
347
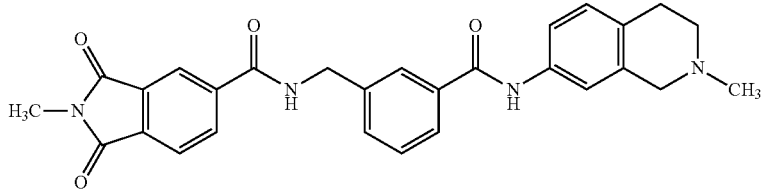
348
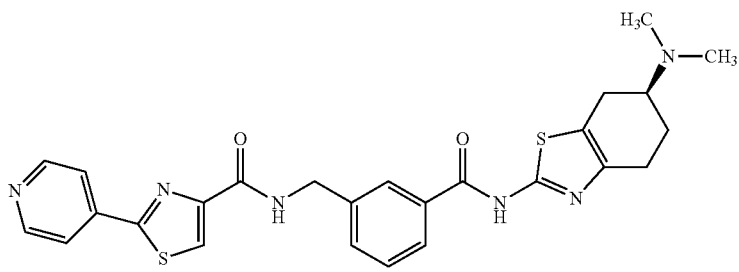 [SMILES: CN(C)[C@H]1CCc2nc(NC(=O)c3cccc(CNC(=O)c4csc(-c5ccncc5)n4)c3)sc2C1]
349
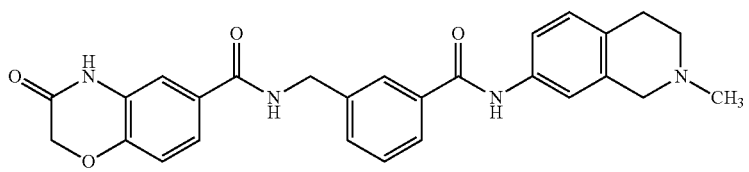 [SMILES: CN1CCc2ccc(NC(=O)c3cccc(CNC(=O)c4ccc5c(c4)NC(=O)CO5)c3)cc2C1]
350
351

-continued
| 352 | 353 |
|---|---|
| 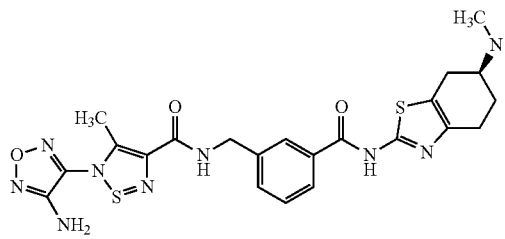 | 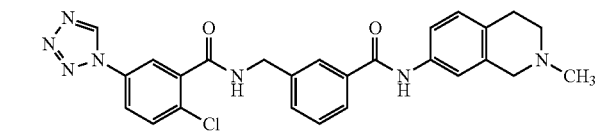 |
| 354 | |
| 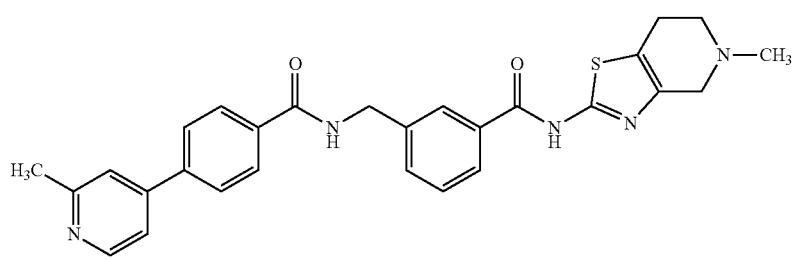 | |
| 355 | 356 |
| 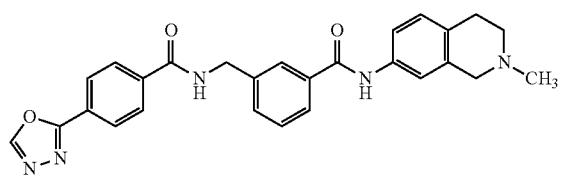 | 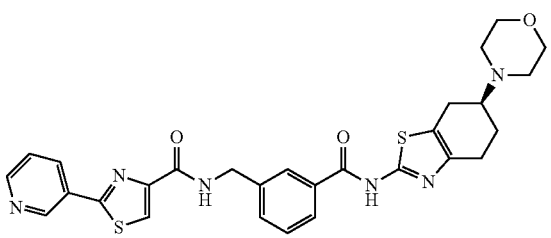 |
| 357 | 358 |
| 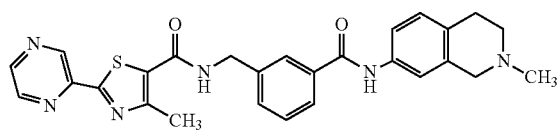 | 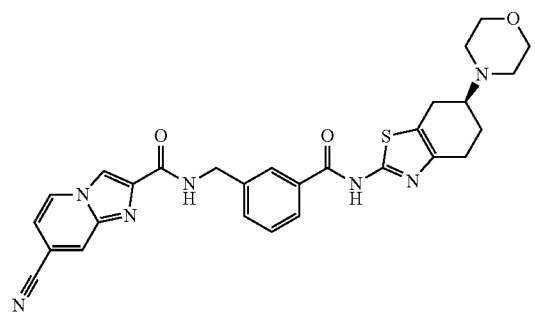 |
| 359 | |
| 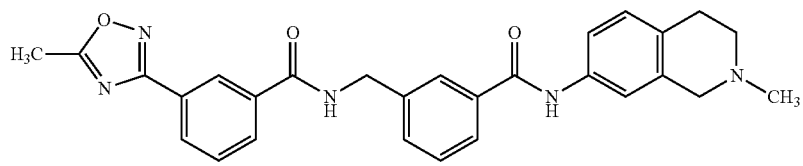 | |
| 360 | |
| 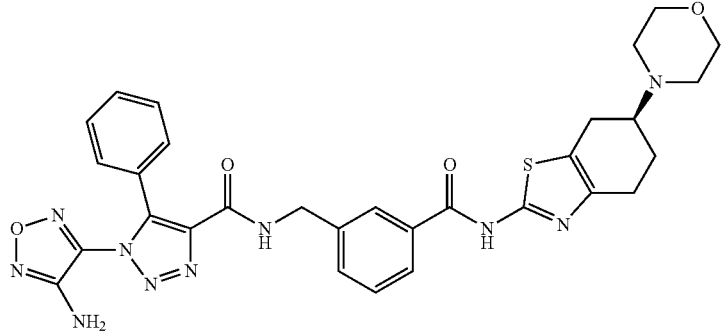 | |

-continued
361
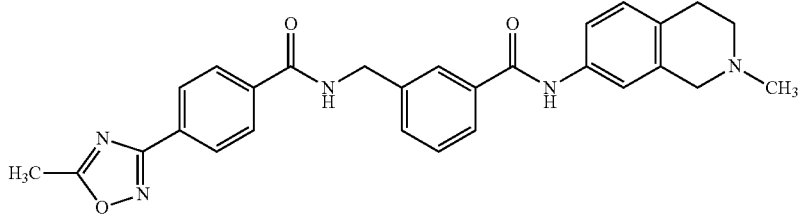
362
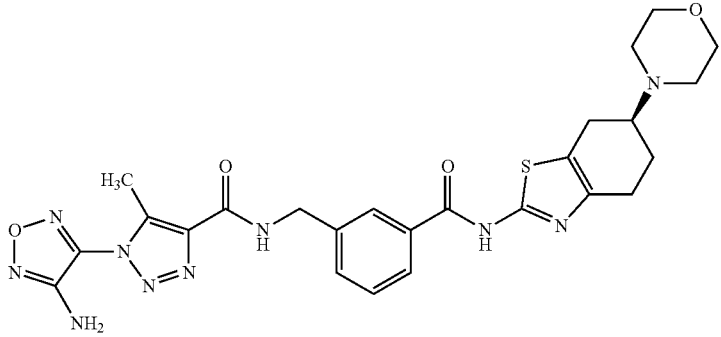
363
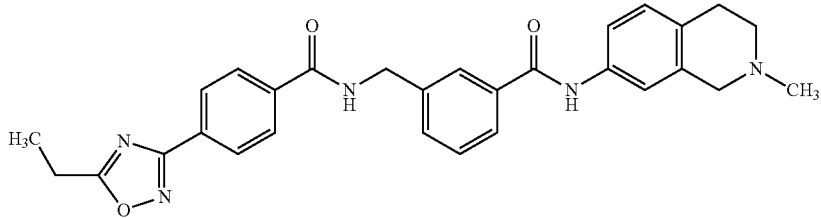
364
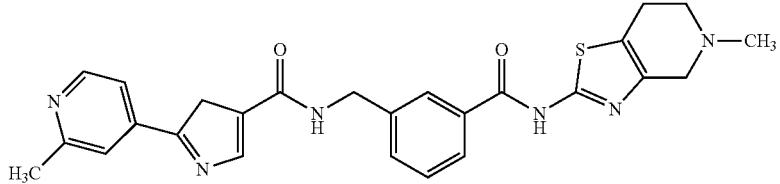
365 366
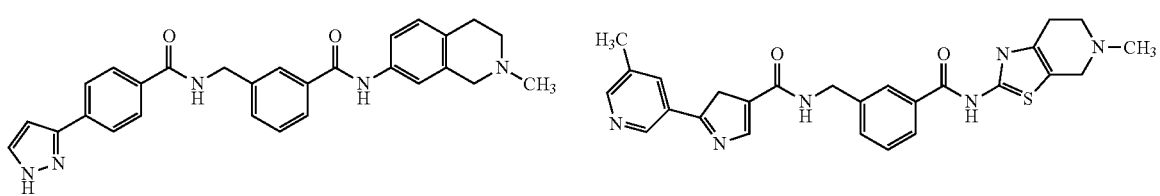
367
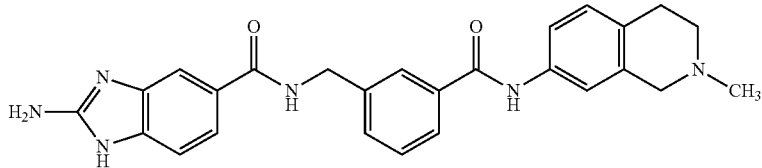 [SMILES: CN1CCc2ccc(NC(=O)c3cccc(CNC(=O)c4ccc5[nH]c(N)nc5c4)c3)cc2C1]
368 369
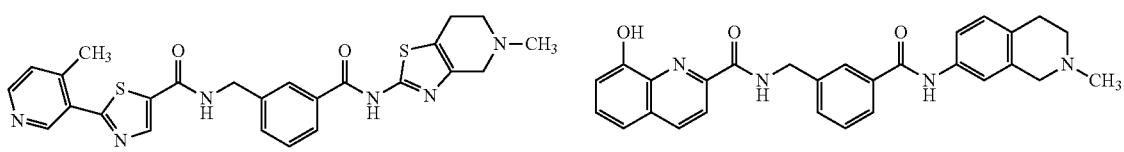

-continued
370 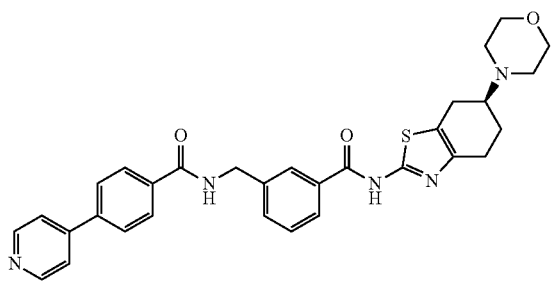 [SMILES: O=C(NCc1cccc(C(=O)Nc2nc3c(s2)C[C@@H](N2CCOCC2)CC3)c1)c1ccc(-c2ccncc2)cc1]
371 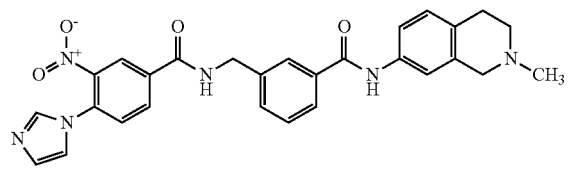
372 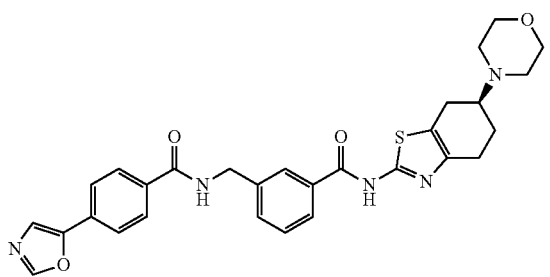 [SMILES: O=C(NCc1cccc(C(=O)Nc2nc3c(s2)C[C@@H](N2CCOCC2)CC3)c1)c1ccc(-c2cnco2)cc1]
373 
374 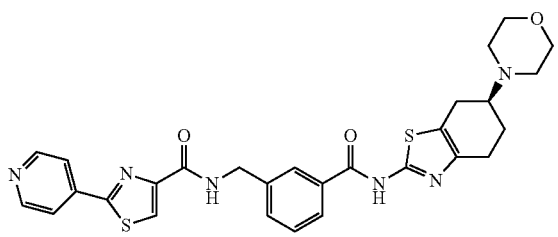 [SMILES: O=C(Nc1nc2c(s1)C[C@@H](N1CCOCC1)CC2)c1cccc(CNC(=O)c2csc(-c3ccncc3)n2)c1]
375 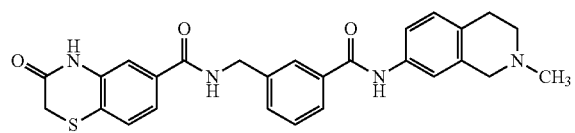
376 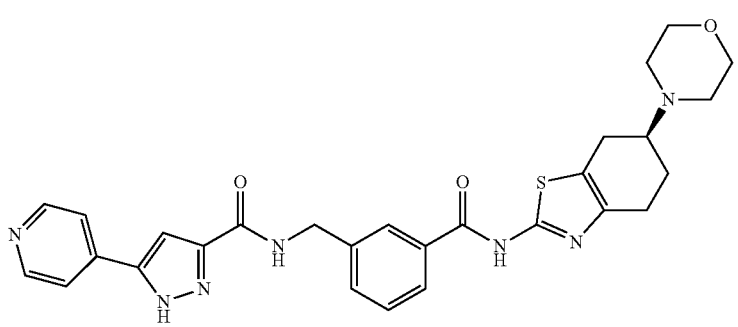 [SMILES: O=C(Nc1nc2c(s1)C[C@@H](N1CCOCC1)CC2)c1cccc(CNC(=O)c2cc(-c3ccncc3)[nH]n2)c1]
377 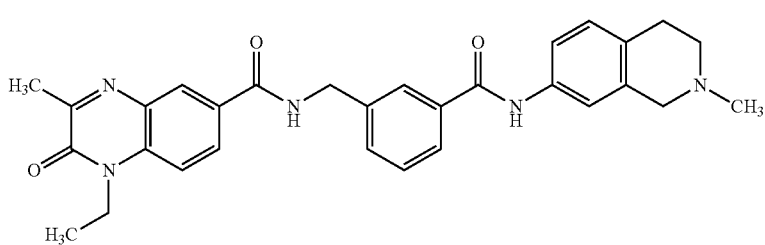 [SMILES: CCn1c(=O)c(C)nc2cc(C(=O)NCc3cccc(C(=O)Nc4ccc5c(c4)CN(C)CC5)c3)ccc21]

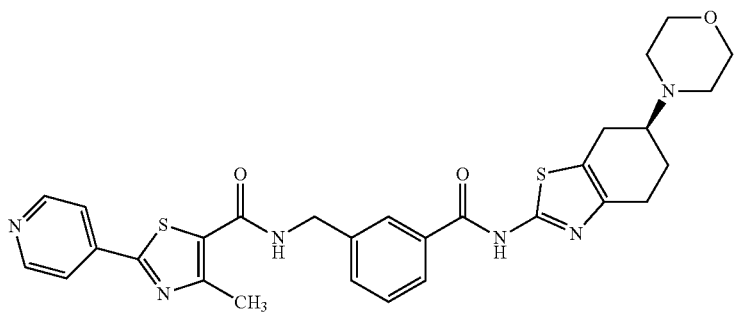 [SMILES: Cc1nc(-c2ccncc2)sc1C(=O)NCc1cccc(C(=O)Nc2nc3c(s2)C[C@@H](N2CCOCC2)CC3)c1]
378
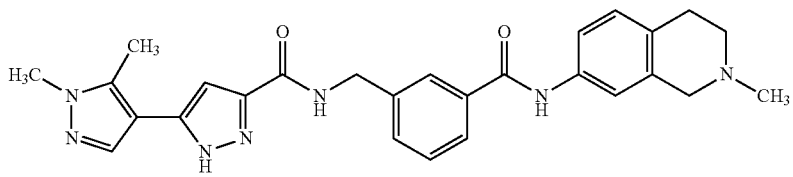
379
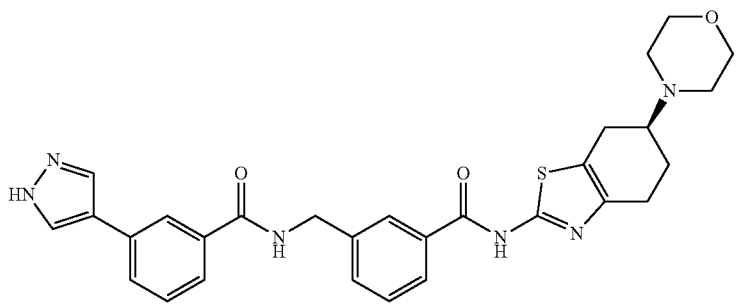 [SMILES: O=C(NCc1cccc(C(=O)Nc2nc3c(s2)C[C@@H](N2CCOCC2)CC3)c1)c1cccc(-c2cn[nH]c2)c1]
380
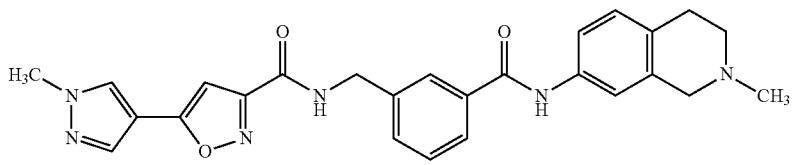
381
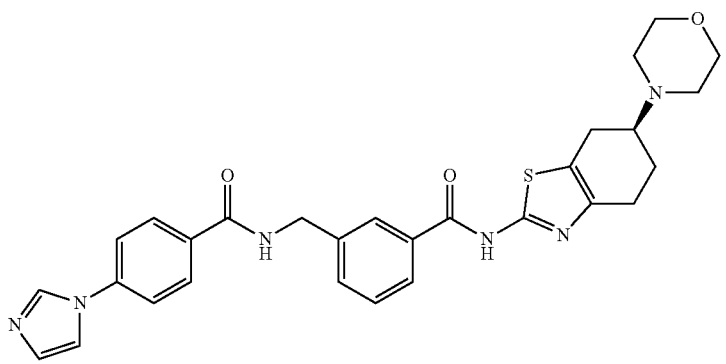 [SMILES: O=C(NCc1cccc(C(=O)Nc2nc3c(s2)C[C@@H](N2CCOCC2)CC3)c1)c1ccc(-n2ccnc2)cc1]
382
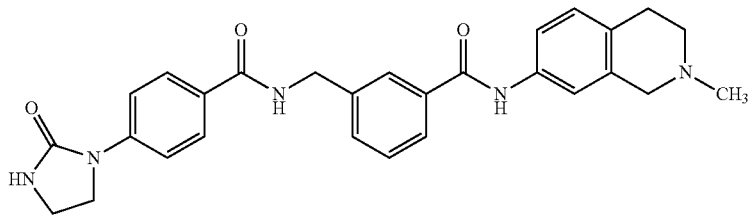 [SMILES: CN1CCc2ccc(NC(=O)c3cccc(CNC(=O)c4ccc(N5CCNC5=O)cc4)c3)cc2C1]
383

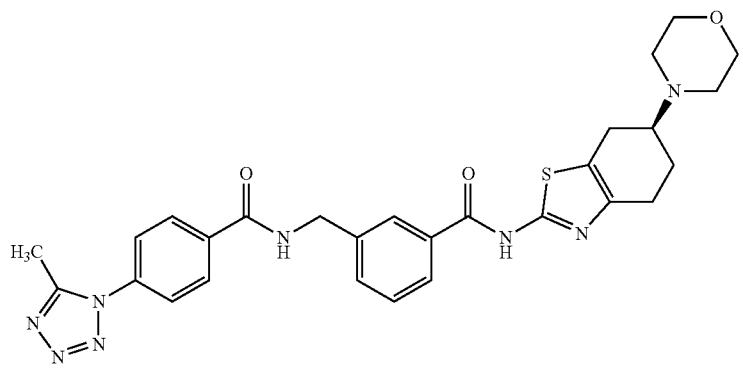
384
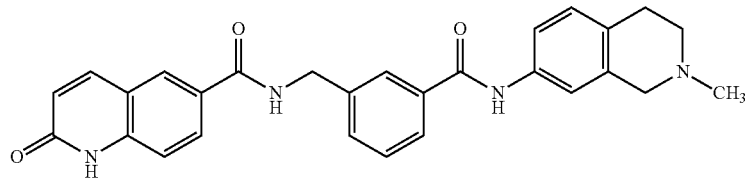 [SMILES: CN1CCc2ccc(NC(=O)c3cccc(CNC(=O)c4ccc5[nH]c(=O)ccc5c4)c3)cc2C1]
385
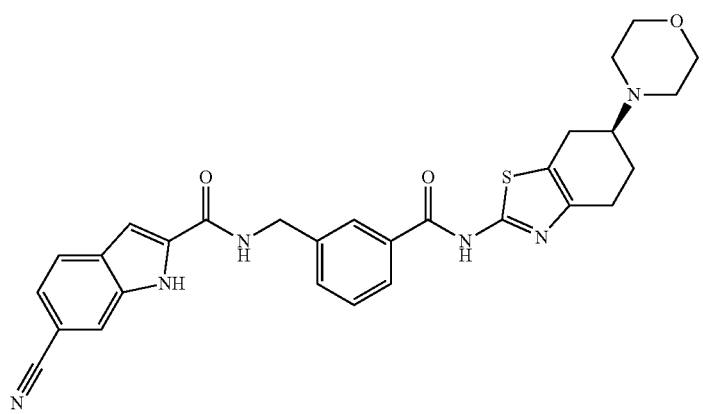 [SMILES: N#Cc1ccc2cc(C(=O)NCc3cccc(C(=O)Nc4nc5c(s4)C[C@@H](N4CCOCC4)CC5)c3)[nH]c2c1]
386
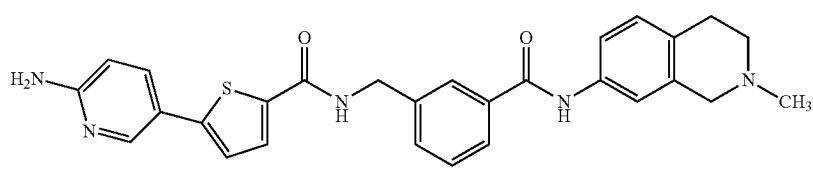 [SMILES: CN1CCc2ccc(NC(=O)c3cccc(CNC(=O)c4ccc(-c5ccc(N)nc5)s4)c3)cc2C1]
387
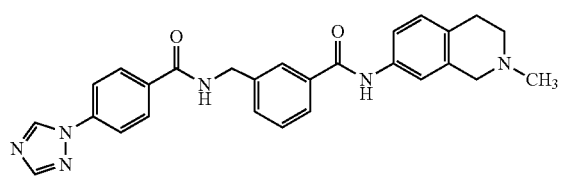
388
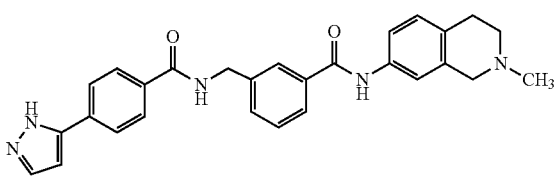
389
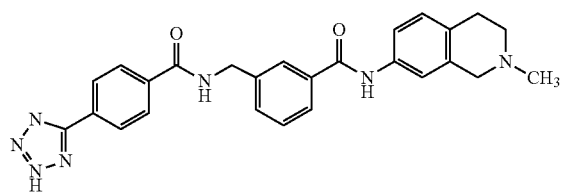
390
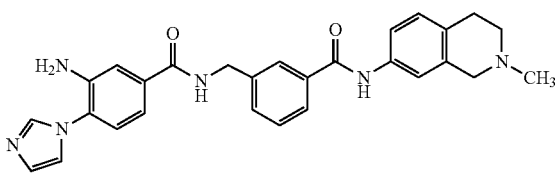
391

392 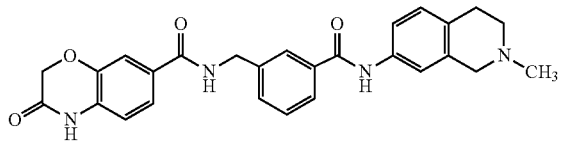
393 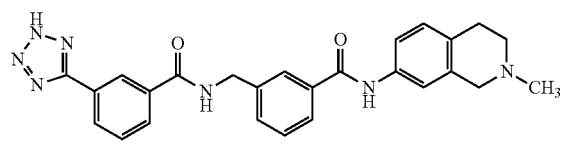
394 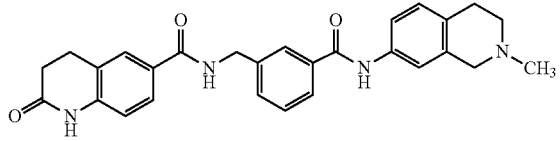
395 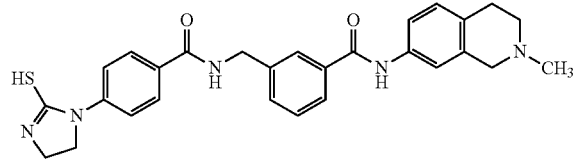
396 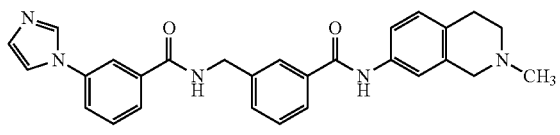
397 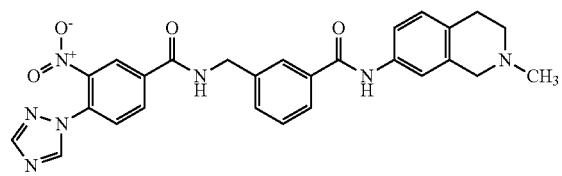
398 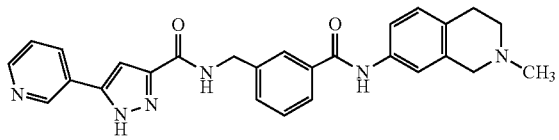
399 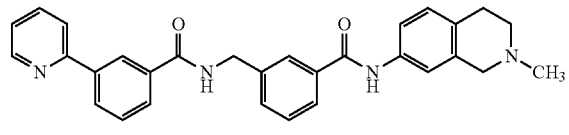
400 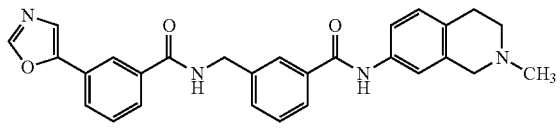
401 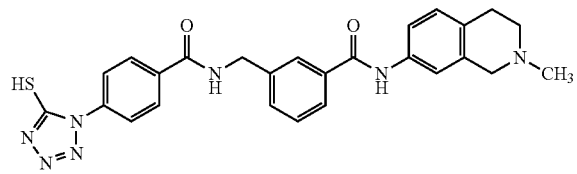
402 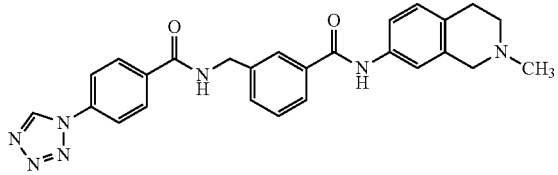
403 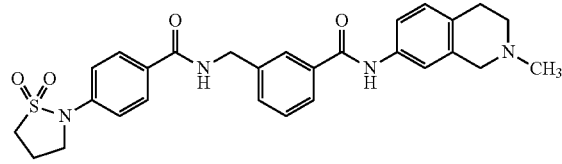
404 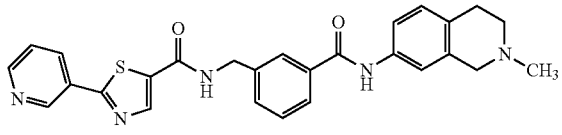
405 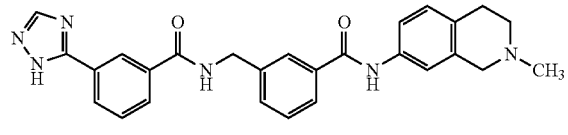
406 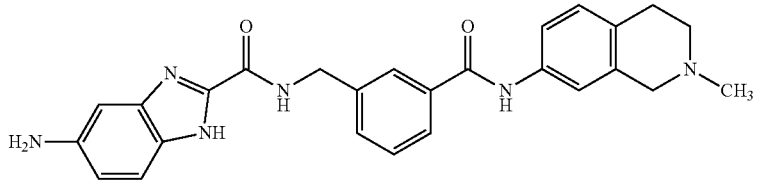 [SMILES: CN1CCc2ccc(NC(=O)c3cccc(CNC(=O)c4nc5cc(N)ccc5[nH]4)c3)cc2C1]

-continued
407
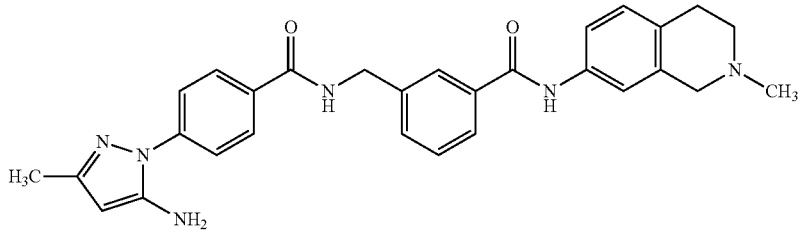
408
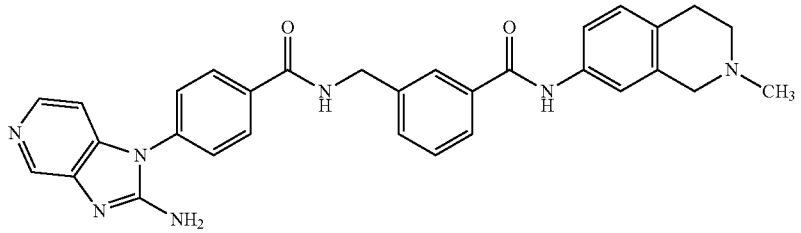 [SMILES: Cc1nc2cnccc2n1-c1ccc(C(=O)NCc2cccc(C(=O)Nc3ccc4c(c3)CN(C)CC4)c2)cc1]
409
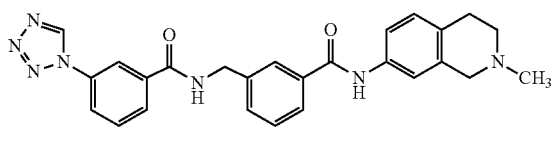
410
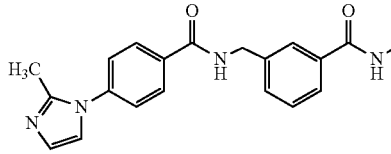
411
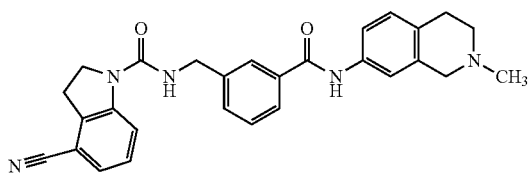
412
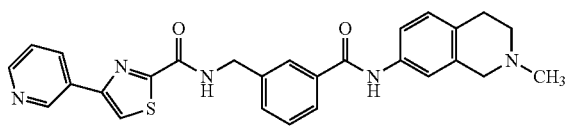
413
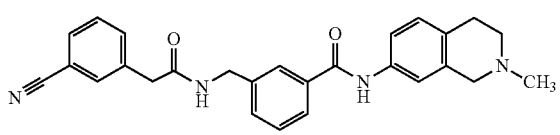
414
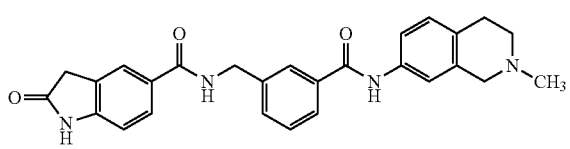
415
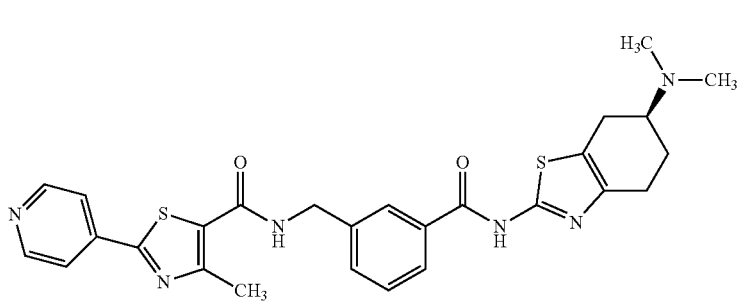 [SMILES: Cc1nc(-c2ccncc2)sc1C(=O)NCc1cccc(C(=O)Nc2nc3c(s2)C[C@@H](N(C)C)CC3)c1]
416
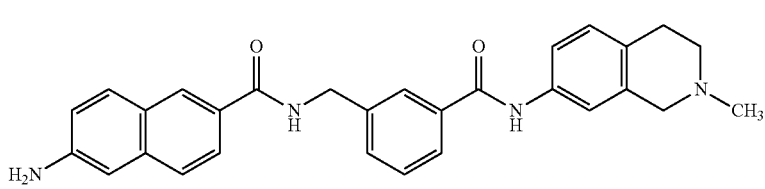 [SMILES: CN1CCc2ccc(NC(=O)c3cccc(CNC(=O)c4ccc5cc(N)ccc5c4)c3)cc2C1]

-continued
417
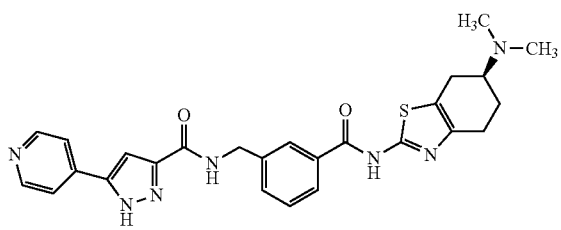
418
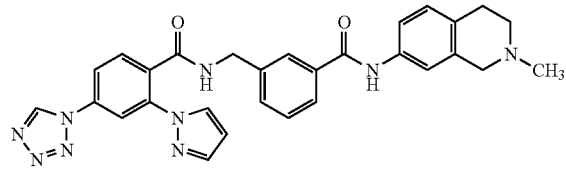
419
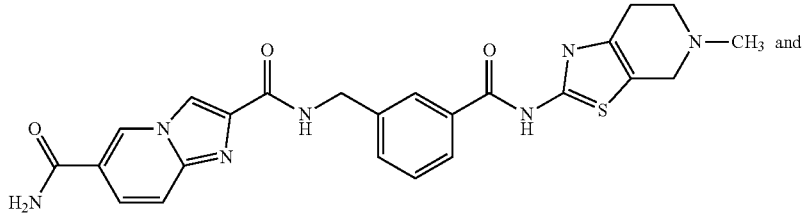
and
420
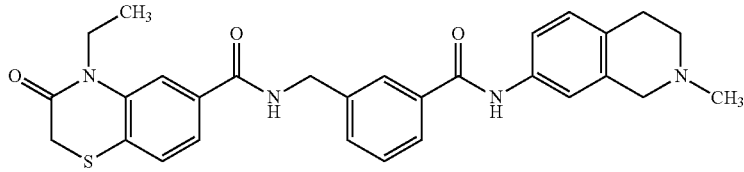 [SMILES: CCN1C(=O)CSc2ccc(C(=O)NCc3cccc(C(=O)Nc4ccc5c(c4)CN(C)CC5)c3)cc21]
and the pharmaceutically acceptable salts thereof.
12. The compound according to claim 11 selected from compound numbers 2-4, 6, 8, 12, 14, 18, 20-22, 24, 26-34, 36-40, 42, 44, 46, 48-50, 52-54, 56, 58, 62, 64, 66, 68-70, 74, 76, 78, 80, 84, 86, 88, 90, 92, 94-96, 98, 100, 102, 104, 106, 108, 110, 112, 114, 116, 118-120, 122-126, 128-130, 132-134, 136, 138, 140, 142, 144-146, 148, 150, 152, 154, 155, 160, 162, 164, 166, 168, 170, 172, 174-179, 182, 184, 186, 188, 190, 194, 198, 200-202, 205, 207, 209 and 210 and the pharmaceutically acceptable salts thereof.
* * * * *